United States Patent
Saito et al.

(10) Patent No.: US 11,046,889 B2
(45) Date of Patent: *Jun. 29, 2021

(54) POLYMERIZABLE COMPOUND AND OPTICALLY ANISOTROPIC BODY

(71) Applicant: DIC Corporation, Tokyo (JP)

(72) Inventors: Yoshitaka Saito, Kita-adachi-gun (JP); Tatsufumi Yamazaki, Kita-adachi-gun (JP); Masahiro Horiguchi, Kita-adachi-gun (JP); Junichi Mamiya, Kita-adachi-gun (JP); Toru Tsuruta, Kita-adachi-gun (JP)

(73) Assignee: DIC CORPORATION, Tokyo (JP)

( * ) Notice: Subject to any disclaimer, the term of this patent is extended or adjusted under 35 U.S.C. 154(b) by 151 days.

This patent is subject to a terminal disclaimer.

(21) Appl. No.: 16/060,265

(22) PCT Filed: Dec. 1, 2016

(86) PCT No.: PCT/JP2016/085717
§ 371 (c)(1),
(2) Date: Jun. 7, 2018

(87) PCT Pub. No.: WO2017/098988
PCT Pub. Date: Jun. 15, 2017

(65) Prior Publication Data
US 2018/0362847 A1    Dec. 20, 2018

(30) Foreign Application Priority Data
Dec. 8, 2015    (JP) .............................. JP2015-239359

(51) Int. Cl.
| | | |
|---|---|---|
| *C09K 19/38* | (2006.01) | |
| *C09K 19/34* | (2006.01) | |
| *C07D 277/66* | (2006.01) | |
| *C07D 277/82* | (2006.01) | |
| *C07D 417/04* | (2006.01) | |
| *C07D 409/04* | (2006.01) | |
| *C07D 339/06* | (2006.01) | |
| *C08F 20/30* | (2006.01) | |
| *C07D 277/84* | (2006.01) | |

(Continued)

(52) U.S. Cl.
CPC ........ *C09K 19/3497* (2013.01); *C07D 277/64* (2013.01); *C07D 277/66* (2013.01); *C07D 277/82* (2013.01); *C07D 277/84* (2013.01); *C07D 339/06* (2013.01); *C07D 409/04* (2013.01); *C07D 417/04* (2013.01); *C08F 20/30* (2013.01); *C08F 222/1006* (2013.01); *C09K 19/3491* (2013.01); *C09K 2019/0448* (2013.01); *C09K 2019/122* (2013.01); *C09K 2019/2035* (2013.01); *C09K 2019/3004* (2013.01); *C09K 2019/548* (2013.01); *C09K 2219/03* (2013.01); *G02F 1/133633* (2021.01)

(58) Field of Classification Search
CPC ....................................................... C09K 19/54
See application file for complete search history.

(56) References Cited

U.S. PATENT DOCUMENTS

| 5,445,854 A | 8/1995 | Newsham et al. |
| 2007/0111199 A1 | 5/2007 | Housey |
(Continued)

FOREIGN PATENT DOCUMENTS

| CN | 101279901 A | 10/2008 |
| GB | 1016964 A | 1/1966 |
(Continued)

OTHER PUBLICATIONS

International Search Report dated Jan. 31, 2017, issued in counterpart International Application No. PCT/JP2016/085717 (3 pages).
Notification of Reasons for Refusal dated Oct. 26, 2017, issued in counterpart Japanese Patent Application No. 2017-549348, w/English translation (6 pages).
Decision of Refusal dated Mar. 20, 2018, issued in counterpart Japanese Patent Application No. 2017-549348, w/English translation (4 pages).
Calvin, Joel et al., "Rhodium-Catalyzed and Zinc(II)-Triflate-Promoted Asymmetric Hydrogenation of Tetrasubstituted a, b-Unsaturated Ketones", Oranic Letters, 2012, vol. 14, No. 4, pp. 1038-1041, (counterpart to U.S. Appl. No. 15/517,441). (4 pages).

(Continued)

*Primary Examiner* — Chanceity N Robinson
(74) *Attorney, Agent, or Firm* — Westerman, Hattori, Daniels & Adrian, LLP

(57) ABSTRACT

The polymerizable liquid crystal compound has reverse wavelength dispersion or low wavelength dispersion and has high solubility in various solvents. The polymerizable liquid crystal compound provides an optically anisotropic body having high adhesiveness to substrates (or alignment films), by adding the polymerizable liquid crystal compound to a polymerizable composition and polymerizing the polymerizable composition using ultraviolet light. The invention provides a polymerizable composition containing the polymerizable liquid crystal compound having reverse wavelength dispersion or low wavelength dispersion, a polymer obtained by polymerizing the polymerizable composition, and an optically anisotropic body using the polymer. The present invention provides a polymerizable low wavelength dispersion or polymerizable reverse wavelength dispersion compound having in the molecule a partial structure represented by the general formula (AO-1); and also provides a composition containing the compound, a polymer obtained by polymerizing the composition, and an optically anisotropic body and the like using the polymer.

$$\text{---}\!\!\left(\!R^0\!\!-\!\!O\right)_{\!\!n^0}\!\!\text{---} \qquad \text{(AO-1)}$$

9 Claims, No Drawings

(51) Int. Cl.
*C07D 277/64* (2006.01)
*C08F 222/10* (2006.01)
*G02F 1/13363* (2006.01)
*C09K 19/04* (2006.01)
*C09K 19/12* (2006.01)
*C09K 19/20* (2006.01)
*C09K 19/30* (2006.01)
*C09K 19/54* (2006.01)

(56) References Cited

U.S. PATENT DOCUMENTS

| | | | |
|---|---|---|---|
| 2007/0176145 | A1 | 8/2007 | Nishikawa et al. |
| 2009/0189120 | A1 | 7/2009 | Takeuchi |
| 2010/0045901 | A1 | 2/2010 | Uehira et al. |
| 2010/0047478 | A1 | 2/2010 | Tomita et al. |
| 2010/0072422 | A1 | 3/2010 | Parri et al. |
| 2011/0240918 | A1* | 10/2011 | Ootsuki ............ C09K 19/2021 252/299.61 |
| 2012/0224245 | A1 | 9/2012 | Adlem et al. |
| 2014/0107247 | A1 | 4/2014 | Sakamoto et al. |
| 2014/0142266 | A1* | 5/2014 | Sakamoto ............ C07D 215/38 526/257 |
| 2014/0200320 | A1 | 7/2014 | Sakamoto et al. |
| 2014/0309396 | A1 | 10/2014 | Sakamoto et al. |
| 2015/0115199 | A1 | 4/2015 | Choi et al. |
| 2015/0175564 | A1 | 6/2015 | Sakamoto et al. |
| 2015/0183902 | A1 | 7/2015 | Sakamoto et al. |
| 2015/0274647 | A1 | 10/2015 | Sakamoto et al. |
| 2015/0274872 | A1 | 10/2015 | Sakamoto et al. |
| 2015/0277006 | A1* | 10/2015 | Takasago ............ G02B 1/12 349/194 |
| 2015/0277007 | A1 | 10/2015 | Matsuyama et al. |
| 2015/0277010 | A1 | 10/2015 | Aimatsu et al. |
| 2015/0285979 | A1 | 10/2015 | Aimatsu |
| 2016/0002374 | A1 | 1/2016 | Sakamoto et al. |
| 2016/0200841 | A1 | 7/2016 | Sakamoto |
| 2016/0257659 | A1 | 9/2016 | Sakamoto et al. |
| 2017/0003418 | A1 | 1/2017 | Yamamoto et al. |
| 2017/0008833 | A1 | 1/2017 | Sakamoto et al. |
| 2017/0166815 | A1 | 6/2017 | Sakamoto et al. |
| 2017/0260150 | A1 | 9/2017 | Nose et al. |
| 2017/0306233 | A1 | 10/2017 | Horiguchi et al. |
| 2017/0369783 | A1* | 12/2017 | Horiguchi ............ C07C 69/753 |
| 2018/0022716 | A1* | 1/2018 | Horiguchi ............ C07C 243/20 526/257 |

FOREIGN PATENT DOCUMENTS

| | | | |
|---|---|---|---|
| JP | S63-55543 | A | 3/1988 |
| JP | 2005-289980 | A | 10/2005 |
| JP | 2007-328053 | A | 12/2007 |
| JP | 2008-107767 | A | 5/2008 |
| JP | 2008-127336 | A | 6/2008 |
| JP | 2008-239873 | A | 10/2008 |
| JP | 2008-273925 | A | 11/2008 |
| JP | 2009-029795 | A | 2/2009 |
| JP | 2009-506125 | A | 2/2009 |
| JP | 2009-062508 | A | 3/2009 |
| JP | 2009-179563 | A | 8/2009 |
| JP | 2010-31223 | A | 2/2010 |
| JP | 2010-100541 | A | 5/2010 |
| JP | 2010-522892 | A | 7/2010 |
| JP | 2011-006361 | A | 1/2011 |
| JP | 2011-207765 | A | 10/2011 |
| JP | 2011-225520 | A | 11/2011 |
| JP | 2011-246381 | A | 12/2011 |
| JP | 2012-8525 | A | 1/2012 |
| JP | 2012-077055 | A | 4/2012 |
| JP | 2013-509458 | A | 3/2013 |
| JP | 2015-110531 | A | 6/2015 |
| JP | 2015-110532 | A | 6/2015 |
| JP | 2015-151383 | A | 8/2015 |
| JP | 2015-200877 | A | 11/2015 |
| JP | 2016-113583 | A | 6/2016 |
| JP | 2017-88591 | A | 5/2017 |
| JP | 6164509 | B2 | 7/2017 |
| JP | 6217999 | B2 | 10/2017 |
| WO | 2005/112540 | A1 | 12/2005 |
| WO | 2012/141245 | A1 | 10/2012 |
| WO | 2012/147904 | A1 | 11/2012 |
| WO | 2012/176679 | A1 | 12/2012 |
| WO | 2013/157888 | A1 | 10/2013 |
| WO | 2013/180217 | A1 | 12/2013 |
| WO | 2014/010325 | A1 | 1/2014 |
| WO | 2014/061709 | A1 | 4/2014 |
| WO | 2014/065176 | A1 | 5/2014 |
| WO | 2014/065243 | A1 | 5/2014 |
| WO | 2014/069515 | A1 | 5/2014 |
| WO | 2014/126113 | A1 | 8/2014 |
| WO | 2014/132978 | A1 | 9/2014 |
| WO | 2015/025793 | A1 | 2/2015 |
| WO | 2015/064698 | A1 | 5/2015 |
| WO | 2015/098702 | A1 | 7/2015 |
| WO | 2015/122384 | A1 | 8/2015 |
| WO | 2015/122385 | A1 | 8/2015 |
| WO | 2016/056542 | A1 | 4/2016 |
| WO | 2016/088749 | A1 | 6/2016 |
| WO | WO-2016104317 | A1 * | 6/2016 | ........... C07D 277/64 |
| WO | WO-2016136533 | A1 * | 9/2016 | ........... C07C 251/86 |
| WO | 2017/068860 | A1 | 4/2017 |

OTHER PUBLICATIONS

Szelinski, Helga et al., "Porphyrins Linked to High Acceptor Strength Cyano Quinones as Models for the Photosynthetic Reaction Center", Pergamon, Tetrahedron, vol. 52, No. 25, pp. 8497-8516, (counterpart to U.S. Appl. No. 15/517,441). (20 pages).

Kallitsis, J.K. et al., "Soluble Polymers with Laterally Attached Oligophenyl Units for Potential Use as Blue Luminescent Materials", Macromolecules, 1997, vol. 30, No. 10, pp. 2989-2996, (counterpart to U.S. Appl. No. 15/517,441). (8 pages).

Benbow, John W. et al., "An Approach to Dibenzofuran Heterocycles. 1. Electron-Transfer Processes en Route to Dibenzofuran-1, 4-diones", J. Org. Chem, Jul. 1, 1997, vol. 62, No. 26, pp. 9345-9347, (counterpart to U.S. Appl. No. 15/517,441). (3 pages).

Yu, Sze-Chit et al., "Self-Assembled Electroluminescent Polymers Derived from Terpyridine-Based Moieties", Advanced Materials, Oct. 2, 2003, vol. 15, No. 19, pp. 1643-1647, (counterpart to U.S. Appl. No. 15/517,441). (5 pages).

Benbow, John W. et al., "Biaryl Formation Using the Suzuki Protocol: Considerations of Base, Halide, and Protecting Group", Pergamon, Tetrahedron Letters, 1996, vol. 37, No. 49, pp. 8829-8832, (counterpart to U.S. Appl. No. 15/517,441). (4 pages).

MacDonald, Dwight et al., "Substituted 2, 2-bisaryl-bicycloheptanes as novel and potent inhibitors of 5-lipoxygenase activating protein", Elsevier, Bioorganic & Medicinal Chemistry Letters, Jan. 29, 2008, pp. 2023-2027, (counterpart to U.S. Appl. No. 15/517,441). (5 pages).

International Search Report dated Feb. 16, 2016, issued in Application No. PCT/JP2015/085342 (counterpart to U.S. Appl. No. 15/517,441), with English translation (17 pages).

International Search Report dated May 17, 2016, issued in Application No. PCT/JP2016/054399 (counterpart to U.S. Appl. No. 15/517,441). (2 pages).

Notification of Reasons for Refusal dated Jan. 24, 2017, issued in JP Application No. 2016-567448 (counterpalt to U.S. Appl. No. 15/517,441), with English translation. (8 pages).

Decision to Grant a Patent dated May 25, 2017, issued in JP Application No. 2016-567448 (counterpart to U.S. Appl. No. 15/517,441), with English translation. (6 pages).

Non-Final Office Action dated Jun. 15, 2018, issued in U.S. Appl. No. 15/517,441. (13 pages).

International Search Report dated Dec. 22, 2015, issued in Application No. PCT/JP2015/078322 (counterpart to U.S. Appl. No. 15/517,441). (3 pages).

(56) References Cited

OTHER PUBLICATIONS

International Search Report dated Nov. 8, 2016, issued in Application No. PCT/JP2016/077247(counterpart to U.S. Appl. No. 15/764,755). (2 pages).

\* cited by examiner

POLYMERIZABLE COMPOUND AND OPTICALLY ANISOTROPIC BODY

TECHNICAL FIELD

The present invention relates to a compound having a polymerizable groups a polymerizable composition and a polymerizable liquid crystal composition containing the compound, and an optically anisotropic body using the polymerizable liquid crystal composition.

BACKGROUND ART

A compound having a polymerizable group (polymerizable compound) is used in various optical materials. For example, a polymerizable composition containing at polymerizable compound, which is in a liquid crystal state, is subjected to alignment, and then subjected to polymerization, thereby making it possible to produce a polymer having a uniform alignment. Such a polymer can be used for polarization plates, retardation plates and the like which are necessary for displays. In many cases, for satisfying necessary optical characteristics, polymerization speed, solubility, melting point, glass transition temperature, polymer transparency, mechanical strength, surface hardness, heat resistance and lightfastness, a polymerizable, composition containing two or more kinds of polymerizable compounds is used. In such a case, the polymerizable compound to be used, is required to impart good properties to the polymerizable composition without imposing any negative influence on the other characteristics thereof.

For improving the view angle of a liquid crystal display, the wavelength dispersion in terms of birefringence of a retardation film is required to be lowered or reversed. As a material for that purpose, various polymerizable liquid crystal compounds having low wavelength dispersion or reverse wavelength dispersion have been developed.

However, such polymerizable compounds have low solubility in various types of solvents, and thus have a limitation in the solvent to be used in production of an optically anisotropic body, resulting in poor versatility. In addition, precipitations are generated therein after drying, which leads to problems when the optically anisotropic body is used in a display, such as unevenness in lightness of a screen, unnatural hue, or unsatisfactory optical characteristics, resulting in significantly reduced quality of display products. Such optically anisotropic bodies also have low adhesiveness to glass, plastics, or various other substrates (or alignment films), leading to a problem of poor durability of itself. Although the problems may be solved by addition of additives in some cases, the addition of additives has resulted in new problems of reduced optical characteristics due to reduced liquid crystallinity and of complexity in the production process. For the reasons, there has been a need for development of a polymerizable liquid crystal compound having reverse wavelength dispersion and low wavelength dispersion which can solve the above problems (PTLs 1 to 3).

CITATION LIST

Patent Literature

[PTL 1] WO2014-010325A1
[PTL 2] JP-A-2010-31223
[PTL 3] JP-A-2008-273925

SUMMARY OF INVENTION

Technical Problems

A problem to be solved by the present invention is to provide a polymerizable liquid crystal compound having reverse wavelength dispersion or low wavelength dispersion and having high solubility in various solvents. Another problem is to provide a polymerizable liquid crystal compound having reverse wavelength dispersion or low wavelength dispersion and providing an optically anisotropic body having high adhesiveness to substrates (or alignment films), by adding the polymerizable liquid crystal, compound to a polymerizable composition and polymerizing the polymerizable, composition using ultraviolet light. Still another problem is to provide a polymerizable composition that contains the polymerizable liquid crystal compound having reverse wavelength dispersion or low wavelength dispersion, a polymer produced by polymerizing the polymerizable composition, and an optically anisotropic body using the polymer.

Solution to Problems

As a result of assiduous studies for solving the above-mentioned problems, the present inventors have reached development of a low wavelength dispersion and/or reverse wavelength dispersion compound having a partial structure represented by the formula (AO-1) in the molecule. Specifically, the present invention provides a polymerizable low wavelength dispersion or polymerizable reverse wavelength dispersion compound having, in the molecule, a partial structure represented by the following formula (AO-1):

[Chem. 1]

(wherein $n^0$ represents an integer of 2 or more; $R^0$ represents a linear or branched alkylene group having 2 to 20 carbon atoms, arbitrary hydrogen atoms in the alkylene group may be substituted with a fluorine atom or a chlorine atom, and the plural $R^0$'s may be the same or different), and also provides a polymerizable composition containing the compound, as well as resins, resin additives, oils, filters, adhesives, pressure-sensitive adhesives, oils and fats, inks, medicines, cosmetics, detergents, building materials, wrapping materials, liquid crystal materials, organic EL materials, organic semiconductor materials, electronic materials, display elements, electronic devices, communication devices, automotive parts, aircraft parts, machine parts, agricultural chemicals and foods using the compound, and products using these, and provides a polymerizable liquid crystal composition, a polymer obtained through polymerization of the polymerizable liquid crystal composition, and an optically anisotropic body using the polymer.

Advantageous Effects of Invention

The compound of the present invention has high solubility in various solvents and is unlikely to generate precipitations in production of an optically anisotropic body. In addition, the optically anisotropic body has high adhesiveness to glass, plastics, and various other substrates (or alignment films), and thus is useful in applications for optical materials such as retardation films.

DESCRIPTION OF EMBODIMENTS

The present invention provides a reverse dispersion compound having a specific structure in the molecule, and also provides not only a polymerizable composition containing the compound, but also resins, resin additives, oils, filters, adhesives, pressure-sensitive adhesives, oils and fats, inks, medicines, cosmetics, detergents, building materials, wrapping materials, liquid crystal materials, organic EL materials, organic semiconductor materials, electronic materials, display elements, electronic devices, communication devices, automotive parts, aircraft parts, machine parts, agricultural chemicals and foods each using the compound, products using these, a polymerizable liquid crystal composition, a polymer obtained through polymerization of the polymerizable liquid crystal composition, and an optically anisotropic body using the polymer.

In a graph drawn by plotting a wavelength λ of an incident light running on a retardation film on the horizontal axis and plotting a birefringence Δn thereof on the vertical axis, in the case where the birefringence Δn becomes larger while the wavelength λ becomes shorter, the film is generally referred to as "normal dispersion" by those skilled in the art, and in the case where the birefringence Δn becomes smaller while: the wavelength λ becomes shorter, the film is generally referred to as "reverse wavelength dispersion" or "reverse dispersion". In the present invention, a compound which constitutes a retardation film having a Re(450)/Re(550) of 0.95 or less, which is the value calculated by dividing the in-plane phase difference thereof at a wavelength of 450 nm (Re(450)) by the in-plane phase difference thereof at a wavelength of 550 nm (Re(550)), is referred to as a reverse wavelength dispersion compound, and a compound which constitutes a retardation film having a Re(450)/Re(550) of more than 0.95 or less and 1.05 or less is referred to as a low wavelength dispersion compound. The measurement method for phase difference is as described below.

<<Measurement of Phase Difference>>

A polyimide solution for an alignment film is applied onto a glass substrate having a thickness of 0.7 mm according to a spin coating method, then dried at 100° C. for 10 minutes, and thereafter baked at 200° C. for 60 minutes to form a coating film. The resultant coating film is rubbed using a commercially available rubbing device.

A cyclopentanone solution containing 20% by mass of a target compound to be evaluated is applied onto the rubbed substrate by a spin coating method, and dried at 100° C. for 2 minutes. The resultant coating film is cooled down to room temperature, and then, using a high-pressure mercury lamp, this is irradiated with UV rays at an intensity of 30 mW/cm² for 30 seconds to give a target film to be evaluated. The phase difference of the resultant film is measured using a retardation film/optical material inspection apparatus RETS-100 (manufactured by Otsuka Electronics Co., Ltd.).

In the case where the target compound to be evaluated does not dissolve in cyclopentanone, chloroform is used as the solvent. In the case where the target compound does not exhibit liquid crystallinity by itself, a composition prepared by adding the target compound (10% by mass, 20% by mass or 30% by mass) to a matrix liquid crystal composed of a compound represented by the following formula (A) (50% by mass) and a compound represented by the following formula (B) (50% by mass) is formed into a film:

[Chem. 2]

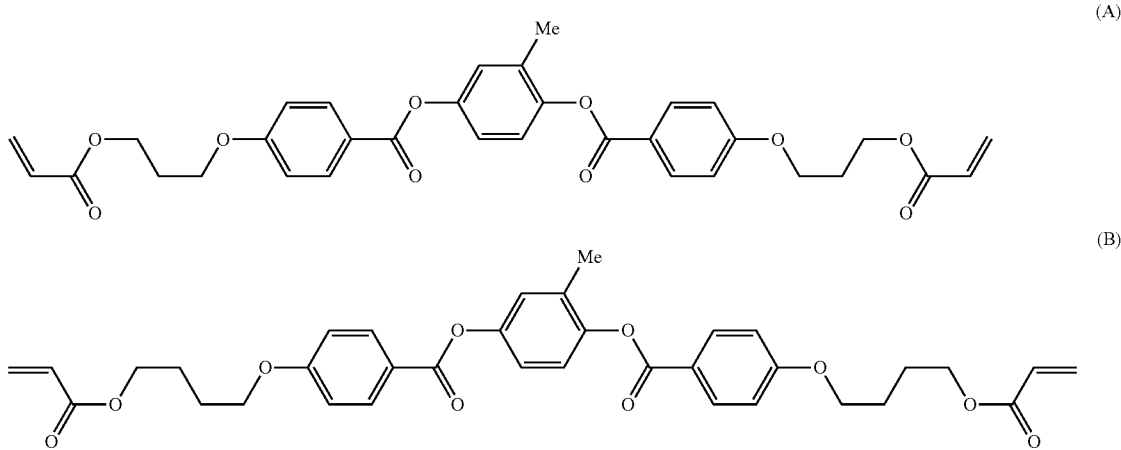

and the phase difference of the compound is determined by extrapolation.

In the general formula (AO-1), $R^0$ represents a linear or branched alkylene group having 2 to 20 carbon atoms, arbitrary hydrogen atoms in the alkylene group may be substituted with a fluorine atom or a chlorine atom, and the plural $R^0$'s represent groups which may be the same or different. From the viewpoints of liquid crystallinity, easy synthesis, solubility in various solvents, and adhesiveness to various substrates (or alignment films), $R^0$ preferably represents a linear or branched alkylene group having 2 to 6 carbon atoms in which arbitrary hydrogen atoms may be substituted with a fluorine atom or a chlorine atom, more preferably represents a linear or branched alkylene group having 2 to 6 carbon atoms, and further preferably represents a linear alkylene group having 2 or 3 carbon atoms. In the general formula (AO-1), $n^0$ represents an integer of 2 or more, and plural $n^0$'s, if any, may be the same or different. From the viewpoints of liquid crystallinity, easy synthesis, solubility in Various solvents, and adhesiveness to various substrates (or alignment films), $n^0$ preferably represents an integer of 2 or more and 6 or less, and more preferably represents 2 or 3.

From the viewpoints of mechanical strength and liquid crystallinity when formed into an optical film, the compound preferably has in the molecule at least one group represented by the following general formula (I-0-R):

[Chem. 3]

(I-0-R)

(wherein $P^0$ represents a polymerizable group; $k^0$ represents an integer of 0 to 10; $Sp^0$ represents a linear or branched alkylene group having 1 to 30 carbon atoms or a single bond, one —$CH_2$— or two or more (—$CH_2$—)'s not adjacent, to each other in the alkylene group may be each independently substituted with —O—, —S—, —CO—, —COO—, —OCO—, —CO—S—, —S—CO—, —O—CO—O—, —CO—NH—, —NH—CO—, —$CF_2$O—, —O$CF_2$—, —$CF_2$S—, —S$CF_2$—, —CH═CH—COO—, —CH═CH—OCO—, —COO—CH═CH—, —OCO—CH═CH—, —CH═CH—, —N═N—, —CH═N—N═CH—, —CF═CF—, or —C≡C—, and plural $Sp^0$'s, if any, may be the same or different; and $(Sp^0)_{k0}$ may be a group having a partial structure represented by the general formula (AO-1), provided that $P^0$—$(Sp^0)_{k0}$— contains no —O—O— bond).

In the general formula (I-0-R), $P^0$ represents a polymerizable group, and preferably represents a group selected from the following formulae (P-1) to (P-20):

[Chem. 4]

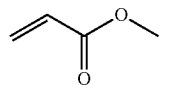
(P-1)

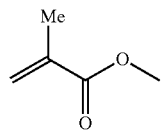
(P-2)

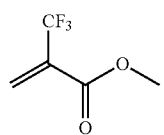
(P-3)

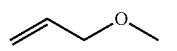
(P-4)

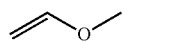
(P-5)

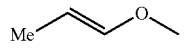
(P-6)

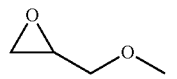
(P-7)

-continued

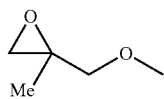
(P-8)

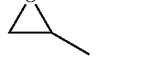
(P-9)

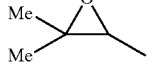
(P-10)

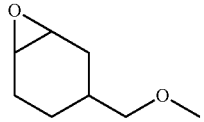
(P-11)

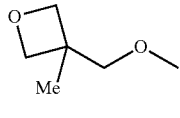
(P-12)

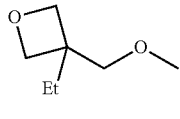
(P-13)

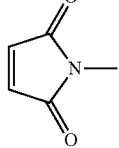
(P-14)

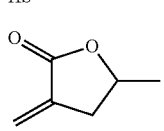
(P-15)

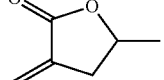
(P-16)

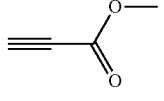
(P-17)

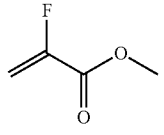
(P-18)

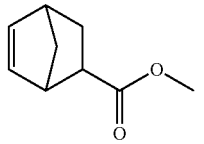
(P-19)

(P-20)

and these polymerizable groups polymerize through radical polymerization, radical addition polymerization, cationic polymerization, and anionic polymerization. Particularly in the case of using UV polymerization as the polymerization process, the formula (P-1), (P-2), (P-3), (P-4), (P-5), (P-7), (P-11), (P-13), (P-15), or (P-18) is preferred, the formula (P-1), (P-2), (P-7), (P-11), or (P-13) is more preferred, the formula (P-1), (P-2), or (P-3) is further preferred, and the formula (P-1) or (P-2) is particularly preferred.

In the (I-0-R), $Sp^0$ represents a linear or branched alkylene group having 1 to 30 carbon atoms or a single bond, one —$CH_2$— or two or more (—$CH_2$—)'s not adjacent to each other in the alkylene group may be each independently substituted with —O—, —S—, —CO—, —COO—, —OCO—, —CO—S—, —S—CO—, —O—CO—O—, —CO—NH—, —NH—CO—, —$CF_2$O—, —$OCF_2$—, —$CF_2$S—, —$SCF_2$—, —CH=CH—COO—, —CH=CH—OCO—, —COO—CH=CH—, —OCO—CH=CH—, —CH=CH—, —N=K—, —CH=N—N=CH—, —CF=CF—, or —C≡C, and plural $Sp^0$'s, if any, may be the same or different. From the viewpoints of availability of the raw materials, easy synthesis, and liquid crystallinity, $Sp^0$ preferably represents a linear or branched alkylene group having 1 to 20 carbon atoms in which one —$CH_2$— or two or more (—$CH_2$—)'s not adjacent to each other may be each independently substituted with —O—, —S—, —COO—, —OCO—, —CO—S—, —S—CO—, —O—CO—O—, —CO—NH—, —NH—CO—, —CH=CH—, or —C≡C or a single bond, more preferably represents a linear or branched alkylene group having 1 to 20 carbon atoms in which one —$CH_2$— or two or more (—$CH_2$—)'s not adjacent to each other may be each independently substituted with —O—, —COO—, —OCO—, —O—CO—O—, —CO—NH—, —NH—CO—, —CH=CH—, or —C≡C s or a single bond, and particularly preferably an alkylene group having 1 to 12 carbon atoms in which one —$CH_2$— or two or more, (—$CH_2$—)'s not adjacent to each other may be each independently substituted with —O—, —COO—, or —OCO— or a single bond.

In the general formula (I-0-R), $k^0$ represents an integer of 0 to 10, preferably represents an integer of 0 to 5, more preferably represents an integer of 0 to 3, and particularly preferably represents an integer of 1 to 3.

In the general formula (I-0-R), from the viewpoints of liquid crystallinity, solubility in various solvents, and adhesiveness to various substrates (or alignment films), the $(Sp^0)_{k0}$ group moiety preferably includes a partial structure represented by the general formula (AO-1), and the general formula (I-0-R) is more preferably a group represented by $P^0$—$((CH_2)_{k01})_{m0}$— where $P^0$ represents the aforementioned polymerizable group, the polymerizable group is preferably the same group as defined above for $P^0$, m0 represents an integer of 2 to 10, k01 represents an integer of 2 to 3, and plural m0's, if any, may be the same or different. From the viewpoints of liquid crystallinity, solubility in various solvents, and adhesiveness to various substrates (or alignment films), the low wavelength dispersion and/or reverse wavelength dispersion compound in the present invention is preferably a compound represented by the general formula (I):

[Chem. 5]

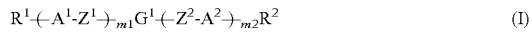

(I)

(wherein $R^1$ and $R^2$ each independently represent a hydrogen atom or a hydrocarbon group having 1 to 80 carbon atoms, the group may have a substituent, and arbitrary carbon atoms may be substituted with a hetero atom, provided that at least one of $R^1$ and $R^2$ represents a group represented by the general formula (I-0-R);

$A^1$ and $A^2$ each independently represent a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, or a 1,3-dioxane-2,5-diyl group, these groups may be unsubstituted or substituted with one or more substituents L's, L represents a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms in which one —$CH_2$— or two or more (—$CH_2$—)'s not adjacent to each other may be each independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, and arbitrary hydrogen atoms in the alkyl group may be substituted with a fluorine atom, or L may represent a group represented by $P^L$—$(Sp^L$—$X^L)_{kL}$— where $P^L$ represents a polymerizable group, the polymerizable group preferably represents the same group as defined above for $P^0$, $Sp^L$ represents a linear alkylene group having 1 to 10 carbon atoms in which one —$CH_2$— or two or more (—$CH_2$—)'s not adjacent to each other may be each independently substituted with —O—, —COO—, or —OCO— or a single bond, plural $Sp^L$'s, if any, may be the same or different, $X^L$ represents —O—, —S—, —$OCH_2$—, —$CH_2$O—, —CO—, —COO—, —OCO—, —CO—S—, —S—CO—, —O—CO—O—, —CO—NH—, —NH—CO—, —$SCH_2$—, —$CH_2$S—, —$CF_2$O—, —$OCF_2$—, —$CF_2$S—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —N=N—, —CH=N—N=CH—, —CF=CF—, —C≡C—, or a single bond, plural $X^L$'s, if any, may be the same or different (provided that $P^L$—$(Sp^L$—$X^L)_{kL}$— contains no —O—O— bond), and kL represents an integer of 0 to 10, plural L's in the compound, if any, may be the same or different, and the substituent L preferably represents a fluorine atom, a chlorine atom, a pentafluorosulfuranyl group, a nitro group, a methylamino group, a dimethylamino group, a diethylamino group, a diisopropylamino group, or a linear or branched alkyl group having 1 to 20 carbon atoms in which arbitrary hydrogen atoms may be substituted with a fluorine atom and one —$CH_2$— or two or more (—$CH_2$—) s not adjacent to each other may be each independently substituted with a group selected from —O—, —S—, —CO—, —COO—, —OCO—, —O—CO—O—, —CH=CH—, —CF=CF—, and —C≡C—, more preferably represents a fluorine atom, a chlorine atom, or a linear or branched alkyl group having 1 to 12 carbon atoms in which arbitrary hydrogen atoms may be substituted with a fluorine atom and one —$CH_2$— or two or more (—$CH_2$—)'s not adjacent to each other may be each independently substituted with a group selected from —O—, —COO—, and —OCO—, further preferably represents a fluorine atom, a chlorine atom, or a linear or branched alkyl group or alkoxy group having 1 to 12 carbon atoms in which arbitrary hydrogen atoms may be substituted with a fluorine atom, and particularly preferably represents a fluorine atom, a chlorine atom, or a linear alkyl group or linear alkoxy group having 1 to 8 carbon atoms; $Z^1$ and $Z^2$ each independently represent —O—, —S—, —OCH$_2$—, —CH$_2$O—, —CH$_2$CH$_2$—, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—, —N=CH—, —CH=N—N=CH—, —CF=CF—, —C≡C—, or a single bond, plural $Z^1$'s, if any, may be the same or different, and plural $Z^2$'s, if any, may be the same or different;

$G^1$ represents a divalent group having at least one aromatic ring selected from the group consisting of aromatic hydrocarbon rings and aromatic hetero rings, the number of π electrons contained in the aromatic ring(s) in the group represented by is 12 or more, the group represented by $G^1$ may be unsubstituted or substituted with one or more substituents $L^G$'s, the substituent $L^G$ represents a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms in which one —CH$_2$— or two or more (—CH$_2$—)'s not adjacent to each other may be each independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, and arbitrary hydrogen atoms in the alkyl group may be substituted: with a fluorine atop, or $L^G$ may represent a group represented by $P^{LG}$—(Sp$^{LG}$—X$^{LG}$)$_{kLG}$— where $P^{LG}$ represents a polymerizable group, the polymerizable group preferably represents the same group as defined above for $P^0$, Sp$^{LG}$ represents a linear alkylene group having 1 to 10 carbon atoms in which one —CH$_2$— or two or more (—CH$_2$—)'s not adjacent to each other may be each independently substituted with —O—, —COO—, or —OCO— or a single bond, plural Sp$^{LG}$'s, if any, may be the same or different, $X^{LG}$ represents —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, —C≡C—, or a single bond, plural $X^{LG}$'s, if any, may be the same or different (provided that $P^{LG}$—(Sp$^{LG}$—X$^{LG}$)$_{kLG}$— contains no —O—O— bond), kLG represents an integer of 0 to 10, and plural $L^G$'s in the compound, if any, may be the same or different; and m1 and m2 each independently represent an integer of 0 to 6, provided that m1+m2 is an integer of 0 to 6).

In the general formula (I), and $R^1$ and $R^2$ each independently represent a hydrogen atom or a hydrocarbon group having 1 to 80 carbon atoms, the hydrocarbon group may have a substituent, and arbitrary carbon atoms may be substituted with a hetero atom, provided that at least one of $R^1$ and $R^2$ and represents the group represented by the general; formula (I-0-R). When $R^1$ or $R^2$ represents a group other than the group represented by the general formula (I-0-R), from the viewpoints of liquid crystallinity and easy synthesis, $R^1$ or $R^2$ preferably each independently represents a hydrogen atom, a fluorine atom, a chlorine atom, a bromine atom, an iodine atom, a pentafluorosulfuranyl group, a cyano group, a nitro group, an isocyano group, a thioisocyano group, or a linear or branched alkyl group having 1 to 20 carbon atoms in which arbitrary hydrogen atoms in the group may be substituted with a fluorine atom and one —CH$_2$— or two or more (—CH$_2$—)'s not adjacent to each other may be each independently substituted with —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, or —C≡C—, more preferably each independently represents a hydrogen atom, a fluorine atom, a chlorine atom, or a linear or branched alkyl group having 1 to 12 carbon atoms in which one —CH$_2$— or two or more (—CH$_2$—)'s not adjacent to each other may be each independently substituted with —O—, —COO—, —OCO—, or —O—CO—O—, further preferably represents a hydrogen atom, a fluorine atom, a chlorine atom, or a linear alkyl group or linear alkoxy group, having 1 to 12 carbon atoms, and particularly preferably represents a linear alkyl group or linear alkoxy group having 1 to 12 carbon atoms. From the viewpoints of mechanical strength and liquid crystallinity when formed into optical film, $R^1$ and $R^2$ more preferably each independently represent the group represented by the general formula (I-0-R).

In the general formula (I), $A^1$ and $A^2$ each independently represent a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, or a 1,3-dioxane-2,5-diyl group, and these groups may be unsubstituted or substituted with one or more substituents L's as described above. $A^1$ and $A_2$ preferably each independently represent a 1,4-phenylene group, a 1,4-cyclohexylene group, or a naphthalene-2,6-diyl group which may be unsubstituted or substituted with one or more substituents L's, more preferably each independently represent a group selected from the following formulae (A-1) to (A-11):

[Chem. 6]

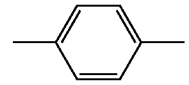

(A-1)

(A-2)

(A-3) 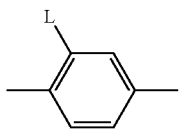

(A-4) 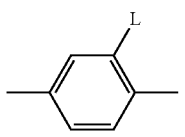

(A-5) 

(A-6) 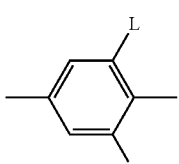

(A-7) 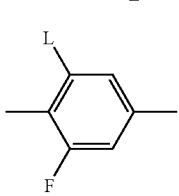

(A-8) 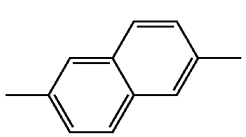

(A-9) 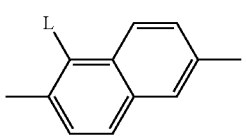

(A-10) 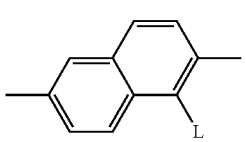

(A-11) 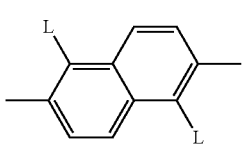

further preferably each independently represent a group selected from the formulae (A-1) to (A-8), and particularly preferably each independently represent a group selected from the formulae (A1) to (A-4). From the viewpoint of reverse dispersion, the group represented by $A^1$ bound to the group represented by $Z^1$ adjacent to the group represented by $G^1$ and the group represented by $A^2$ bound to the group represented by $Z^2$ adjacent to the group represented by $G^1$ preferably each independently represent a 1,4-cyclohexylene group which may be unsubstituted or substituted with one or more substituents L's as described above, and more preferably represent the group represented by the formulae (A-2). If any plural groups represented by $A^1$ and $A^2$ are present, from the viewpoints of refractive index anisotropy, easy synthesis, and solubility in solvents, the groups represented by $A^1$ and $A^2$ other than the aforementioned $A^1$ and $A^2$ preferably each independently represent a 1,4-phenylene group or a naphthalene-2,6-diyl group which may be unsubstituted or substituted with one or more substituents L's, more preferably each independently represent a group selected from the formulae (A-1) and (A-3) to (A-11), further preferably each independently represent a group selected from the formulae (A-1) and (A-3) to (A-8), and particularly preferably each independently represent a group selected from the formulae (A-1), (A-3), and (A-4).

In the general formula (I), $Z^1$ and $Z^2$ each independently represent a group represented by —O—, —S—, —OCH$_2$—, —CH$_2$O—, —CH$_2$CH$_2$—, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—, —N=CH—, —CH=N—N=CH—, —CF=CF—, —C≡C—, or a single bond, plural $Z^2$'s, if any, may be the same or different, and plural $Z^2$'s, if any, may be the same or different. From the viewpoints of liquid crystallinity, availability of the raw materials, and easy synthesis, $Z^1$ and $Z^2$ preferably represent —OCH$_2$—, —CH$_2$O—, —COO—, —OCO—, —CF$_2$O—, —OCF$_2$—, —CH$_2$CH$_2$—, —CF$_2$CF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —CH=CH—, —CF=CF—, —C≡C—, or a single bond, more preferably represent —OCH$_2$—, —CH$_2$O—, —COO—, —OCO—, —CF$_2$O—, —OCF$_2$—, —CH$_2$CH$_2$—, —COO—CH$_2$CH$_2$—, —OCO—CH$_2$CH$_2$—, —CH$_2$CH$_2$—COO—, —CH$_2$CH$_2$—OCO—, —CH=CH—, —C≡C—, or a single bond, further preferably represent —OCH$_2$—, —CH$_2$O—, —COO—, —OCO—, —CF$_2$O—, —OCF$_2$—, or a single bond, furthermore preferably represent —OCH$_2$—, —CH$_2$O—, —COO—, —OCO—, or a single bond, and particularly preferably represent —OCH$_2$—, —CH$_2$O—, —COO—, or —OCO—.

In the general formula (I), m1 and m2 each independently represent, an integer of 0 to 6, provided that m1+m2 is an integer of 0 to 6. From the viewpoints of solubility in solvents, liquid crystallinity, and adhesiveness to various substrates (or alignment, films), m1 and m2 each independently represent an integer of 1 to 3, and particularly preferably each independently represent 1 or 2. From the viewpoint of easy synthesis, m1 and m2 are more preferably the same.

In the general formula (I), $G^1$ represents a divalent group having at least one aromatic ring selected from aromatic hydrocarbon rings and aromatic hetero rings, the number or π electrons contained in the aromatic ring(s) in the group represented by $G^1$ is 12 or more, and the group represented by $G^1$ may be unsubstituted or substituted with one or more substituents $L^G$'s as described above. From the viewpoint of reverse wavelength dispersion, $G^1$ is preferably a group having the maximum absorptivity within 300 nm to 900 nm, and more preferably a group having the maximum absorptivity within 310 nm to 500 nm. From, the viewpoints of liquid crystallinity, availability of the raw materials, and easy synthesis of the compound, $G^1$ more preferably represents a group selected from the following general formulae (M-1) to (M-6):

[Chem. 7]

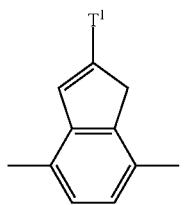
(M-1)

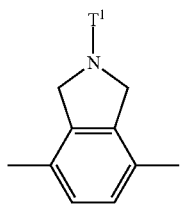
(M-2)

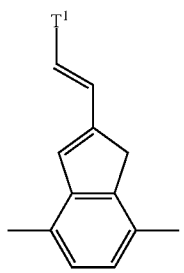
(M-3)

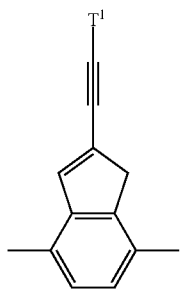
(M-4)

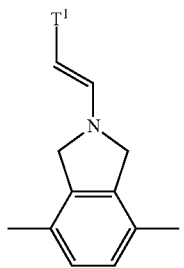
(M-5)

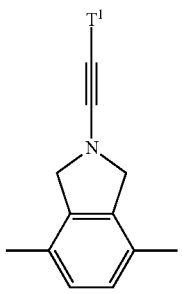
(M-6)

(wherein these groups may be unsubstituted or substituted with one or more substituents $L^G$'s as described above, arbitrary (—CH=)'s may be each independently substituted with —N=, —CH$_2$— may be each independently substituted with —O—, —S—, —NR$^T$— (where in R$^T$ represents a hydrogen atom or an alkyl group having 1 to 20 carbon atoms), —CS—, or —CO—, and $T^1$ represents a group selected from the following formulae (T1-1) to (T1-6):

[Chem. 8]

(T1-1)

(T1-2)

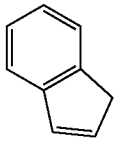
(T1-3)

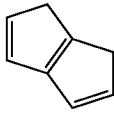
(T1-4)

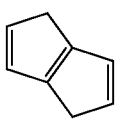
(T1-5)

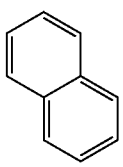
(T1-6)

(wherein these groups may have a bonding at an arbitrary position, arbitrary (—CH=)'s may be each independently substituted with —N=, (—CH$_2$—)'s each independently substituted with —O—, —S—, —NR$^T$— (wherein R$^T$ represents a hydrogen atom or alkyl group having 1 to 20 carbon atoms), —CS—, or —CO— ("may have a bonding at an arbitrary position", as used herein, means that, when, for example, the formula (T1-1) is bound to $T^1$ in the formulae (M-1) to (M-6), the formula (T1-1) has one bonding at an arbitrary position (hereinafter, "may have a bonding at an arbitrary position" in the present invention has the same meaning)), and these groups may be unsubstituted or substituted with one or more substituents as described above)), or a group selected from the following general formulae (M-7) to (M-14):

[Chem. 9]

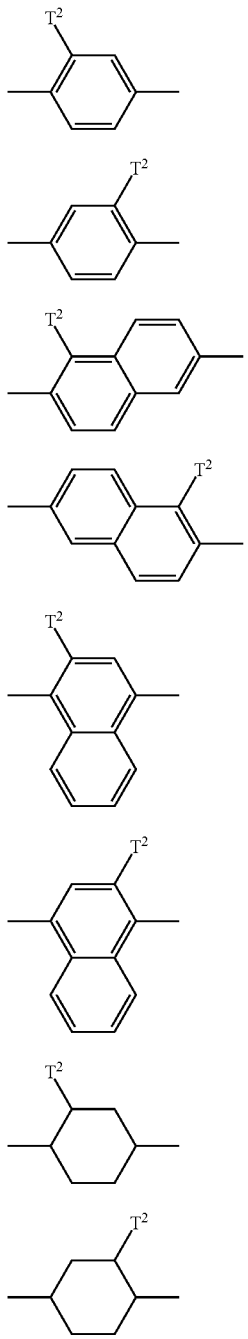

(M-7)
(M-8)
(M-9)
(M-10)
(M-11)
(M-12)
(M-13)
(M-14)

(wherein these groups may be unsubstituted or substituted with one or more substituents L+s as described above, arbitrary (—CH═)'s may be each independently substituted with —N═, (—CH$_2$—) s each independently represent —O—, —S—, —NR$^T$— (wherein R$^T$ represents a hydrogen atom or an alkyl group having 1 to 20 carbon atoms), —CS—, or —CO—, and T$^2$ represents a group selected from the general formulae (T2-1) and (T2-2):

[Chem. 10]

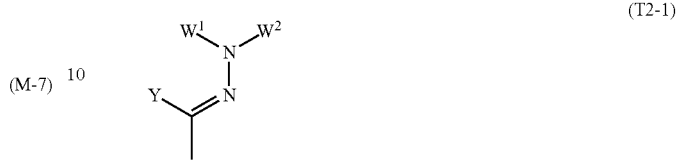

(T2-1)

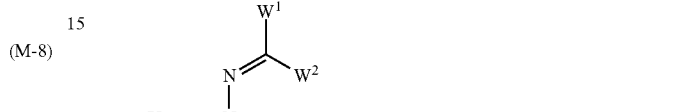

(T2-2)

(wherein W$^1$ represents a group containing an aromatic group and/or nonaromatic group having 1 to 40 carbon atoms which may be substituted, the aromatic group may be a hydrocarbon ring or a hetero ring, the nonaromatic group may be a hydrocarbon group or a hydrocarbon group in which arbitrary carbon atoms therein are substituted with a heteroatom (provided that any oxygen atoms do not directly bind to each other); W$_2$ represents a hydrogen atom or a linear or branched alkyl group having 1 to 20 carbon atoms in which one —CH$_2$— or two or more (—CH$_2$—)'s not adjacent to each other may be each independently substituted with —O—, —S—, —CO—, —COO—, —OCO—, —CO—S—, —S—CO—, —O—CO—O—, —CO—NH—, —NH—CO—, —CH═CH—COO—, —CH═CH—OCO—, —COO—CH═CH—, —OCO—CH═CH—, —CH═CH—, —CF═CF—, or —C≡C—, and arbitrary hydrogen atoms in the alkyl group may be substituted with a fluorine atom, or W$^2$ may represent a group having 2 to 30 carbon atoms and having at least one aromatic group, and the group may be unsubstituted or substituted with one or more substituents L$^W$'s, or may represent a group represented by P$^W$—(Sp$^W$—X$^W$)$_{kW}$— where P$^W$ represents a polymerizable group, Sp$^W$ represents a spacer group or a single bond, plural Sp$^W$'s, if any, may be the same or different, X$^W$ represents —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH═CH—COO—, —CH═CH—OCO—, —COO—CH═CH—, —OCO—CH═CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH═CH—, —N═N—, —CH═N—N═CH—, —CF═CF—, —C≡C—, or a single bond, plural X$^W$'s, if any, may be the same or different (provided that P$^W$—(Sp$^W$—X$^W$)$_{kW}$— contains no —O—O— bond), and kW represents an integer of 0 to 10, the substituent L$^W$ represents a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms in which one —$CH_2$— or two or more (—$CH_2$—)'s not adjacent to each other may be each independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, and arbitrary hydrogen atoms in the alkyl group may be substituted with a fluorine atom, or $L^W$ may represents a group represented by $P^{LW}$—($Sp^{LW}$—$X^{LW}$) where $P^{LW}$ represents a polymerizable group, the polymerizable group preferably represents the same group as defined above for $P^0$, $Sp^{LW}$ represents a linear alkylene group having 1 to 10 carbon atoms in which one —$CH_2$— or two or more (—$CH_2$—)'s not adjacent to each other may be each independently substituted with —O—, —COO—, or —OCO— or a single bond, plural $Sp^{LW}$'s, if any, may be the same or different, $X^{LW}$ represents —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —N=N—, —CH=N—N=CH—, —CF=CF—, —C≡C—, or a single bond, plural $X^{LW}$'s, if any, may be the same or different (provided that $P^{LW}$—($Sp^{LW}$—$X^{LW}$)$_{kL}$— contains no —O—O— bond), and kLW represents an integer of 0 to 10, and plural substituents $L^W$'s in the compound, if any, may be the same or different; Y represents a hydrogen atom, a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethyl amino group, a diisopropylamino group, a trimethylsilyl group, a dimethylsilyl group, a thioisocyano group, or a linear or branched alkyl group having 1 to 20 carbon atoms in which one —$CH_2$— or two or more (—$CH_2$—)'s not adjacent to each other may be each independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, and arbitrary hydrogen atoms in the alkyl group may be substituted with a fluorine atom, or Y may represent a group represented by $P^Y$—($Sp^Y$—$X^Y$)$_{kY}$— where $P^Y$ represents a polymerizable group, the polymerizable group preferably represents the same group as defined, above for $P^0$, $SP^Y$ represents a linear, alkylene group having 1 to 10 carbon atoms in which one —$CH_2$— or two or more (—$CH_2$—)'s not adjacent to each other may be each independently substituted with —O—, —COO—, or —OCO— or a single bond, plural $Sp^Y$'s, if any, may be the same or different, $X^Y$ represents —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$— OCO—, —CH=CH—, —N=N—, —CH=N—N=CH—, —CF=CF—, —C≡C—, or a single bond, plural $X^Y$'s, if any, may be the same or different (provided that $P^Y$—($Sp^Y$—$X^Y$)$_{kY}$— contains no —O—O— bond), and kY represents an integer of 0 to 10; and $W^1$ and $W^2$ may be linked together to form a ring structure)). From the viewpoints of solubility in solvents and easy synthesis, $G^1$ further preferably represents a group selected from the formulae (M-1), (M-3), (M-4), (M-7), and (M-8), furthermore preferably represents a group selected from the formulae (M-1), (M-7), and (M-8), and particularly preferably a group selected from the formulae (M-7) and (M-8).

More specifically, the group represented by the formula (M-1) preferably represents a group selected from the following formulae (M-1-1) to (M-1-6):

[Chem. 11]

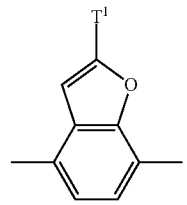

(M-1-1)

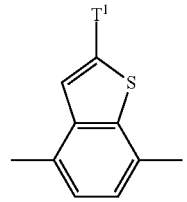

(M-1-2)

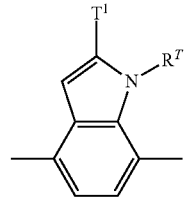

(M-1-3)

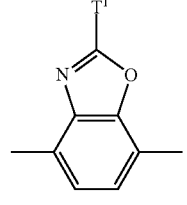

(M-1-4)

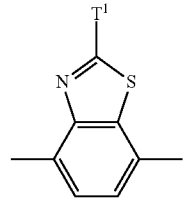

(M-1-5)

-continued (M-1-6)

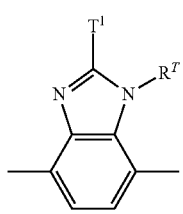

(wherein T¹ represents the same meaning as described above, and $R^T$ preferably represents a hydrogen atom or an alkyl group having 1 to 20 carbon atoms), more preferably represents a group selected from the formulae (M-1-4) and (M-1-5), and particularly preferably represents a group represented by the formulae (M-1-5). The group represented by the formula (M-3) preferably represents a group selected from the following formulae (M-3-1) to (M-3-6):

[Chem. 12]

(M-3-1)

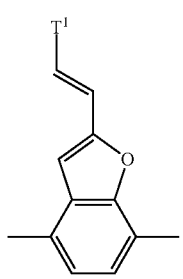

(M-3-2)

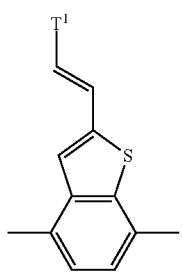

(M-3-3)

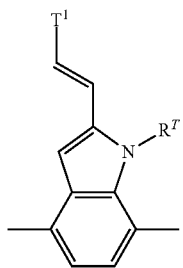

(M-3-4)

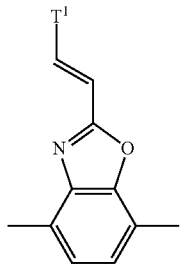

-continued (M-3-5)

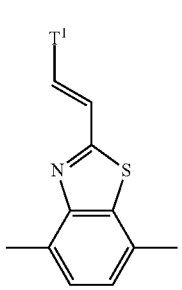

(M-3-6)

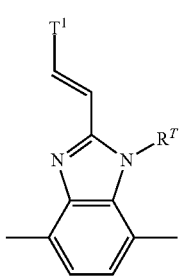

(wherein T¹ represents the same meaning as described above, and $R^T$ represents a hydrogen atom or an alkyl group having 1 to 20 carbon atoms), more preferably represents a group selected from the formulae (M-3-4) and (M-3-5), and particularly preferably a group represented, by the formula (M-3-5).

The group represented by the formulae (M-4) preferably represents a group selected from the following formulae (M-4-1) to (M-4-6):

[Chem. 13]

(M-4-1)

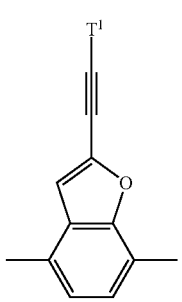

(M-4-2)

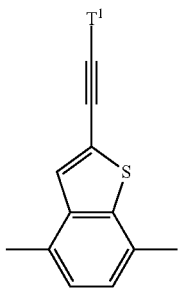

-continued

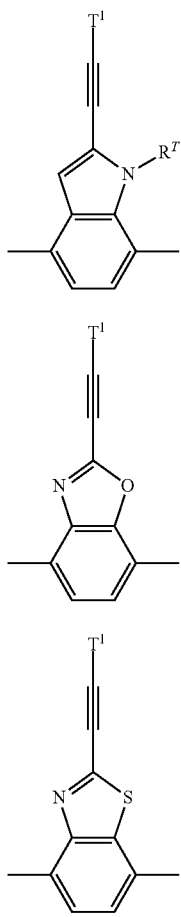

(M-4-3)

(M-4-4)

(M-4-5)

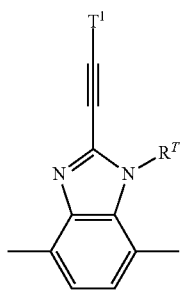

(M-4-6)

(wherein $T^1$ represents the same meaning as described above, and $R^T$ represents a hydrogen atom or an alkyl group having 1 to 20 carbon atoms), more preferably represents a group selected from the formulae (M-4-4) and (M-4-5), and particularly preferably represents a group represented by the formula (M-4-5).

In the formulae (M-1) to (M-6), from the viewpoints: of wavelength dispersion and easy synthesis, $T^1$ preferably represents a group selected from the formulae (T1-1), (T1-2), (T1-3), and (T1-6), more preferably represents a group selected from the formulae (T1-3) and (T1-5), and particularly preferably represents: the formula. (T1-3). More specifically, the group, represented by the formula (T1-1) preferably represents a group selected from the following formulae (T1-1-1) to (T1-1-7):

[Chem. 14]

 (T1-1-1)

 (T1-1-2)

 (T1-1-3)

 (T1-1-4)

 (T1-1-5)

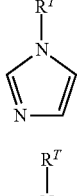 (T1-1-6)

(T1-1-7)

(wherein these groups may have a bonding at an arbitrary position, $R^T$ represents a hydrogen atom or an alkyl group having 1 to 20 carbon atoms, and these groups may be unsubstituted or substituted with one or more substituents $L^G$'s as described above), and more preferably represents a group selected from the formulae (T1-1-2), (T1-1-4), (T1-1-5), (T1-1-6), and (T1-1-7). The group represented by the formulae (T1-2) preferably represents a group selected from the following formulae (T1-2-1) to (T1-2-8):

[Chem. 15]

 (T1-2-1)

 (T1-2-2)

 (T1-2-3)

 (T1-2-4)

-continued

(T1-2-5)

(T1-2-6)

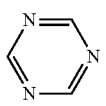
(T1-2-7)

(T1-2-8)

(wherein these groups may have a bonding at an arbitrary position, and these groups may be unsubstituted or substituted with one or more substituents $L^G$'s as described above), and more preferably a group represented, by the formula (T1-2-1). The group represented by the formula (T1-3) preferably represents a group selected from the following formulae (T1-3-1) to (T1-3-8):

[Chem. 16]

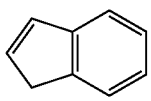
(T1-3-1)

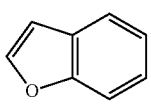
(T1-3-2)

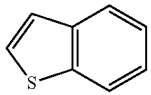
(T1-3-3)

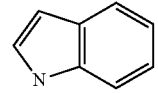
(T1-3-4)

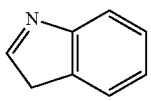
(T1-3-5)

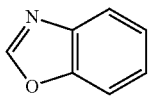
(T1-3-6)

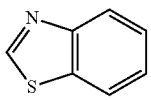
(T1-3-7)

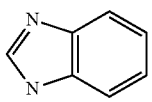
(T1-3-8)

(wherein these groups may have a bonding at an arbitrary position, $R^T$ represents a hydrogen atom or an alkyl group having 1 to 20 carbon atoms, and these groups may be unsubstituted or substituted with one or more substituents $L^G$'s as described above), and more preferably represents a group represented by the formulae (T1-3-2), (T1-3-3), (T1-3-6), or (T1-3-7). The group represented by the formula (T1-4) preferably represents a group selected from the following formulae (T1-4-1) to (T1-4-6):

[Chem. 17]

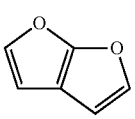
(T1-4-1)

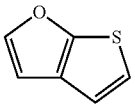
(T1-4-2)

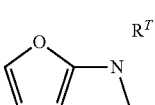
(T1-4-3)

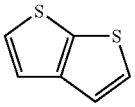
(T1-4-4)

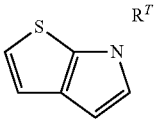
(T1-4-5)

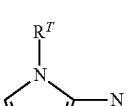
(T1-4-6)

(wherein these groups may have a bonding at an arbitrary position, $R^T$ represents a hydrogen atom or an alkyl group having 1 to 20 carbon atoms, and these groups may be unsubstituted or substituted with one or more substituents $L^G$'s as described above). The group represented by the formulae (T1-5) preferably represents a group selected from the following formulae (T1-5-1) to (T1-5-9):

[Chem. 18]

(T1-5-1) 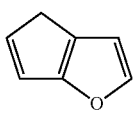

(T1-5-2) 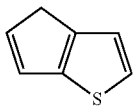

(T1-5-3) 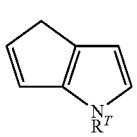

(T1-5-4) 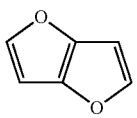

(T1-5-5) 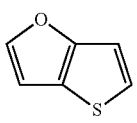

(T1-5-6) 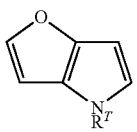

(T1-5-7) 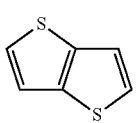

(T1-5-8) 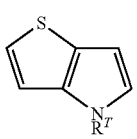

(T1-5-9) 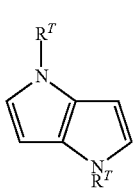

(wherein these groups may have a bonding at an arbitrary position, $R^T$ represents a hydrogen atom or an alkyl group having 1 to 20 carbon atoms, and these groups may be unsubstituted or substituted with one or more substituents $L^G$'s as described above.). The group represented by the formulae (T1-6) preferably represents a group selected from the following formulae (T1-6-1) to (T1-6-7):

[Chem. 19]

(T1-6-1) 

(T1-6-2) 

(T1-6-3) 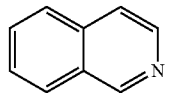

(T1-6-4) 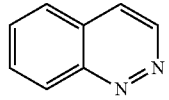

(T1-6-5) 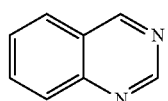

(T1-6-6) 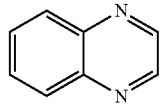

(T1-6-7) 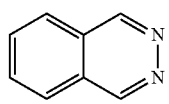

(wherein these groups may have a bonding at an arbitrary position, and these groups may be unsubstituted or substituted with one or more substituents $L^G$'s as described above).

In the general formula (I), from, the viewpoints of liquid crystallinity and easy synthesis, the substituent $L^G$ preferably represents a fluorine atom, a chlorine atom, a pentafluorosulfuranyl group, a nitro group, a methylamino group, a dimethylamino group, a diethylamino group, a diisopropylamino group, or a linear or branched alkyl group having 1 to 20 carbon atoms in which arbitrary hydrogen atoms may be substituted with a fluorine atom and one —CH$_2$— or two or more (—CH$_2$—)'s not adjacent to each other may be each independently substituted with a group selected from —O—, —S—, —CO—, —COO—, —OCO—, —O—CO—O—, —CH=CH—, —CF=CF—, and —C≡C—, more preferably represents a fluorine atom, a chlorine atom, or a linear or branched alkyl group having 1 to 12 carbon atoms in which arbitrary hydrogen atoms may be substituted with a fluorine atom and one —CH$_2$— or two or more (—CH$_2$—)'s not adjacent to each other may be each independently substituted with a group selected from —O—, —COO—, and —OCO—, further preferably represents a fluorine atom, a chlorine atom, or a linear or branched alkyl group or alkoxy group having 1 to 12 carbon atoms in which arbitrary hydrogen atoms may be substituted with a fluorine atom, and particularly preferably represents a fluorine atom, a chlorine atom, or a linear alkyl group or linear alkoxy group having 1 to 8 carbon atoms.

The group represented by the formulae (M-7) to (M-14) preferably represents a group represented by the following formulae (M-7-1) to (M-14-1):

[Chem. 20]

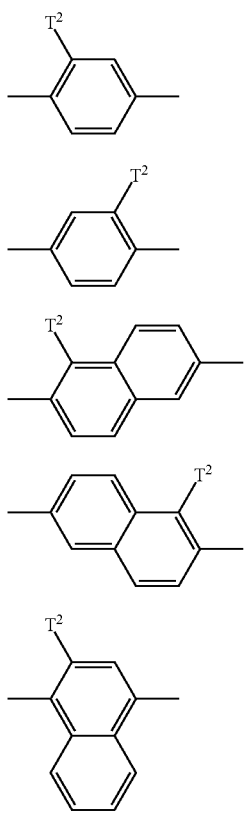

(M-7-1)

(M-8-1)

(M-9-1)

(M-10-1)

(M-11-1)

(M-12-1)

(M-13-1)

(M-14-1)

(wherein T² has the same meaning as described above), more preferably represents a group selected from the formulae (M-7-1) to (M-12-1), and particularly preferably represents a group represented by the formula (M-7-1) or (M-8-1).

In the formula (T2-1) or (T2-2), from the viewpoints of liquid crystallinity and easy synthesis, Y preferably represents a hydrogen atom, a fluorine atom, a chlorine atom, a nitro group, a cyano group, or a linear or branched alkyl group having 1 to 20 carbon atoms in which arbitrary hydrogen atoms in the group may be substituted with a fluorine atom and one —CH$_2$— or two or more (—CH$_2$—)'s not adjacent to each other may be each independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C— or a group represented by P$^Y$—(Sp$^Y$—X$^Y$)$_{kY}$—, Y more preferably represents a hydrogen atom or a linear or branched alkyl group having 1 to 12 carbon atoms in which arbitrary hydrogen atoms in the group may be substituted with a fluorine atom and one —CH$_2$— or two or more (—CH$_2$—)'s not adjacent, to each other may be each independently substituted with —O—, —COO—, or —OCO—, Y further preferably represents a hydrogen atom or a linear or branched alkyl group having 1 to 12 carbon atoms in which arbitrary hydrogen atoms in the group may be substituted with a fluorine atom, and Y particularly preferably represents a hydrogen atom or a linear alkyl group having 1 to 12 carbon atoms.

In the formulae (T2-1) or (T2-2), from the viewpoints of liquid crystallinity and easy synthesis, W$^1$ represents a group having 1 to 80 carbon atoms and containing an aromatic and/or a nonaromatic carbon ring or hetero ring which may be substituted, arbitrary carbon atoms in the carbon ring or hetero ring may be substituted with a hetero atom. From the viewpoints of availability of the raw materials and easy synthesis, the aromatic group contained in W$^1$ preferably represents a group selected from the following formulae (W-1) to (W-18) which may fee unsubstituted or substituted with one or more substituents L$^W$'s:

[Chem. 21]

 (W-1)

 (W-2)

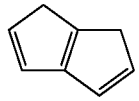 (W-3)

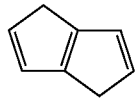 (W-4)

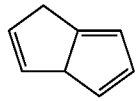 (W-5)

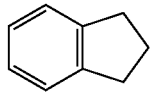 (W-6)

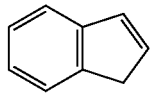 (W-7)

-continued

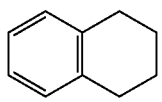 (W-8)

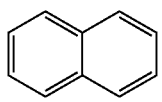 (W-9)

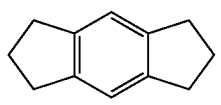 (W-10)

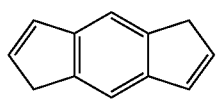 (W-11)

 (W-12)

 (W-13)

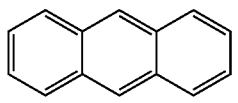 (W-14)

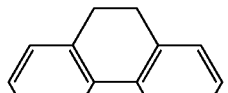 (W-15)

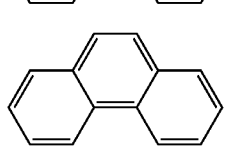 (W-16)

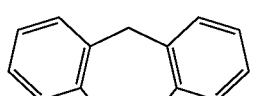 (W-17)

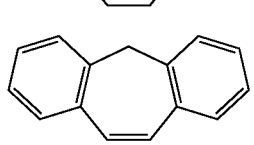 (W-18)

(wherein the ring structures may have a bonding at an arbitrary position, and may form a group in which two or more aromatic groups selected from the groups are linked via a single bond, arbitrary (—CH═)'s may be each independently substituted with —N═, (—CH$_2$—)'s each independently substituted with —O—, —S—, —NR$^T$— (wherein R$^T$ represents a hydrogen atom or an alkyl group having 1 to 20 carbon atoms), —CS—, or —CO—, provided that no —O—O— bond is contained, and these groups may be unsubstituted or substituted with one or more substituents L$^W$'s as described above). The group represented by the formula (W-1) preferably represent a group selected from the following formulae (W-1-1) to (W-1-7) which may be unsubstituted or substituted with one of more substituents L$^W$'s as described above:

[Chem. 22]

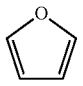 (W-1-1)

 (W-1-2)

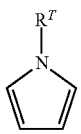 (W-1-3)

 (W-1-4)

 (W-1-5)

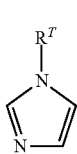 (W-1-6)

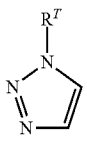 (W-1-7)

(wherein these groups may have a bond at any position, and R$^T$ represents a hydrogen atom or an alkyl group having 1 to 8 carbon atoms.) Preferably, the group represented by the above-mentioned formula (W-2) is a group selected from the following formulae (W-2-1) to (W-2-8), which may be unsubstituted or substituted with one or more of the above-mentioned substituents L$^W$'s:

[Chem. 23]

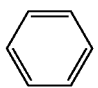 (W-2-1)

 (W-2-2)

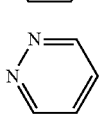 (W-2-3)

-continued

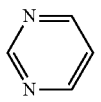 (W-2-4)

 (W-2-5)

 (W-2-6)

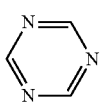 (W-2-7)

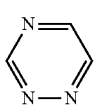 (W-2-8)

(wherein these groups may have a bond at any position.) Preferably, the group represented by the above-mentioned formula (W-3) is a group selected from the following formulae (W-3-1) to (W-3-6), which may be unsubstituted or substituted with one or more of the above-mentioned substituents $L^{W}$'s:

[Chem. 24]

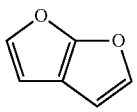 (W-3-1)

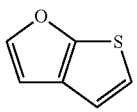 (W-3-2)

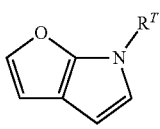 (W-3-3)

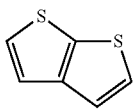 (W-3-4)

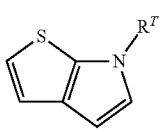 (W-3-5)

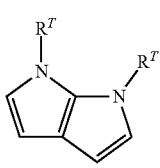 (W-3-6)

(wherein these groups may have a bond at any position, and $R^T$ represents a hydrogen atom or an alkyl group having 1 to 8 carbon atoms.) Preferably, the group represented by the above-mentioned formula (W-4) is a group selected from the following formulae (W-4-1) to (W-4-9), which may be unsubstituted or substituted with one or more of the above-mentioned substituents if $L^{W}$'s:

[Chem. 25]

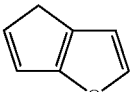 (W-4-1)

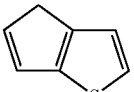 (W-4-2)

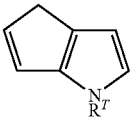 (W-4-3)

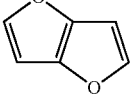 (W-4-4)

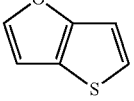 (W-4-5)

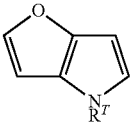 (W-4-6)

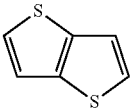 (W-4-7)

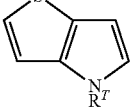 (W-4-8)

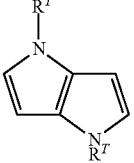 (W-4-9)

(wherein these groups may have a bond at any position, and $R^T$ represents a hydrogen atom or an alkyl group having 1 to 8 carbon atoms.) Preferably, the group represented by the above-mentioned formula (W-5) is a group selected from the following formulae (W-5-1) to (W-5-13), which may be unsubstituted or substituted with one or more of the above-mentioned substituents $L^{W}$'s:

[Chem. 26]

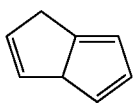 (W-5-1)

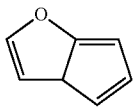 (W-5-2)

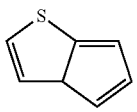 (W-5-3)

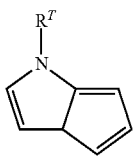 (W-5-4)

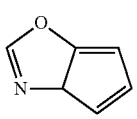 (W-5-5)

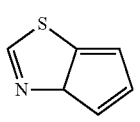 (W-5-6)

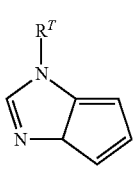 (W-5-7)

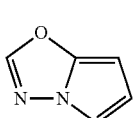 (W-5-8)

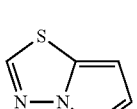 (W-5-9)

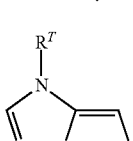 (W-5-10)

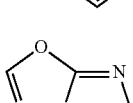 (W-5-11)

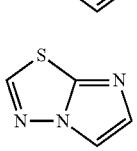 (W-5-12)

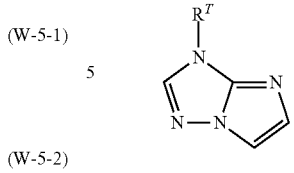 (W-5-13)

(wherein these groups may have a bond at any position, and $R^T$ represents a hydrogen atom or an alkyl group having 1 to 8 carbon atoms.) Preferably, the group represented by the above-mentioned formula (W-6) is a group selected from the following formulae (W-6-1) to (W-6-12), which may be unsubstituted or substituted with one or more of the above-mentioned substituents $L^W$'s:

[Chem. 27]

 (W-6-1)

 (W-6-2)

 (W-6-3)

 (W-6-4)

 (W-6-5)

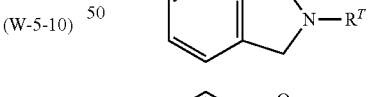 (W-6-6)

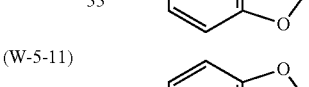 (W-6-7)

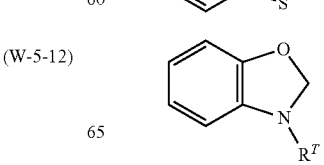 (W-6-8)

(W-6-9)

(W-6-10)

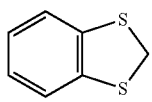 (W-6-11)

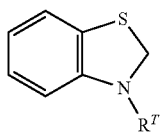 (W-6-12)

(wherein these groups may have a bond at any position, and $R^T$ represents a hydrogen atom or an alkyl group having 1 to 8 carbon atoms.) Preferably, the group represented by the above-mentioned formula (W-7) is a group selected from the following formulae (W-7-1) to (W-7-8), which may be unsubstituted or substituted with one or more of the above-mentioned substituents $L^W$'s:

[Chem. 28]

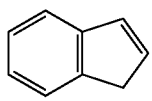 (W-7-1)

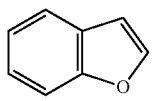 (W-7-2)

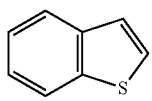 (W-7-3)

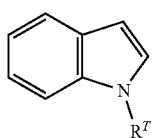 (W-7-4)

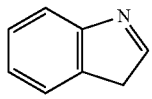 (W-7-5)

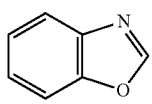 (W-7-6)

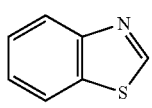 (W-7-7)

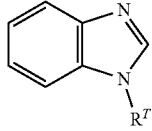 (W-7-8)

(wherein these groups may have a bond at any position, and $R^T$ represents a hydrogen atom or an alkyl group having 1 to 8 carbon atoms.) Preferably, the group represented by the above-mentioned formula (W-8) is a group selected from the following formulae (W-8-1) to (W-8-19), which may be unsubstituted or substituted with one or more of the above-mentioned substituents $L^W$'s:

[Chem. 29]

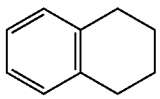 (W-8-1)

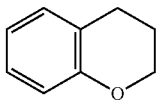 (W-8-2)

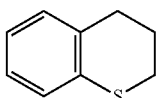 (W-8-3)

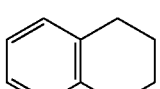 (W-8-4)

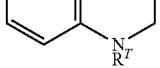 (W-8-5)

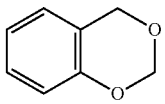 (W-8-6)

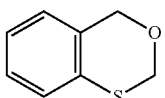 (W-8-7)

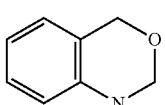 (W-8-8)

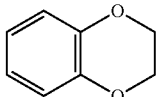 (W-8-9)

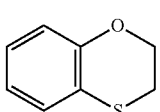 (W-8-10)

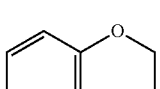 (W-8-11)

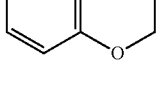 (W-8-12)

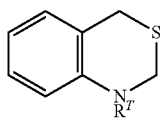
(W-8-13)

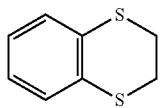
(W-8-14)

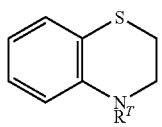
(W-8-15)

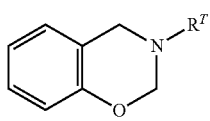
(W-8-16)

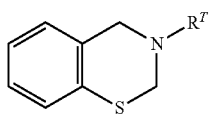
(W-8-17)

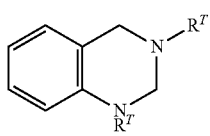
(W-8-18)

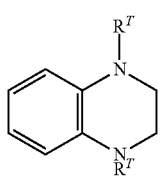
(W-8-19)

(wherein these groups may have a bond at any position, and $R^T$ represents a hydrogen atom or an alkyl group having 1 to 8 carbon atoms.) Preferably, the group represented by the above-mentioned formula (W-9) is a group selected from the following formulae (W-9-1) to (W-9-7), which may be unsubstituted or substituted with one or more of the above-mentioned substituents $L^{W}$'s:

[Chem. 30]

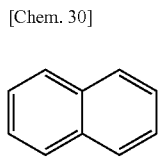
(W-9-1)

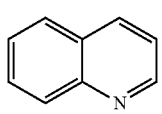
(W-9-2)

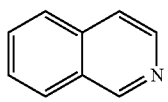
(W-9-3)

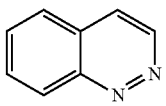
(W-9-4)

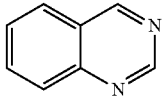
(W-9-5)

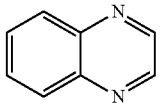
(W-9-6)

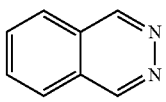
(W-9-7)

(wherein these groups may have a bond at any position.) Preferably, the group represented by the above-mentioned formula (W-10) is a group selected from the following formulae (W-10-1) to (W-10-16), which may be unsubstituted or substituted with one or more of the above-mentioned substituents $L^{W}$'s:

[Chem. 31]

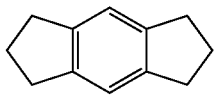
(W-10-1)

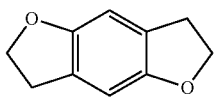
(W-10-2)

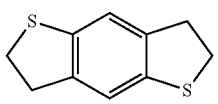
(W-10-3)

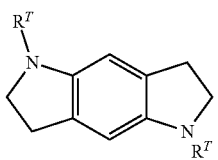
(W-10-4)

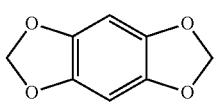
(W-10-5)

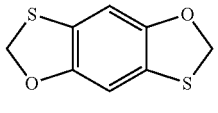
(W-10-6)

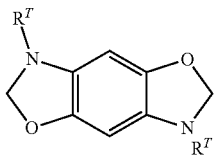
(W-10-7)

-continued

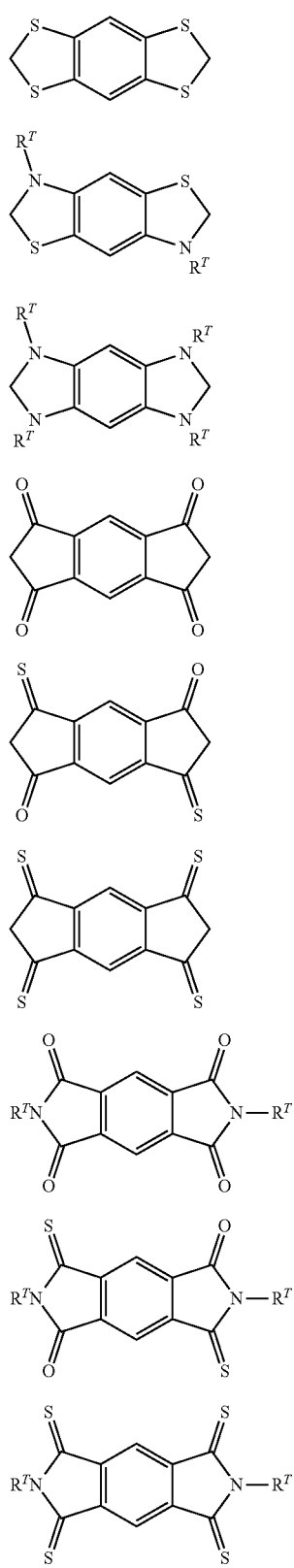

(wherein these groups may have a bond at any position, and $R^T$ represents a hydrogen atom or an alkyl group having 1 to 8 carbon atoms.) Preferably, the group represented by the above-mentioned formula (W-11) is at group selected from the following formulae (W-11-1) to (W-11-10), which may be unsubstituted or substituted with one or more of the above-mentioned substituents $L^W$'s:

[Chem. 32]

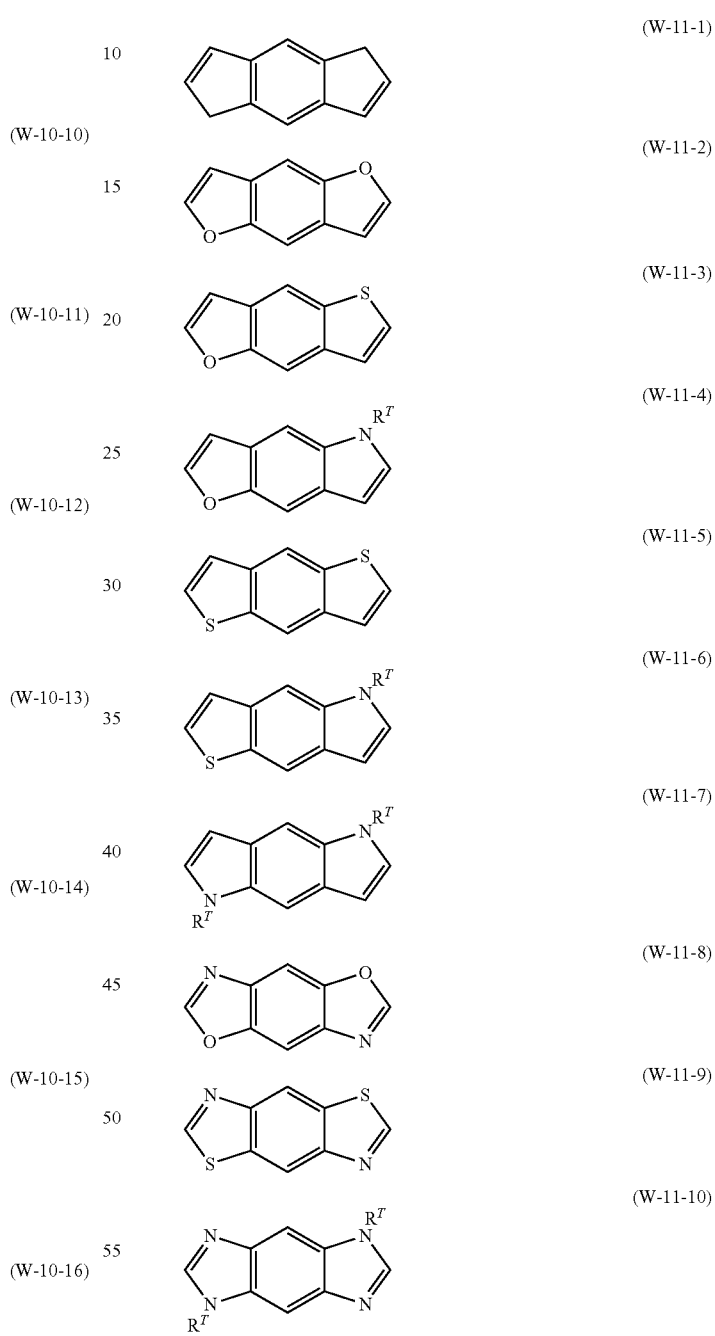

(wherein these groups may have a bond at any position, and $R^T$ represents a hydrogen atom or an alkyl group having 1 to 8 carbon atoms.) Preferably, the group represented by the above-mentioned formula (W-12) is a group selected from the following formulae (W-12-1) to (W-12-4), which may be unsubstituted or substituted with one or more of the above-mentioned substituents $L^W$'s:

[Chem. 33]

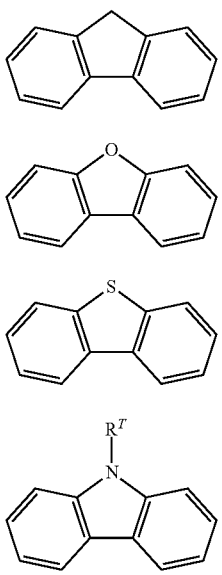

(W-12-1)
(W-12-2)
(W-12-3)
(W-12-4)

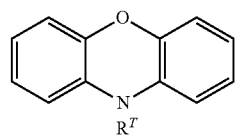
(W-13-7)

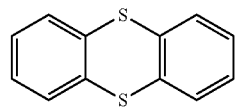
(W-13-8)

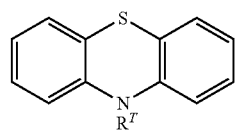
(W-13-9)

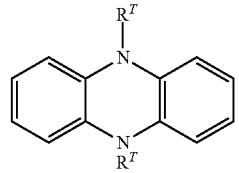
(W-13-10)

(wherein these groups may have a bond at any position, and $R^T$ represents a hydrogen atom or an alkyl group having 1 to 8 carbon atoms.) Preferably, the group represented by the above-mentioned formula (W-13) is a group selected from the following formulae (W-13-1) to (W-13-10), which may be unsubstituted or substituted with one or more of the above-mentioned substituents $L^W$'s:

(wherein these groups may have a bond at any position, and $R^T$ represents a hydrogen atom or an alkyl group having 1 to 8 carbon atoms.) Preferably, the group represented by the above-mentioned formula (W-17) is a group selected from the following formulae (W-17-1) to (W-17-16), which may be unsubstituted or substituted with one or more of the above-mentioned substituents $L^W$'s:

[Chem. 34]

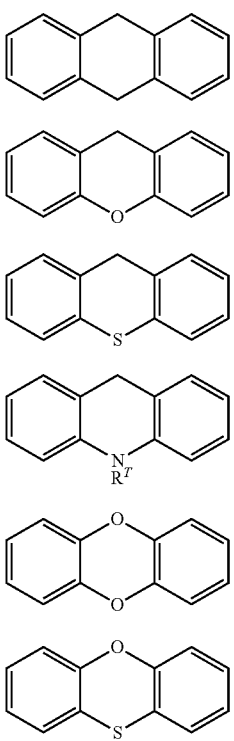

(W-13-1)
(W-13-2)
(W-13-3)
(W-13-4)
(W-13-5)
(W-13-6)

[Chem. 35]

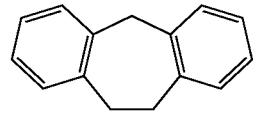
(W-17-1)

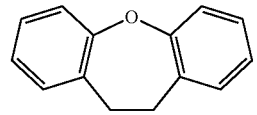
(W-17-2)

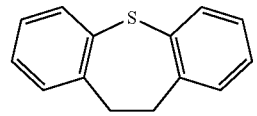
(W-17-3)

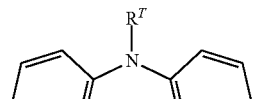
(W-17-4)

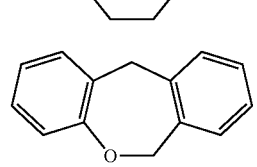
(W-17-5)

(W-17-6) 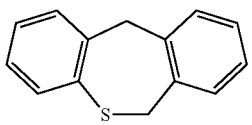

(W-17-7) 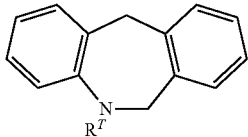

(W-17-8) 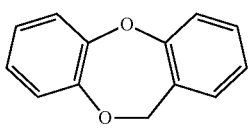

(W-17-9) 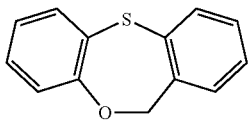

(W-17-10) 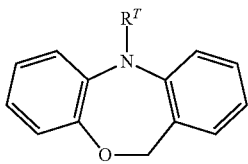

(W-17-11) 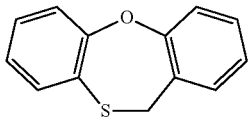

(W-17-12) 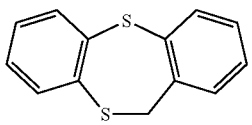

(W-17-13) 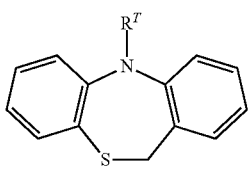

(W-17-14) 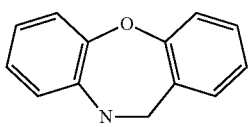

(W-17-15) 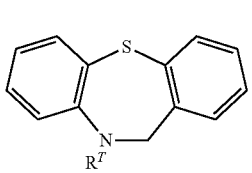

(W-17-16) 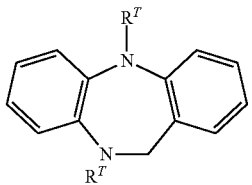

(wherein these groups may have a band at any position, and $R^T$ represents a hydrogen atom or an alkyl group having 1 to 8 carbon atoms.) Preferably, the group represented by the above-mentioned formula (W-18) is a group selected from the following formulae (W-18-1) to (W-18-4), which may be unsubstituted or substituted, with one or more of the above-mentioned substituents $L^W$'s:

[Chem. 36]

(W-18-1) 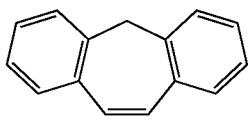

(W-18-2)

(W-18-3) 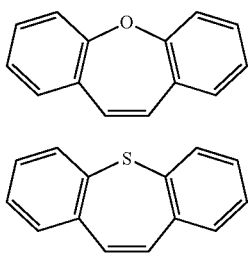

(W-18-4)

(wherein these groups may have a bond, at any position, and $R^T$ represents a hydrogen atom or an alkyl group having 1 to 8 carbon atoms.)

The group containing a carbon, ring or hetero ring contained in $W^1$ preferably represents a group selected from the formulae (W-1-1), (W-1-2), (W-1-3), (W-1-4), (W-1-5), (W-1-6), (W-2-1), (W-6-9), (W-6-11), (W-6-12), (W-7-2), (W-7-3), (W-7-4), (W-7-6), (W-7-7), (W-7-8), (W-9-1), (W-12-1), (W-12-2), (W-12-3), (W-12-4), (W-13-7), (W-13-9), (W-13-10), (W-14), (W-18-1), and (W-18-4) which may be unsubstituted or substituted with one or more substituents $L^W$'s as described above, more preferably represents a group selected from the formulae (W-2-1), (W-7-3), (W-7-7), and (W-14) which may be unsubstituted or substituted with one or more substituents $L^W$'s as described above, further preferably represents a group selected from the formulae (W-7-3), (W-7-7), and (W-14) which may be unsubstituted or substituted with one or more substituents $L^W$'s as described above, furthermore preferably represents a group represented by the formula (W-7-7) which may be unsubstituted or substituted with one or more substituents $L^W$'s as described above, and particularly preferably represents a group represented by the following formula (W-7-7-1):

[Chem. 37]

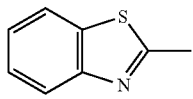
(W-7-7-1)

which may be unsubstituted or substituted with one or more substituents $L^W$'s as described above.

In the formulae (T-1) or (T-2), from the viewpoints of availability of the raw materials and easy synthesis, $W^2$ more preferably represents a hydrogen atom or a linear or branched alkyl group having 1 to 20 carbon atoms in which arbitrary hydrogen atoms in the group may be substituted with a fluorine atom and one —$CH_2$— or two or more (—$CH_2$—)'s not adjacent to each other may be each independently substituted with —O—, —CO—, —COO—, —OCO—, —O—CO—O—, —CH=CH—COO—, —CH=CH—OCO—, —COO—CH=CH—, —OCO—CH=CH—, —CH=CH—, —CF=CF—, or —C≡C—, or a group represented by $P^W$—$(Sp^W-X^W)_{kW}$—, $W^2$ further preferably represents a hydrogen atom or a linear or branched alkyl group having 1 to 20 carbon atoms in which arbitrary hydrogen atoms in the group may be substituted with a fluorine atom and one —$CH_2$— or two or more (—$CH_2$—)'s not adjacent to each other may be each independently substituted with —O—, —CO—, —COO—, or —OCO—, or a group represented by $P^W$—$(Sp^W-X^W)_{kW}$—, and $W^2$ furthermore preferably represents a hydrogen atom or a linear alkyl group having 1 to 12 carbon atoms in which one —$CH_2$— or two or more (—$CH_2$—)'s not adjacent to each other may be each independently substituted with —O— or a group represented by $P^W$—$(Sp^W-X^W)_{kW}$—. In the formula, $P^W$ represents a polymerizable group, the polymerizable group preferably represents the same group as defined above for $P^O$, $Sp^W$ represents a linear or branched alkylene group having 1 to 30 carbon atoms or a single bond, one —$CH_2$— or two or more (—$CH_2$—)'s not adjacent to each other in the alkylene group may be each independently substituted with —O—, —S—, —CO—, —COO—, —OCO—, —CO—S—, —S—CO—, —O—CO—O—, —CO—NH—, —NH—CO—, —$CF_2$O—, —$OCF_2$—, —$CF_2$S—, —$SCF_2$—, —CH=CH—COO—, —CH=CH—OCO—, —COO—CH=CH—, —OCO—CH=CH—, —CH=CH—, —N=N—, —CH=N—N=CH—, —CF=CF—, or —C≡C, plural $Sp^W$'s, if any, may be the same or different, $X^W$ represents —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —N=N—, —CH=N—N=CH—, —CF=CF—, —C≡C—, or a single bond, and kW represents an integer of 0 to 10, provided that $P^W$—$(Sp^W-X^W)_{kW}$— contains no —O—O— bond. From the viewpoints of liquid crystallinity, solubility in various solvents, and adhesiveness to various substrates (or alignment films), $P^W$ is preferably a group selected from the formulae (P-1), (P-2), (P-7), (P-11), and (P-13) as defined for $P^O$, more preferably the formulae (P-1), (P-2), or (P-3), and particularly preferably the formulae (P-1) or (P-2), $Sp^W$ preferably an alkylene group having 1 to 10 carbon atoms or a single bond, more preferably an alkylene group having 1 to 8 carbon atoms or a single bond, particularly preferably an alkylene group having 1 to 6 carbon atoms or a single bond, and plural $Sp^W$, if any, may be the same or different, $X^W$ is preferably —O— or a single bond, kW is preferably an integer of 0 to 5, more preferably an integer of 0 to 3, and kW is particularly preferably an integer of 1 to 3.

In the formula (T-1) or (T-2), in view of not only availability of the raw materials and easy synthesis, but also liquid crystallinity, solubility in various solvents, and adhesiveness to various substrates (or alignment films), $W^2$ preferably contains a partial structure represented by the general formula (AO-1), specifically, is more preferably the group represented by $P^W$—$(Sp^W-X^W)_{kW}$— containing a partial structure represented by the general formula (AO-1), or more preferably a group represented by H—$((CH_2)_{m2}$—$O)_{k2}$—$(CH_2)_{m3}$— where k2 represents an integer of 2 to 10, m2 represents an integer of 1 to 10, plural m2 may be the same or different integer, and m3 represents an integer of 0 to 10, and when m3 is 0, —$(CH_2)_{m3}$— represents a single bond. m2 is more preferably an integer of 1 to 6, k2 is more preferably an integer of 2 to 4, m3 is more preferably an integer of 0 to 8, and m3 is particularly preferably an integer of 0 to 6.

$W^1$ and $W^2$ may be linked together to form a ring structure, and in this case, a cyclic group represented by —$NW^1W^2$ preferably represents a group selected from the following formulae (W-19) to (W-40) which may be unsubstituted or substituted with one or more substituents $L^W$'s as described above:

[Chem. 38]

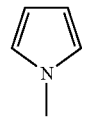
(W-19)

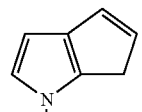
(W-20)

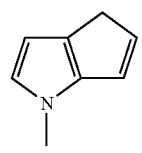
(W-21)

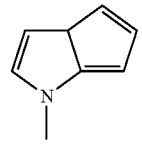
(W-22)

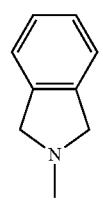
(W-23)

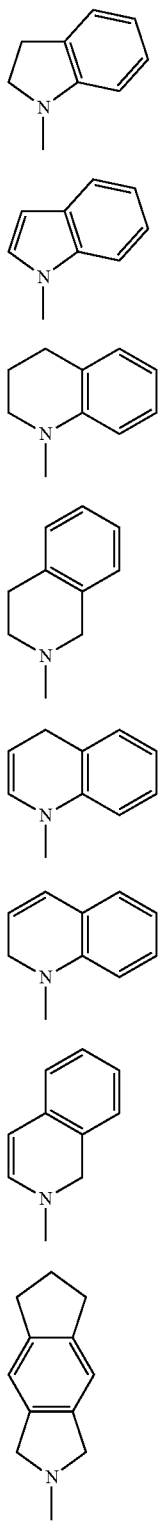
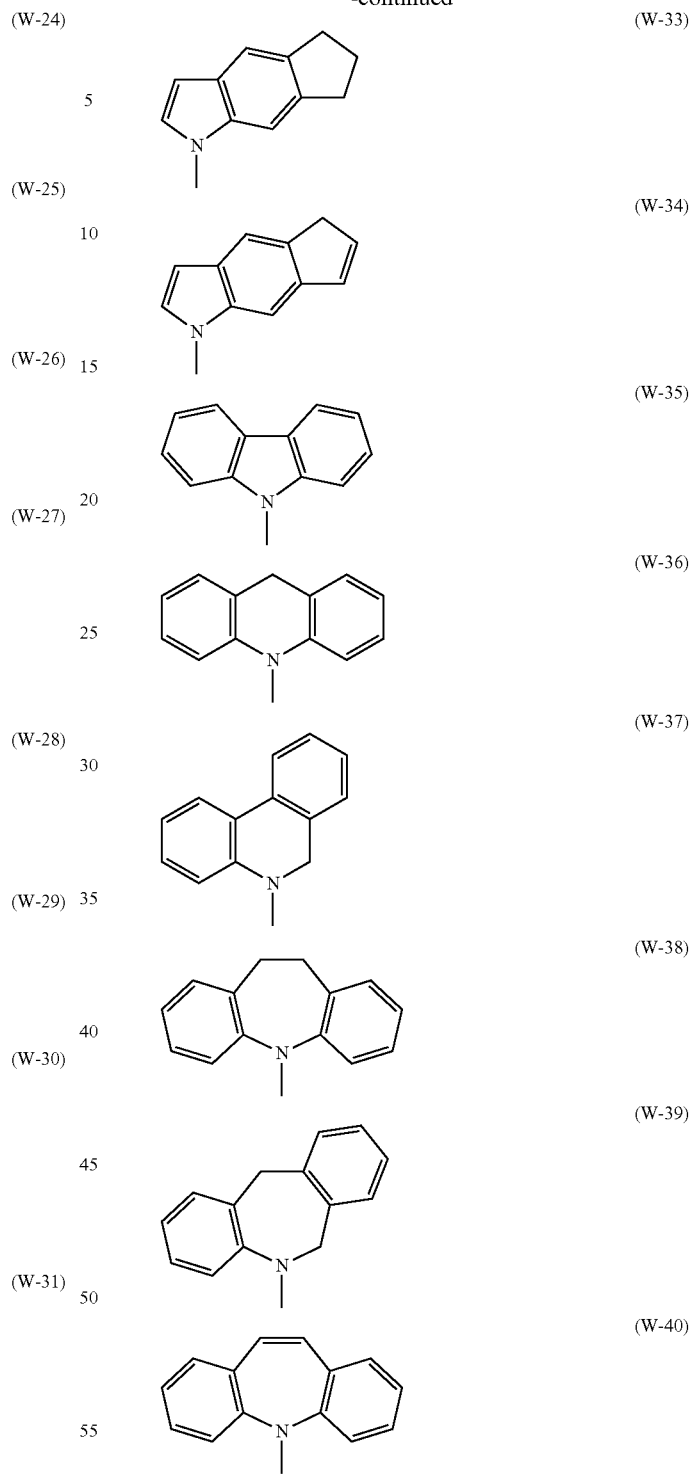

(wherein arbitrary (—CH=)'s may be each independently substituted with —N=, (—CH$_2$—)'s may be each independently substituted with —O—, —S—, —NR$^T$— (wherein R$^T$ represents a hydrogen atom or an alkyl group having 1 to 20 carbon atoms), —CS—, or —CO—, provided that no —O—O— is contained, and these groups may be unsubstituted or substituted with one or more substituents L$^W$'s as described above). The group represented by the formula (W-19) preferably represents a group selected from the following formulae (W-19-1) to (W-19-3) which may be unsubstituted or substituted with one or more substituents $L^W$'s as described above:

[Chem. 39]

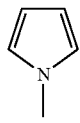
(W-19-1)

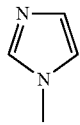
(W-19-2)

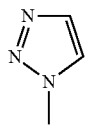
(W-19-3)

the group represented by the formula (W-20) preferably represents a group selected from the following formulae (W-20-1) to (W-20-4) which may be unsubstituted or substituted with one or more substituents $L^W$'s as described above:

[Chem. 40]

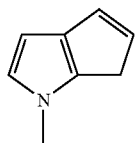
(W-20-1)

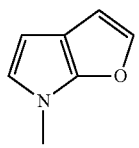
(W-20-2)

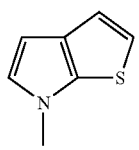
(W-20-3)

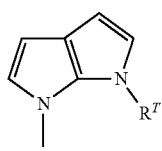
(W-20-4)

(wherein $R^T$ represents a hydrogen atom or an alkyl group having 1 to 8 carbon atoms), and the group represented by the formula (W-21) preferably represents a group selected from the following formulae (W-21-1) to (W-21-4) which may be unsubstituted or substituted with one or more substituents $L^W$'s as described above:

[Chem. 41]

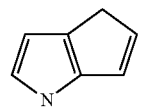
(W-21-1)

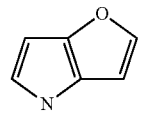
(W-21-2)

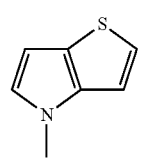
(W-21-3)

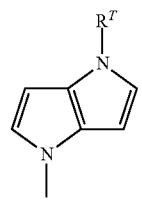
(W-21-4)

(wherein $R^T$ represents a hydrogen atom or an alkyl group having 1 to 8 carbon atoms), the group represented by the formula (W-22) preferably represents a group selected from the following formulae (W-22-1) to (W-22-4) which may be unsubstituted or substituted with one or more substituents $L^W$'s as described above:

[Chem. 42]

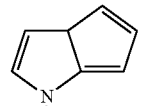
(W-22-1)

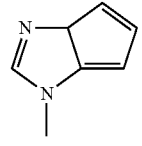
(W-22-2)

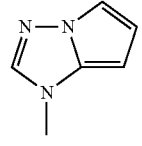
(W-22-3)

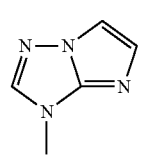
(W-22-4)

the group represented by the formula (W-23) preferably represents a group selected from the following formulae (W-23-1) to (W-23-3) which may be unsubstituted or substituted with one or more substituents $L^W$'s as described above:

[Chem. 43]

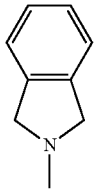
(W-23-1)

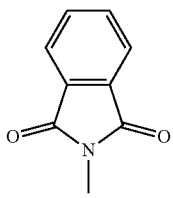
(W-23-2)

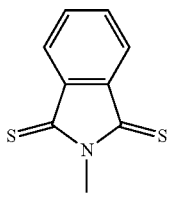
(W-23-3)

the group represented by the formula (W-24) preferably represents a group selected from the following formulae (W-24-1) to (W-24-4) which may be unsubstituted or substituted with one or more substituents $L^W$'s as described above:

[Chem. 44]

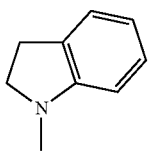
(W-24-1)

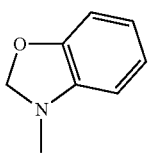
(W-24-2)

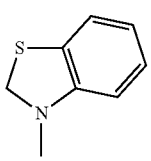
(W-24-3)

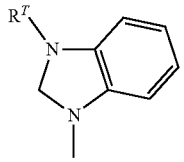
(W-24-4)

(wherein $R^T$ represents a hydrogen atom or an alkyl group having 1 to 8 carbon atoms), the group represented by the formula (W-25) preferably represents a group selected from the following formulae (W-25-1) to (W-25-3) which may be unsubstituted or substituted with one or more substituents $L^W$'s as described above:

[Chem. 45]

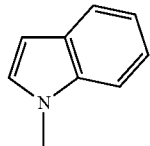
(W-25-1)

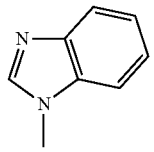
(W-25-2)

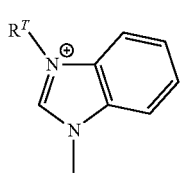
(W-25-3)

(wherein $R^T$ represents a hydrogen atom or an alkyl group having 1 to 8 carbon atoms), the group represented by the formula (W-26) preferably represents a group selected from the following formulae (W-26-1) to (W-26-7) which may be unsubstituted or substituted with one or more substituents $L^W$'s as described above:

[Chem. 46]

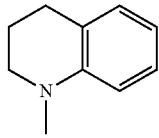
(W-26-1)

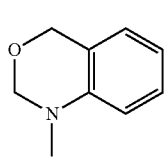
(W-26-2)

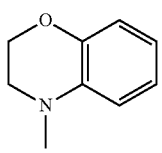 (W-26-3)

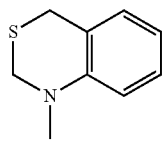 (W-26-4)

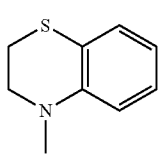 (W-26-5)

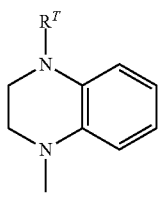 (W-26-6)

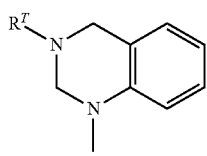 (W-26-7)

(wherein $R^T$ represents a hydrogen atom or an alkyl group having 1 to 8 carbon atoms), the group represented by the formula (W-27) preferably represents a group selected from, the following formulae (W-27-1) to (W-27-4) which may be unsubstituted or substituted with one or more substituents $L^W$'s as described above:

[Chem. 47]

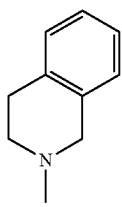 (W-27-1)

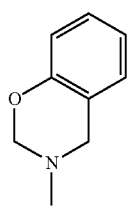 (W-27-2)

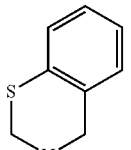 (W-27-3)

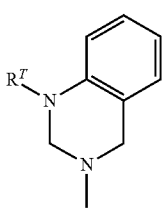 (W-27-4)

(wherein $R^T$ represents a hydrogen atom or an alkyl group having 1 to 8 carbon atoms), the group represented by the formula (W-28) preferably represents a group selected from the following formulae (W-28-1) to (W-28-6) which may be unsubstituted or substituted with one or more substituents $L^W$'s as described above:

[Chem. 48]

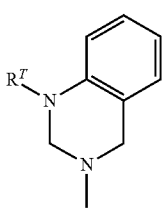 (W-28-1)

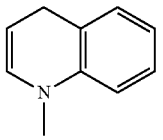 (W-28-2)

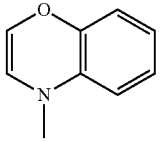 (W-28-3)

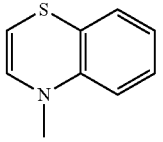 (W-28-4)

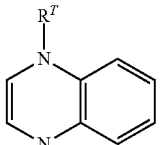 (W-28-5)

(wherein $R^T$ represents a hydrogen atom or an alkyl group having 1 to 8 carbon atoms), the group represented by the formula (W-29) preferably represents a group selected from the following formulae (W-29-1) to (W-29-3) which may be unsubstituted or substituted with one or more substituents $L^W$'s as described above:

the group represented by the formula (W-31) preferably represents a group selected from the following formulae (W-31-1) to (W-31-4) which may be unsubstituted or substituted with one or more substituents $L^W$'s as described above:

the group represented by the formula (W-30) preferably represents a group selected from the following formulae (W-30-1) to (W-30-3) which may be unsubstituted or substituted with one or more substituents $L^W$'s as described above:

(W-31-4)

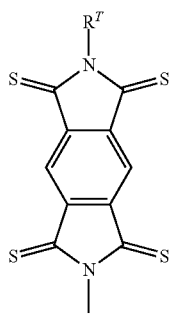

(wherein $R^T$ represents a hydrogen atom or an alkyl group having 1 to 8 carbon atoms), the group represented by the formula (W-32) preferably represents a group selected from the following formulae (W-32-1) to (W-32-5) which may be unsubstituted or substituted with one or more substituents $L^W$'s as described above:

[Chem. 52]

(W-32-1)

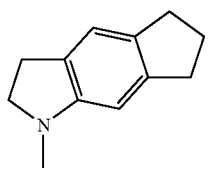

(W-32-2)

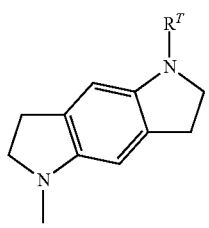

(W-32-3)

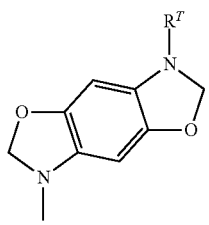

(W-32-4)

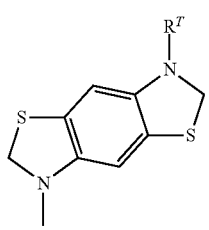

(W-32-5)

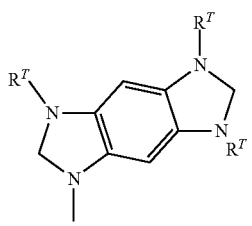

(wherein $R^T$ represents a hydrogen atom or an alkyl group having 1 to 8 carbon atoms), the group represented by the formula (W-33) preferably represents a group selected from the following formulae (W-33-1) to (W-33-3) which may be unsubstituted or substituted with one or more substituents $L^W$'s as described above:

[Chem. 53]

(W-33-1)

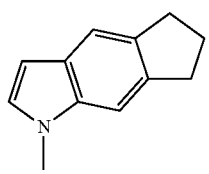

(W-33-2)

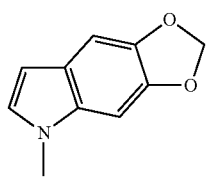

(W-33-3)

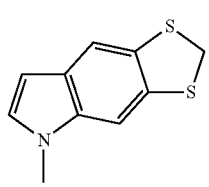

the group represented by the formula (W-34) preferably represents a group selected from the following formulae (W-34-1) to (W-34-5) which may be unsubstituted or substituted with one or more substituents $L^W$'s as described above:

[Chem. 54]

(W-34-1)

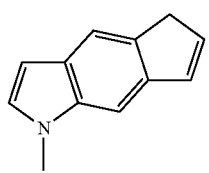

(W-34-2)

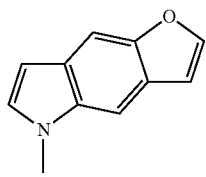

(W-34-3)

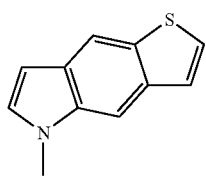

(W-34-4)

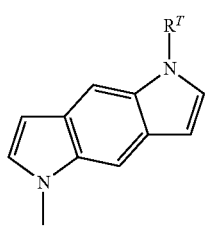

(W-34-5)

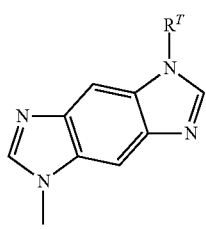

(wherein $R^T$ represents a hydrogen atom or an alkyl group having 1 to 8 carbon atoms), the group represented by the formula (W-35) preferably represents the following formula (W-35-1) which may be unsubstituted or substituted with one or more substituents $L^W$'s as described above:

[Chem. 55]

(W-35-1)

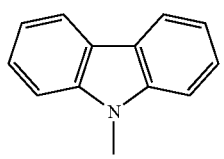

the group represented by the formula (W-36) preferably represents a group selected from the following formulae (W-36-1) to (W-36-6) which may be unsubstituted or substituted with one or more substituents $L^W$'s as described above:

[Chem. 56]

(W-36-1)

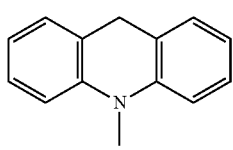

(W-36-2)

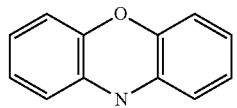

(W-36-3)

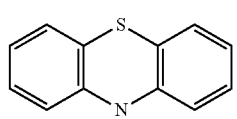

(W-36-4)

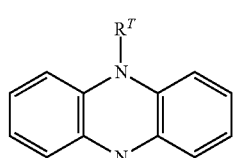

(W-36-5)

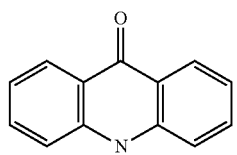

(W-36-6)

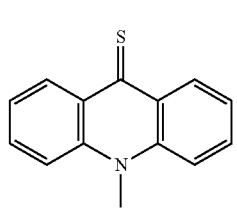

(wherein $R^T$ represents a hydrogen atom or an alkyl group having 1 to 8 carbon atoms), the group represented by the formula (W-37) preferably represents a group selected from the following formulae (W-37-1) to (W-37-3) which may be unsubstituted or substituted with one or more substituents $L^W$'s as described above:

[Chem. 57]

(W-37-1)

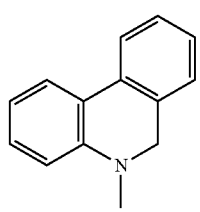

(W-37-2)

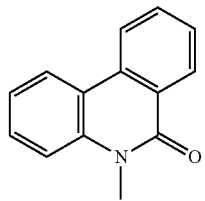

(W-37-3)

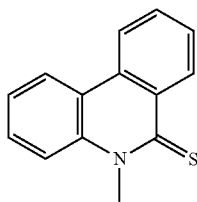

the group represented by the formula (W-38) preferably represents a group selected from the following: formulae (W-38-1) to (W-38-4) which may be unsubstituted or substituted with one or more substituents $L^W$'s as described above:

[Chem. 58]

(W-38-1)

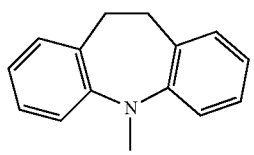

(W-38-2)

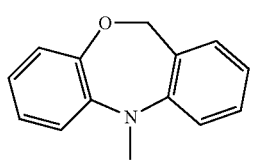

(W-38-3)

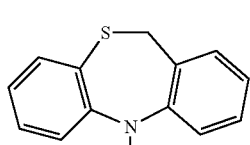

(W-38-4)

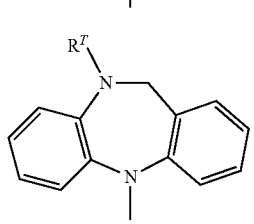

(wherein $R^T$ represents a hydrogen atom or an alkyl group having 1 to 8 carbon atoms), the group represented by the formula (W-39) preferably represents a group selected from the following formulae (W-39-1) to (W-39-4) which may be unsubstituted or substituted with one or more substituents $L^W$'s as described above:

[Chem. 59]

(W-39-1)

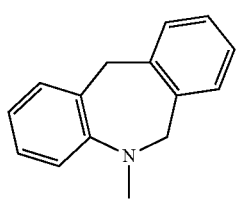

(W-39-2)

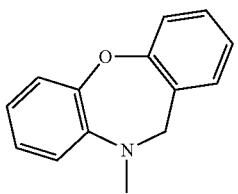

(W-39-3)

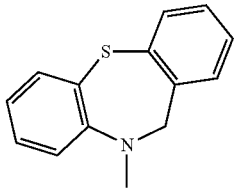

(W-39-4)

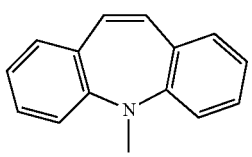

(wherein $R^T$ represents a hydrogen atom or an alkyl group having 1 to 8 carbon atoms), the group represented by the formula (W-40) preferably represents the following formula (W-40-1):

[Chem. 60]

(W-40-1)

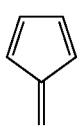

which may be unsubstituted or substituted with one or more substituents $L^W$'s as described above.

From the viewpoints of availability of the raw materials and easy synthesis, a cyclic group represented by preferably represents a group selected from the formulae (W-19-1), (W-21-2), (W-21-3), (W-21-4), (W-23-2), (W-23-3), (W-25-1), (W-25-2), (W-25-3), (W-30-2), (W-30-3), (W-35-1), (W-36-2), (W-36-3), (W-36-4), and (W-40-1) which may be unsubstituted or substituted with one or more substituents $L^W$'s as described above.

$W^1$ and $W^2$ may be linked together to form a ring structure, and in this case, a cyclic group represented by $=CW^1W^2$ preferably represents a group selected from the following formulae (W-41) to (W-62) which may be unsubstituted or substituted with one or more substituents $L^W$'s as described above:

[Chem. 61]

(W-41)

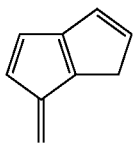 (W-42)
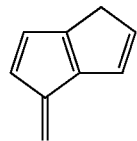 (W-43)
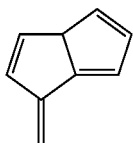 (W-44)
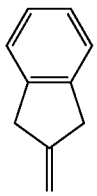 (W-45)
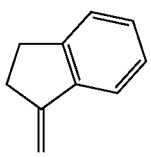 (W-46)
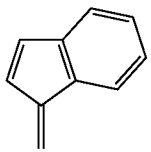 (W-47)
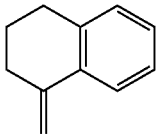 (W-48)
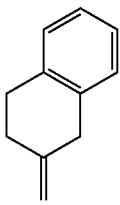 (W-49)
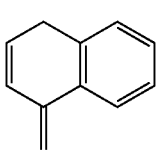 (W-50)
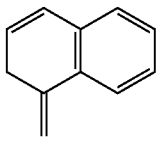 (W-51)
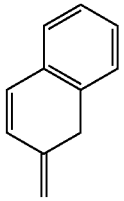 (W-52)
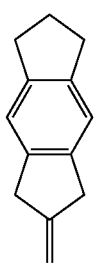 (W-53)
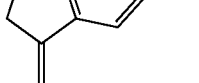 (W-54)
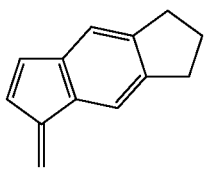 (W-55)
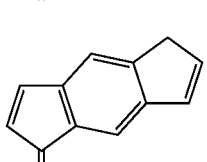 (W-56)
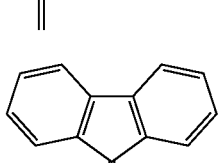 (W-57)
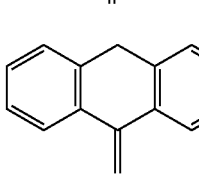 (W-58)

-continued (W-59)
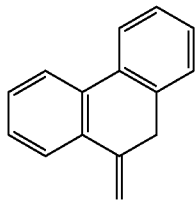

(W-60)
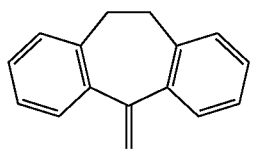

(W-61)
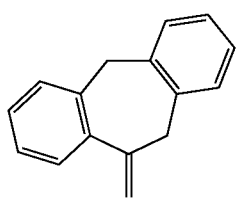

(W-62)
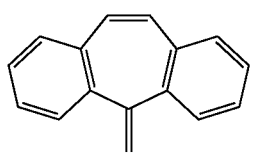

(wherein arbitrary (—CH═)'s may be each independently substituted with —N═, (—CH$_2$—)'s each independently substituted with —O—, —S—, —NR$^T$— (wherein R$^T$ represents a hydrogen atom or an alkyl group having 1 to 20 carbon, atoms), —CS—, or —CO—, provided that no —O—O— bond is contained, and these groups may be unsubstituted or substituted with one or more substituents L$^W$'s as described above). The group represented by the formula (W-41) preferably represents a group selected from the following formulae (W-41-1) to (W-41-3) which may be unsubstituted or substituted with one or more substituents L$^W$'s as described above:

[Chem. 62]

(W-41-1)

(W-41-2)

(W-41-3)
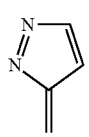

the group represented by the formula (W-42) preferably represents a group selected from the following formulae (W-42-1) to (W-42-4) which may be unsubstituted or substituted with one or more substituents ifs as described above:

[Chem. 63]

(W-42-1)
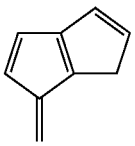

(W-42-2)
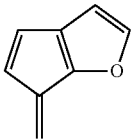

(W-42-3)
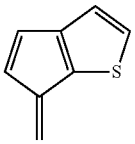

(W-42-4)
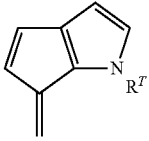

(wherein R$^T$ represents a hydrogen atom or an alkyl group having 1 to 8 carbon atoms), the group represented by the formula (W-43) preferably represents a group selected from the following formulae (W-43-1) to (W-43-4) which may be unsubstituted or substituted with one or more substituents L$^W$'s as described above:

[Chem. 64]

(W-43-1)
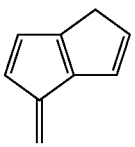

(W-43-2)
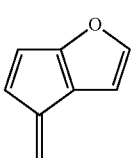

(W-43-3)

(W-43-4)

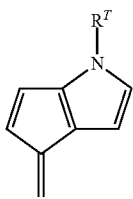

(wherein $R^T$ represents a hydrogen atom or an alkyl group having 1 to 8 carbon atoms), the group represented by the formula (W-44) preferably represents a group selected from the following formulae (W-44-1) to (W-44-4) which may be unsubstituted or substituted with one or more substituents $L^W$'s as described above:

[Chem. 65]

(W-44-1)

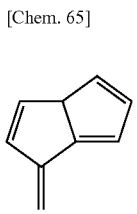

(W-44-2)

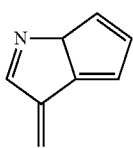

(W-44-3)

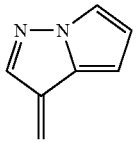

(W-44-4)

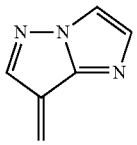

the group represented by the formula (W-45) preferably represents a group selected from the following formulae (W-45-1) to (W-45-4) which may be unsubstituted or substituted with one or more substituents $L^W$'s as described above:

[Chem. 66]

(W-45-1)

(W-45-2)

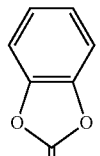

(W-45-3)

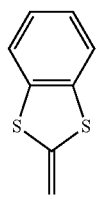

(W-45-4)

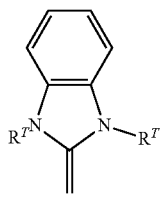

(wherein $R^T$ represents a hydrogen atom or an alkyl group having 1 to 8 carbon atoms), the group represented by the formula (W-46) preferably represents a group selected from the following formulae (W-46-1) to (W-46-4) which may be unsubstituted or substituted with one or more substituents $L^W$'s as described above:

[Chem. 67]

(W-46-1)

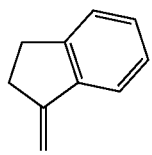

(W-46-2)

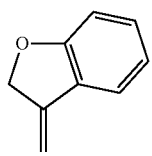

(W-46-3)

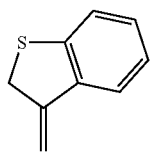

(W-46-4)

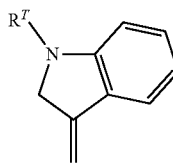

(wherein $R^T$ represents a hydrogen atom or an alkyl group having 1 to 8 carbon atoms), the group represented by the formula (W-47). Preferably represents a group selected from the following formulae (W-47-1) to (W-47-3) which may be unsubstituted or substituted with one or more substituents $L^W$'s as described above:

[Chem. 68]

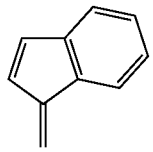
(W-47-1)

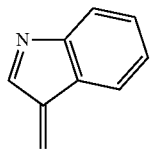
(W-47-2)

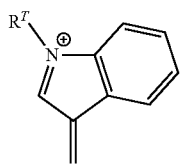
(W-47-3)

(wherein $R^T$ represents a hydrogen atom or an alkyl group having 1 to 8 carbon atoms), the group represented by formula (W-48) preferably represents a group selected from the following formulae (W-48-1) to (W-48-7) which may be unsubstituted or substituted with one or more substituents $L^W$'s as described above:

[Chem. 69]

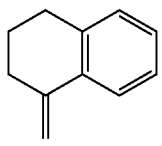
(W-48-1)

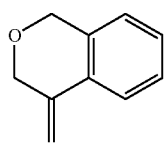
(W-48-2)

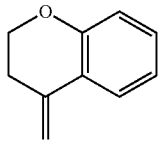
(W-48-3)

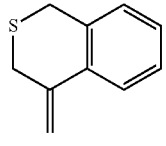
(W-48-4)

-continued

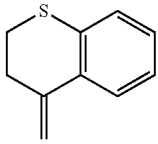
(W-48-5)

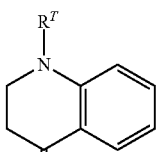
(W-48-6)

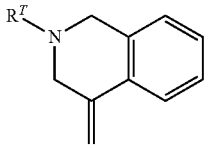
(W-48-7)

(wherein $R^T$ represents a hydrogen atom or an alkyl group having 1 to 8 carbon atoms), the group represented by the formula (W-49) preferably represents a group selected from the following formulae (W-49-1) to (W-49-4) which may be unsubstituted or substituted with one or more substituents $L^W$'s as described above:

[Chem. 70]

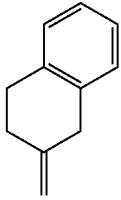
(W-49-1)

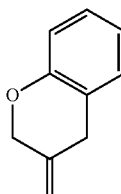
(W-49-2)

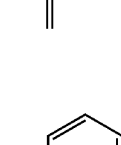
(W-49-3)

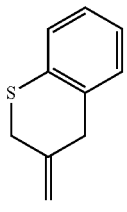

-continued (W-49-4)

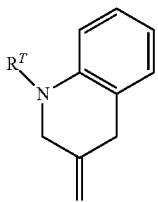

(wherein $R^T$ represents a hydrogen atom or an alkyl group having 1 to 8 carbon atoms), the group represented by the formula (W-50) preferably represents a group selected from the following formulae (W-50-1) to (W-50-6) which may be unsubstituted or substituted with one or more substituents $L^W$'s as described above:

[Chem. 71]

(W-50-1)

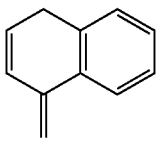

(W-50-2)

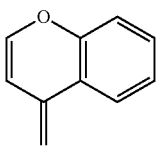

(W-50-3)

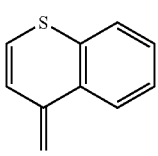

(W-50-4)

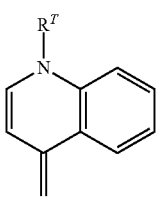

(W-50-5)

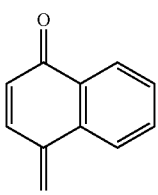

(W-50-6)

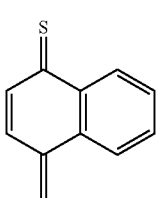

(wherein $R^T$ represents a hydrogen atom or an alkyl group having 1 to 8 carbon atoms), the group represented by the formula (W-51) preferably represents a group selected from the following formulae (W-51-1) to (W-51-3) which may be unsubstituted or substituted with one or more substituents $L^W$'s as described above:

[Chem. 72]

(W-51-1)

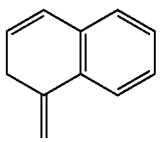

(W-51-2)

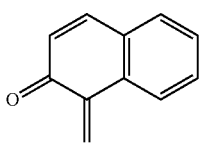

(W-51-3)

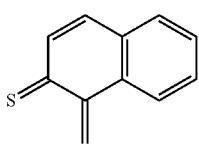

the group represented by the formula (W-52) preferably represents a group selected from the following formulae (W-52-1) to (W-52-3) which may be unsubstituted or substituted with one or more substituents $L^W$'s as described above:

[Chem. 73]

(W-52-1)

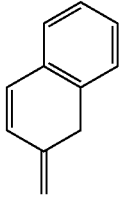

(W-52-2)

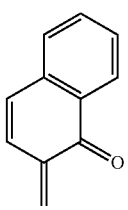

(W-52-3)

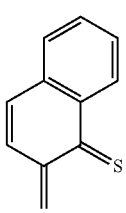

the group represented by the formula (W-53) preferably represents a group selected from the following formulae (W-53-1) to (W-53-8) which may be unsubstituted or substituted with one or more substituents $L^W$'s as described above:

[Chem. 74]
(W-53-1) 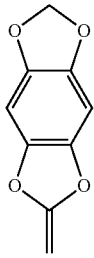
(W-53-2) 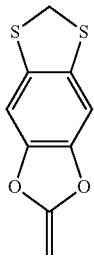
(W-53-3) 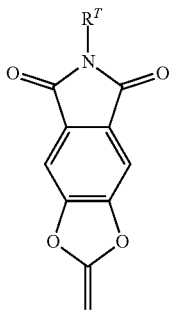
(W-53-4) 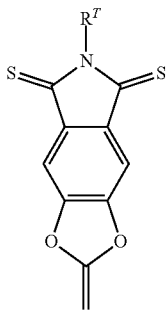
(W-53-5) 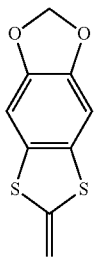
(W-53-6) 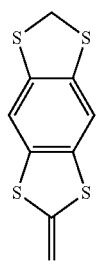
(W-53-7)
(W-53-8)
(wherein $R^T$ represents a hydrogen atom or an alkyl group having 1 to 8 carbon atoms), the group represented by the formula (W-54) preferably represents a group selected from the following formulae (W-54-1) to (W-54-5) which may be unsubstituted or substituted with one or more substituents $L^W$'s as described above:
[Chem. 75]
(W-54-1) 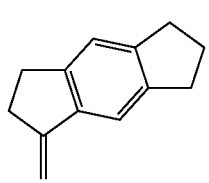
(W-54-2) 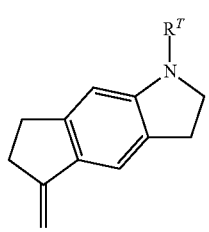

(W-54-3)

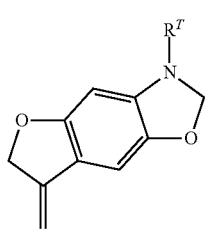

(W-54-4)

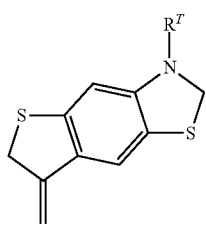

(W-54-5)

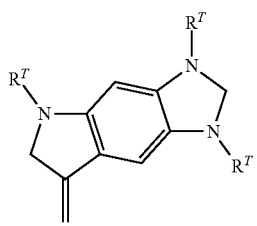

(wherein $R^T$ represents a hydrogen atom or an alkyl group having 1 to 8 carbon atoms), the group represented by the formula (W-55) preferably represents a group selected from the following formulae (W-55-1) to (W-55-3) which may be unsubstituted or substituted with one or more substituents $L^W$'s as described above:

[Chem. 76]

(W-55-1)

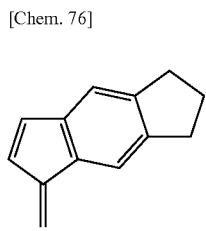

(W-55-2)

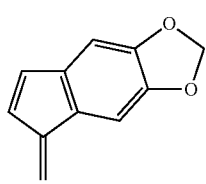

(W-55-3)

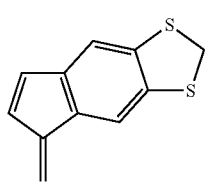

the group represented by the formula (W-56) preferably represents a group selected from the following formulae (W-56-1) to (W-56-5) which may be unsubstituted or substituted with one or more substituents: $L^W$'s as described above:

[Chem. 77]

(W-56-1)

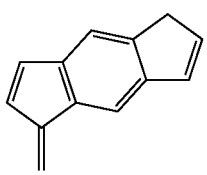

(W-56-2)

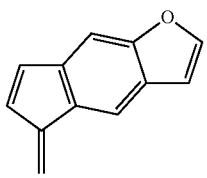

(W-56-3)

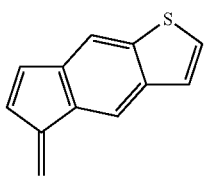

(W-56-4)

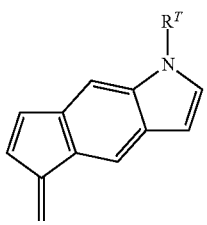

(W-56-5)

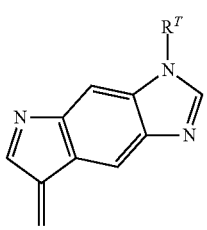

(wherein $R^T$ represents a hydrogen atom or an alkyl group having 1 to 8 carbon atoms), the group represented by the formula (W-57) preferably represents the formula (W-57-1) which may be unsubstituted or substituted with one or more substituents $L^W$'s as described above:

[Chem. 78]

(W-57-1)

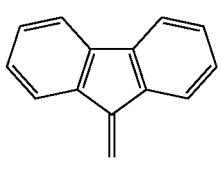

the group represented by the formula (W-58) preferably represents a group selected from the following formulae (W-58-1) to (W-58-6) which may be unsubstituted or substituted with one or more substituents $L^W$'s as described above:

[Chem. 79]

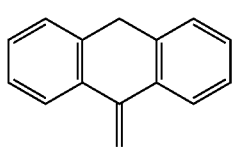
(W-58-1)

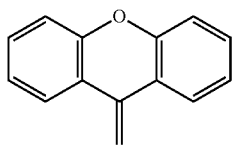
(W-58-2)

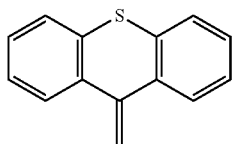
(W-58-3)

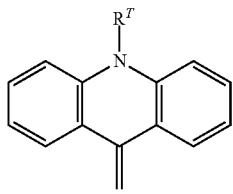
(W-58-4)

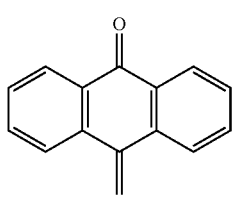
(W-58-5)

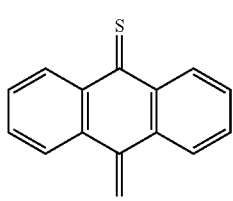
(W-58-6)

(wherein $R^T$ represents a hydrogen atom or an alkyl group having 1 to 8 carbon atoms), the group represented by the formula (W-59) preferably represents a group selected front the following formulae (W-59-1) to (W-59-3) which may be unsubstituted or substituted with one or more substituents $L^W$'s as described above:

[Chem. 80]

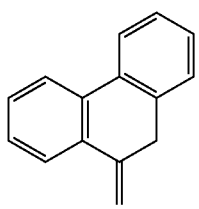
(W-59-1)

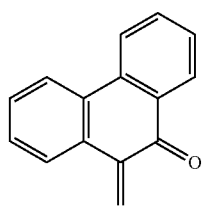
(W-59-2)

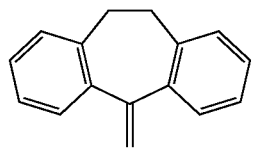
(W-59-3)

the group represented by the formula (W-60) preferably represents a group selected from the following formulae (W-60-1) to (W-60-4) which may be unsubstituted or substituted with one or more substituents $L^W$'s as described above:

[Chem. 81]

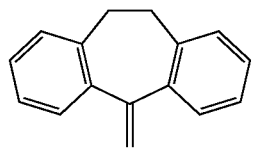
(W-60-1)

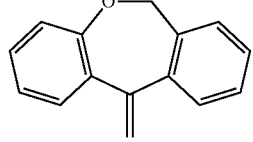
(W-60-2)

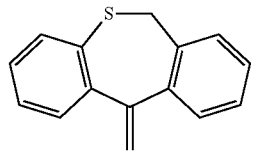
(W-60-3)

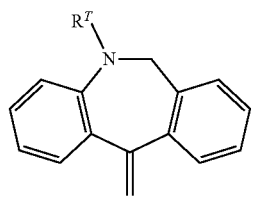
(W-60-4)

(wherein $R^T$ represents a hydrogen atom or an alkyl group having 1 to 8 carbon atoms), the group represented by the formula (W-61) preferably represents a group selected from the following formulae (W-61-1) to (W-61-4) which may be unsubstituted or substituted with one or more substituents $L^W$'s as described above;

[Chem. 82]

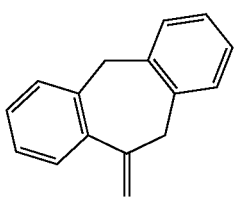
(W-61-1)

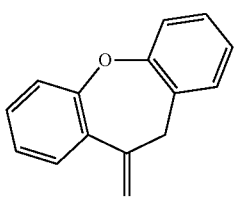
(W-61-2)

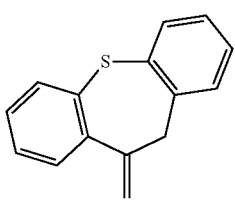
(W-61-3)

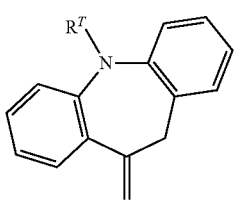
(W-61-4)

(wherein $R^T$ represents a hydrogen atom or an alkyl group having 1 to 8 carbon atoms), the group represented by the formula (W-62) preferably represents the formula (W-62-1):

[Chem. 83]

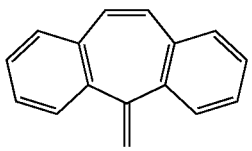
(W-62-1)

which may be unsubstituted or substituted with one or more substituents $L^W$'s as described above.

From the viewpoints of availability of the raw materials and easy synthesis, a cyclic group represented by $=CW^1W^2$ more preferably represents a group selected from the formulae (W-42-2), (W-42-3), (W-43-2), (W-43-3), (W-45-3), (W-45-4), (W-57-1), (W-58-2), (W-58-3), (W-58-4), and (W-62-1) which may be unsubstituted or substituted with one or more substituents $L^W$'s as described above, further preferably represents a group selected from the formulae (W-57-1) and (W-62-1) which may be unsubstituted or substituted with one or more substituents $L^W$'s as described above, and furthermore preferably represents a group represented by the formula (W-57-1) which may be unsubstituted or substituted with one or more substituents $L^W$'s as described above.

From the viewpoints of wavelength dispersion characteristics, storage stability, liquid crystallinity, and easy synthesis, the total number of π electrons contained in $W^1$ and $W^2$ is preferably 4 to 24.

From the viewpoints of liquid crystallinity and easy synthesis, the substituent if preferably represents a fluorine atom, a chlorine atom, a pentafluorosulfuranyl group, a nitro group, a methylamino group, a dimethylamino group, a diethylamino group, a diisopropylamino group, or a linear or branched alkyl group having 1 to 20 carbon, atoms in which arbitrary hydrogen atoms may be substituted with a fluorine atom and one —$CH_2$— or two or more (—$CH_2$—)'s not adjacent to each other may be each independently substituted with a group selected from —O—, —S—, —CO—, —COO—, —OCO—, —O—CO—O—, —CH=CH—, —CF=CF—, and —C≡C—, more preferably represents a fluorine atom, a chlorine atom, or a linear or branched alkyl group having 1 to 12 carbon atoms in which arbitrary hydrogen atoms may be substituted with a fluorine atom and one —$CH_2$— or two or more (—$CH_2$—)'s not adjacent to each other may be each independently substituted with a group selected from —O—, —COO—, and —OCO—, further preferably represents a fluorine atom, a chlorine atom, or a linear or branched alkyl group or alkoxy group having 1 to 12 carbon atoms in which arbitrary hydrogen atoms may be substituted with a fluorine atom, and particularly preferably represents a fluorine atom, a chlorine atom, or a linear alkyl group or linear alkoxy group having 1 to 8 carbon atoms.

In the general formula (I), $G^1$ more preferably represents a group selected from the following formulae (G-1) to (G-22):

[Chem. 84]

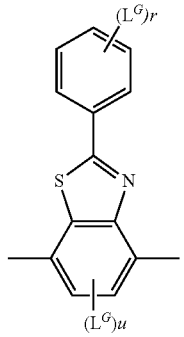
(G-1)

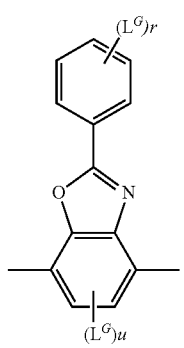
(G-2)

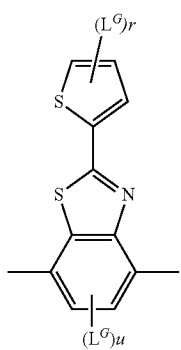 (G-3)
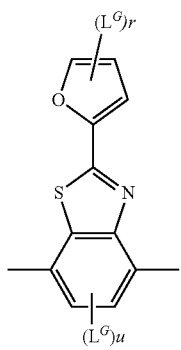 (G-4)
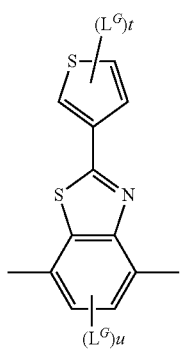 (G-5)
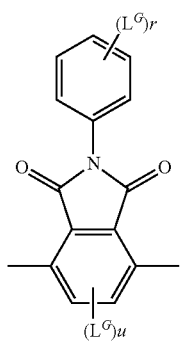 (G-6)
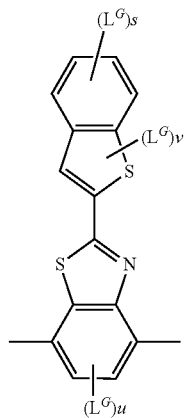 (G-7)
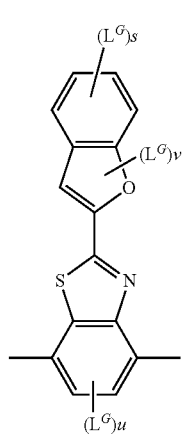 (G-8)
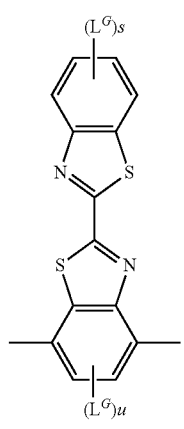 (G-9)

(G-10)
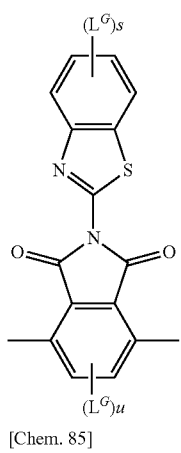
[Chem. 85]
(G-11)
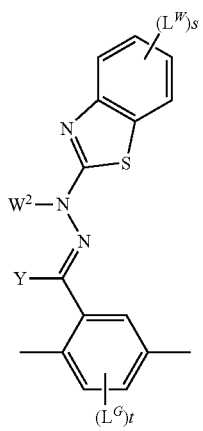
(G-12)
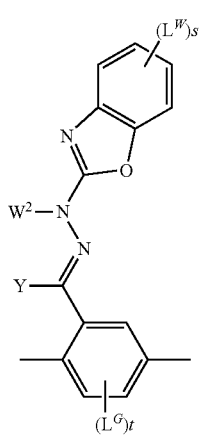
(G-13)
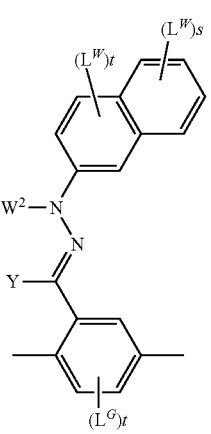
(G-14)
(G-15)
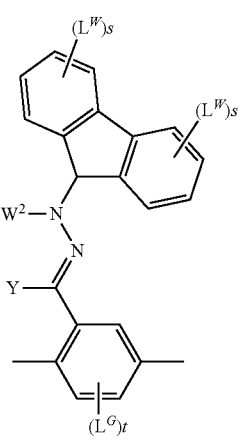

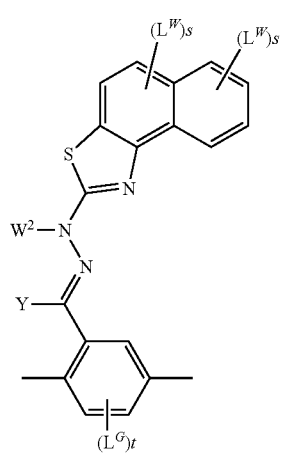
(G-16)
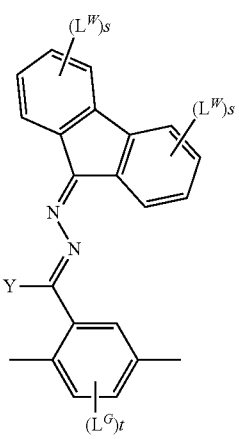
(G-17)
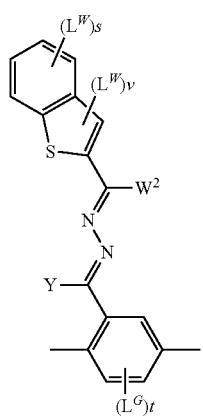
(G-18)
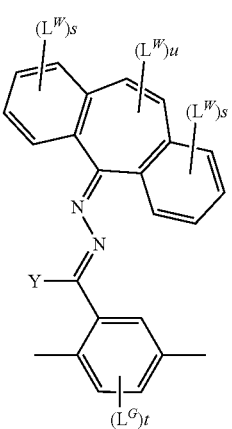
(G-19)
(G-20)
(G-21)

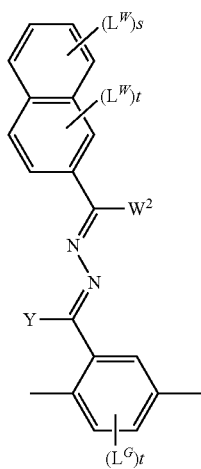
(G-22)

(wherein $L^G$, $L^W$, Y, and $W^2$ have the same meanings as described above, r represents an integer of 0 to 5, s represents an integer of 0 to 4, t represents an integer of 0 to 3, u represents an integer of 0 to 2, v represents 0 or 1, and the right side and the left side of these groups may be reversed). Among the formulae (G-1) to (G-10), a group selected from the formulae (G-1), (G-3), (G-5), (G-6), (G-7), (G-8), and (G-10) is more preferred, those in which u is 0 are further preferred, and a group selected from the following formulae (G-1-1) to (G-10-1) is particularly preferred:

[Chem. 86]

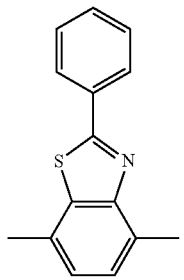
(G-1-1)

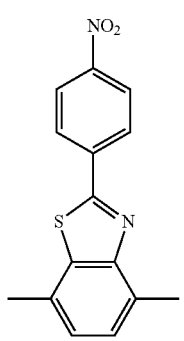
(G-1-2)

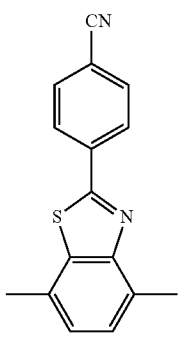
(G-1-3)

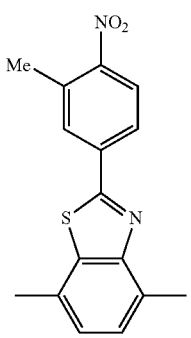
(G-1-4)

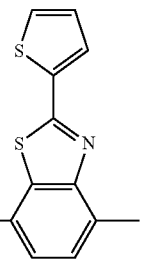
(G-3-1)

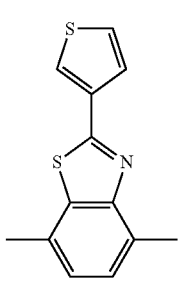
(G-5-1)

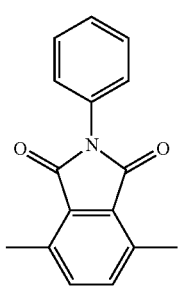
(G-6-1)

(G-7-1)
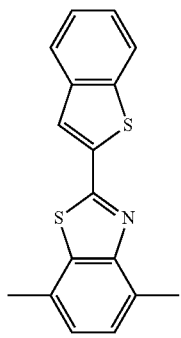
(G-8-1)
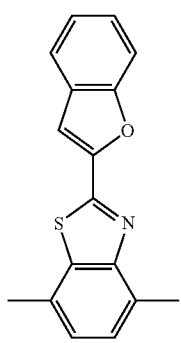
(G-8-2)
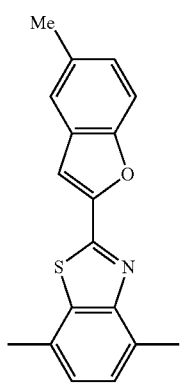
(G-8-2)
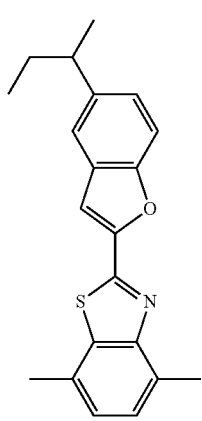
(G-8-3)
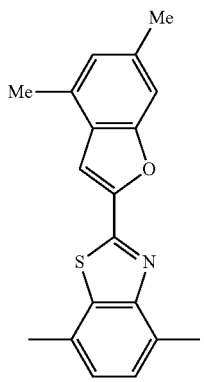
(G-8-4)
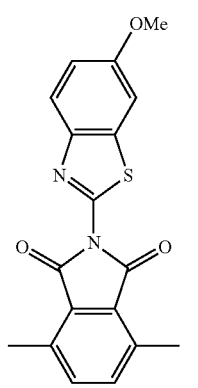
(G-10-1)
(wherein the right side and the left side of these groups may be reversed).
Among the formulae (G-11) to (G-22), those in which Y represents a hydrogen atom are preferred, those in which s, t, u, and v represent 0 are further preferred, and a group selected from the following formulae (G-11-1) to (G-20-1) is particularly preferred:

[Chem. 87]
(G-11-1) 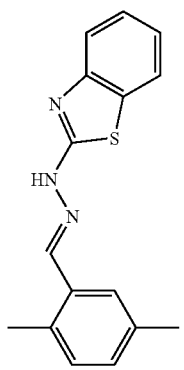
(G-11-2) 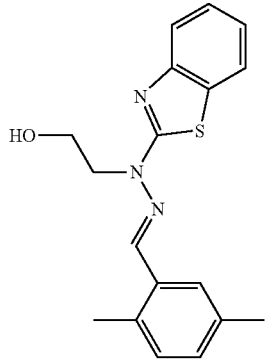
(G-11-3) 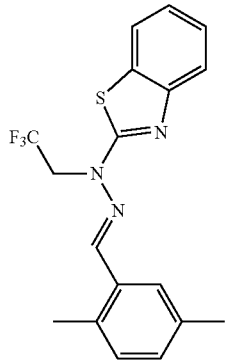
(G-11-4) 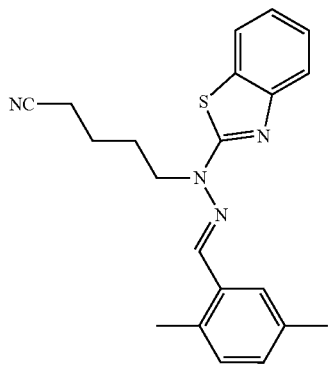
(G-11-5) 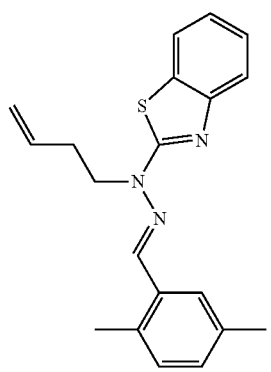
(G-11-6)
(G-11-7)
(G-11-8)

(G-11-9)

(G-11-10)

(G-11-11)

(G-11-12)

(G-11-13)

(G-11-14)

(G-11-15)

(G-11-16)

[Chem. 88]
(G-11-17)
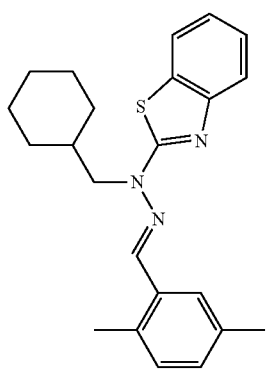
(G-11-18)
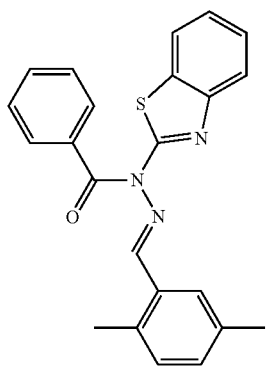
(G-11-19)
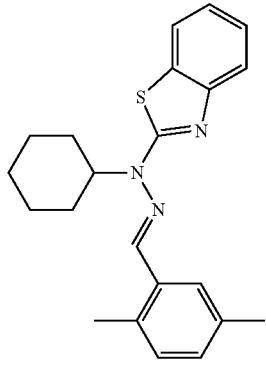
(G-11-20)
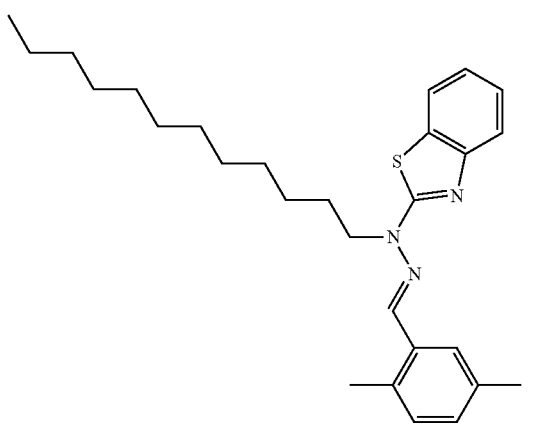
(G-11-21)
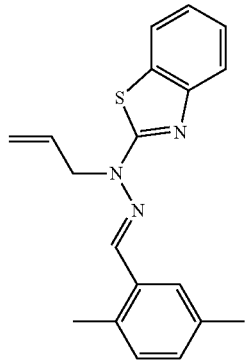
(G-11-22)
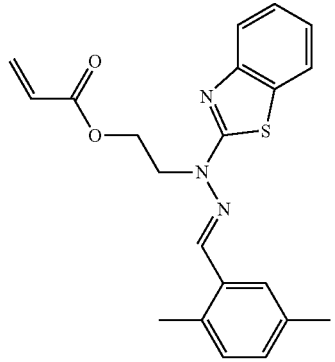
(G-11-23)
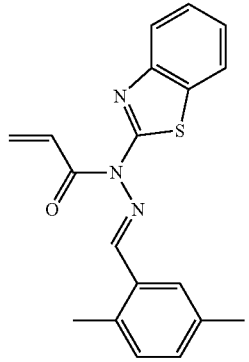
(G-11-24)
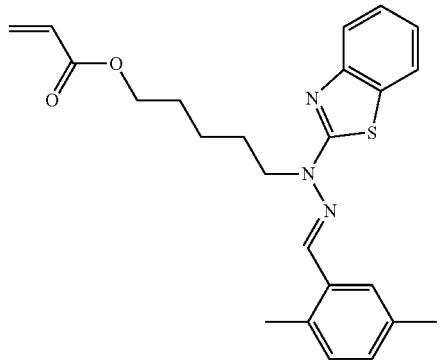

97
-continued
(G-11-25)
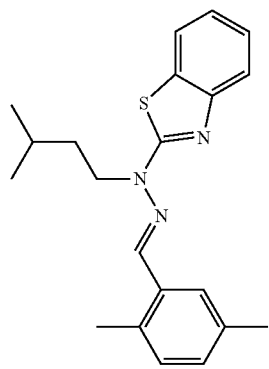
(G-11-26)
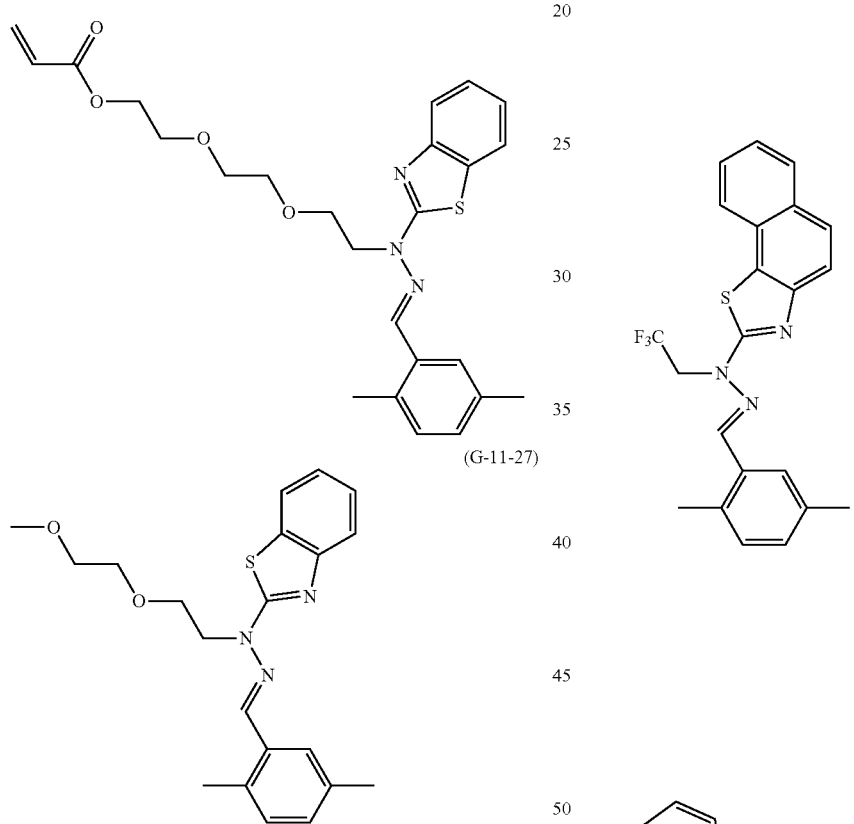
(G-11-27)
[Chem. 89]
(G-15-1)
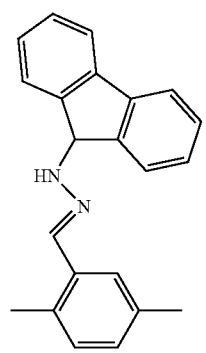
98
-continued
(G-16-1)
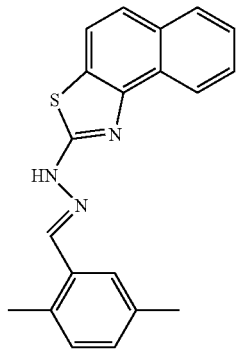
(G-17-1)
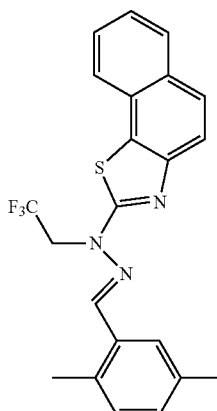
(G-20-1)
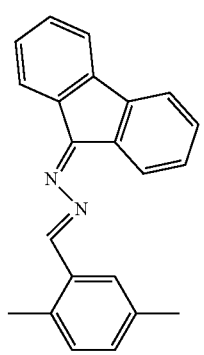
As specific examples of the compound represented by the general formula (I), compounds represented by the following formulae (I-1) to (I-99) are preferred.

[Chem. 90]
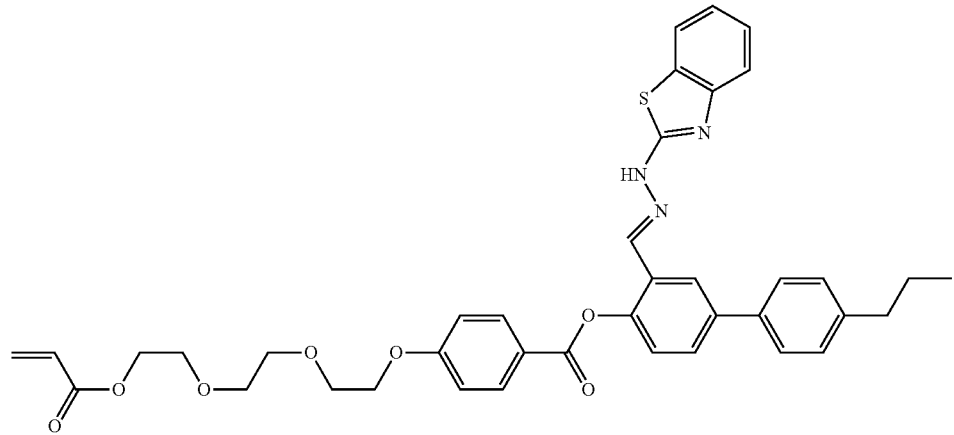
(I-1)
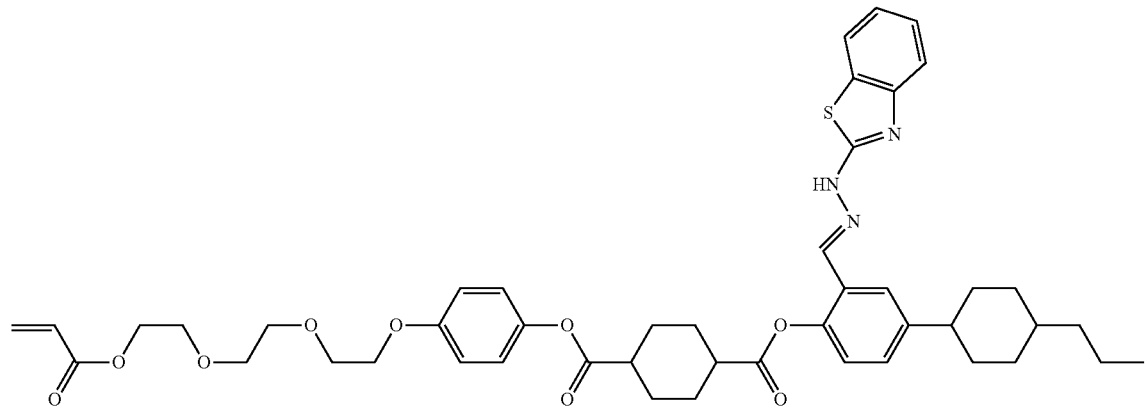
(I-2)
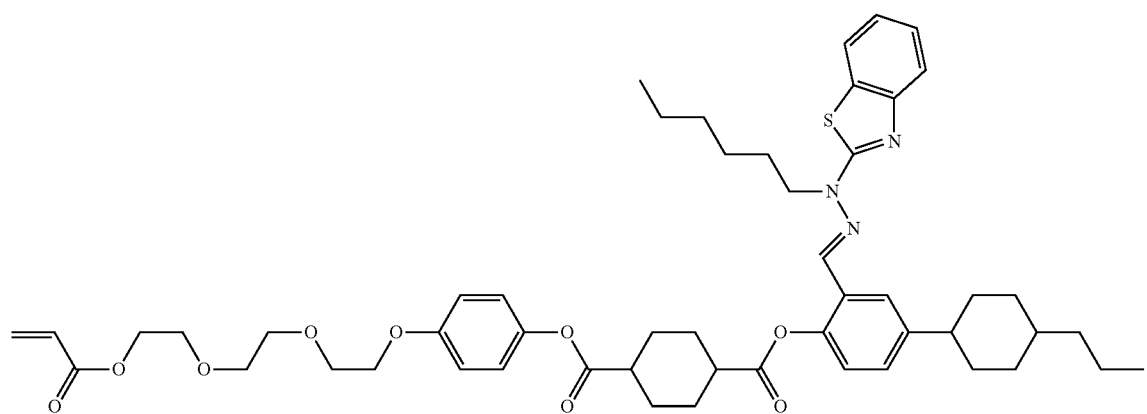
(I-3)

(I-4)
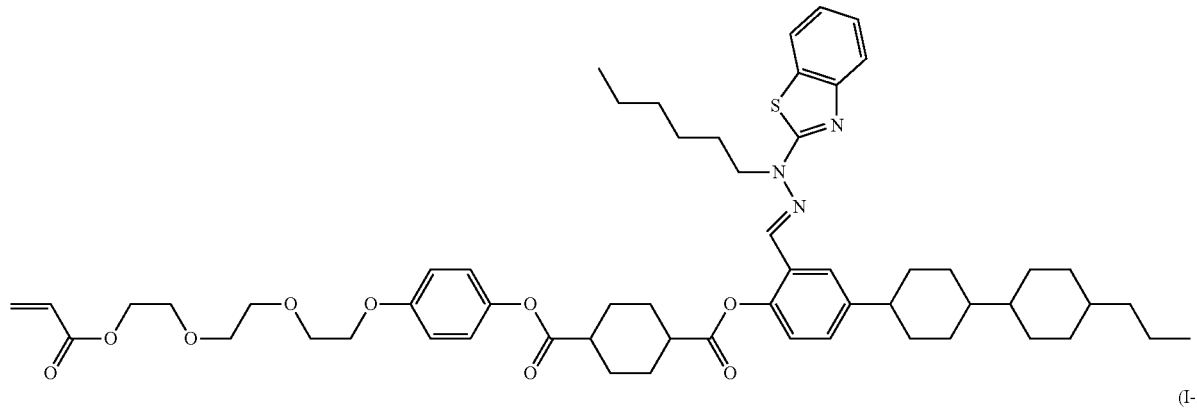
(I-5)
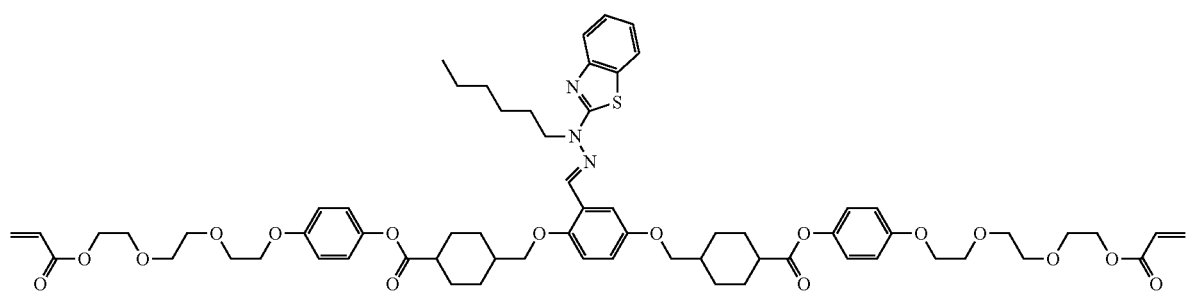
[Chem. 91]
(I-6)
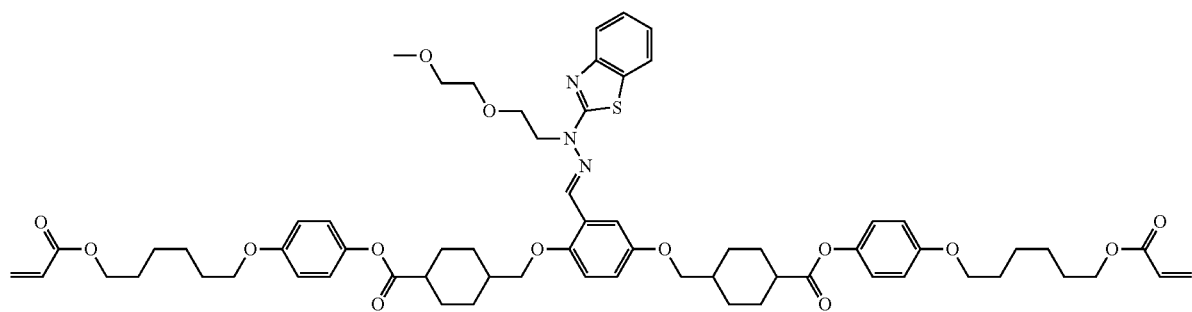
(I-7)
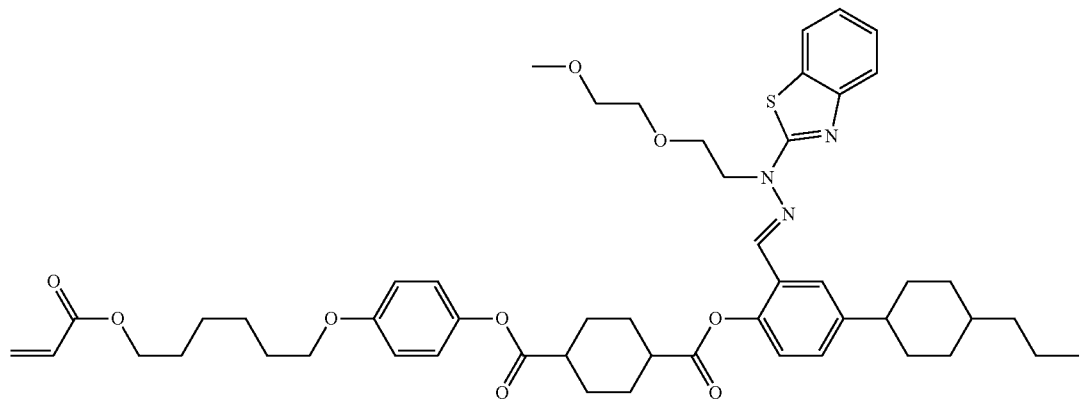

-continued
(I-8)
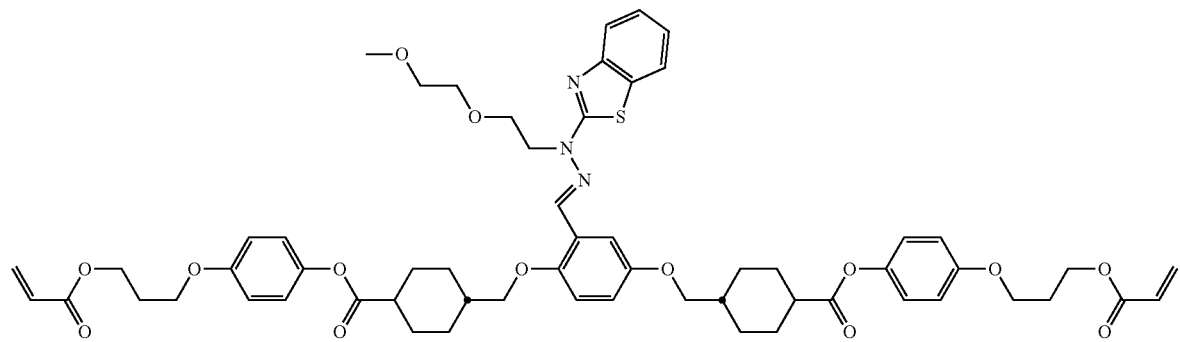
(I-9)
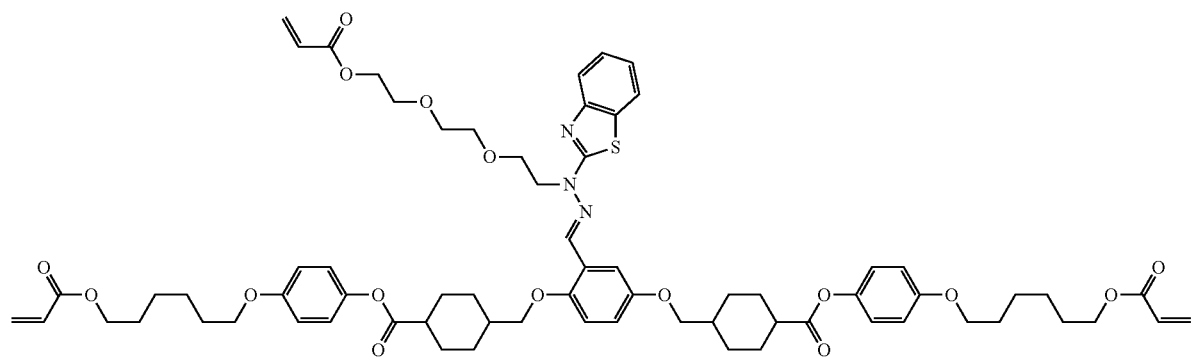
(I-10)
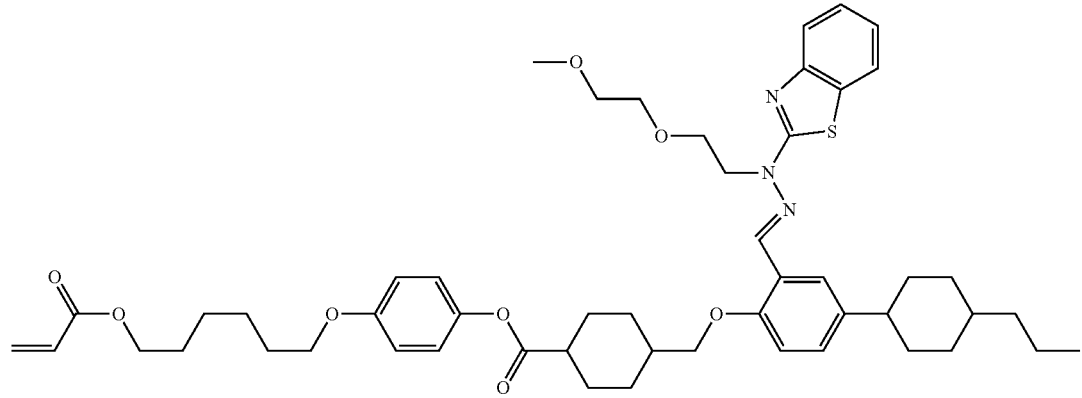
[Chem. 92]
(I-11)
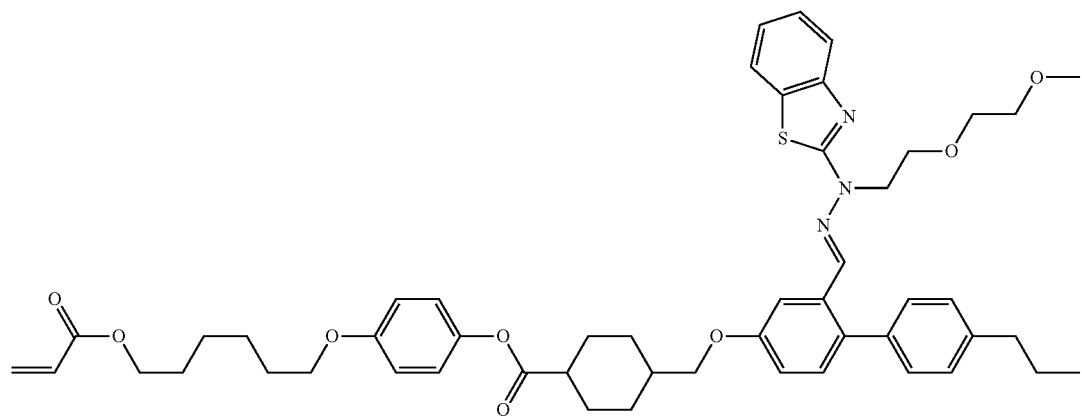

-continued
(I-12)
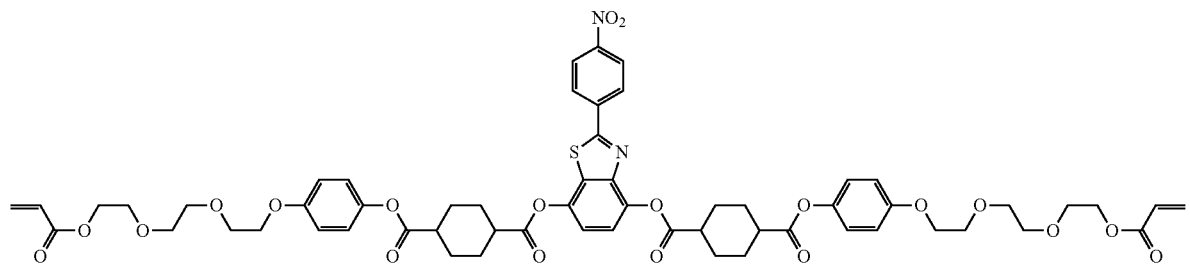
(I-13)
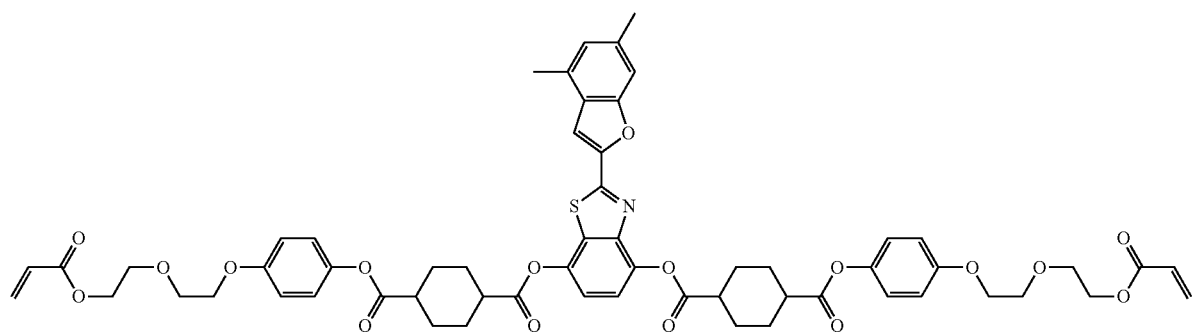
(I-14)
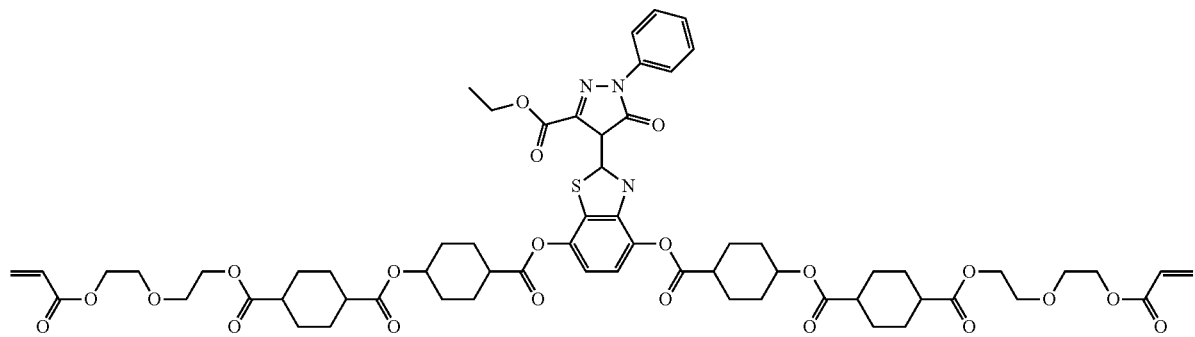
(I-15)
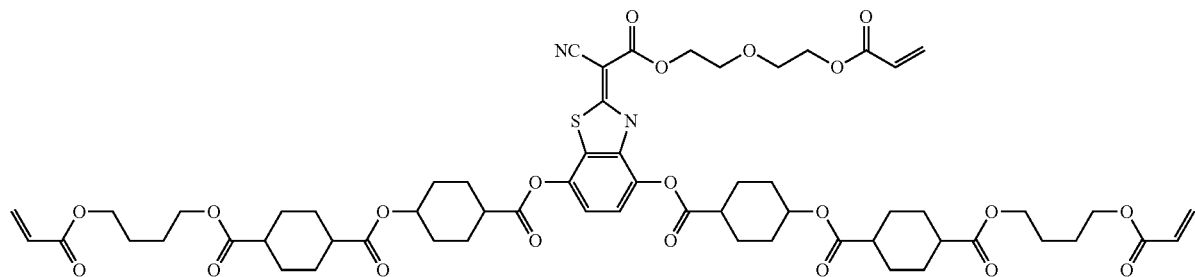

-continued
(I-16)
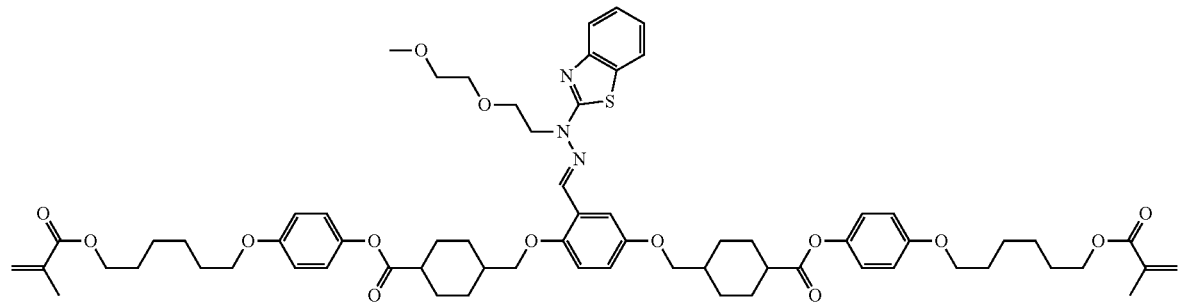
(I-17)
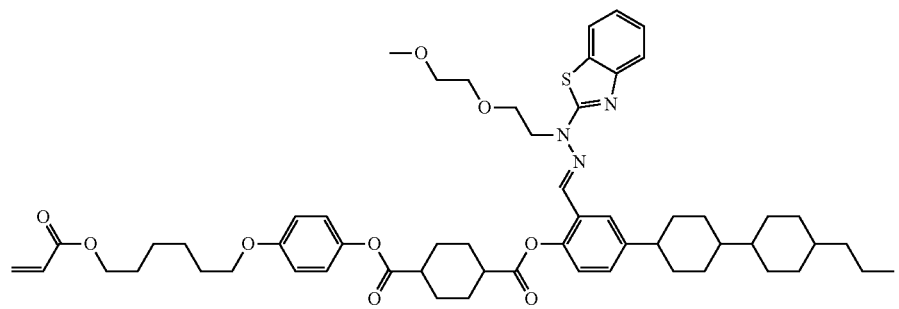
(I-18)
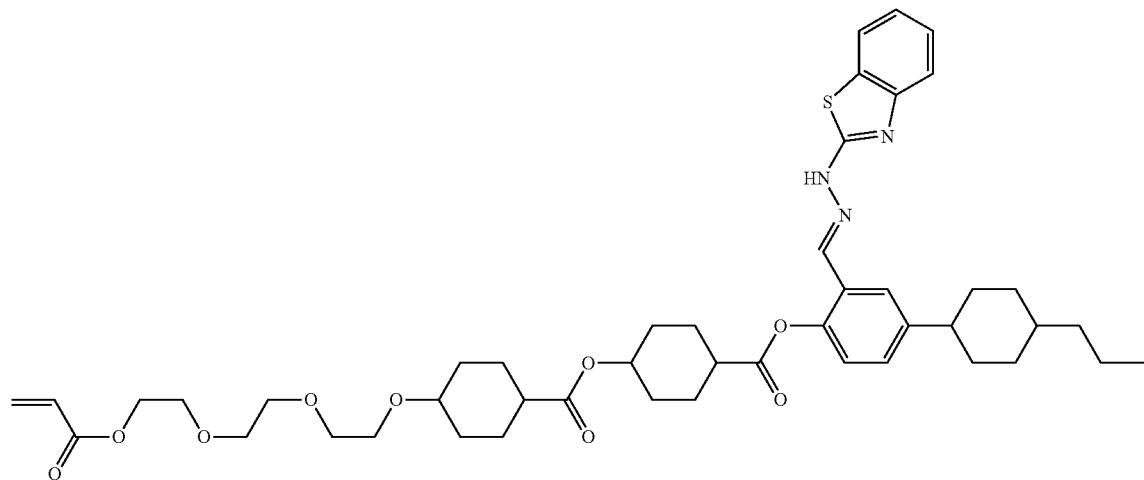
(I-19)
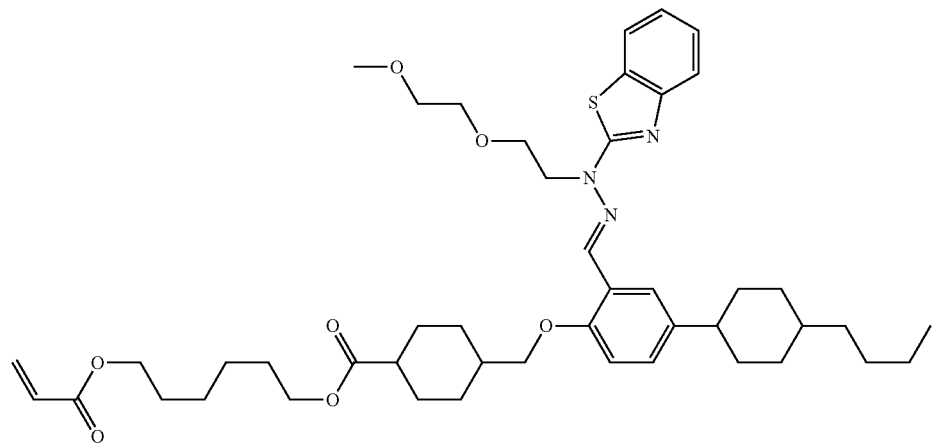

-continued
(I-20)
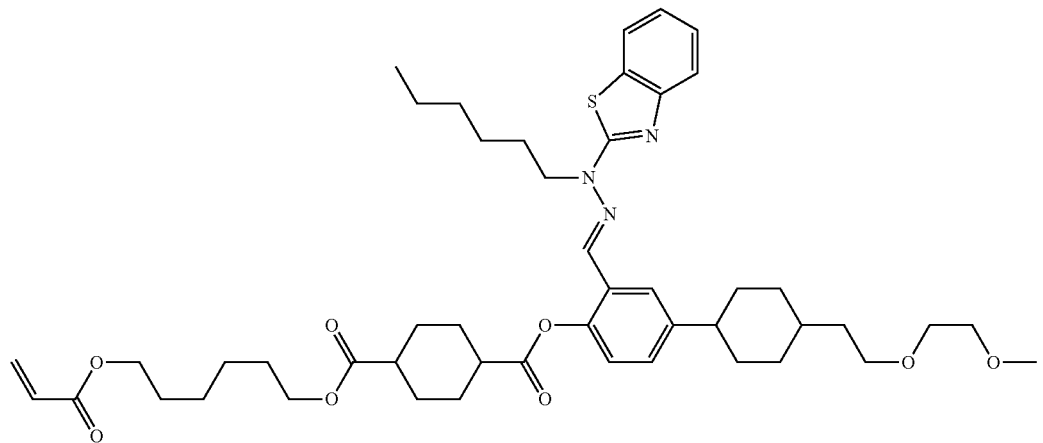
[Chem. 94]
(I-21)
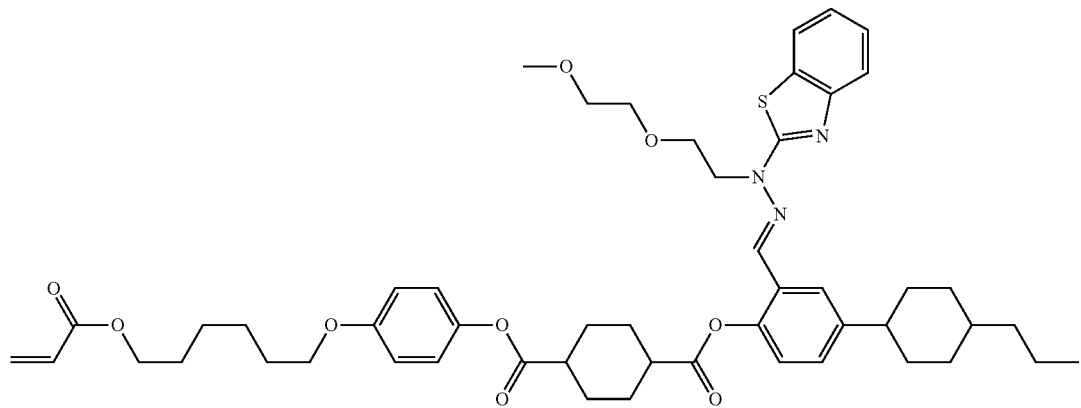
(I-22)
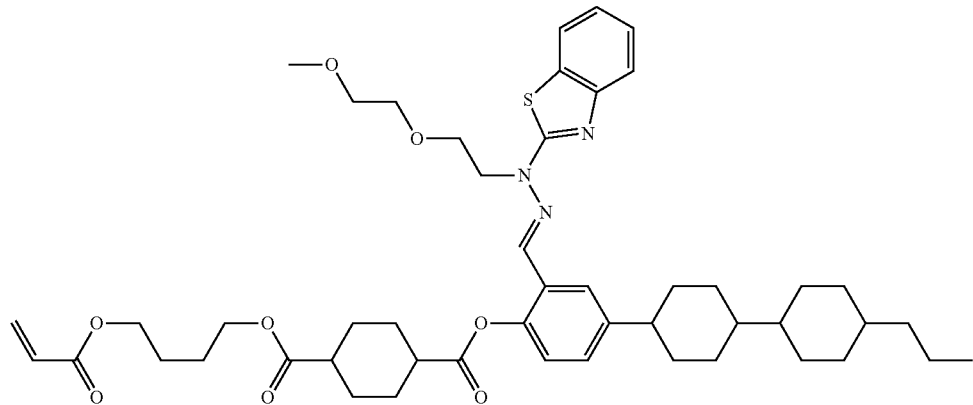

(I-23)
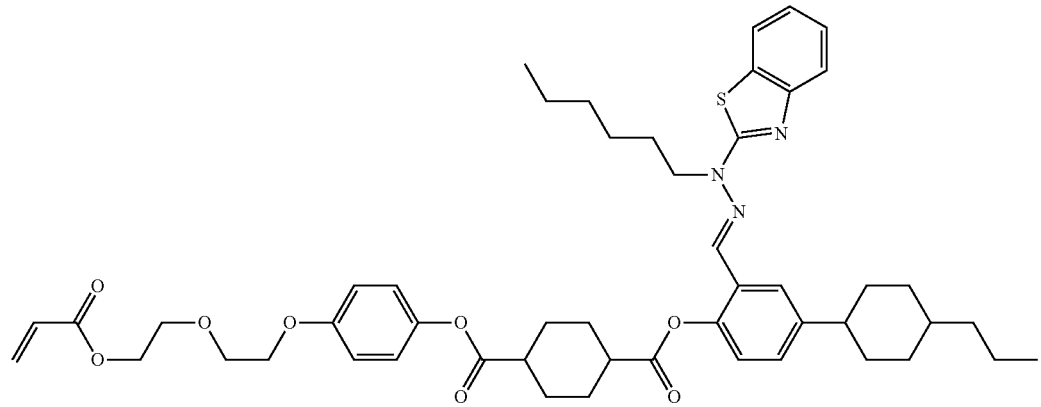
(I-24)
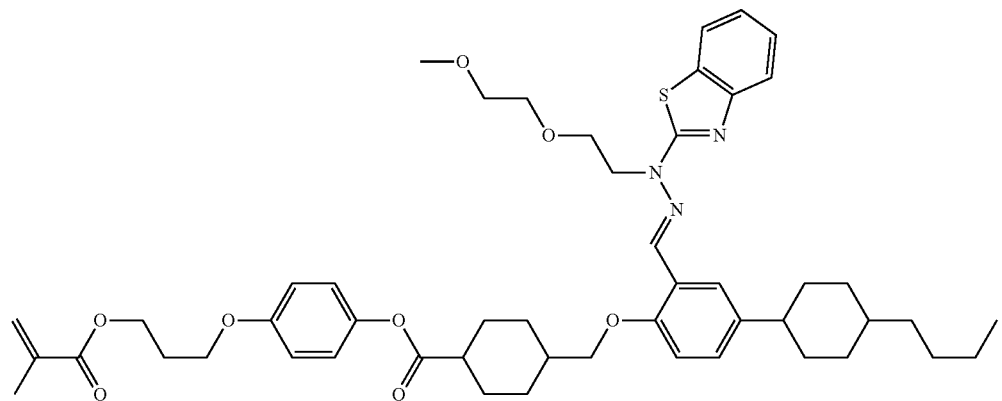
(I-25)
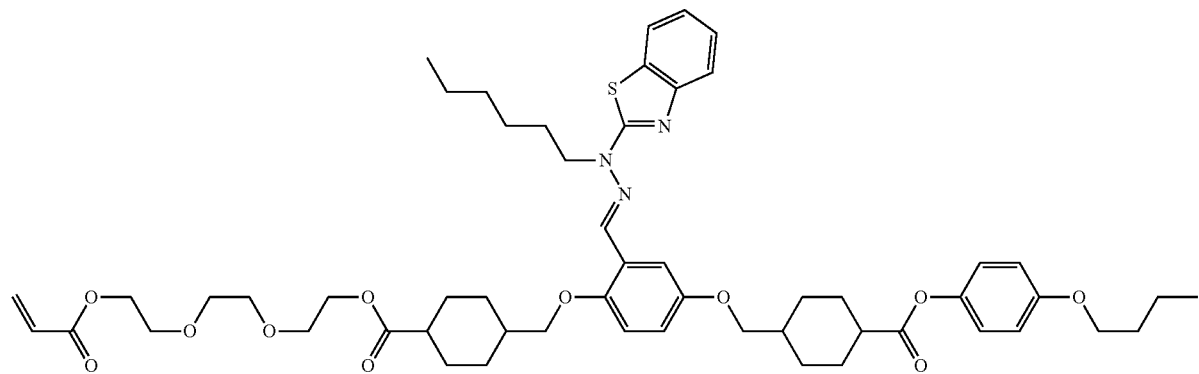
[Chem. 95]
(I-26)
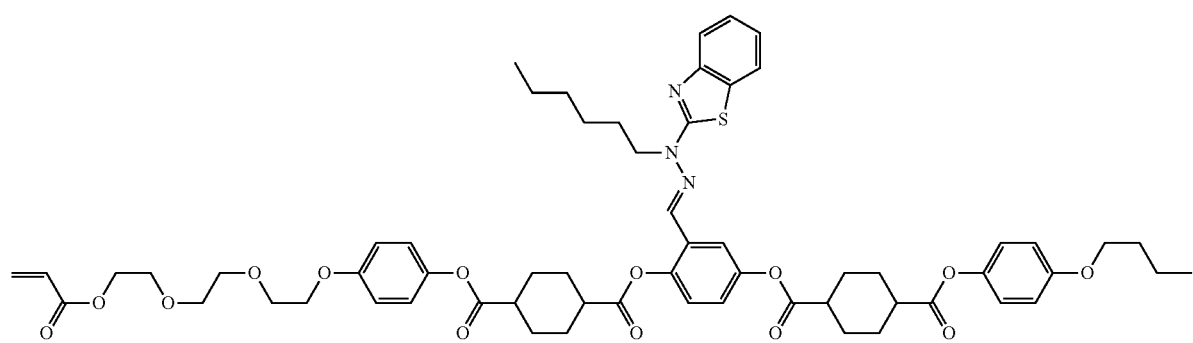

-continued
(I-27)
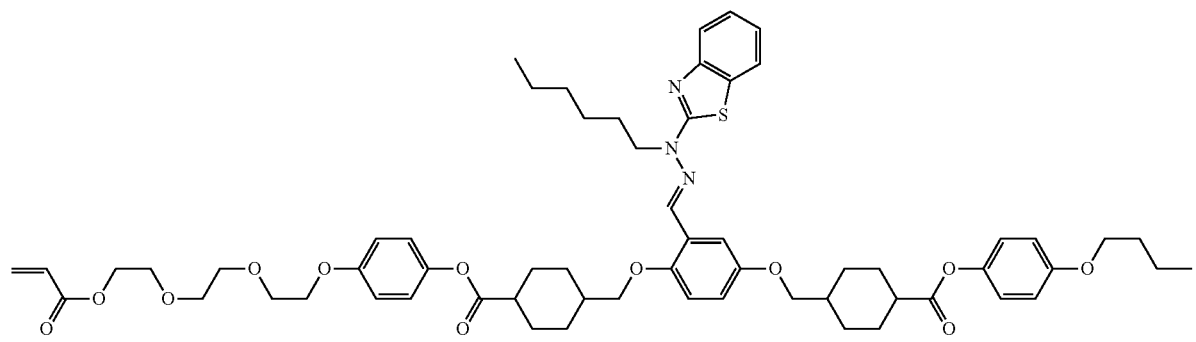
(I-28)
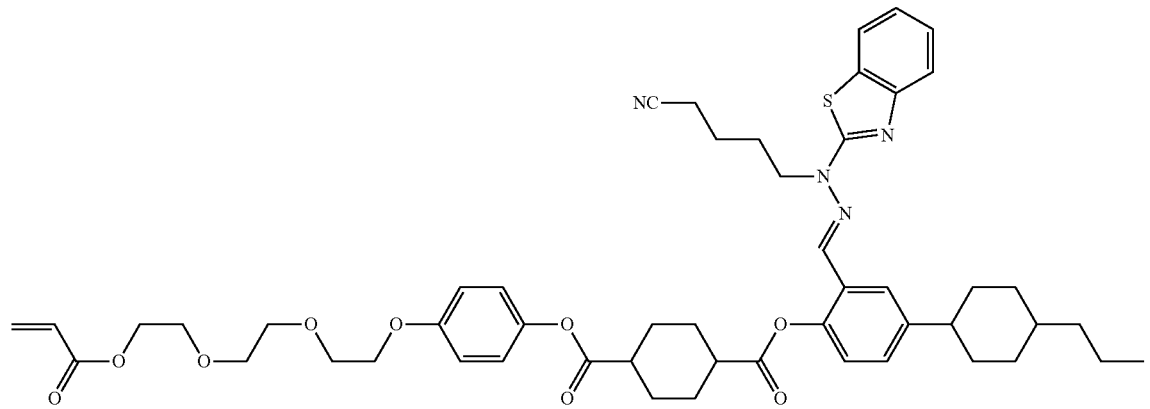
(I-29)
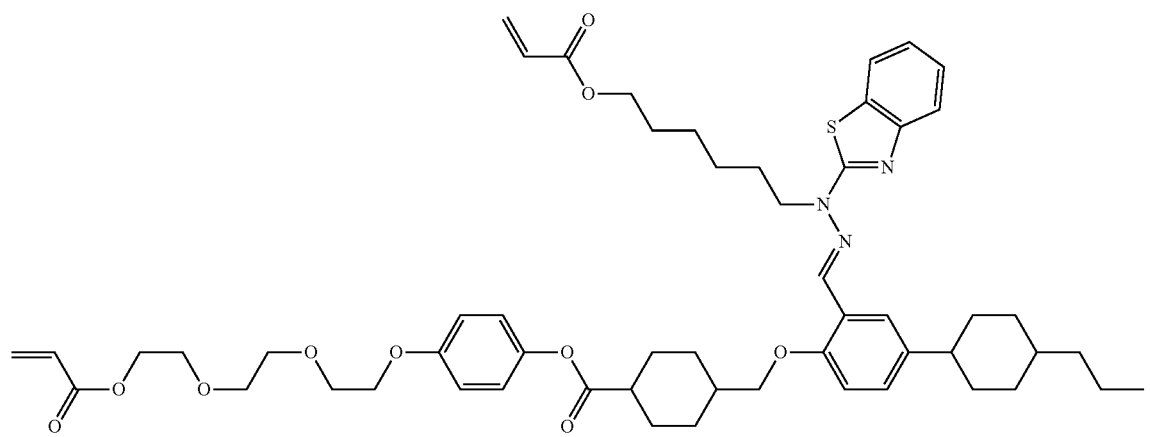
(I-30)
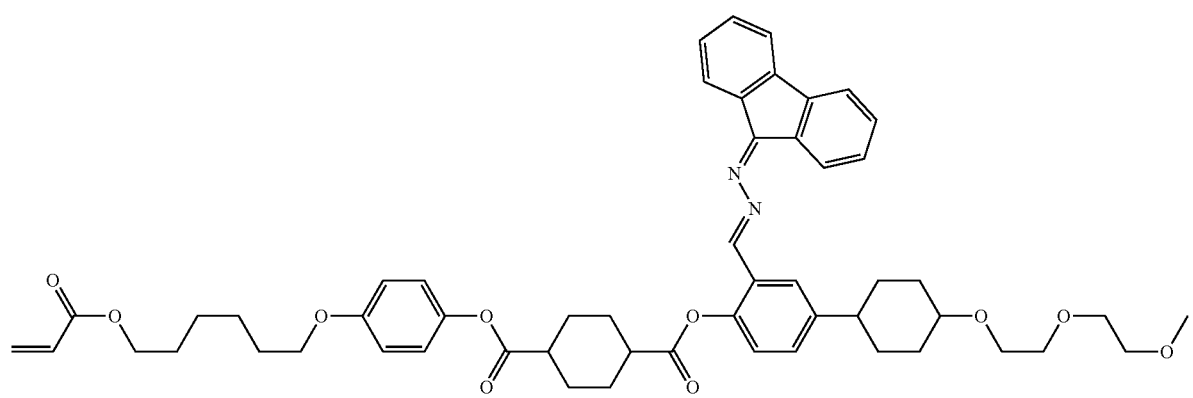

-continued
[Chem. 96]
(I-31)
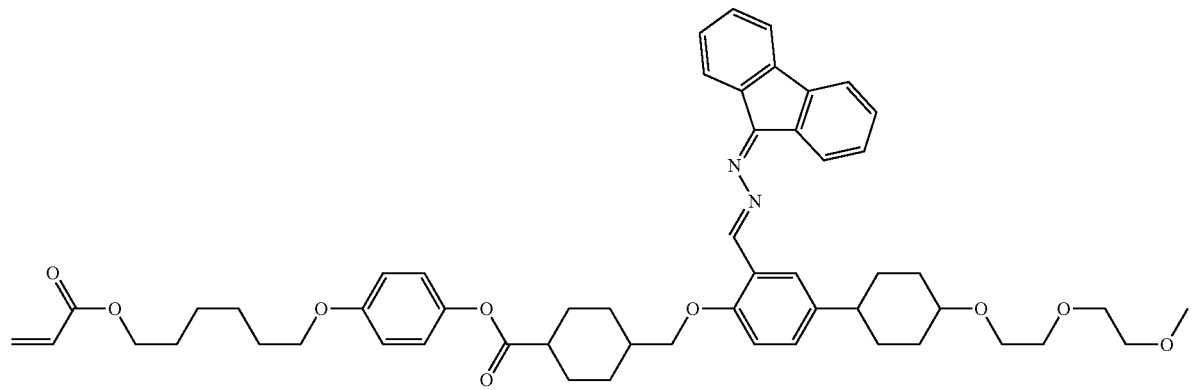
(I-32)
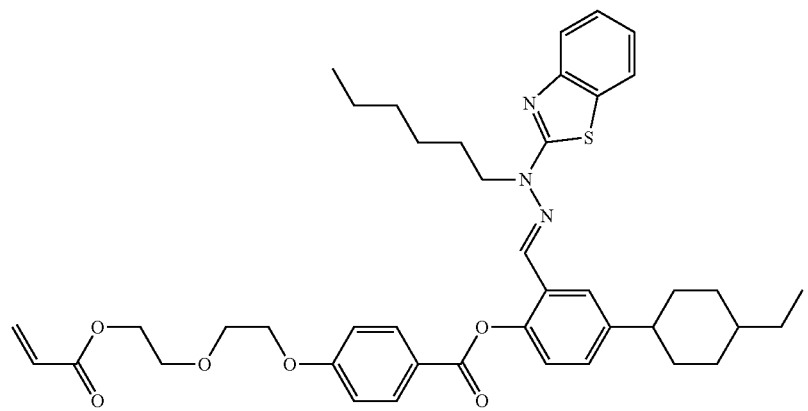
(I-33)
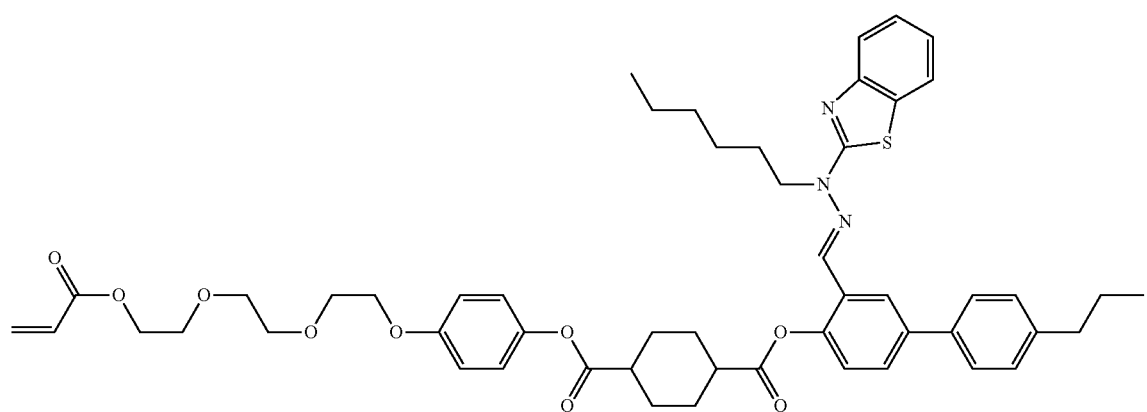

(I-34)
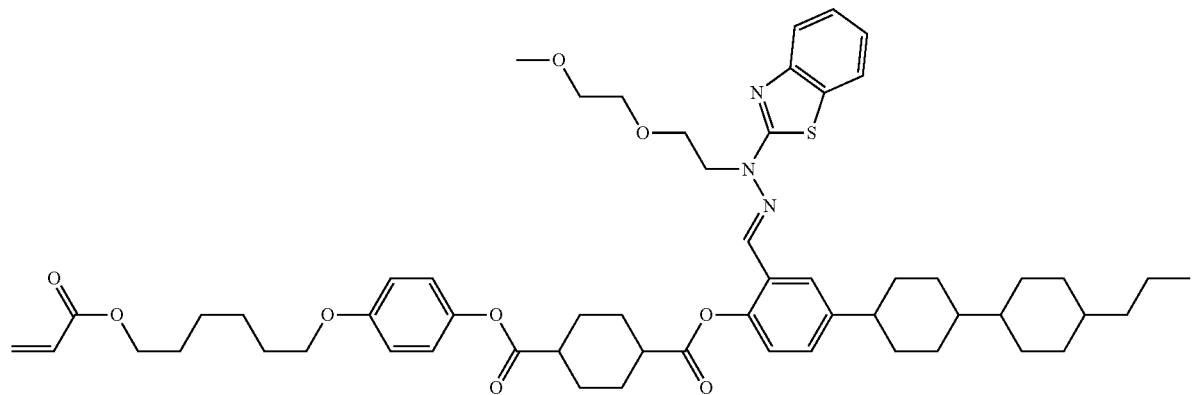
(I-35)
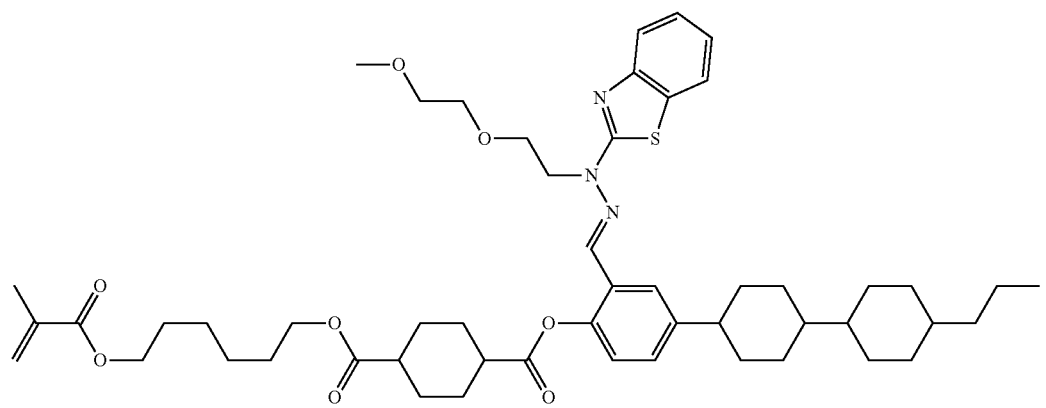
[Chem. 97]
(I-36)
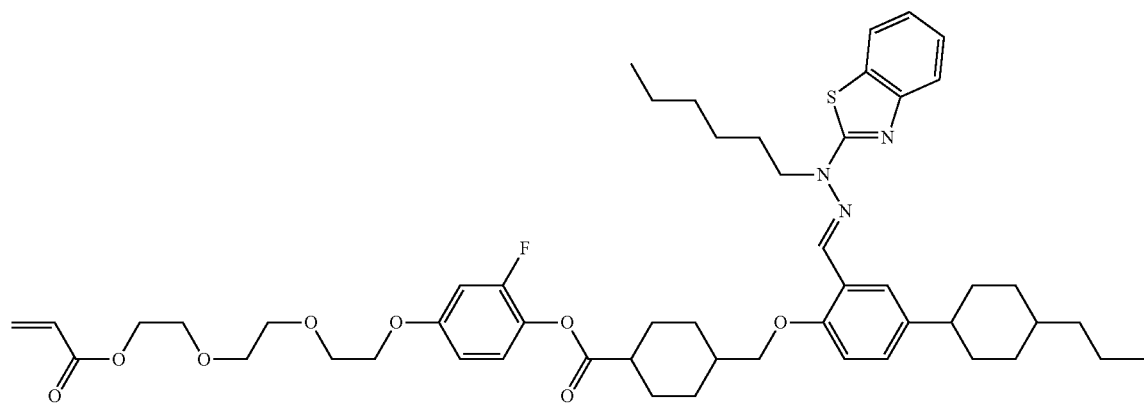

-continued
(I-37)
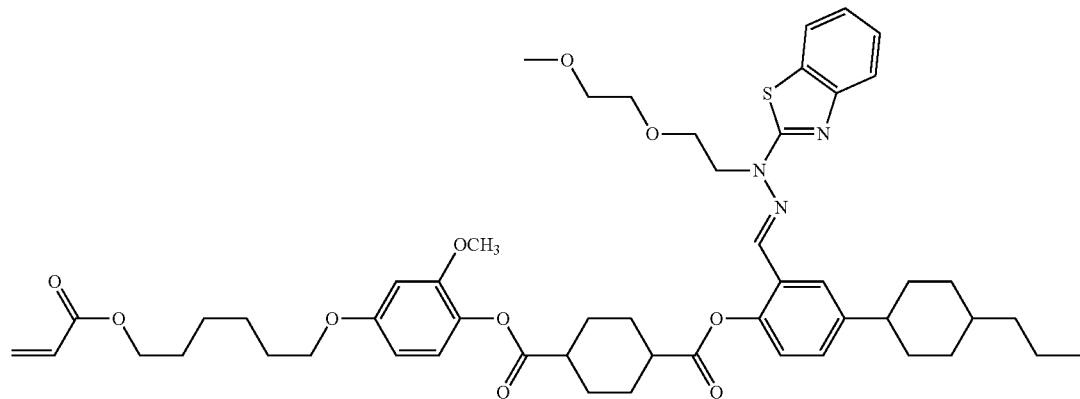
(I-38)
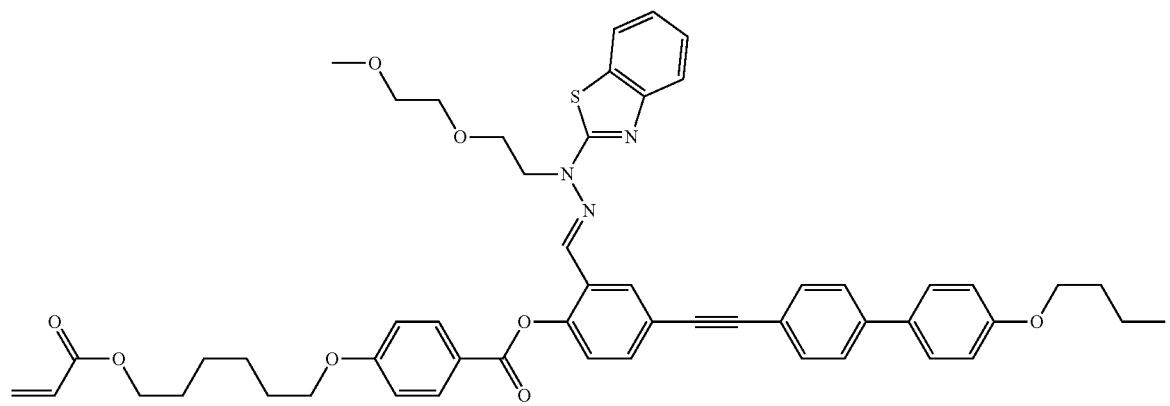
(I-39)
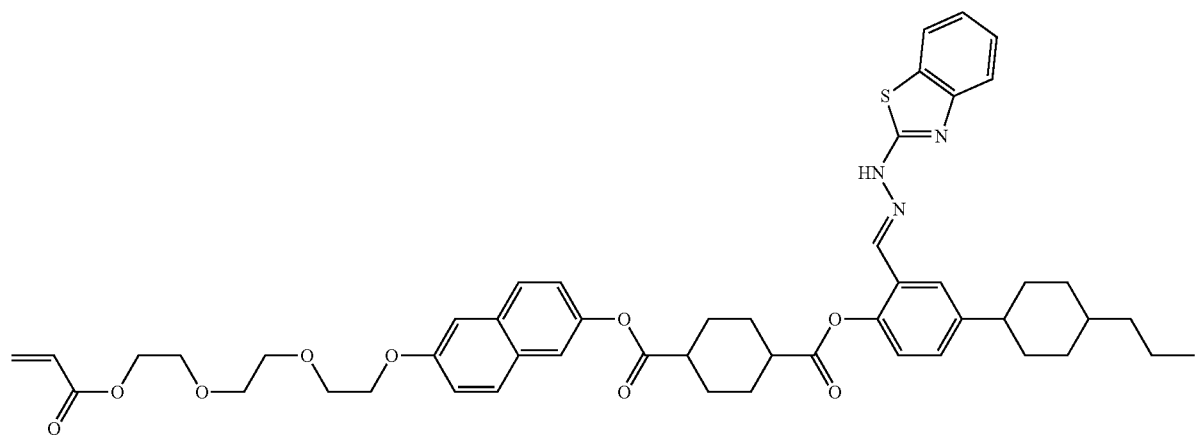

-continued
(I-40)
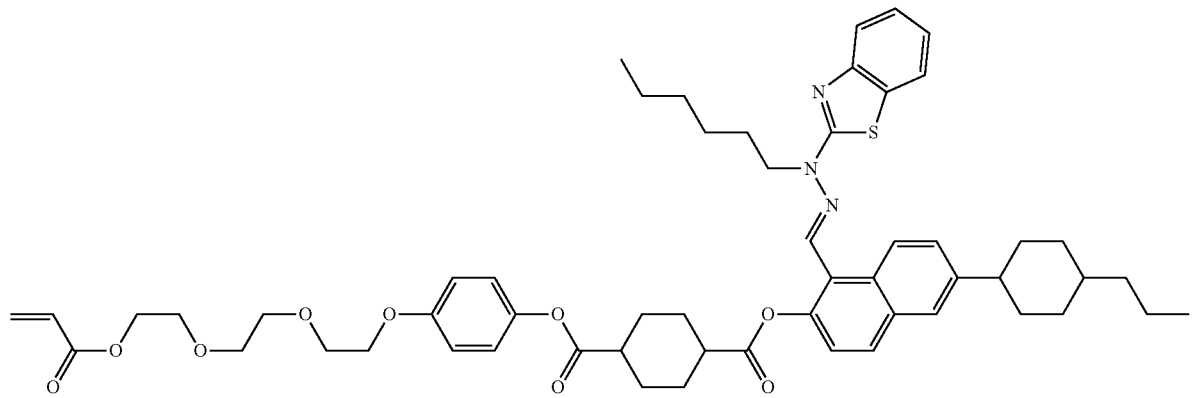
[Chem. 98]
(I-41)
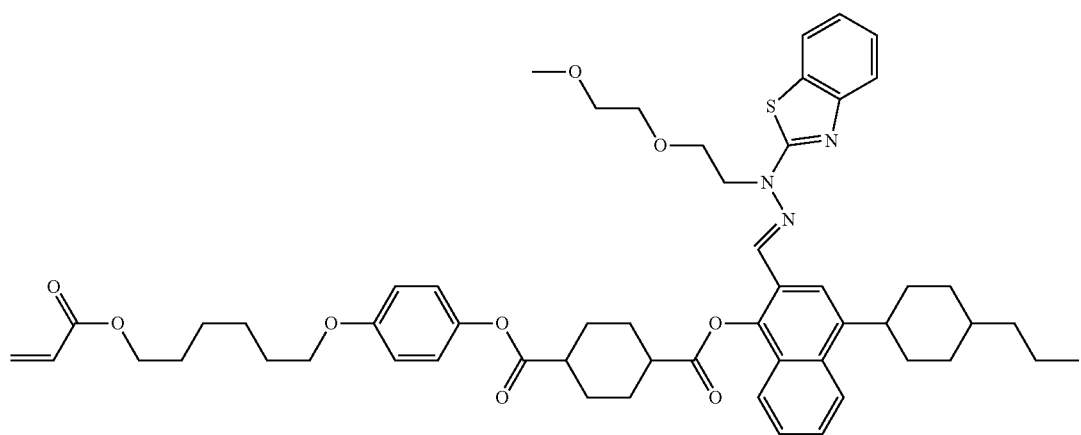
(I-42)
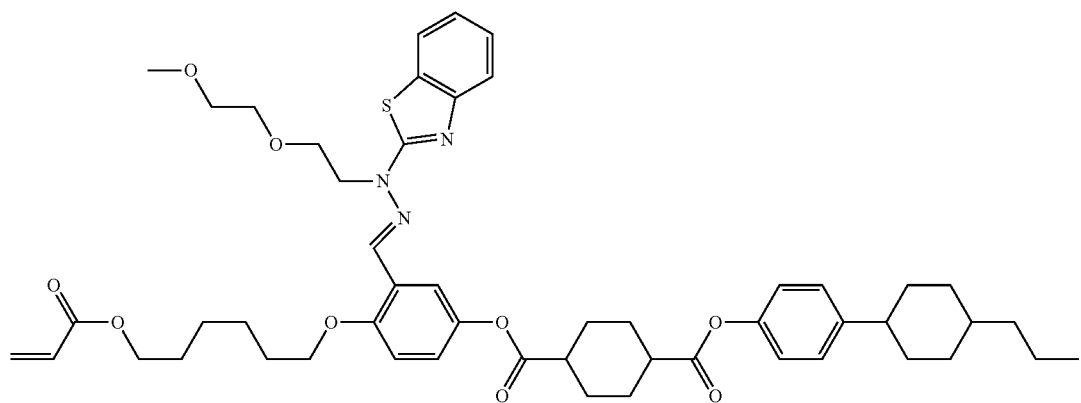

-continued
(I-43)
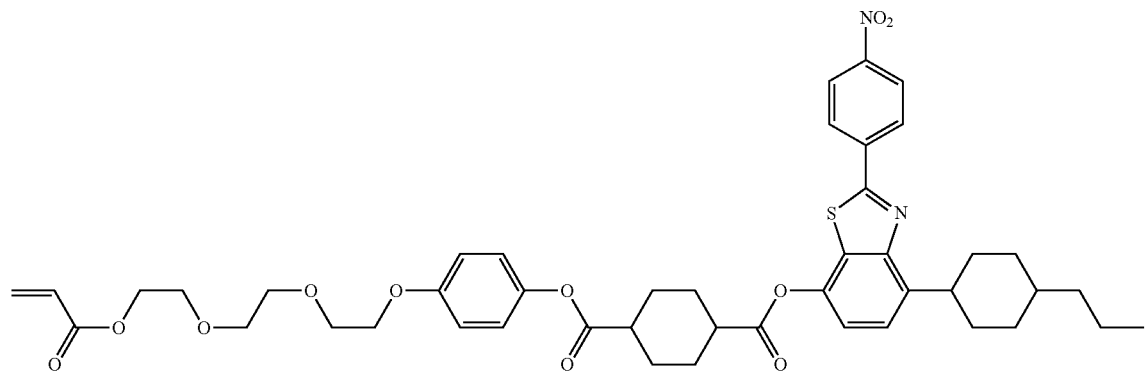
(I-44)
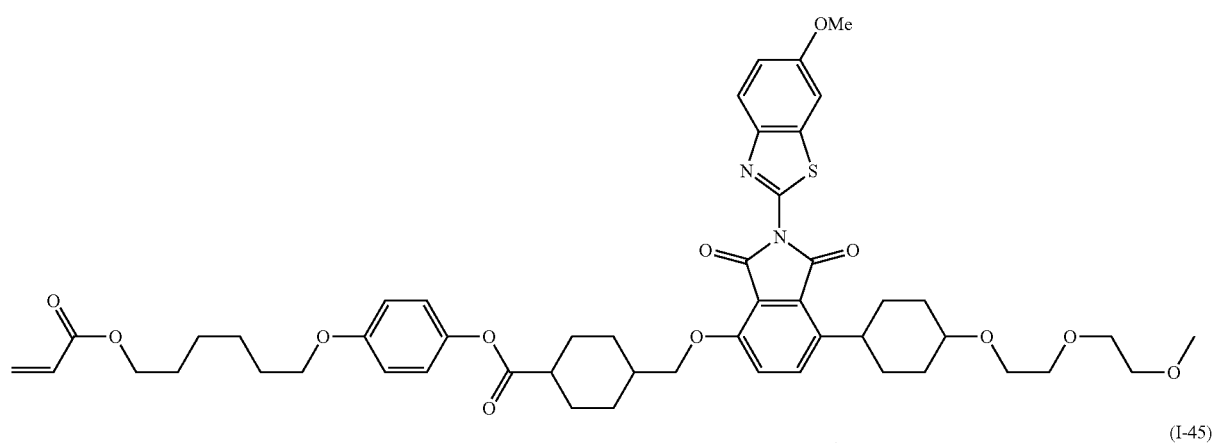
(I-45)
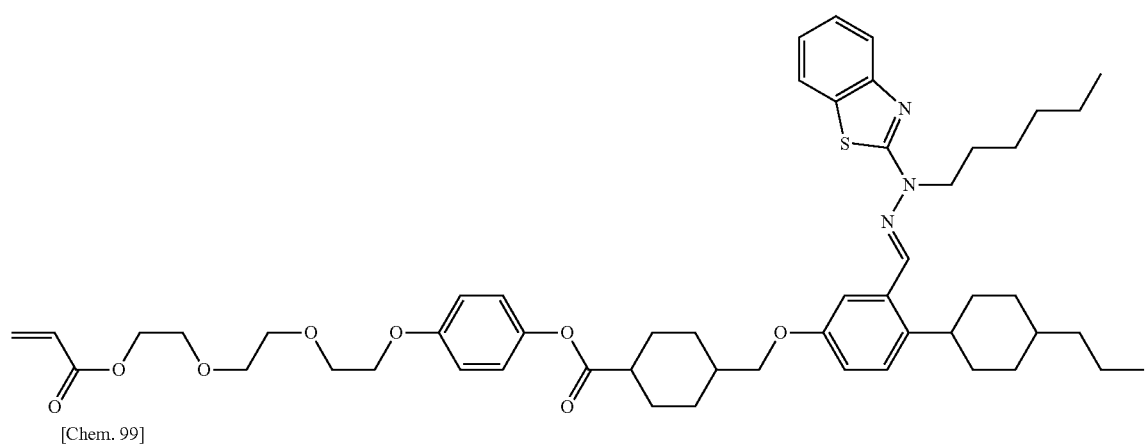
[Chem. 99]
(I-46)
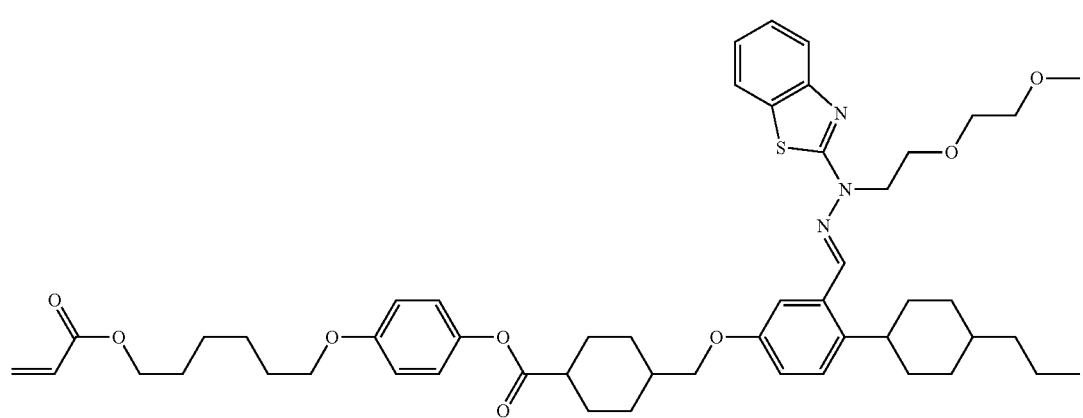

(I-47)
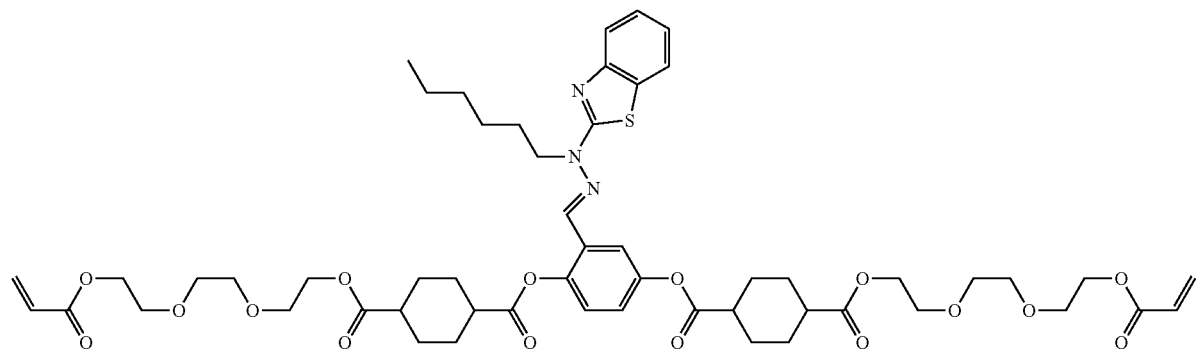
(I-48)
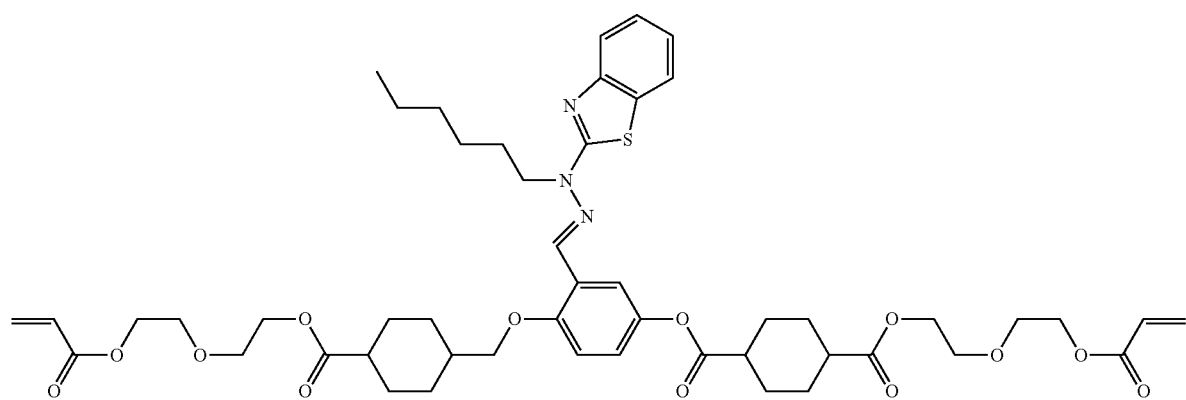
(I-49)
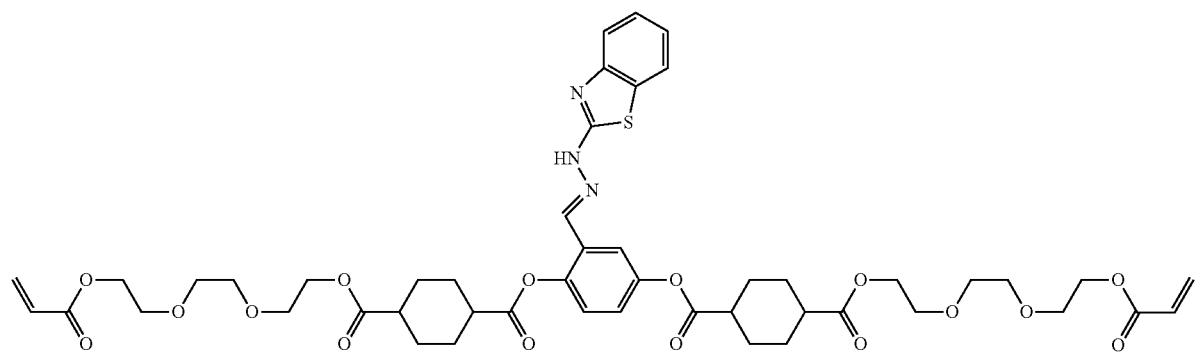
(I-50)
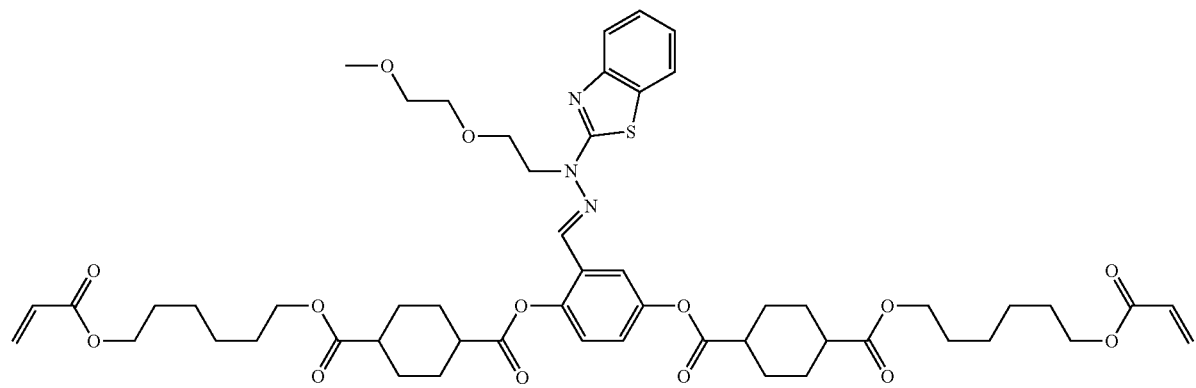

-continued
[Chem. 100]
(I-51)
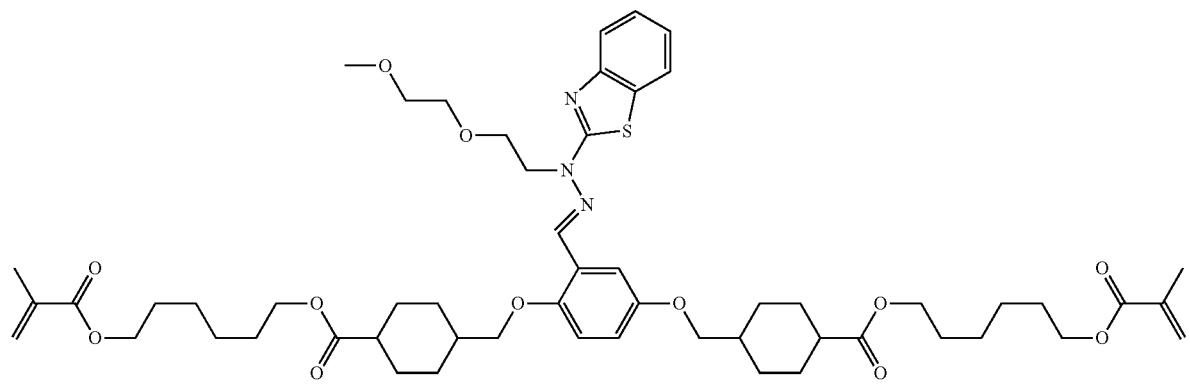
(I-52)
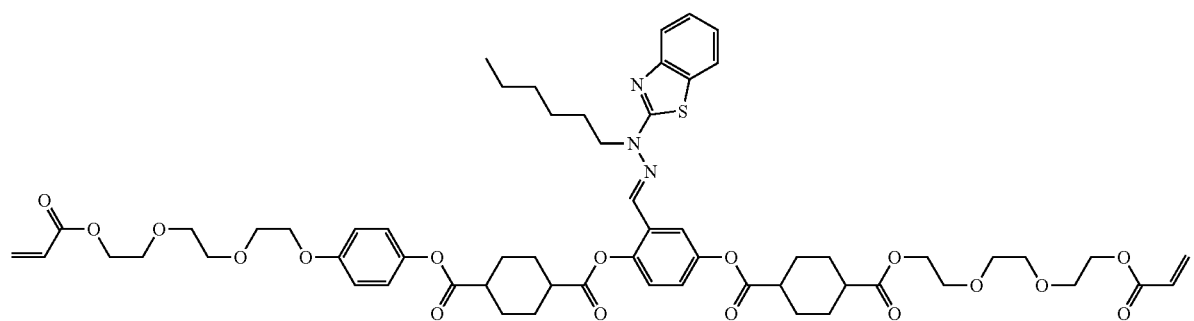
(I-53)
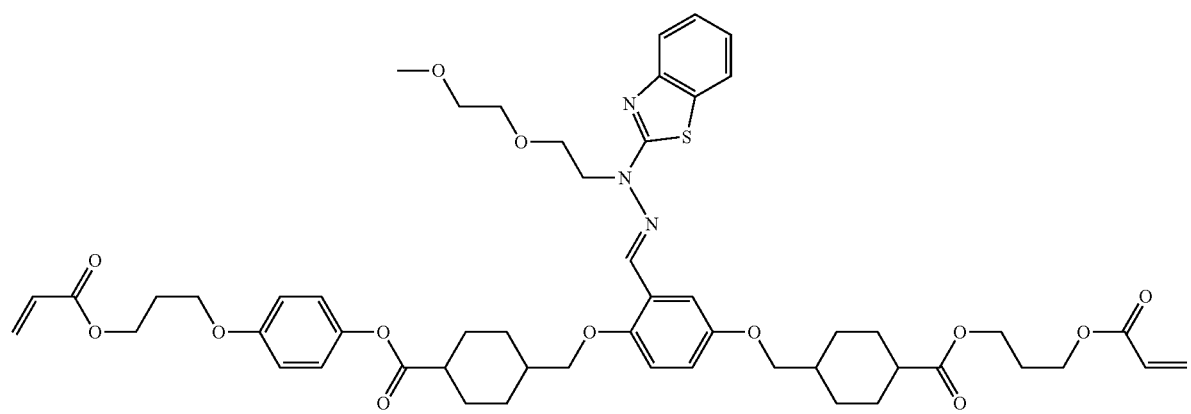
(I-54)
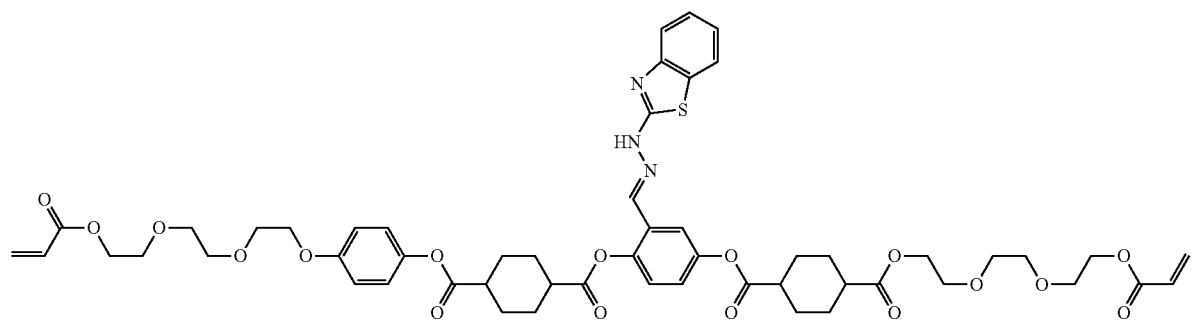

(I-55)
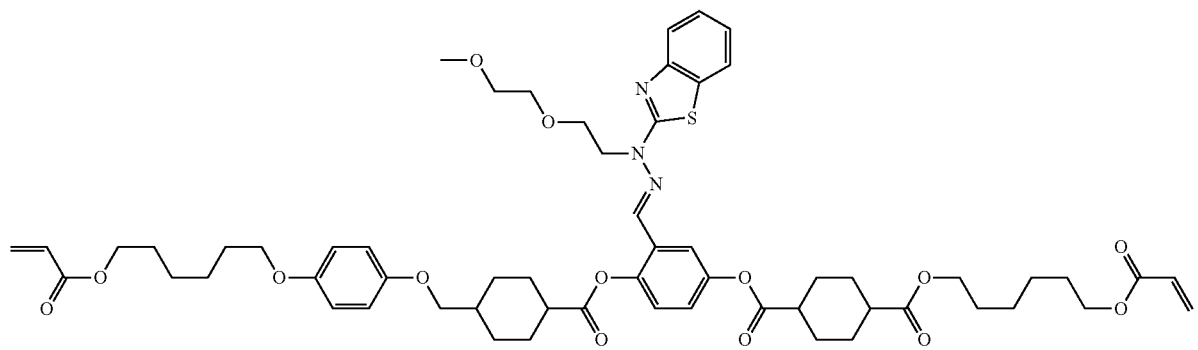
[Chem. 101]
(I-56)
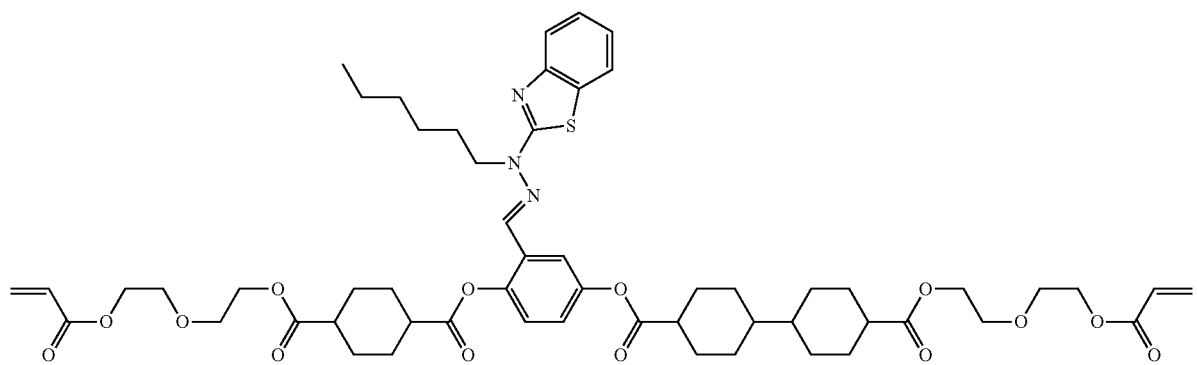
(I-57)
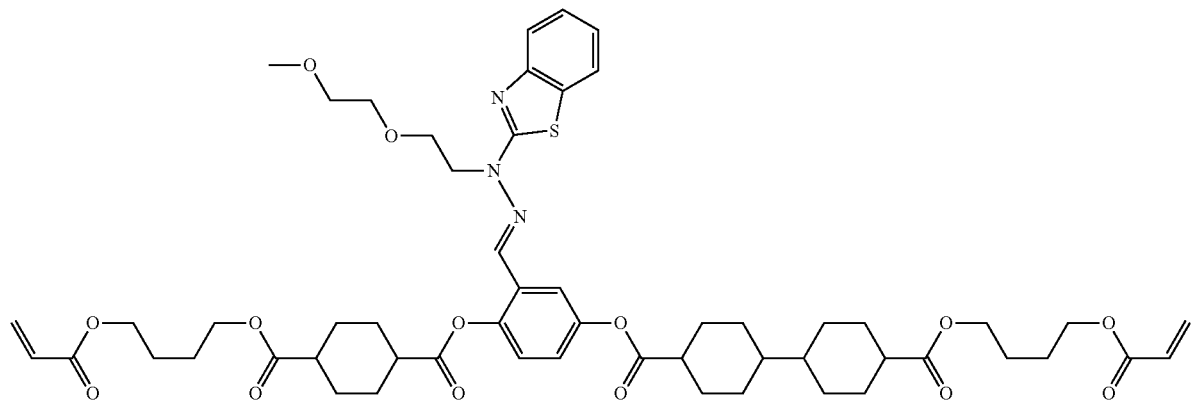
(I-58)
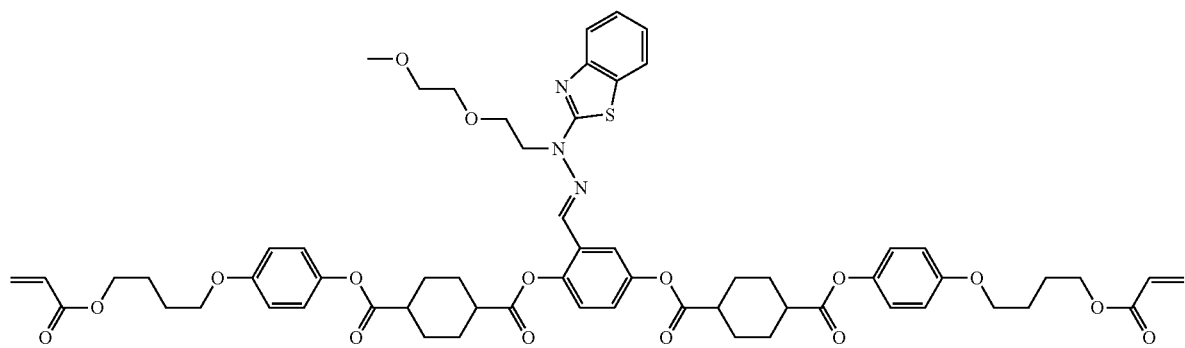

-continued
(I-59)
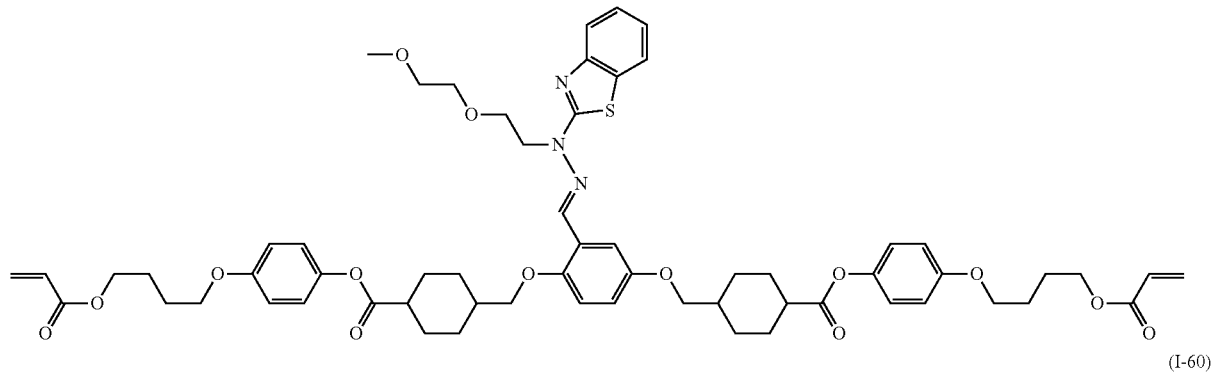
(I-60)
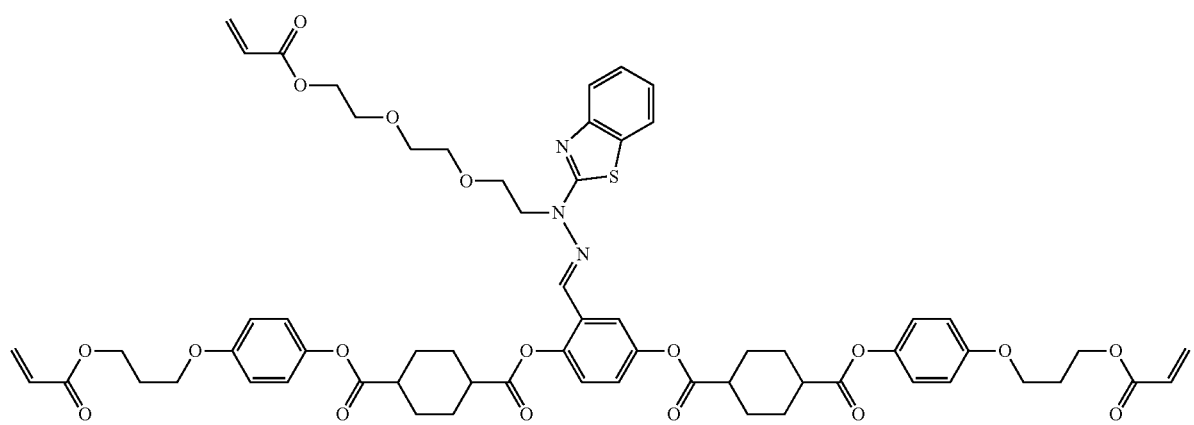
[Chem. 102]
(I-61)
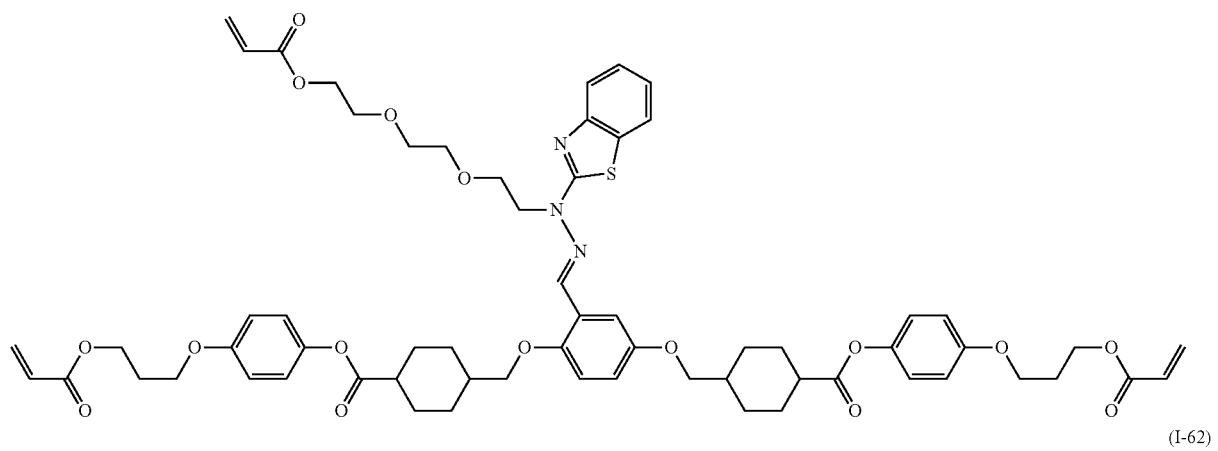
(I-62)
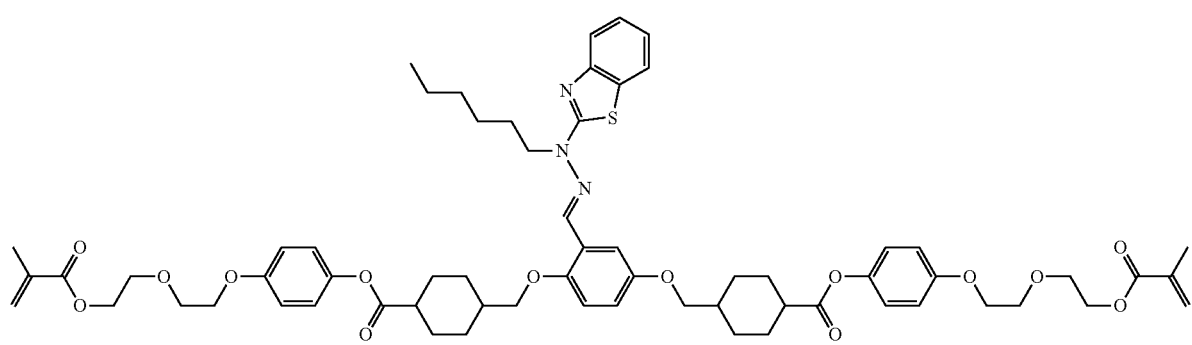

-continued
(I-63)
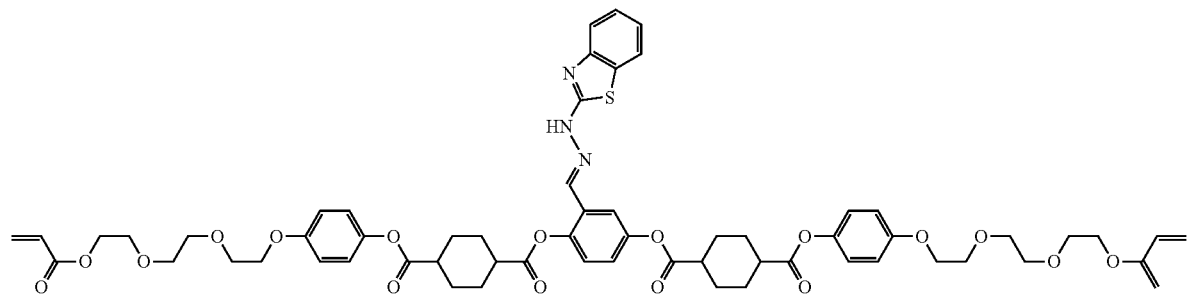
(I-64)
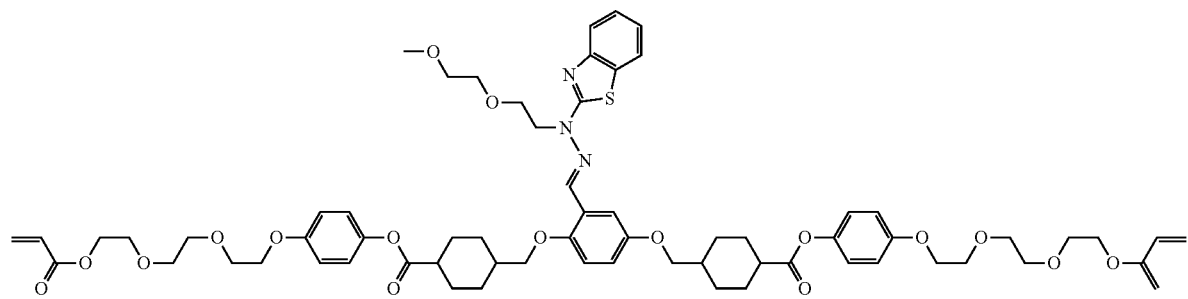
(I-65)
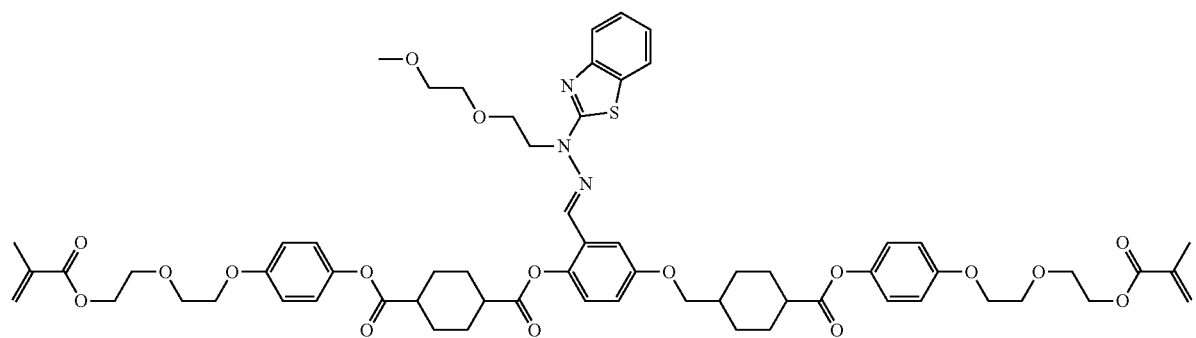
[Chem. 103]
(I-66)
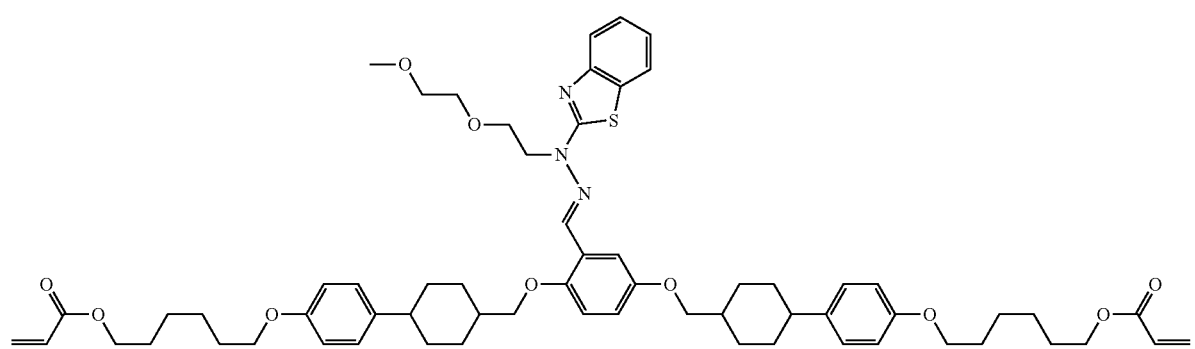

-continued
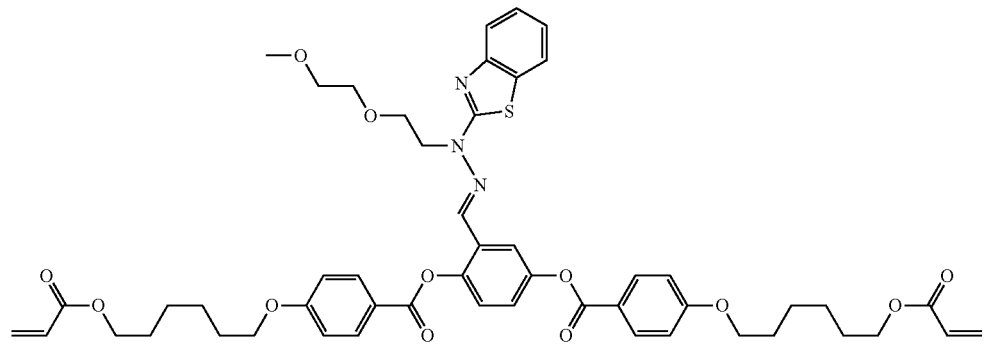
(I-67)
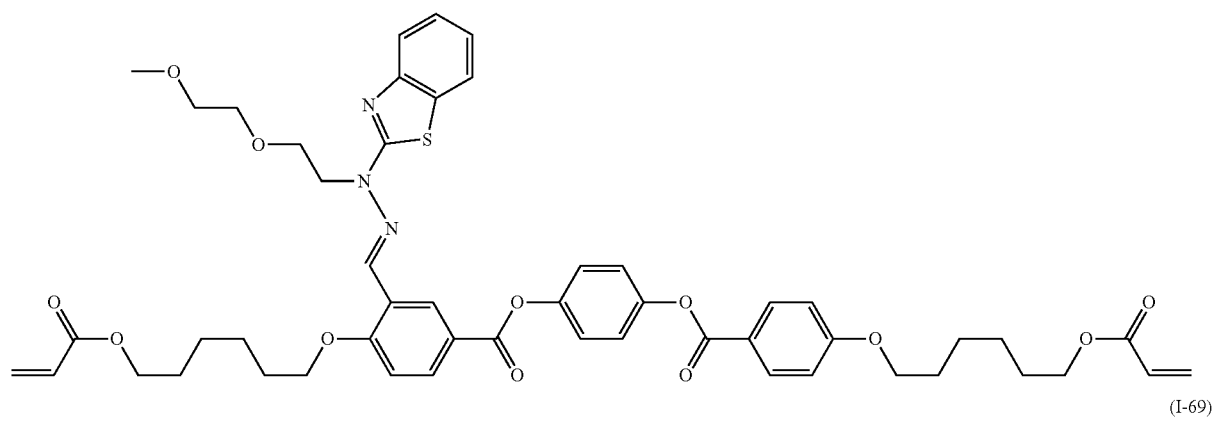
(I-68)
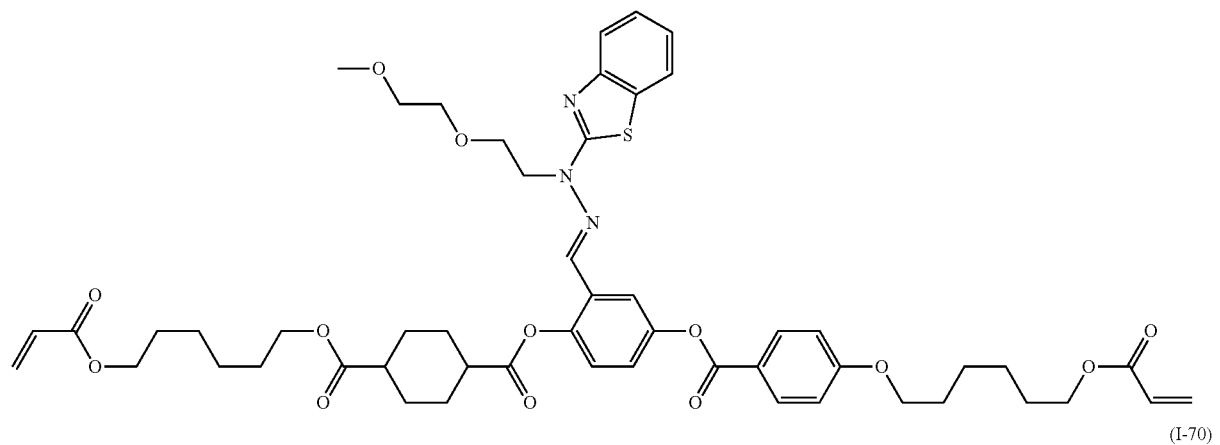
(I-69)
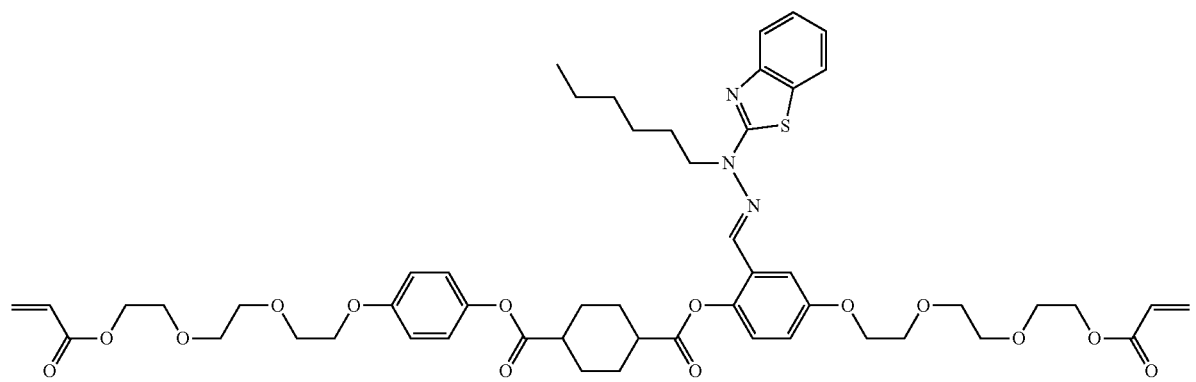
(I-70)

-continued
[Chem. 104]
(I-71)
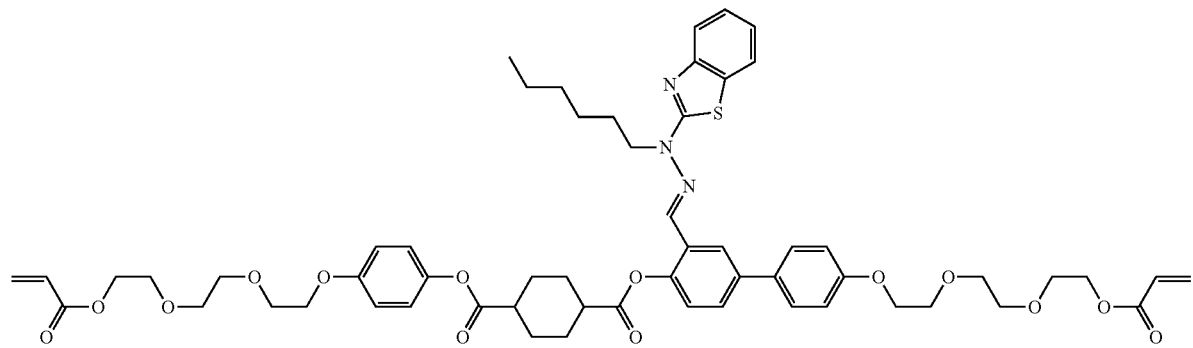
(I-72)
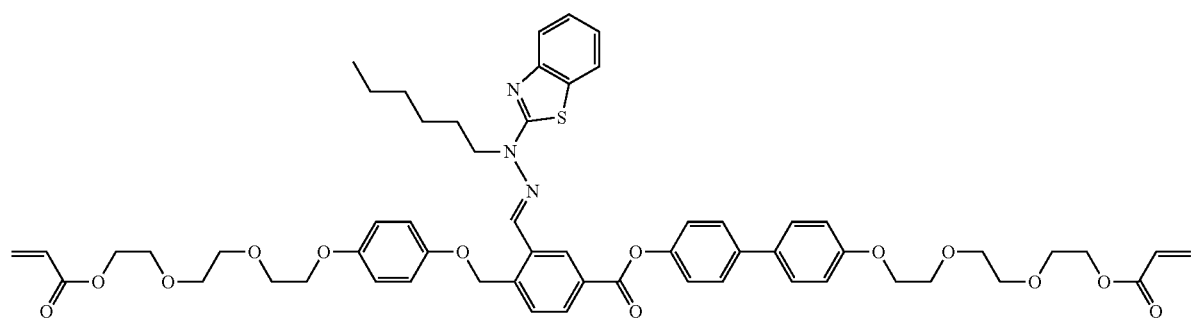
(I-73)
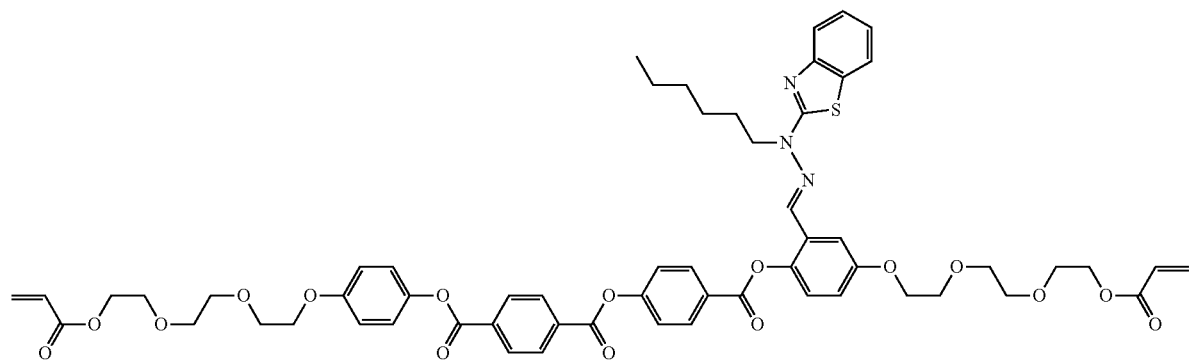
(I-74)
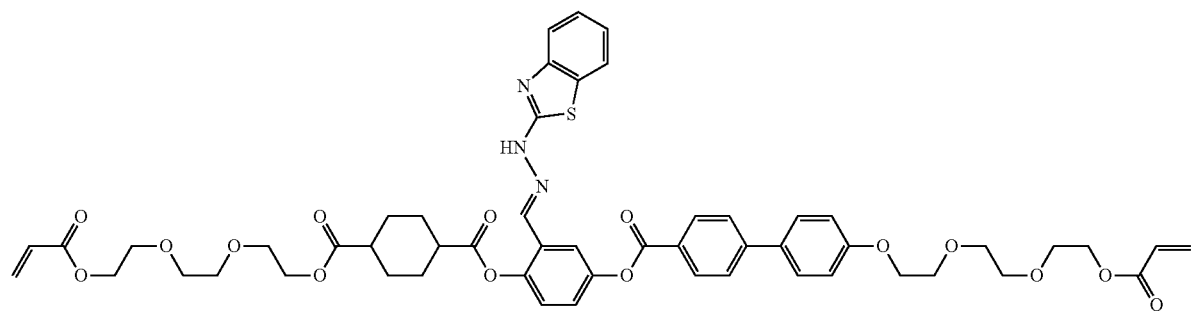

-continued
(I-75)
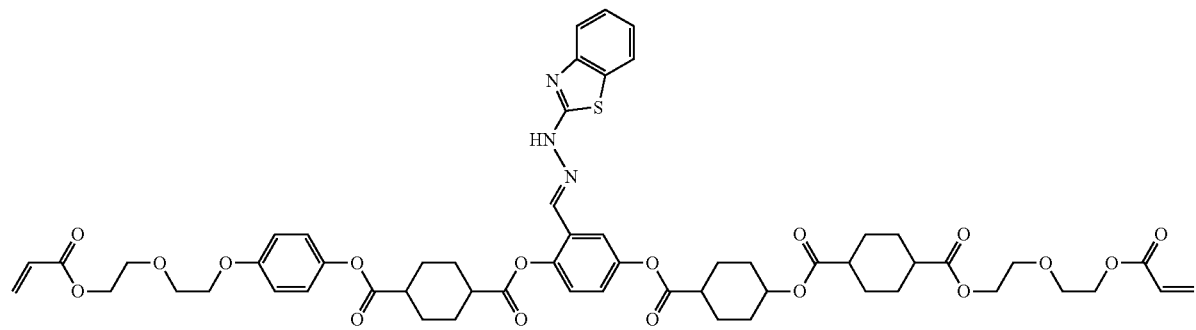
[Chem. 105]
(I-76)
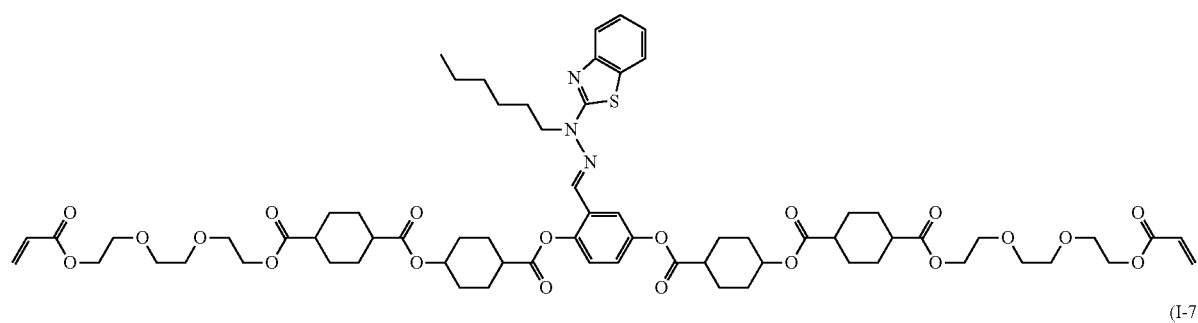
(I-77)
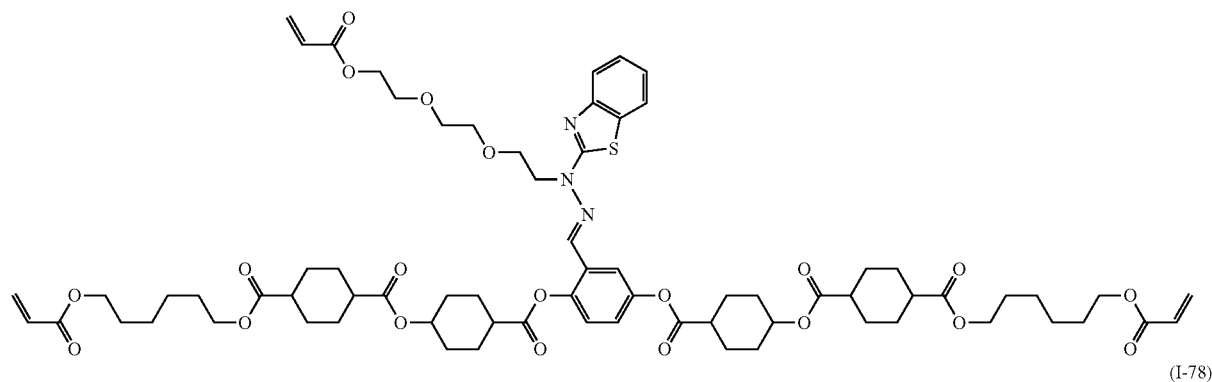
(I-78)
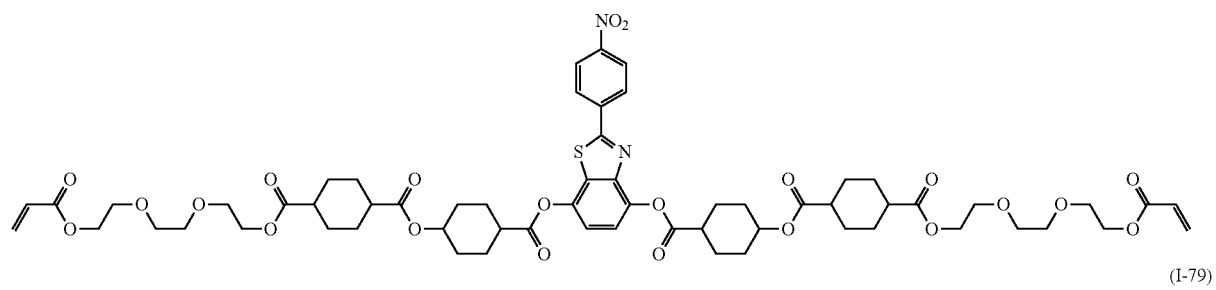
(I-79)
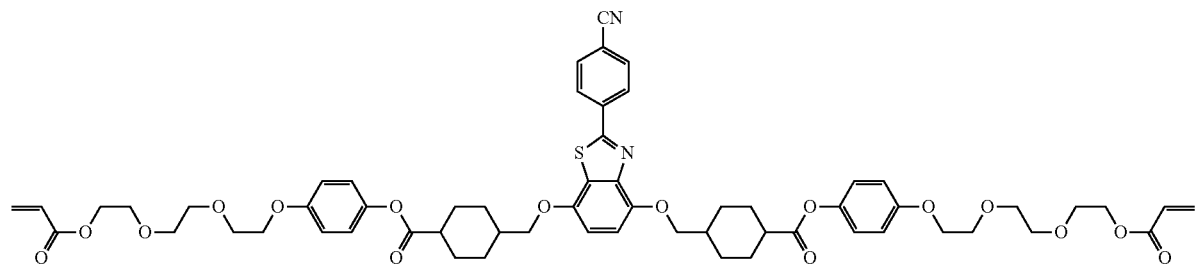

-continued
(I-80)
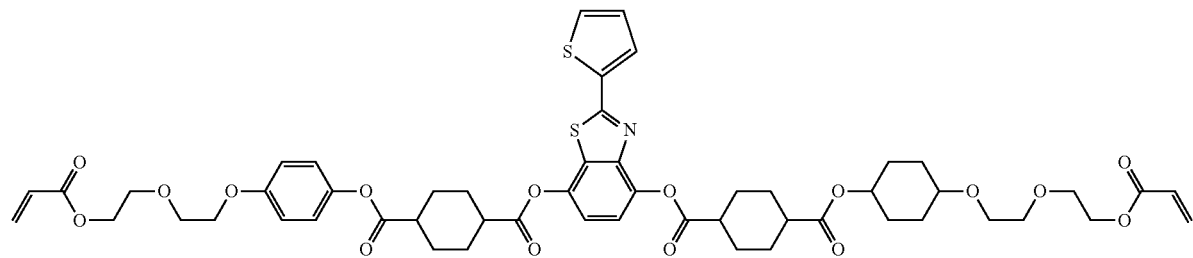
[Chem. 106]
(I-81)
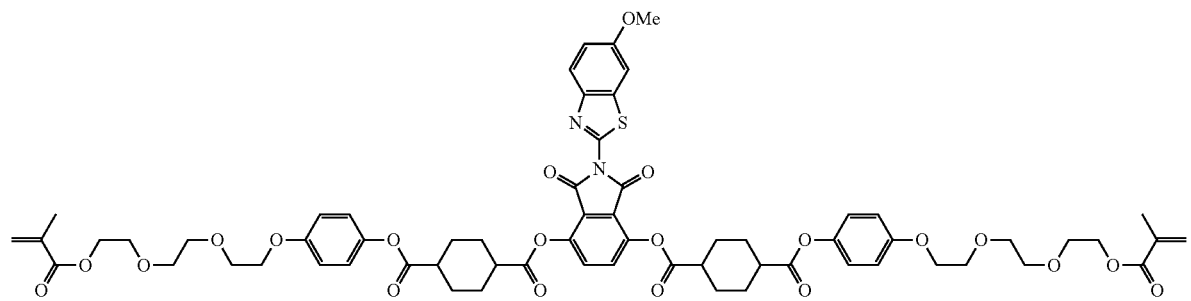
(I-82)
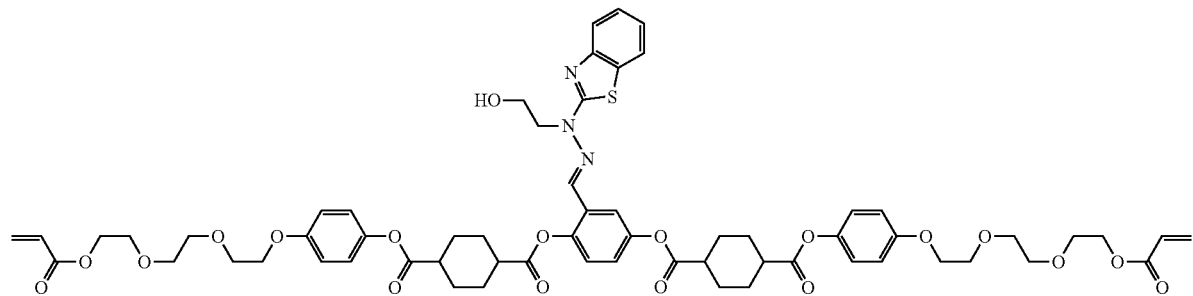
(I-83)
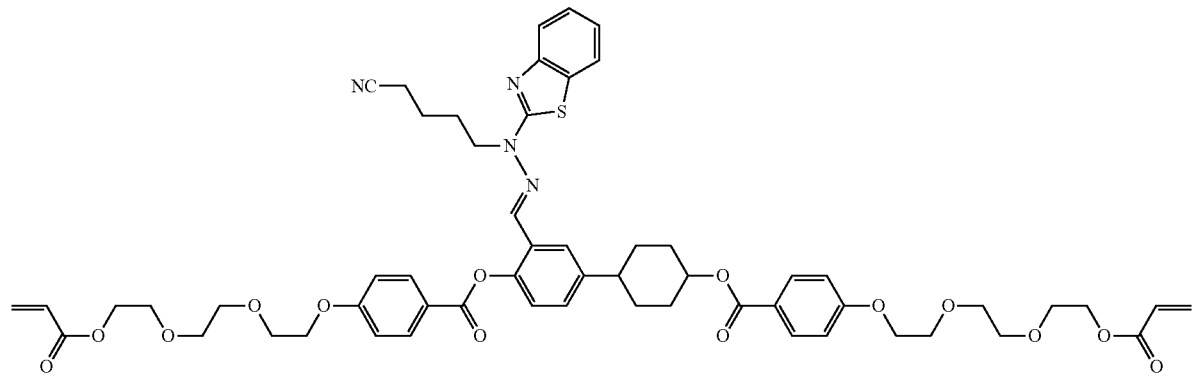

-continued
(I-84)
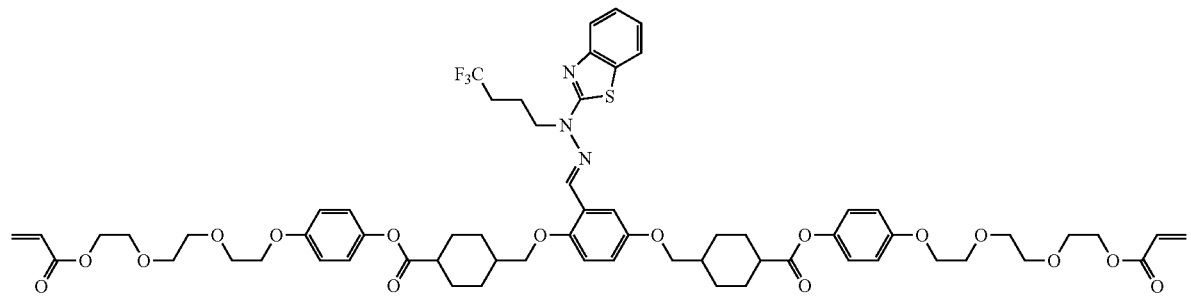
(I-85)
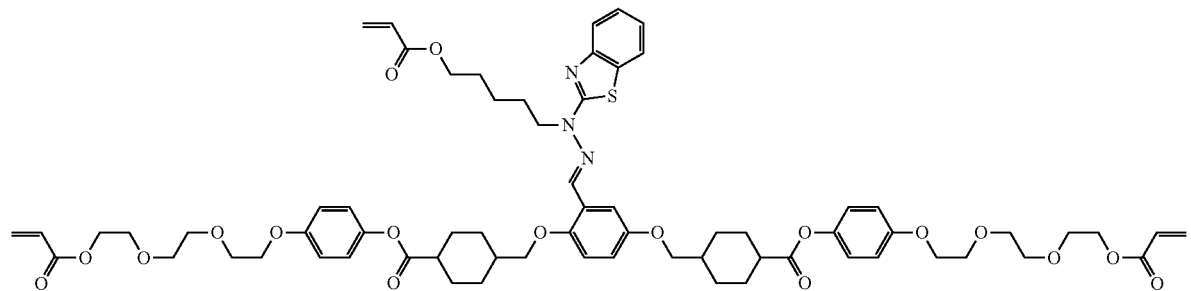
[Chem. 107]
(I-86)
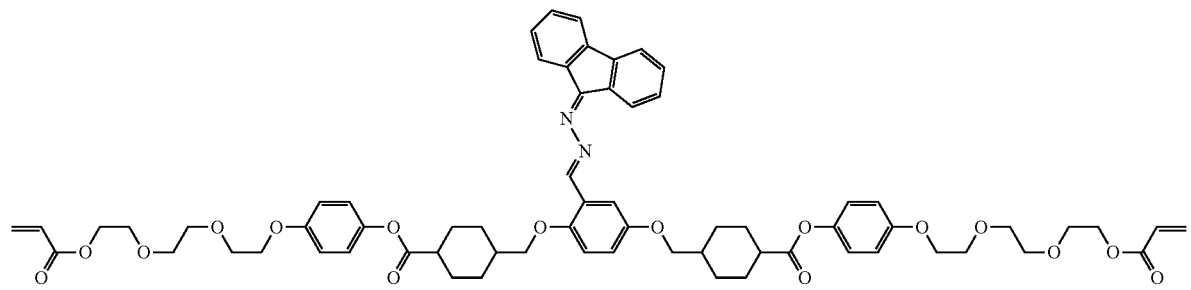
(I-87)
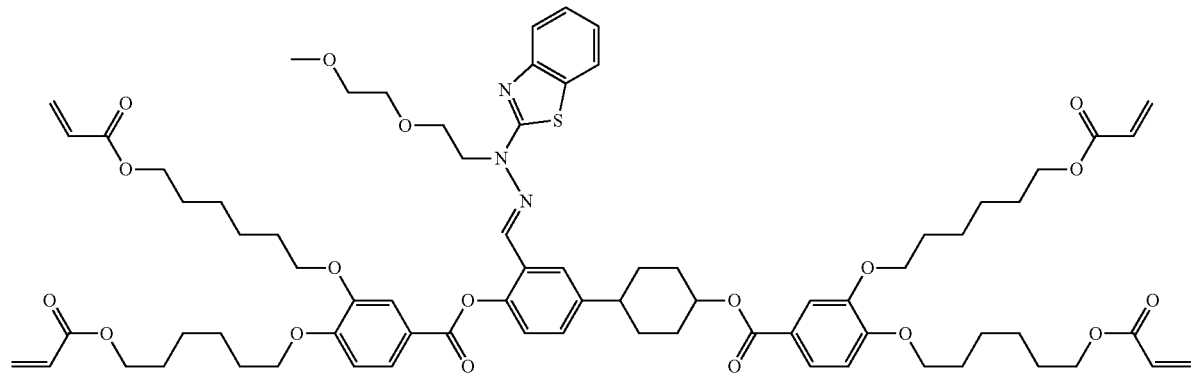

-continued
(I-88)
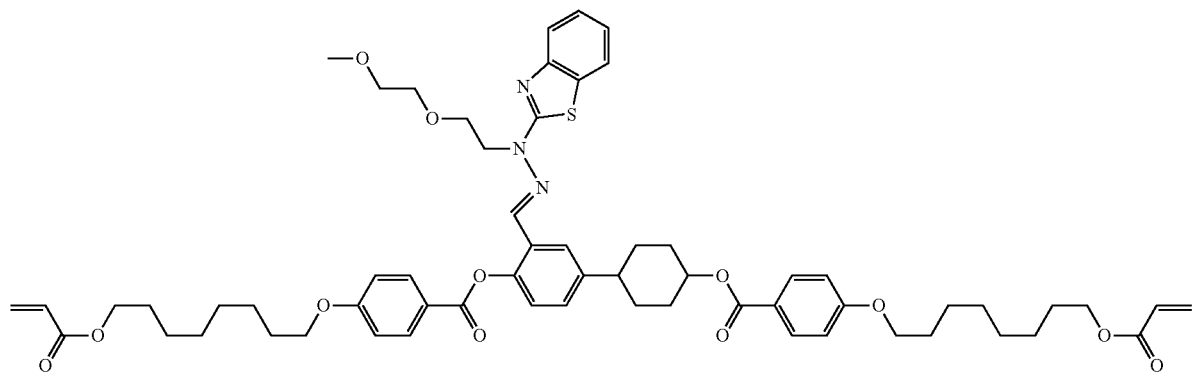
(I-89)
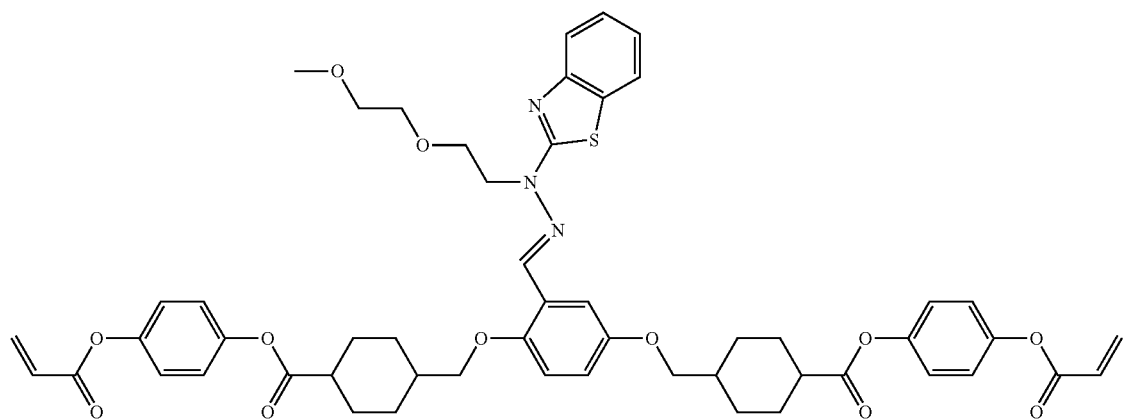
(I-90)
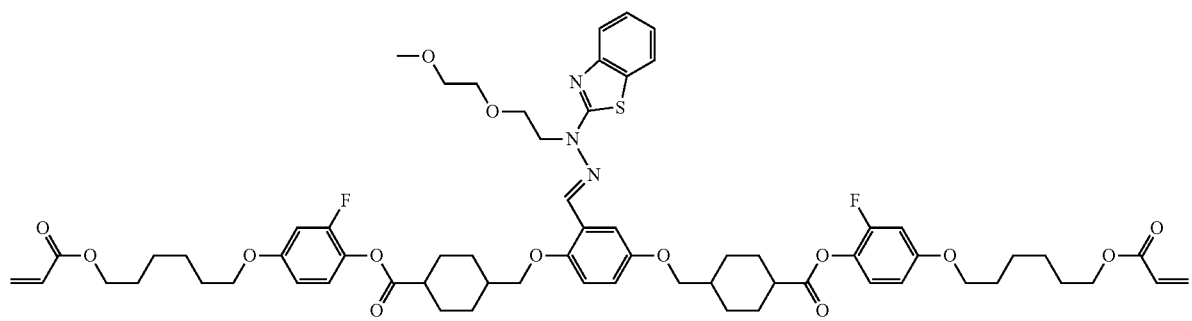
[Chem. 108]
(I-91)
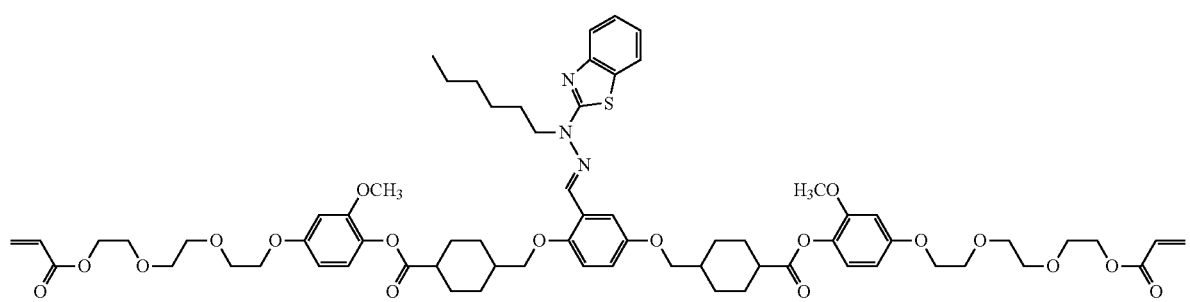

-continued
(I-92)
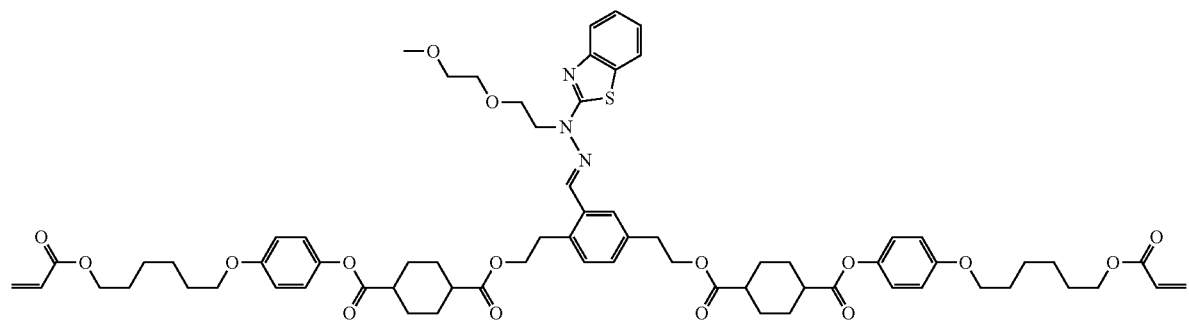
(I-93)
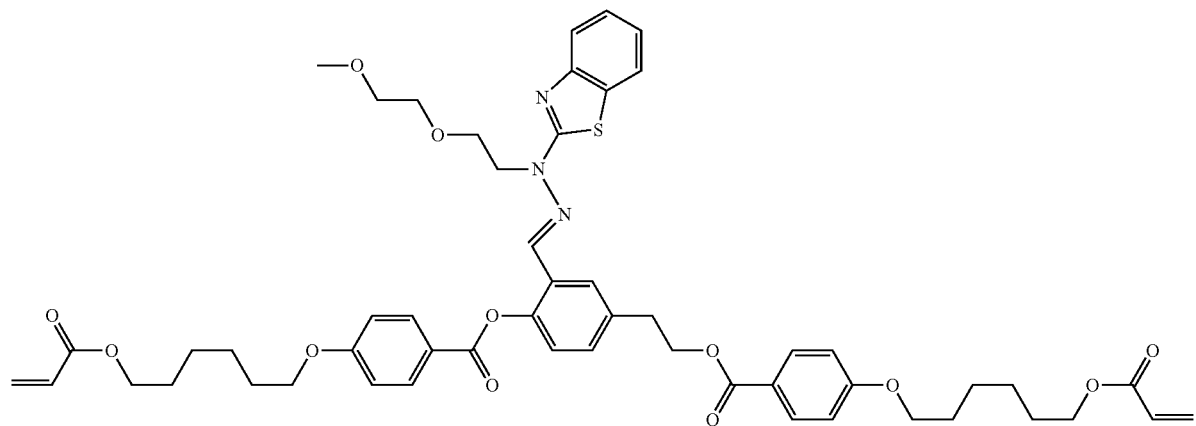
(I-94)
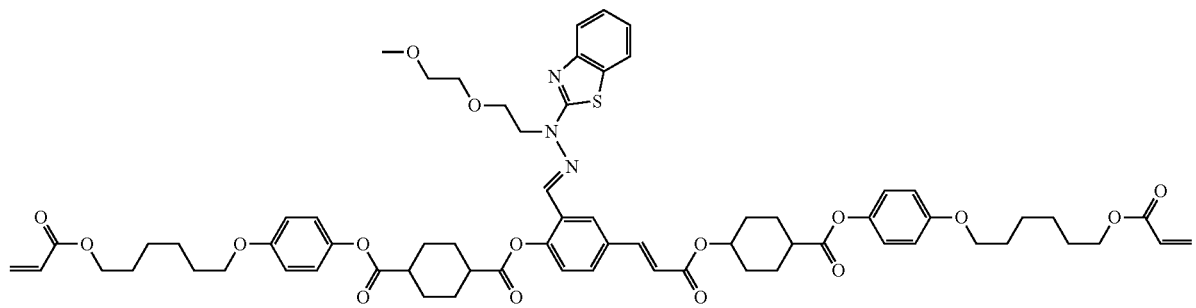
(I-95)
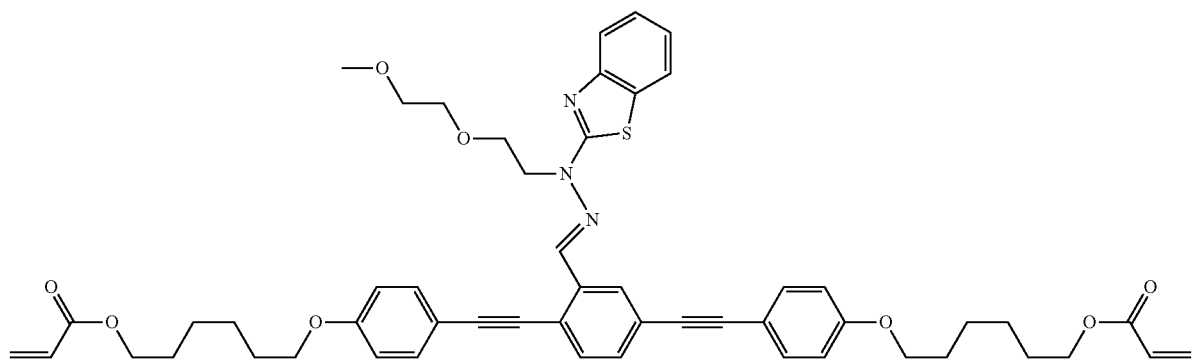

(I-96)
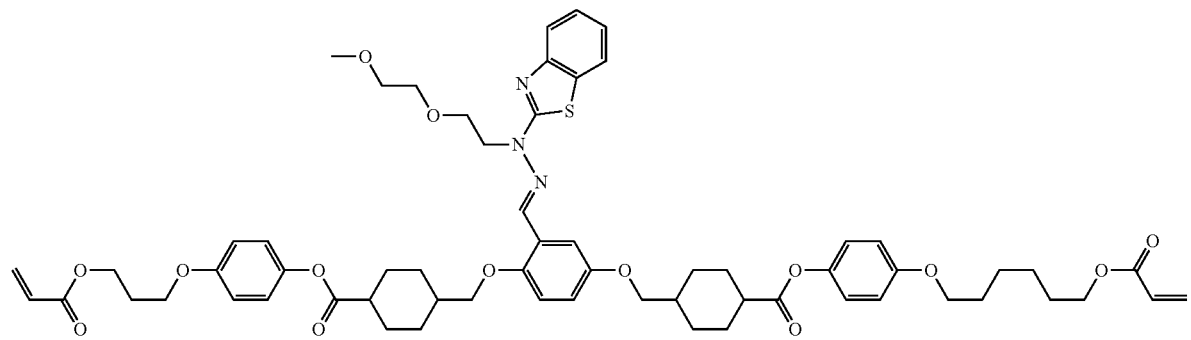
(I-97)
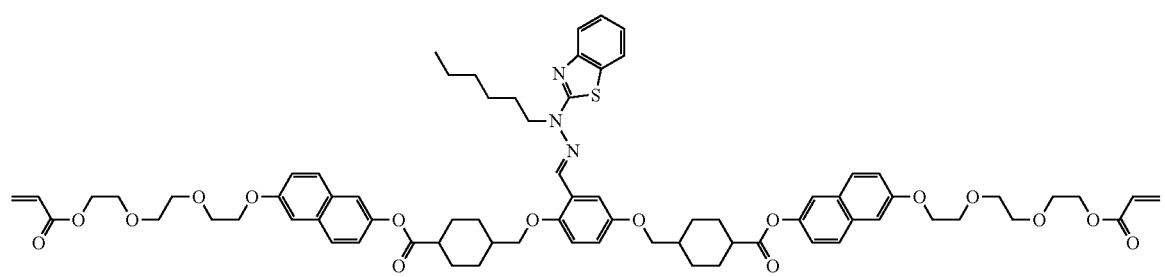
(I-98)
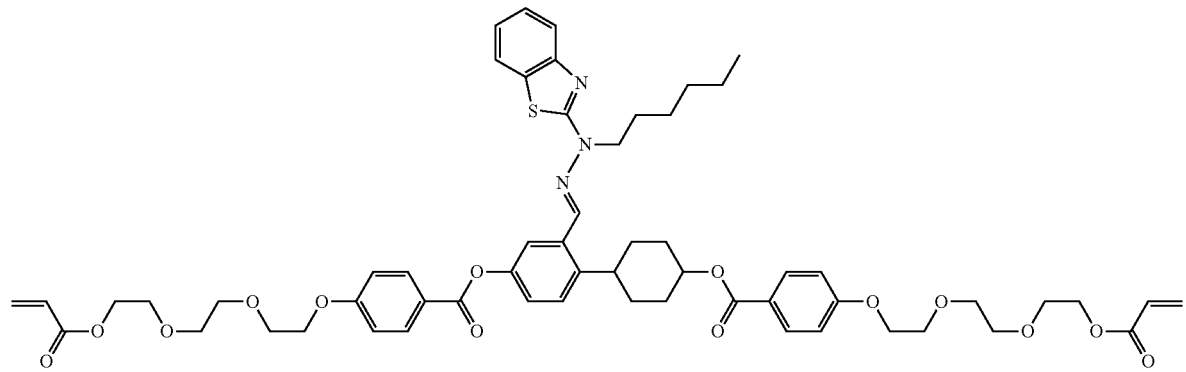
(I-99)
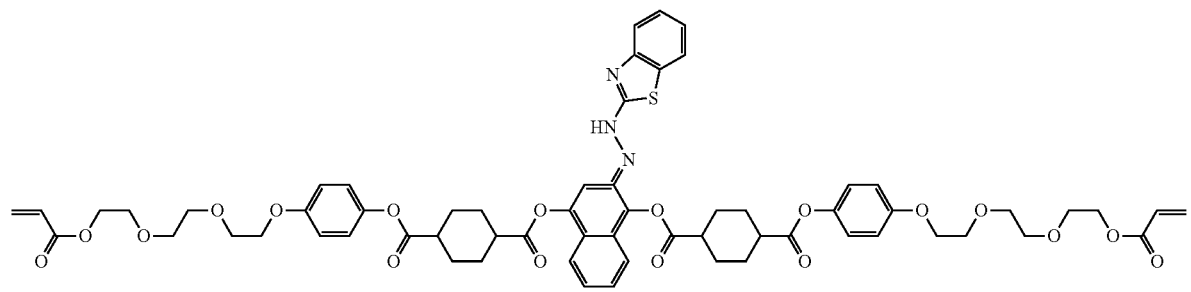

The compound represented by the general formula (I) can be produced by appropriately combining known organic synthesis reactions (for example, a condensation reaction, an esterification reaction, the Williamson reaction, the Wittig reaction, the Sonogashira reaction, the Suzuki-Miyaura reaction, the Friedel-Crafts reaction, the Heck reaction, the Aldol reaction, etc.) described in Organic Reactions, Organic Synthesis, Shin Jikken Kagaku Koza, and the like according to the structure. For example, a compound represented by the formula (I-2) can be produced, according to the following scheme:

[Chem. 110]

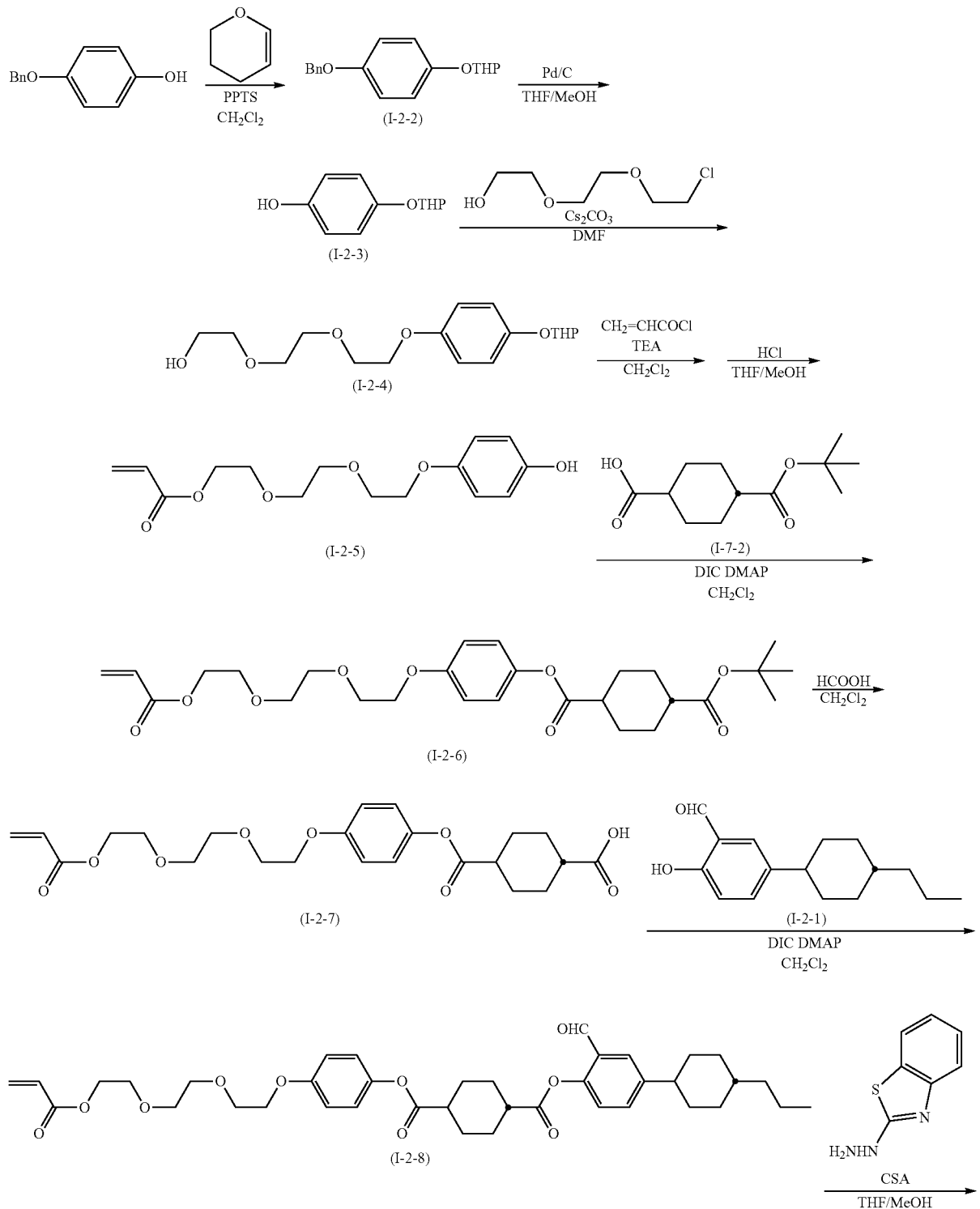

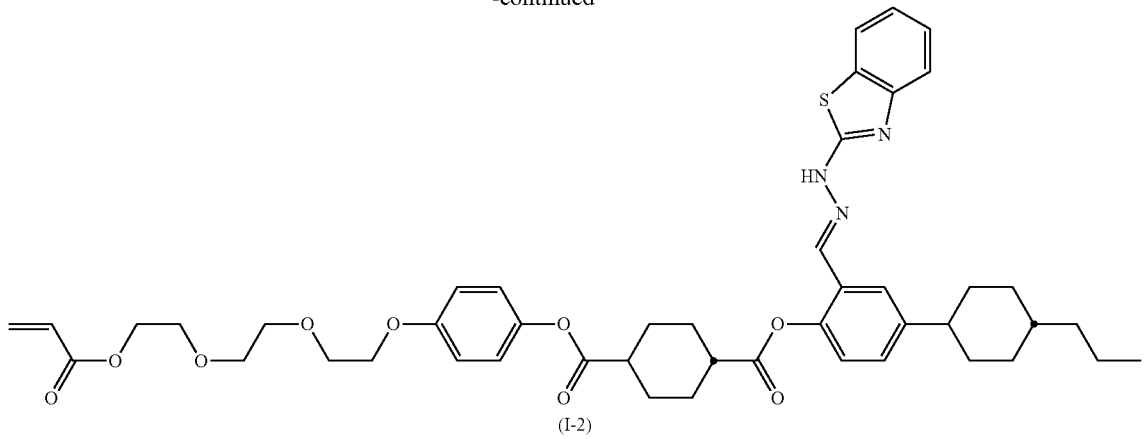

(I-2)

The hydroxy group in benzyloxyphenol is protected by a tetrahydropyranyl group to obtain a compound represented by the formula (I-2-2). The benzyl, group as a protecting group of the compound represented by the formula (I-2-2) is eliminated to obtain a compound represented by the formula (I-2-3). The compound represented by the formula (I-2-3) and 2-[2-(2-chloroethoxy)ethoxy]ethanol are etherified to obtain a compound represented by the formula (I-2-4). An acrylic group is added to the compound represented by the formula (I-2-4) and the tetrahydropyranyl group as a protecting group is eliminated to obtain a compound represented by the formula (I-2-5). The compound represented by the formula (I-2-5) and a compound represented by the formula (I-7-2) are fused to obtain a compound represented by the formula (I-2-6). The t-butyl group as a protecting group of the compound represented by the formula (I-2-6) is eliminated to obtain a compound represented by the formula (I-2-7). The compound represented by the formula (I-2-7) and a compound represented by the formula (I-2-1) are fused to obtain a compound represented by the formula (I-2-8). The compound represented by the formula (I-2-8) and 2-hydrazinobenzothiazole are fused to obtain the compound represented by the formula (I-2).

As another example, a compound represented by the formula (I-6) can be produced according to the following scheme:

[Chem. 111]

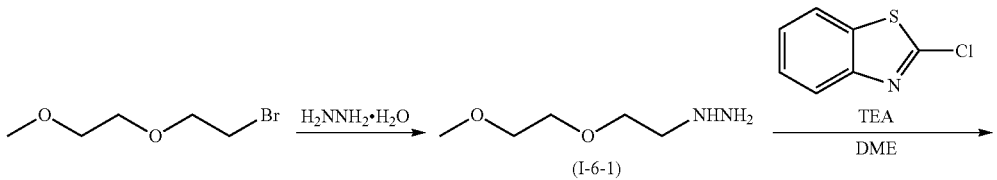

(I-6-1)

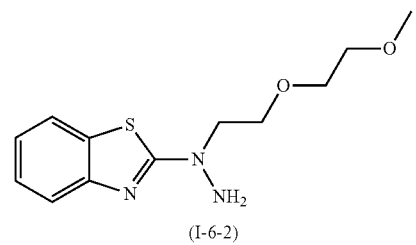

(I-6-2)

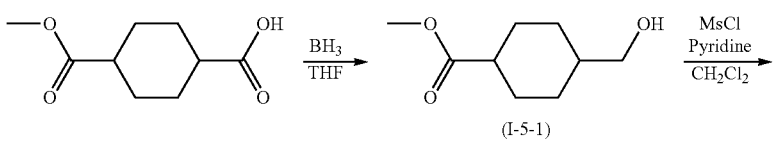

(I-5-1)

-continued
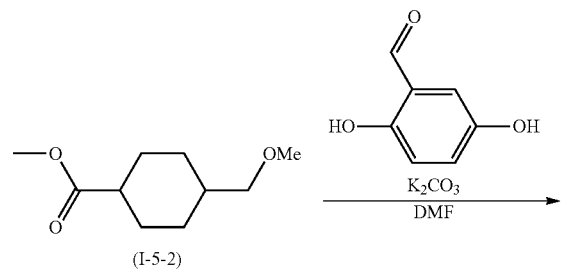
(I-5-2)
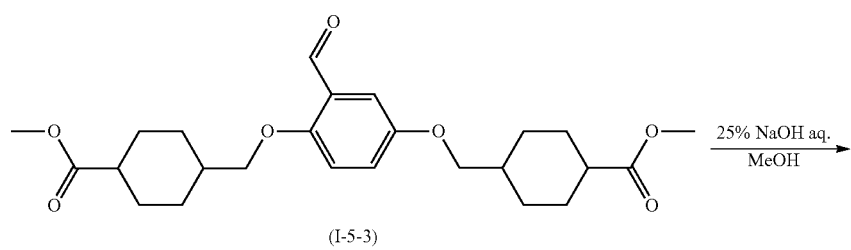
(I-5-3)
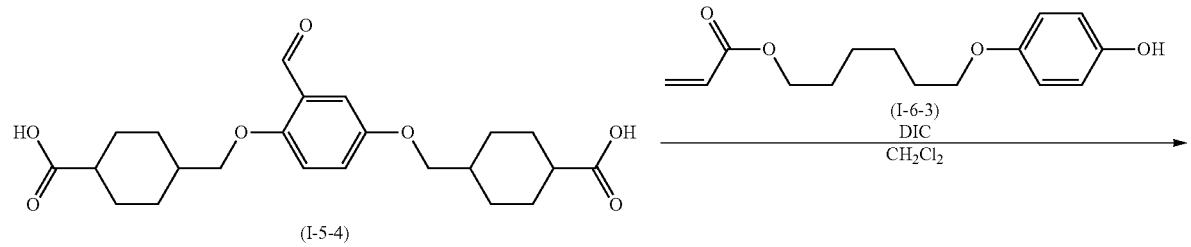
(I-5-4)
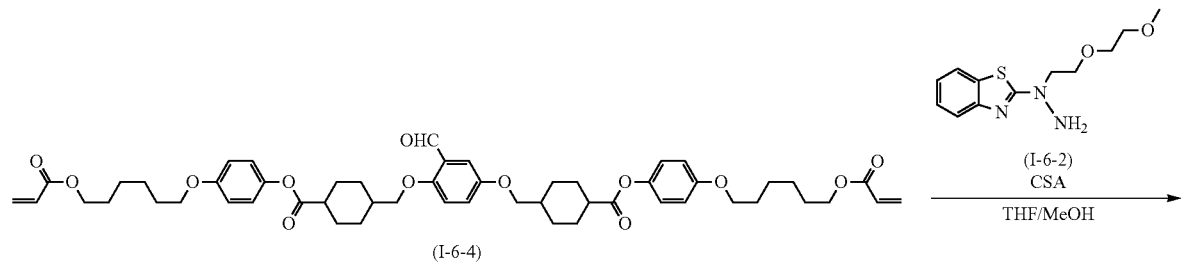
(I-6-4)
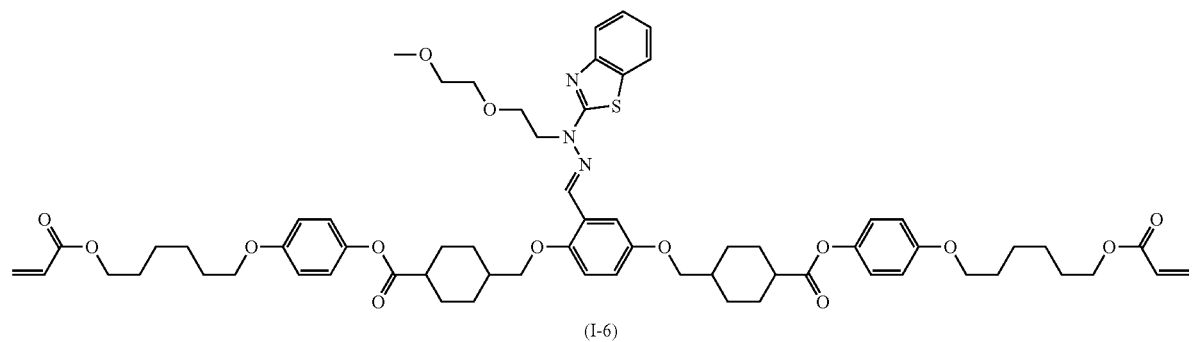 [SMILES: C=CC(=O)OCCCCCCOc1ccc(OC(=O)C2CCC(COc3ccc(OCC4CCC(C(=O)Oc5ccc(OCCCCCCOC(=O)C=C)cc5)CC4)c(/C=N/N(CCOCCOC)c4nc5ccccc5s4)c3)CC2)cc1 ; "(I-6)"]
(I-6)

Hydrazine monohydrate and 1-bromo-2-(2-methoxyethoxy)ethane are reacted to obtain a compound represented by the formula (I-6-1). The compound represented by formula (I-6-1) and 2-chlorobenzothiazole are reacted to obtain a compound represented by the formula (I-6-2). 4-Methoxycarbonylcyclohexane carboxylic acid is reduced to obtain a compound represented by the formula (I-5-1). The compound represented by the formula (I-5-1) is mesylated to obtain a compound represented by the formula (I-5-2). The compound represented by the formula (I-5-2) and 2,5-dihydroxybenzaldehyde are etherified to obtain a compound represented by the formula (I-5-3). The compound represented by the formula (I-5-3) is hydrolyzed to obtain a compound represented by the formula (I-5-4). The compound represented by the formula (I-5-4) and a compound represented by the formula (I-6-3) are fused to obtain a compound represented by the formula (I-6-4). The compound represented by the formula (I-6-4) and the compound represented by the formula (I-6-2) are fused to obtain the compound represented by the formula (I-6).

The compound of the present invention is preferably used in a nematic liquid crystal composition, a smectic liquid crystal composition, a chiral smectic liquid crystal composition and a cholesteric liquid crystal composition. Any other compound than the compound of the present invention may be added to the liquid crystal composition containing the reactive compound of the present invention.

As other polymerizable compounds that may be mixed with the polymerizable compound of the present invention for use herein, specifically, compounds represented by a general formula (X-11):

[Chem. 112]

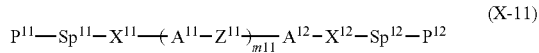

(X-11)

and/or compounds represented by a general formula (X-12):

[Chem. 113]

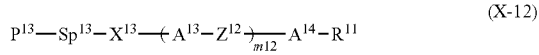

(X-12)

(wherein $P^{11}$, $P^{12}$ and $P^{13}$ each independently represent a polymerizable group, $Sp^{11}$, $Sp^{12}$ and $Sp^{13}$ each independently represent a single bond or an alkylene group having 1 to 20 carbon atoms in which one —$CH_2$— or two or more (—$CH_2$—)'s not adjacent to each other may be each independently substituted with —O—, —COO—, —OCO— or —OCOO—, $X^{11}$, $X^{12}$ and $X^{13}$ each independently represent —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —$CH_2$—OCO—, —CH=CH—, —CF=CF—, —C≡C— or a single bond, $Z^{11}$ and $Z^{12}$ each independently represent —O—, —S—, —$OCH_2$—, —$CH_2O$—, —COO—, —OCO—, —CO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —$CH_2CH_2$—, —$CH_2CF_2$—, —$CF_2CH_2$—, —$CF_2CF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —CF=CF—, —C≡C— or a single bond, $A^{11}$, $A^{12}$, $A^{13}$ and $A^{14}$ each independently represent a 1,4-phenylene group, a 1,4-cyclohexylene group, a bicyclo[2.2.2]octane-1,4-diyl group, a pyridine-2,5-diyl group, a pyrimidine-2,5-diyl group, a naphthalene-2,6-diyl group, a naphthalene-1,4-diyl group, a tetrahydronaphthalene-2,6-diyl group or a 1,3-dioxane-2,5-diyl group, and $A^{11}$, $A^{12}$, $A^{13}$ and $A^{14}$ may be each independently unsubstituted or substituted with an alkyl group, a halogenoalkyl group, an alkoxy group, a halogenoalkoxy group, a halogen atom, a cyano group or a nitro group, $R^{11}$ represents a hydrogen atom, a fluorine atom, a chlorine atom, a bromine atom, an iodine atom, a pentafluorosulfuranyl group, a cyano group, a nitro group, an isocyano group, a thioisocyano group, or a linear or branched alkyl group having 1 to 20 carbon atoms in which one —$CH_2$— or two or more (—$CH_2$—)'s not adjacent to each other may be each independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF— or —C≡C—, m11 and m12 each represent 0, 1, 2 or 3, and in the case where m11 and/or m12 each are 2 or 3, two or three existing groups with respect to each of $A^{11}$, $A^{12}$, $Z^{11}$ and $Z^{12}$ may be the same or different) are preferred; and those where $P^{11}$, $P^{12}$ and $P^{13}$ each are an acrylic group or a methacrylic group are especially preferred. Specifically, the compounds represented by the general formula (X-11) are preferably those represented by a general formula (X-11a):

[Chem. 114]

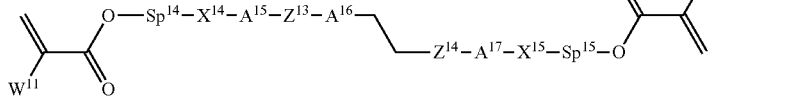

(X-11a)

(wherein $W^{11}$ and $W^{12}$ each independently represent, a hydrogen atom or a methyl group, $Sp^{14}$ and $Sp^{15}$ each independently represent an alkylene group having 2 to 18 carbon atoms, $X^{14}$ and $X^{15}$ each independently represent —O—, —COO—, —OCO— or a single bond, $Z^{13}$ and $Z^{14}$ each independently represent. —COO— or —OCO—, $A^{15}$, $A^{16}$ and $A^{17}$ each independently represent, a 1,4-phenylene group which is unsubstituted or optionally substituted with a fluorine atom, a chlorine atom, a linear or branched alkyl group having 1 to 4 carbon atoms, or a linear or branched alkoxy group having 1 to 4 carbon atoms); and those represented by the following formulae (X-11a-1) to (X-11a-4):

[Chem. 115]

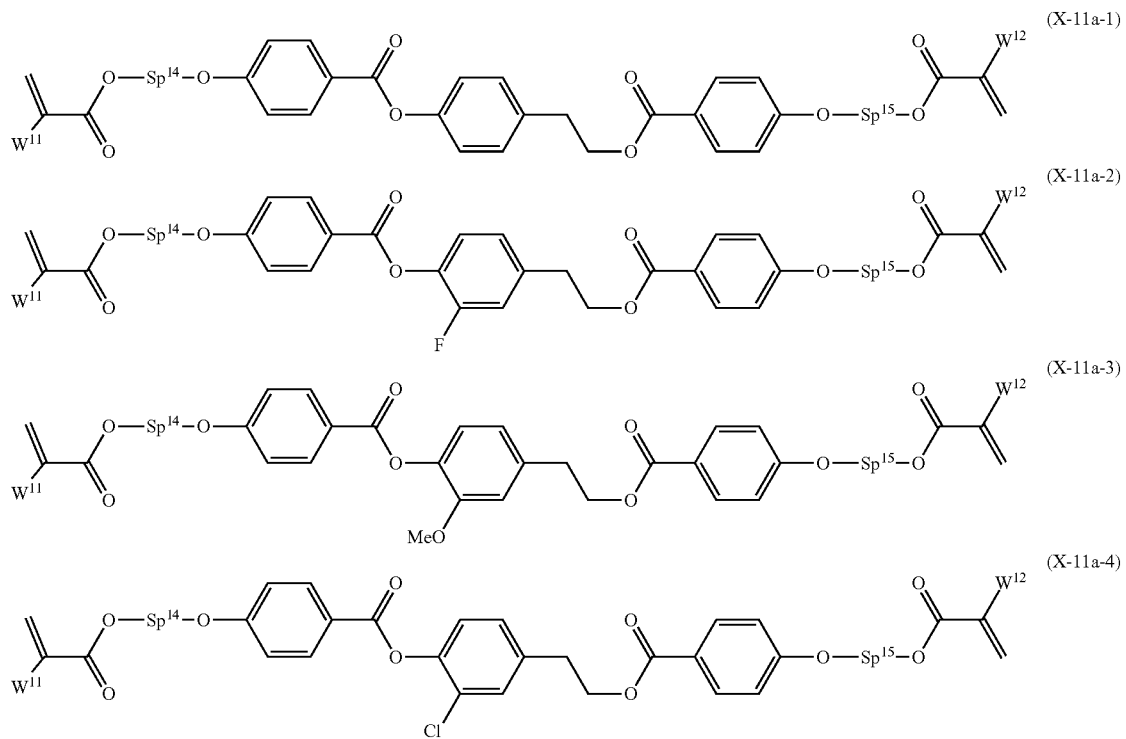

(wherein $W^{11}$, $W^{12}$, $Sp^{14}$ and $Sp^{15}$ each have the same meaning as in the general formula (X-11a) are especially preferred. Compounds of the above formulae (X-11a-1) to (X-11a-4) where $Sp^{14}$ and $Sp^{15}$ each are an alkylene group having 2 to 8 carbon atoms are especially preferred. In addition, as preferred bifunctional polymerizable compounds, there are mentioned compounds represented by the following general formulae (X-11b-1) to (X-11b-3):

[Chem. 116]

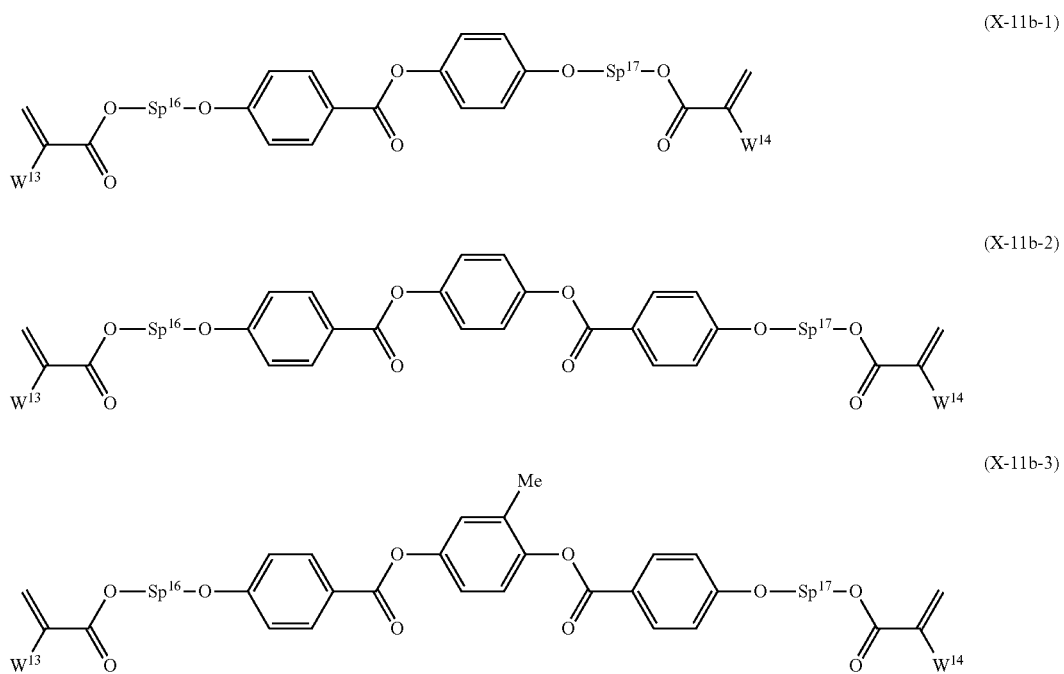

(wherein W$^{13}$ and W$^{14}$ each independently represent a hydrogen atom or a methyl group, Sp$^{16}$ and Sp$^{17}$ each independently represent an alkylene group having 2 to 18 carbon atom). Compounds of the above formulae (X-11b-1) to (X-11b-3) where Sp$^{16}$ and Sp$^{17}$ each are an alkylene group having 2 to 8 carbon atoms are especially preferred.

Specifically, the compounds represented by the general formula (X-12) include compounds represented by the following general formulae (X-12-1) to (X-12-7):

[Chem. 117]

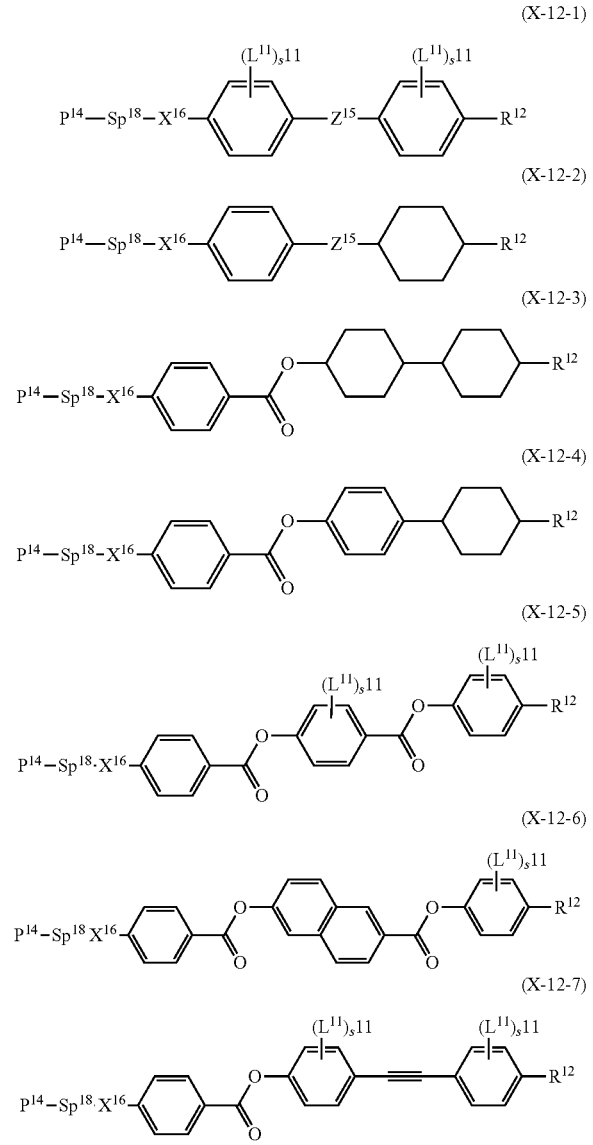

(wherein P$^{14}$ represents a polymerizable group, Sp$^{18}$ represents a single bond or an alkylene group having 1 to 20 carbon atoms, in which one —CH$_2$— or two or more (—CH$_2$—)'s not adjacent to each other may be substituted with —O—, —COO—, —OCO— or —O—CO—O—, X$^{16}$ represents a single bond, —O—, —COO—, or —OCO—, Z$^{15}$ represents a single bond, —COO— or —OCO—, L$^{11}$ represents a fluorine atom, a chlorine atom, or a linear or branched alkyl group having 1 to 10 carbon atoms in which one —CH$_2$— or two or more (—CH$_2$—)'s not adjacent to each other may be each independently substituted with —O—, —COO— or —OCO—, s11 represents an integer of 0 to 4, R$^{12}$ represents a hydrogen atom, a fluorine atom, a chlorine atom, a cyano group, a nitro group, or a linear or branched alkyl group having 1 to 20 carbon atoms in which one —CH$_2$— or two or more (—CH$_2$—)'s not adjacent to each other may be each independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF— or —C≡C—.)

A polymerizable compound not showing liquid crystallinity may be added to the polymerizable liquid crystal composition containing the compound of the present invention within a range not significantly detracting the liquid crystallinity of the composition. Specifically, a compound that can be recognized as a polymer-forming monomer or a polymer-forming oligomer in this technical field can be used with no specific limitation. As specific examples, for example, there are mentioned those described in "Photocurable Technique Data Book, Materials Section (monomer, oligomer, photopolymerization initiator)" (supervised by Kunihiro Ichimura "Kiyoshi Kate, Technonet Co., Ltd.).

The compound of the present invention may be polymerized even though not using a photopolymerization initiator, but depending on the intended purpose, a photopolymerization initiator may be added. In such a case, the concentration of the photopolymerization initiator is preferably 0.1% by mass to 15% by mass relative to the compound of the present invention, more preferably 0.2% by weight to 10% by weight, even more preferably 0.4% by weight to 8% by weight. The photopolymerization initiator includes benzoin ethers, benzophenones, acetophenones, benzyl ketals, acylphosphine oxides, etc. Specific examples of the photopolymerization initiator include 2-methyl-1-(4-methylthiophenyl)-2-morpholinopropan-1-one (IRGACURE 907), [1-[4-(phenylthio)benzoyl]heptylidene]amino-benzoate (IRGACURE OXE 01), etc. A thermal polymerization initiator includes azo compounds, peroxides, etc. Specific examples of the thermal polymerization initiator include 2,2'-azobis(4-methoxy-2,4-dimethylvaleronitrile), 2,2'-azobis(isobutyronitrile), etc. One kind of polymerization initiator may be used, or two or more kinds of polymerization initiators may be used in combination.

A stabilizer may be added to the liquid crystal composition of the present invention for improving the storage stability thereof. Usable stabilizers include, for example, hydroquinones, hydroquinone monoalkyl ethers, tert-butyl catechols, pyrogallols, thiophenols, nitro compounds, β-naphthylamines, β-naphthols, nitroso compounds, etc. in the case where a stabilizer is used, the amount thereof to be added is preferably within a range of 0.005% by mass to 1% by mass relative to the composition, more preferably 0.02% by mass to 0.8% by mass, even more preferably 0.03% by mass to 0.5% by mass. One kind of stabilizer may be used or two or more kinds of stabilizers may be used in combination. As the stabilizer, specifically, compounds represented by formulae (X-13-1) to (X-13-35) are preferred.

[Chem. 118]
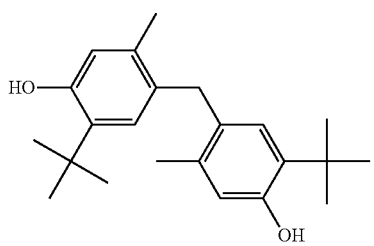 (X-13-1)
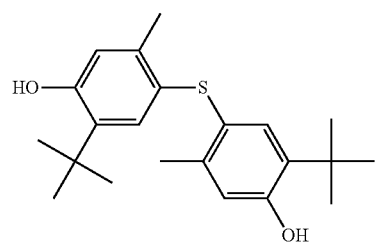 (X-13-2)
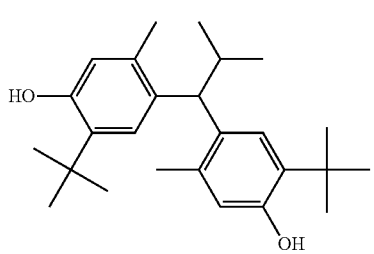 (X-13-3)
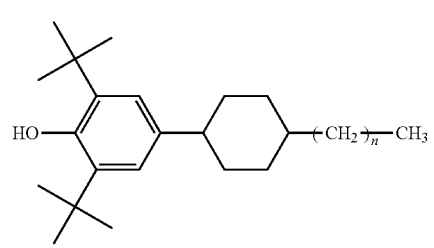 (X-13-4)
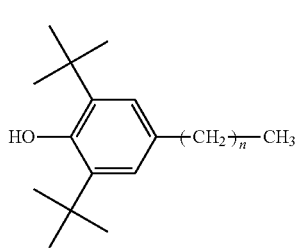 (X-13-5)
[Chem. 119]
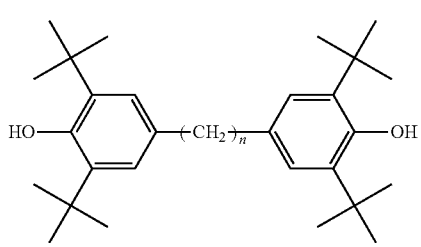 (X-13-6)
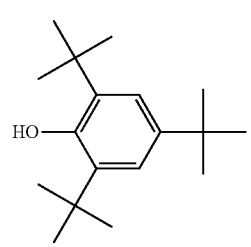 (X-13-7)
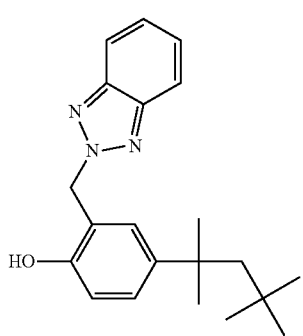 (X-13-8)
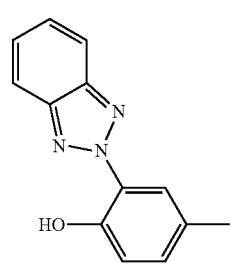 (X-13-9)

-continued
(X-13-10)
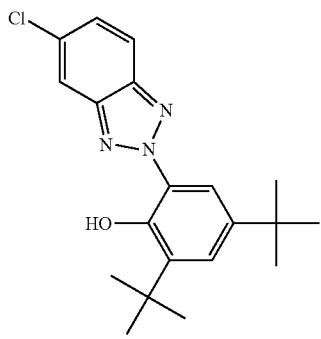
[Chem. 120]
(X-13-11)
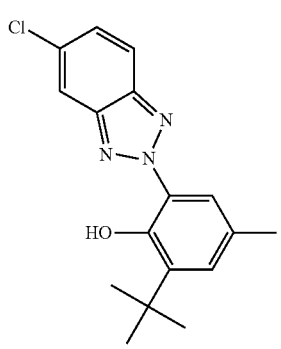
(X-13-12)
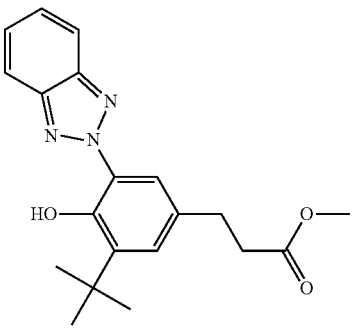
(X-13-13)
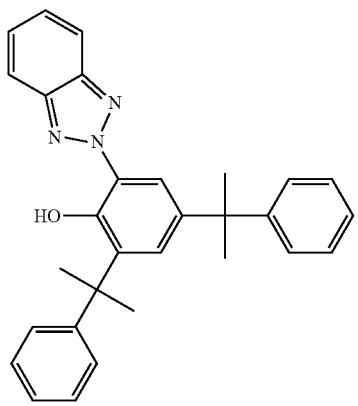
(X-13-14)
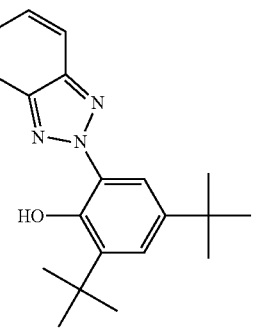
(X-13-15)
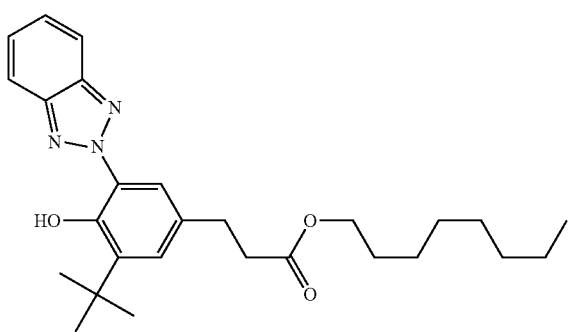

[Chem. 121]
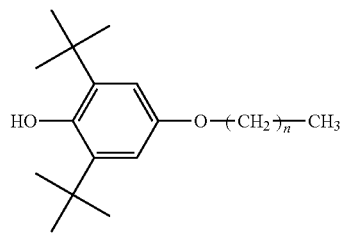 (X-13-16)
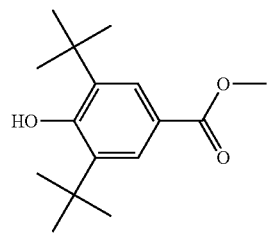 (X-13-17)
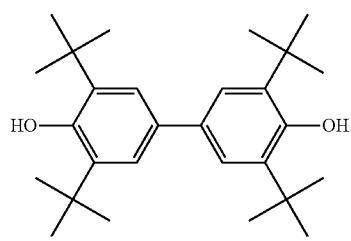 (X-13-18)
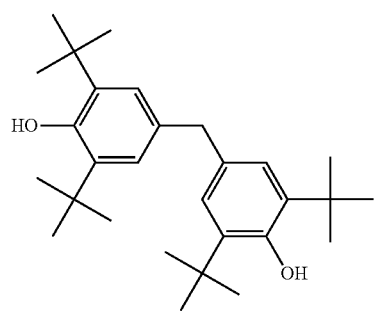 (X-13-19)
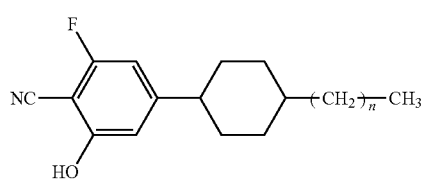 (X-13-20)
[Chem. 122]
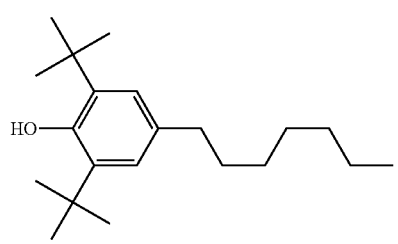 (X-13-21)
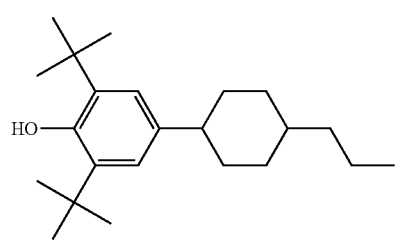 (X-13-22)
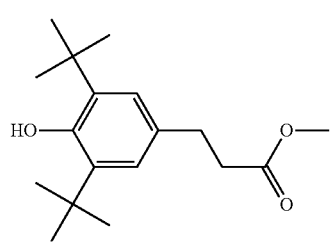 (X-13-23)
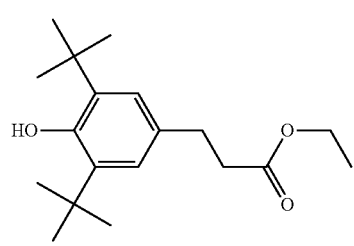 (X-13-24)

-continued
(X-13-25)
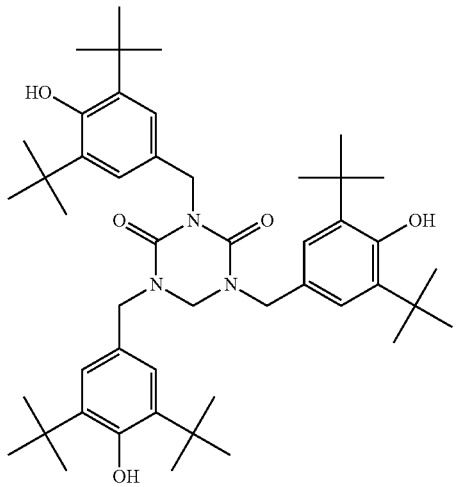
[Chem. 123]
(X-13-26)
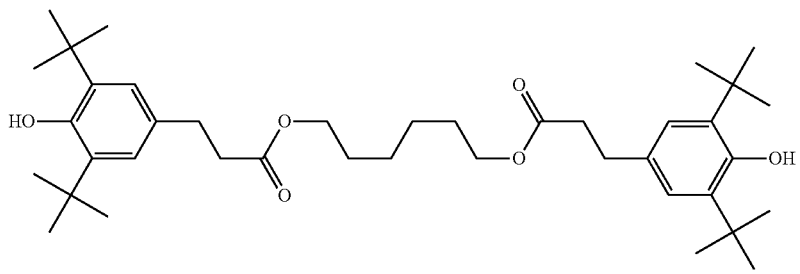
(X-13-27)
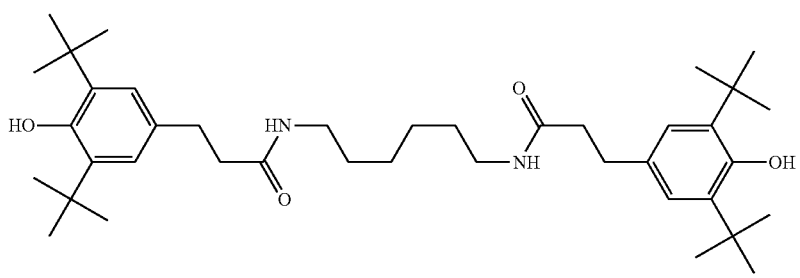
(X-13-28)
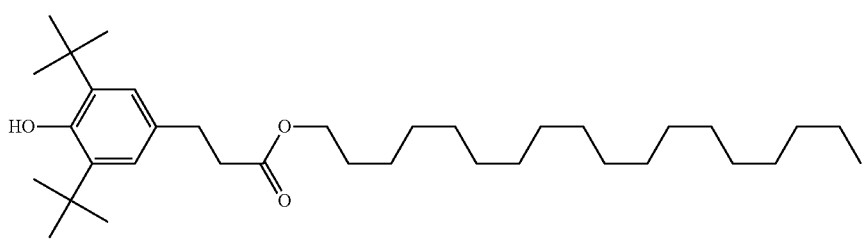

-continued
(X-13-29)
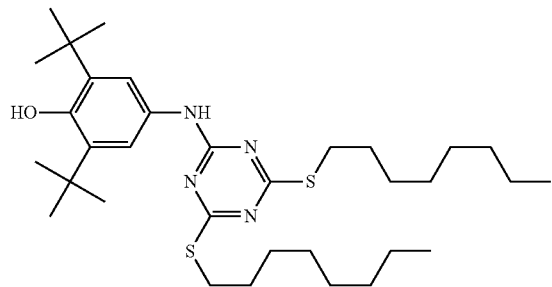
(X-13-30)
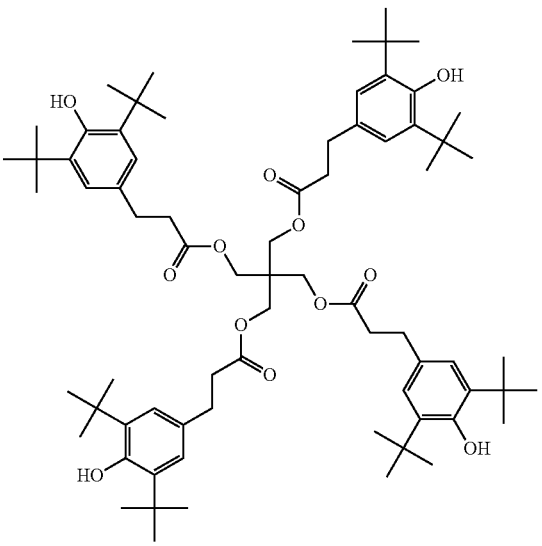
[Chem. 124]
(X-13-31)
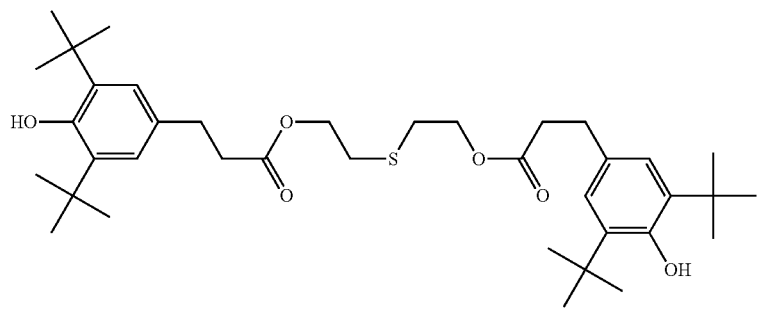
(X-13-32)
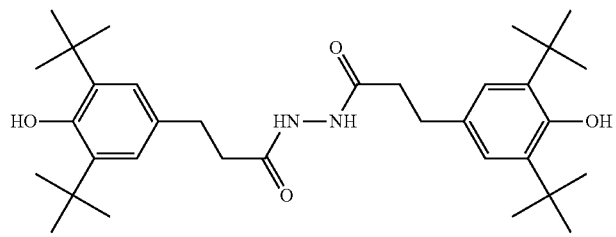
(X-13-33)
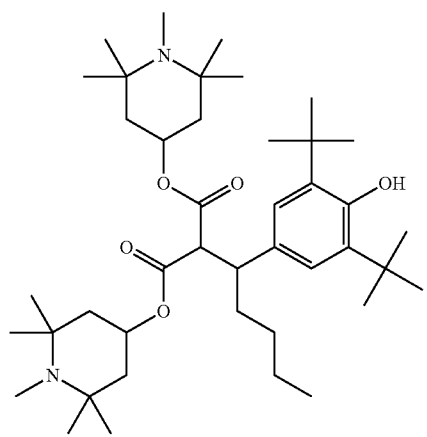
(X-13-34)
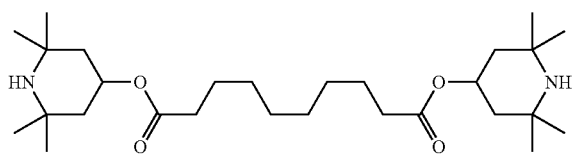

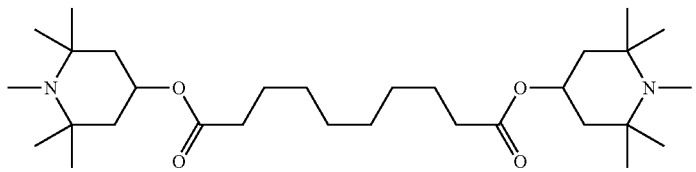

(X-13-35)

(wherein n represents an integer of 0 to 20).

In the case where the polymerizable liquid crystal composition containing the compound of the present invention is used for films, optical elements, functional pigments, medicines, cosmetics, coating agents, synthetic resins and others, a metal, a metal complex, a dye, a pigment, a colorant, a fluorescent material, a phosphorescent material, a surfactant, a leveling agent, a thixotropic agent, a gelling agent, a polysaccharide, a UV absorbent, an IR absorbent, an antioxidant, an ion-exchange resin, a metal oxide such as titanium oxide or the like may be added thereto in accordance with the intended purpose.

Polymers to be obtained through polymerization of the polymerizable liquid crystal composition containing the compound of the present invention can be used in various use applications. For example, polymers obtained through polymerization with no alignment of the polymerizable liquid crystal composition containing the compound of the present invention can be used as light scattering plates, depolarization plates, or more fringe inhibitor plates. Polymers obtained through polymerization after alignment have optical anisotropy and are useful. Such optically anisotropic bodies can be produced, for example, by applying the polymerizable liquid crystal composition containing the compound of the present invention onto a substrate previously rubbed with cloth or the like, a substrate having an organic thin film formed thereon, or a substrate having, as obliquely deposited thereon, an $SiO_2$ alignment film to thereby make the composition supported by the substrate, or by sandwiching the composition between the substrates, and thereafter polymerizing the polymerizable liquid crystal composition.

As a method of making the polymerizable liquid crystal composition supported by a substrate, there are mentioned methods of spin coating, die coating, extrusion coating, roll coating, wire bar coating, gravure coating, spray coating, dipping, printing, etc. In coating, an organic solvent may be added to the polymerizable liquid crystal composition. The organic solvent usable here include hydrocarbon solvents, halogenohydrocarbon solvents, ether solvents, alcohol solvents, ketone solvents, ester solvents, aprotic solvents, etc. For example, hydrocarbon solvents include toluene and hexane; halogenohydrocarbon solvents include methylene chloride; ether solvents include tetrahydrofuran, acetoxy-2-ethoxyethane and propylene glycol monomethyl ether acetate; alcohol solvents include methanol, ethanol and isopropanol; ketone solvents include acetone, methyl ethyl ketone, cyclohexanone, γ-butyrolactone and N-methylpyrrolidinones; ester solvents include ethyl acetate and cellosoive; and aprotic solvents include dimethylformamide and acetonitrile. These may be used, either singly or in combination. In consideration of the vapor pressure thereof and the solubility of the polymerizable liquid crystal composition therein, the solvents may be appropriately selected. As a method of volatilizing the added organic solvent, atmospheric drying, drying under heat, drying under reduced pressure, or drying under heat and reduced pressure may be employed. For further improving the coatability with the polymerizable liquid crystal material, it is also effective to provide an interlayer such as a polyimide thin film or the like on a substrate or to add a leveling agent to the polymerizable liquid crystal material. The method of providing an interlayer such as a polyimide thin film or the like on a substrate is effective for improving the adhesiveness between the polymer obtained through polymerization of the polymerizable liquid crystal material and a substrate.

As the other alignment treatment than the above, there may be mentioned utilization of flow alignment of liquid crystal material, and utilization of electric field or magnetic field. These alignment means may be used singly or may be used in combination an alignment treatment Method substitutable for rubbing, a photo-alignment method may be employed. Regarding the shape of the substrate, the substrate may have, a curved face as a constituent, part in addition, to a tabular plate. As the material to constitute the substrate, an organic material and an inorganic material may be employed with no limitation. The organic material to constitute the substrate includes, for example, polyethylene terephthalate, polycarbonate, polyimide, polyamide, polymethyl methacrylate, polystyrene, polyvinyl chloride, polytetrafluoroethylene, polychlorotrifluoroethylene, polyarylate, polysulfone, triacetyl cellulose, cellulose, polyether ether ketone, etc. The inorganic material includes, for example, silicon, glass, calcite, etc.

In polymerizing the polymerizable liquid crystal composition containing the compound of the present invention, it is desirable that the polymerization runs on rapidly, and therefore, a method of polymerizing the composition through irradiation with active energy rays such as UV rays, electron beams or the like is preferred. In the case of using UV rays, a polarized light source may be used, or a non-polarized light source may also be used. In the case where the liquid crystal composition is polymerized while kept sandwiched between two substrates, at least the substrate on the irradiation face side must have suitable transparency for the active energy rays. If desired, a method of polymerizing only a specific part of the composition via a mask during photo irradiation, then changing the conditions of electric field, magnetic field, temperature and the like to thereby change the alignment state of the unpolymerized part, and further polymerizing the part through irradiation with active energy rays may be employed. The temperature during irradiation is preferably within a temperature range within which the polymerizable liquid crystal composition of the present invention can maintain the liquid crystal state thereof. In particular, in the case of producing an optically anisotropic body through photopolymerization, the polymerization is carried out at a temperature as near as possible to room temperature, typically at a temperature of 25° C. for the purpose of evading induction of any unintended thermal polymerization. The intensity of the active energy rays is preferably 0.1 mW/cm$^2$ to 2 mW/cm$^2$. When the intensity is less than 0.1 mW/cm², much time is taken for completing photopolymerization to worsen productivity, and when more than 2 mW/cm², there is a risk of degradation of the polymerizable liquid crystal compound or the polymerizable liquid crystal composition.

The optically anisotropic body obtained through polymerization may be heat-treated for reducing change in characteristics in the initial stage and for attaining stable characteristics expression. The temperature for the heat treatment, is preferably within a range, of 50 to 250° C., and the heat-treatment time is preferably within a range of 30 seconds to 12 hours.

The optically anisotropic body thus produced according to the method may be used as a simple body after peeled from a substrate, or may be used without peeled. Alternatively, the resultant optically anisotropic body may be laminated or may be stuck to any other substrate.

EXAMPLES

Hereinunder the present invention is described further with reference to Examples, but the present invention is not limited to these Examples. In the following Examples and Comparative Examples, "%" for the compositions means "% by mass". When a substance unstable to oxygen and/or water is handled in each step, preferably, the operation is carried out in an inert gas such as nitrogen gas, argon gas, etc.

Example 1

Production of Compound Represented by the Formula (I-1)

[Chem. 125]

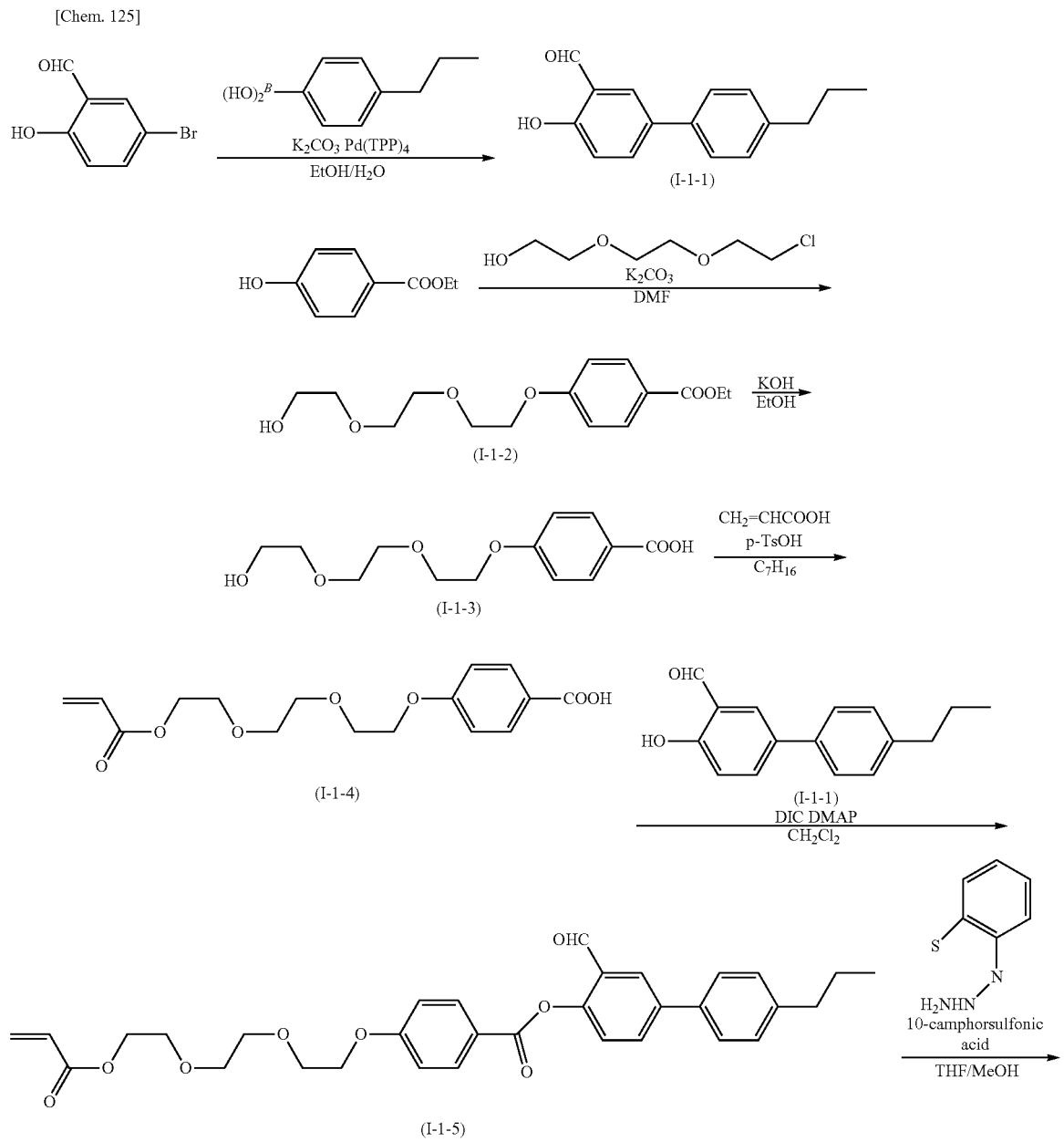

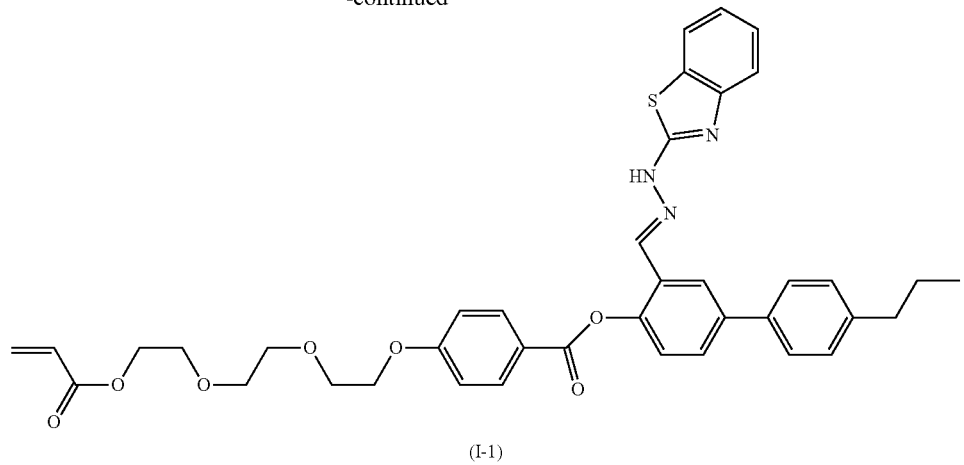

(I-1)

To a reaction vessel, 5.0 g of 5-bromo-2-hydroxybenzaldehyde, 4.1 q of propylphenylboric acid, 5.2 g of potassium carbonate, 0.3 g of tetrakis(triphenylphosphine) palladium (0), 20 mL of ethanol, and 20 mL of water were added and stirred at 60° C. The reaction solution was diluted with ethyl acetate and was washed with hydrochloric acid and a saline solution in this order, and the solvent was evaporated. Purification was performed by column chromatography (silica gel) to yield 4.8 g of a compound represented by the formula (I-1-1).

To a reaction vessel, 70.0 g of ethyl 4-hydroxybenzoate, 74.6 g of 2-[2-(2-chloroethoxy)ethoxy]ethanol, 116.4 g of potassium carbonate, and 350 mL of N,N-dimethylformamide were added and stirred at 90° C. for 19 hours. The reaction solution was diluted with ethyl acetate and washed with hydrochloric acid, a saturated aqueous sodium hydrogen carbonate solution, and a saline solution in this order, and the solvent was evaporated to yield 119.7 g of a compound represented by the formula (I-1-2).

To a reaction vessel, 119.7 g of the compound represented by the formula (I-1-2) and 360 mL of ethanol were added. 180 g of a 15% aqueous potassium hydroxide solution was added dropwise, and the mixture was stirred at room temperature. Ethanol was evaporated from the reaction solution, and the resultant was subjected to acid precipitation with hydrochloric acid. The precipitation was filtered and washed with water to yield 89.2 g of a compound represented by the formula (I-1-3).

To a reaction vessel, 40.5 g of the compound represented by the formula (I-1-3), 129.5 g of acrylic acid, 1.8 g of 4-methoxyphenol, 1.4 g of p-toluenesulfonic acid, and 350 mL of heptane were added and stirred at 95° C. for 4 hours. The reaction solution was diluted with tetrahydrofuran, and was washed with a saturated aqueous sodium hydrogen carbonate solution and a saline solution in this order. After drying over sodium sulfate, the solvent was evaporated.

Purification was performed by recrystallization (toluene/hexane) to yield 6.2 g of a compound represented by the formula (I-1-4).

To a reaction vessel, 6.2 g of the compound represented by the formula (I-1-4), 4.6 g of the compound represented by the formula (I-1-1), 20 mg of N,N-dimethylaminopyridine, and 30 mL of dichloromethane were added 2.9 g of diisopropylcarbodiimide was added dropwise under cooling with ice, and the mixture was stirred at room temperature for 10 hours. The reaction solution was filtered, and the filtrate was purified by column chromatography (silica gel) and recrystallization (dichloromethane/hexane, dichloromethane/methanol) to yield 2.5 g of a compound represented by the formula (I-1-5).

To a reaction vessel, 2.5 g of the compound represented by the formula (I-1-5), 0.8 g of 2-hydrazinobenothiazole, 20 mg of (±)-10-camphorsulfonic acid, 20 mL of tetrahydrofuran, and 1.0 mL of methanol were added, and stirred at room temperature for 4 hours. The solvent, was evaporated from the reaction solution. Purification was performed by column chromatography (silica gel) and recrystallization (dichloromethane/hexane, dichloromethane/methanol) to yield 1.2 g of a compound represented by the formula (I-1). Transition temperature (temperature increase: 5° C./min): C 89-123 I $^1$H NMR (CDCl$_3$) δ 1.05 (t, 3H), 1.70 (m, 2H), 2.70 (t, 2H), 3.58-3.73 (m, 6H), 3.75 (t, 2H), 4.02 (t, 2H), 4.27 (t, 2H), 5.84 (dd, 1H), 6.12 (dd, 1H), 6.42 (dd, 1H), 6.65 (d, 2H), 7.00 (d, 2H), 7.15-7.45 (m, 5H), 7.51-7.70 (m, 5H), 7.78 (dd, 1H), 8.17 (s, 1H), 11.7 (s, 1H) ppm.

LCMS: 694 [M+1]

Example 2

Production of Compound Represented by the Formula (I-2)

[Chem. 126]

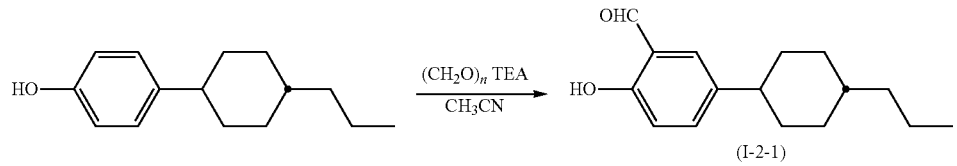

(I-2-1)

-continued
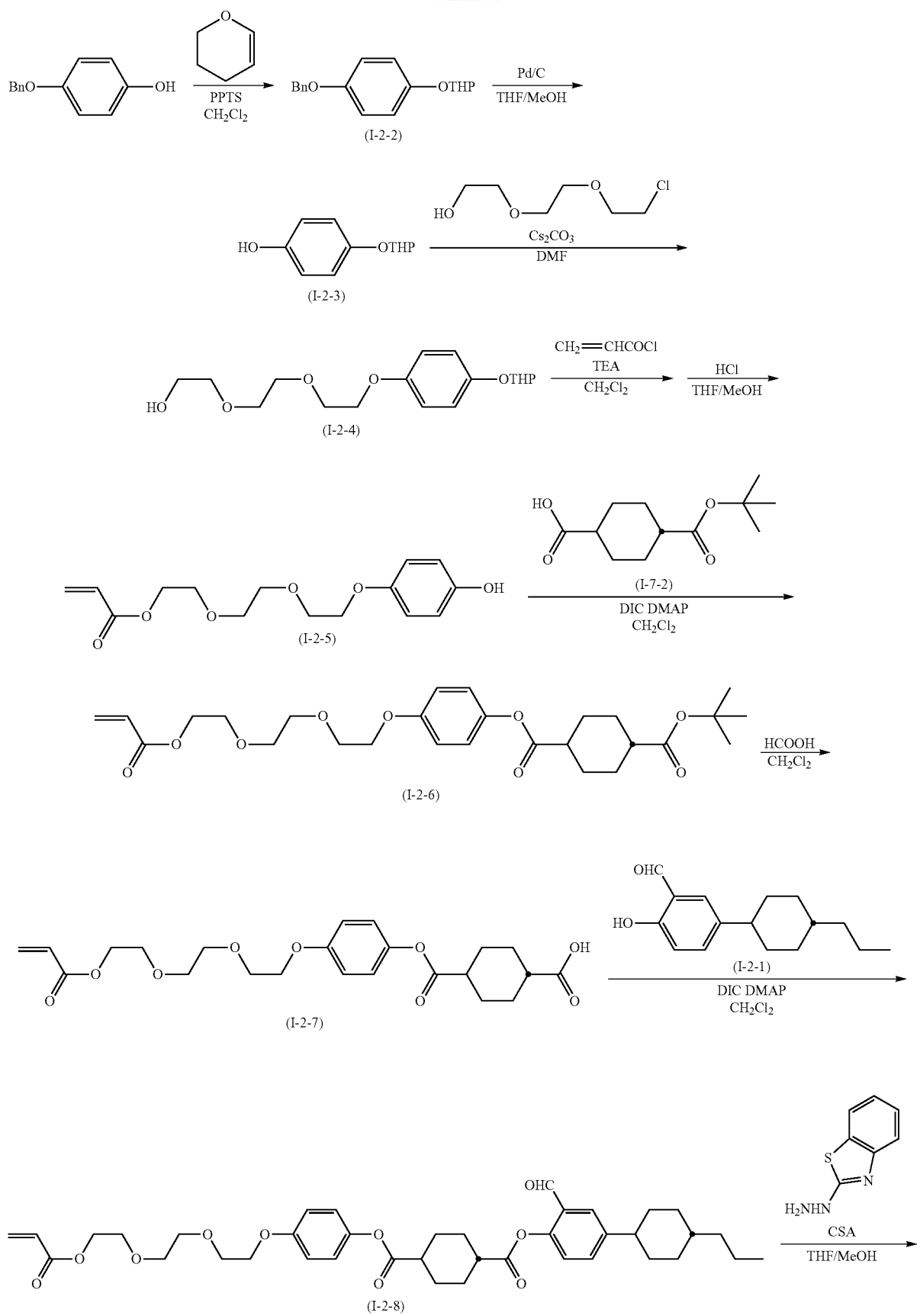

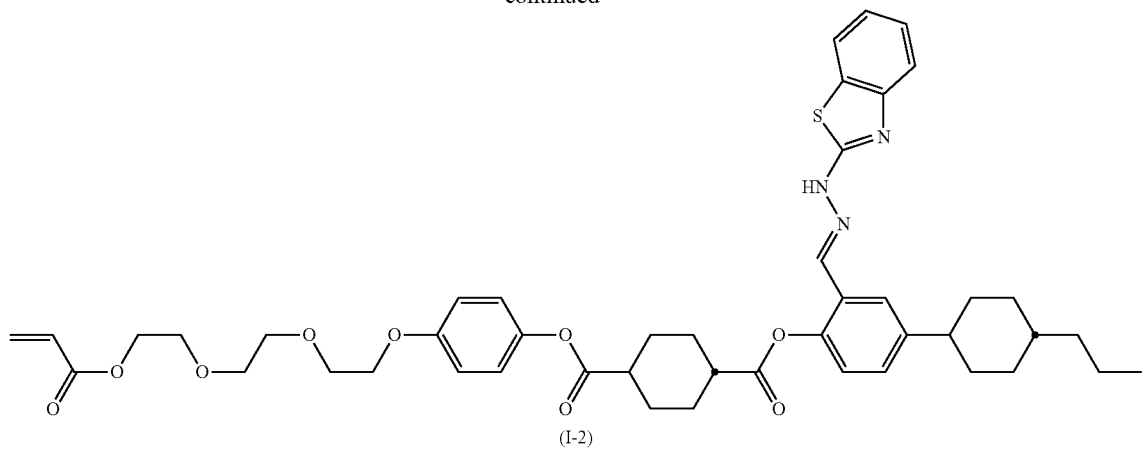

(I-2)

To a reaction vessel, 5.0 g of 4-(4-propylcyclohexyl) phenol, 2.1 g of paraformaldehyde, 3.3 g of magnesium chloride, 20 mL of triethylamine, and 80 mL of acetonitrile were added, and stirred at 60° C. The reaction solution was diluted with ethyl acetate, and was washed with hydrochloric acid and a saline solution in this order, and the solvent was evaporated. Purification was performed by column chromatography (silica gel) to yield 5.4 g of the compound represented by the formula (I-2-1).

To a reaction vessel, 126.0 g of benzyloxyphenol, 7.9 g of pyridinium p-toluenesulfonate, and 630 mL of dichloromethane were added 79.4 g of 3,4-dihydro-2H-pyran was added dropwise under cooling with ice and the mixture was stirred at room temperature for 6 hours. The reaction solution was washed with a saturated aqueous sodium hydrogen carbonate solution, water, and a saline solution in this order. Purification was performed by column chromatography (alumina) to yield 177.9 g of the compound represented by the formula (I-2-2).

To an autoclave reaction vessel, 177.9 g of the compound represented by the formula (I-2-2), 8.8 g of 5% palladium/carbon (50% Wet), 530 mL of tetrahydrofuran, and 530 mL of methanol were added, and stirred at room temperature for 5 hours under 0.5 MPa hydrogen atmosphere. The reaction solution was filtered and the solvent was evaporated. Purification was performed by column chromatography (alumina) to yield 115.9 g of the compound, represented by the formula (I-2-3).

To a reaction vessel, 115.9 g of the compound represented by the formula (I-2-3), 120.7 g of 2-[2-(2-chloroethoxy) ethoxy]ethanol, 272.2 g of cesium carbonate, and 580 mL of N,N-dimethylformamide were added, and stirred at 60° C. for 10 hours. The reaction solution was diluted with dichloromethane, and was washed with water and a saline solution in this order. Purification was performed by column chromatography (alumina) to yield 166.5 g of the compound represented by the formula (I-2-4).

To a reaction vessel, 166.5 g of the compound represented by the formula (I-2-4), 77.4 g of triethylamine, and 830 mL of dichloromethane were added 55.4 g of acryloyl chloride was added dropwise under cooling with ice and the mixture was stirred at room temperature for 4 hours. The reaction solution was washed with a saline solution, and purification was performed by column chromatography (alumina) to yield an oily substance. To the substance, 35 mL of 10% hydrochloric acid, 580 mL of methanol, and 580 mL tetrahydrofuran were added, and the mixture was stirred at room temperature for 2 hours. The reaction solution was washed with a saturated aqueous sodium hydrogen carbonate solution, water, and a saline solution in this order, and the solvent was evaporated. Purification was performed by column chromatography (silica gel) to yield 116.8 g of the compound represented by the formula (I-2-5).

To a reaction vessel, 60.0 g of the compound represented by the formula (I-2-5), 46.2 g of the compound represented by the formula (I-7-2) (the production process was described later), 0.2 g of N,N-dimethylaminopyridine, and 300 mL of dichloromethane were added 30.7 g of diisopropylcarbodiimide was added dropwise under cooling with ice and the mixture was stirred at room temperature for 2 hours. The reaction solution was filtered and the filtrate was washed with hydrochloric acid, water, and a saline solution in this order. Purification was performed by column chromatography (silica gel) and recrystallization (dichloromethane/hexane) to yield 78.4 g of the compound represented by the formula (I-2-6).

To a reaction vessel, 42.5 g of the compound represented by the formula (I-2-6), 170 mL of formic acid, and 210 mL of dichloromethane were added, and stirred at room temperature for 3 hours. Dichloromethane was evaporated from the reaction solution, diisopropyl ether was added to precipitate crystals, thereby obtaining 31.6 g of the compound represented by the formula (I-2-7).

To a reaction vessel, 20.0 g of the compound represented by the formula (I-2-7), 10.9 g of the compound represented by the formula (I-2-1), 50 mg of N,N-dimethylaminopyridine, and 100 mL of dichloromethane were added 6.7 g of diisopropylcarbodiimide was added dropwise under cooling with ice and the mixture was stirred at room temperature for 3 hours. The reaction solution was filtered, and the filtrate was washed with hydrochloric acid, water, and a saline solution in this order. Purification was performed by column chromatography (silica gel) and recrystallization (dichloromethane/hexane, dichloromethane/methanol) to yield 18.4 g of the compound represented by the formula (I-2-8).

To a reaction vessel, 10.0 g of the compound represented by the formula (I-2-8), 2.4 g of 2-hydrazinobenzothiazole, 70 mg of (±)-10-camphorsulfonic acid, 40 mL of tetrahydrofuran, and 10 mL of methanol were added, and stirred at room temperature for 5 hours. The solvent was evaporated form the reaction solution. Purification was performed by column chromatography (silica gel, alumina) and recrystallization (dichloromethane/methanol) to yield 7.9 g of the compound represented by the formula (I-2).

Transition temperature (temperature increase: 5° C./min): C 75-108 N 180 I $^1$H NMR (CDCl$_3$) δ 0.94 (t, 3H), 1.10 (m, 2H), 1.25 (m, 2H), 1.29-1.57 (m, 11H), 1.80-2.08 (m, 6H), 2.30 (m, 2H), 2.54 (m, 1H), 3.67-3.78 (m, 6H), 3.85 (t, 2H), 4.11 (t, 2H), 4.32 (t, 2H), 5.84 (dd, 1H), 6.15 (dd, 1), 6.40 (dd, 1H), 6.82-7.00 (m, 4H), 7.08-7.60 (m, 4H), 7.65-8.10 (m, 3H), 8.40 (s, 1H), 11.6 (s, 1H) ppm.

LCMS: 826 [M+1]

Example 3

Production of Compound Represented by the Formula (I-3)

and a saline solution in this order. After drying over sodium sulfate, the solvent was evaporated to yield 2.8 q of a compound represented by the formula (I-3-1).

To a reaction vessel, 4.1 g of the compound represented by the formula (I-3-1), 20 mL of 1,2-dimethoxyethane, and 10 mL of triethylamine were added 2.8 g of 2-chlorobenzothiazole was added dropwise and the mixture was stirred at 50° C. The reaction solution was poured into water, and the precipitated solid was washed with water and hexane to yield 3.0 g of a compound represented by the formula (I-3-2).

To a reaction vessel, 1.0 g of the compound represented by the formula (I-2-8), 0.4 g of the compound represented by the formula (I-3-2), 0.5 g of (±)-10-camphorsulfonic acid, 20 mL of tetrahydrofuran, and 10 mL of ethanol were added, and stirred at 50° C. The solvent was evaporated from the

[Chem. 127]

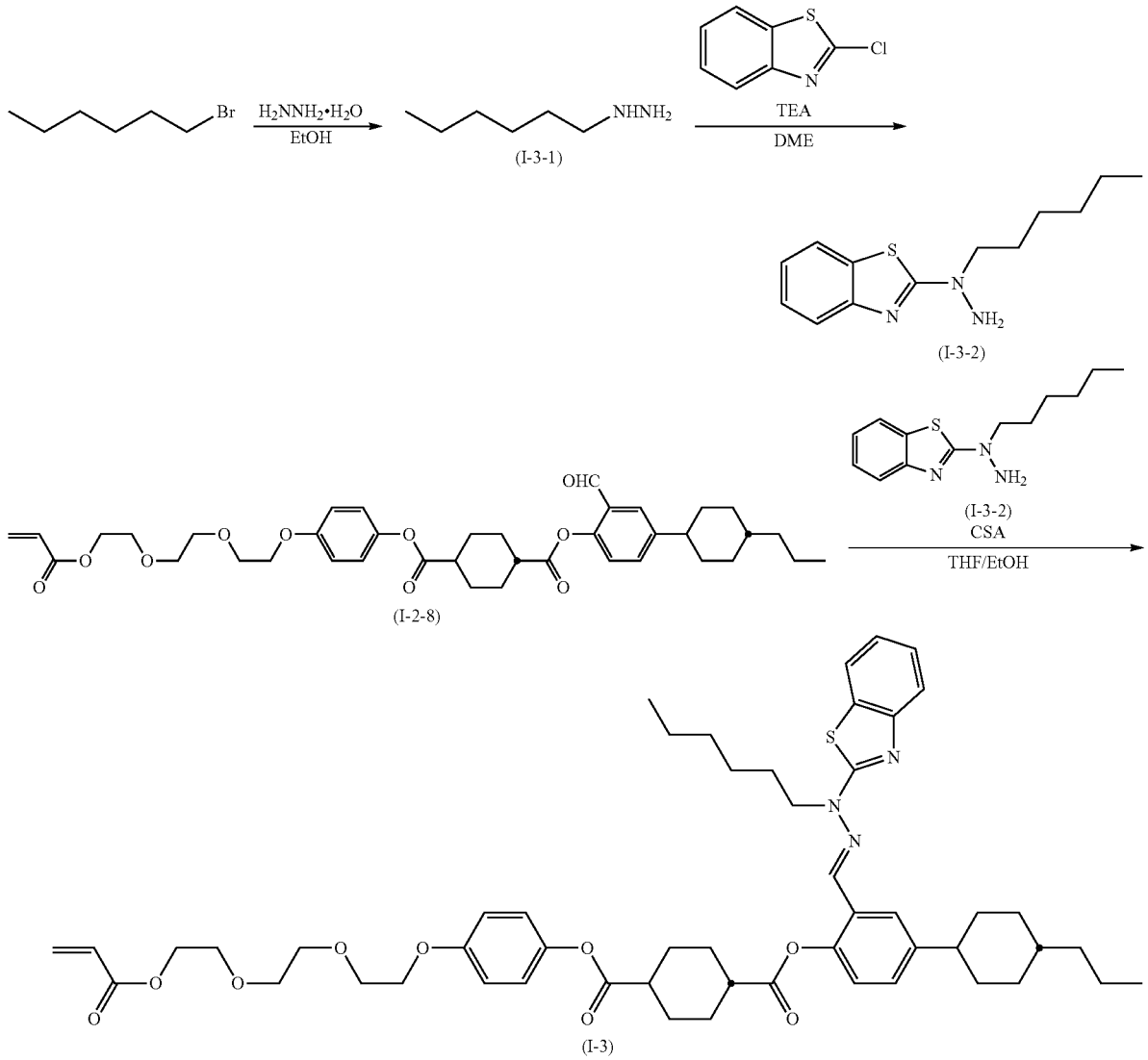

To a reaction vessel, 50 mL of hydrazine monohydrate and 50 mL of ethanol were added. A solution of 5.0 g of 1-bromohexane in ethanol was added dropwise and the mixture was stirred at 50° C. The reaction solution was diluted with dichloromethane and was washed with water reaction solution, and was subjected to dispersion washing with methanol. Purification was performed by column chromatography (silica gel) and recrystallization (dichloromethane/methanol) to yield 0.9 g of a compound represented by the formula (I-3).

Transition temperature (temperature increase: 5° C./min):
C 131 I
$^1$H NMR (CDCl$_3$) δ 0.88-0.94 (m, 6H), 1.10 (m, 2H), 1.22-1.52 (m, 13H), 1.72 (m, 6H), 1.94 (t, 4H), 2.32 (m, 4H), 2.53-2.62 (m, 3H), 3.69-3.77 (m, 6H), 3.86 (t, 2H), 4.12 (t, 2H), 4.27-4.34 (m, 4H), 5.83 (dd, 1H), 6.16 (dd, 1H), 6.43 (dd, 1H), 6.91 (d, 2H), 6.97-7.02 (m, 3H), 7.16 (t, 1H), 7.23 (dd, 1H), 7.33 (t, 1H), 6.66-7.72 (m, 3H), 7.90 (d, 1H) ppm.
LCMS: 910 [M+1]
Example 4
Production of Compound Represented by the Formula (I-4)
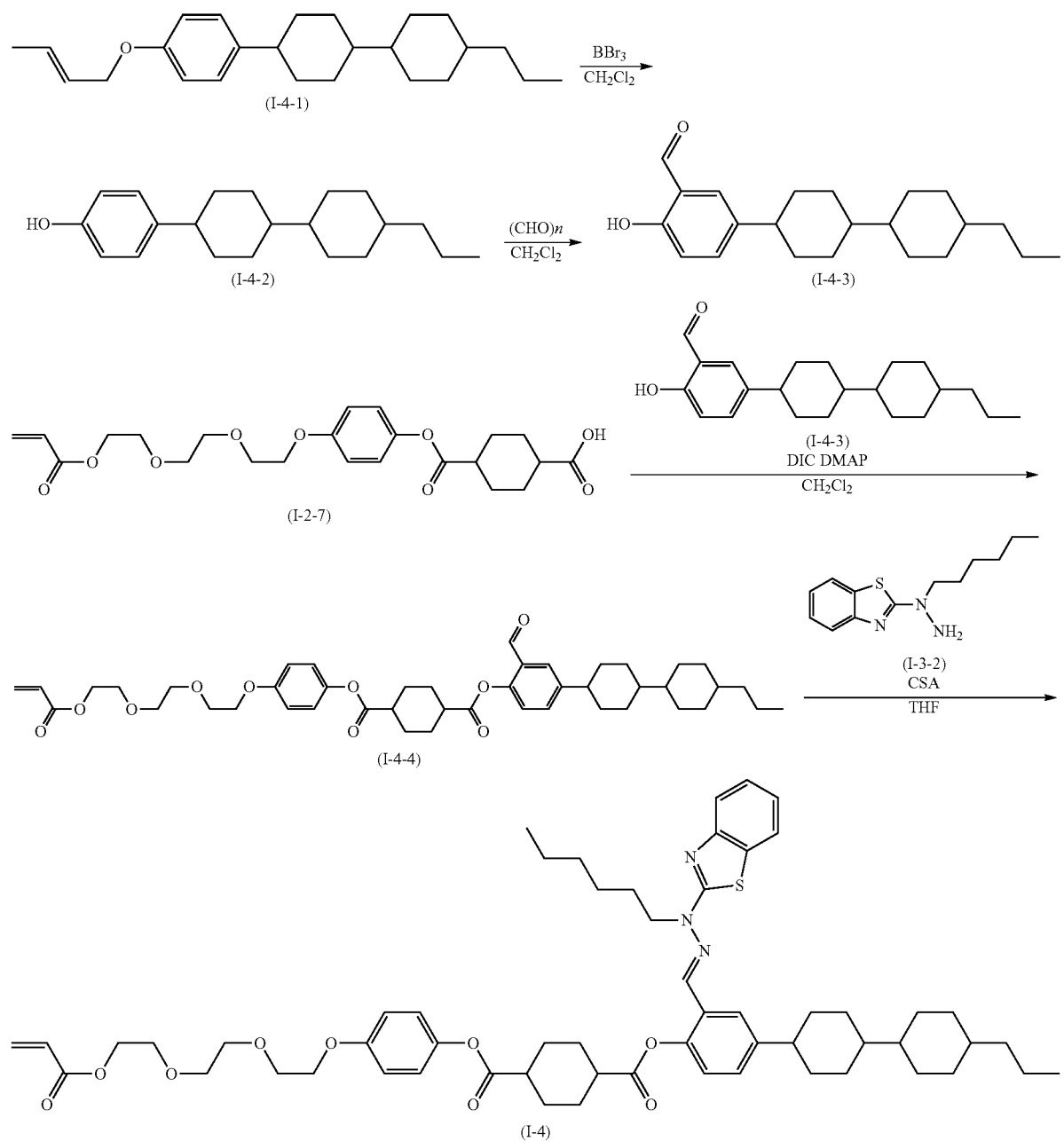

To a reaction vessel, 50 g of a compound represented by the formula (I-4-1) and 250 mL of dichloromethane were added. 50 g of boron tribromide was added dropwise under cooling with ice and the mixture was stirred at room temperature for 5 hours. The reaction solution was poured into water, and a precipitated solid was washed with water to yield 22.8 g of a compound represented by the formula (I-4-2).

To a reaction vessel, 19.8 g of the compound represented by the formula (I-4-2), 5.9 g of paraformaldehyde, 9.4 g of magnesium chloride, 40 mL of triethylamine, and 260 mL of acetonitrile were added, and stirred at 60° C. for 50 hours. The reaction solution was diluted with ethyl acetate and was washed with hydrochloric acid, water, and a saline solution in this order. Purification was performed by column chromatography (silica gel) to yield 11.8 g of a compound represented by the formula (I-4-3).

To a reaction vessel, 3.2 g of the compound represented by the formula (I-4-3), 5.0 g of the compound represented by the formula (I-2-7), 70 mg of N,N-dimethylaminopyridine, and 70 mL of dichloromethane were added 1.5 g of diisopropylcarbodiimide was added dropwise under cooling with ice and the mixture was stirred at room temperature for 10 hours. The reaction solution was filtered and the filtrate was purified by recrystallization (dichloromethane/methanol) to yield 8.4 g of a compound represented by the formula (I-4-4).

To a reaction vessel, 5.1 g of the compound represented by the formula (I-4-4), 1.7 g of the compound represented by the formula (I-3-2), 80 mg of (±)-10-camphorsulfonic acid, and 100 mL of tetrahydrofuran were added, and stirred at room temperature for 1 hour. The reaction solution, was diluted with dichloromethane, and was washed with water and a saline solution in this order, and the solvent was evaporated. Purification was performed by column chromatography (silica gel) and recrystallization (dichloromethane/methanol) to yield 3.7 g of a compound represented by the formula (I-4). Transition temperature (temperature increase: 5° C./min): C 90 Sm 218 N 265 I $^1$H NMR (CDCl$_3$) δ 0.88 (m, 6H), 1.01-1.19 (m, 8H), 1.32-1.45 (m, 6H), 1.71-1.76 (m, 6H), 1.88-1.99 (m, 3H), 2.17 (m, 12H), 2.31 (m, 4H), 2.53 (m, 2H), 2.67 (m, 1H), 3.70-3.76 (m, 6H), 3.85 (t, 2H), 4.11 (t, 2H), 4.31 (m, 4H), 5.82 (d, 2H), 6.15 (q, 2H), 6.43 (d, 2H), 6.92 (m, 5H), 7.14-7.26 (m, 2H), 7.33 (t, 1H), 7.68 (m, 3H), 7.38 (s, 1H) ppm.

Example 5

Production of Compound Represented by the Formula (I-5)

[Chem. 129]

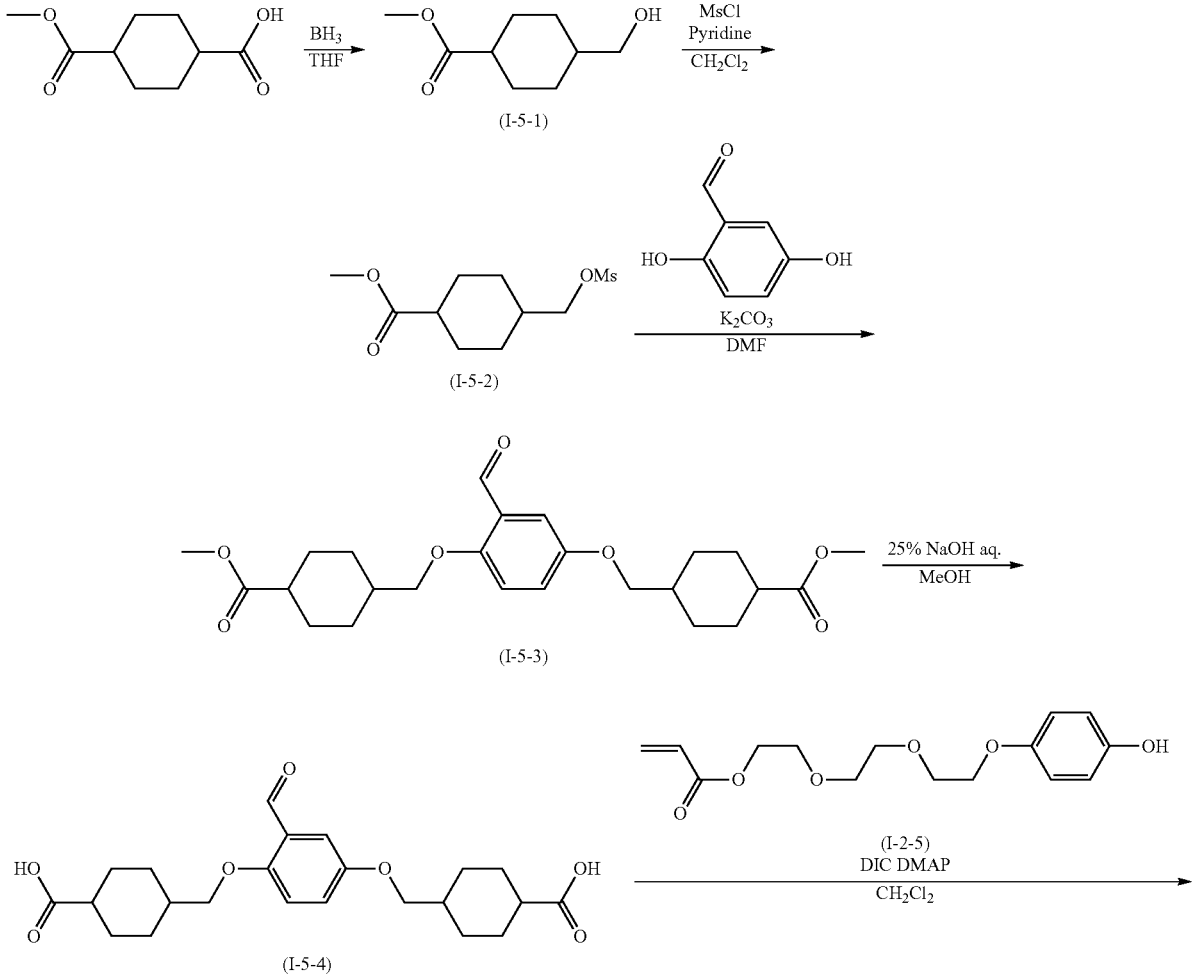

-continued

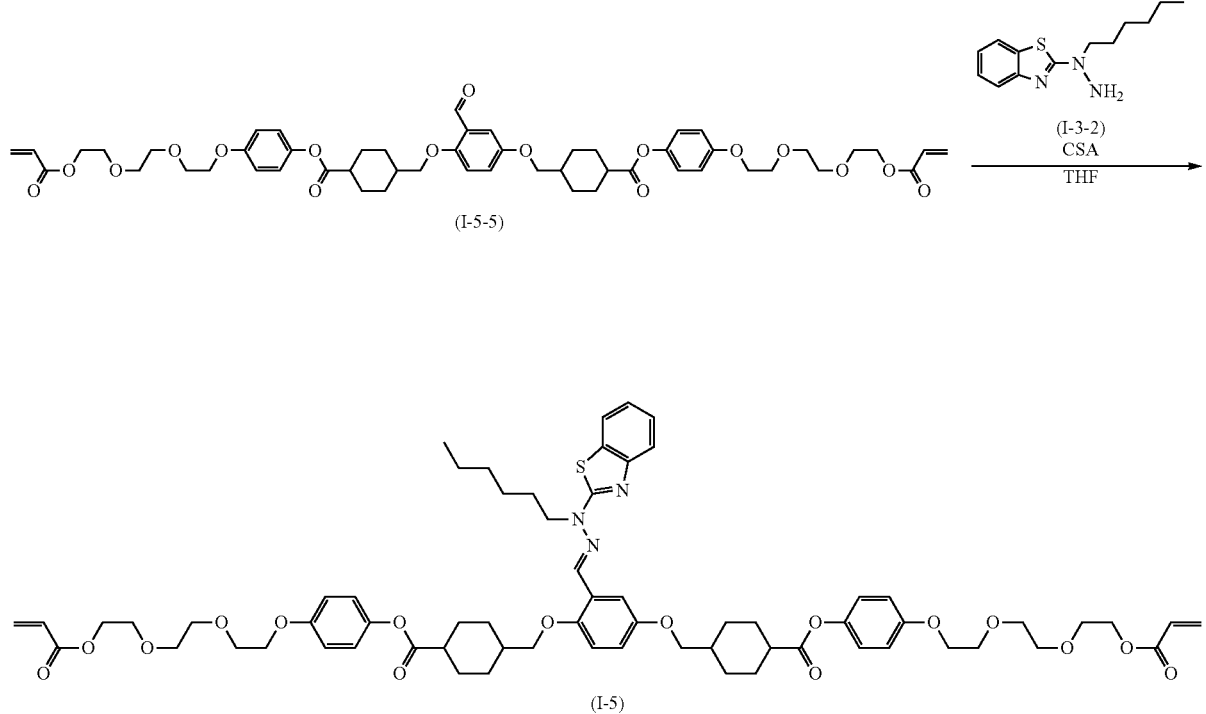

To a reaction vessel, 100.0 g of 4-methoxycarbonylcyclohexane carboxylic acid and 400 mL of tetrahydrofuran were added. A 1 mol/L solution of borane in tetrahydrofuran was added dropwise under cooling with ice and the mixture was stirred at room temperature for 3 hours. The reaction solution was diluted with dichloromethane, and was washed, with hydrochloric acid, a saturated aqueous sodium hydrogen carbonate solution, and a saline solution in this order. After drying over sodium sulfate, the solvent was evaporated. Purification was performed by distillation to yield 64.6 g of the compound represented by the formula (I-5-1).

To a reaction vessel, 127.0 g of the compound represented by the formula (I-5-1), 70 g of pyridine, and 250 mL of dichloromethane were added 92.9 g of methanesulfonyl-chloride was added dropwise under cooling with ice and the mixture was stirred at room temperature for 3 hours. The reaction solution was washed with hydrochloric acid, a saturated aqueous sodium hydrogen carbonate solution, and a saline solution in this order. After drying over sodium sulfate, the solvent was evaporated. Purification was performed by column chromatography (silica gel) and recrystallization (acetone/methanol, toluene/hexane) to yield 141.7 g of the compound represented by the formula (I-5-2).

To a reaction vessel, 100.1 g of the compound represented by the formula (I-5-2), 27.6 g of 2,5-dihydroxybenzaldehyde, 127.4 g of potassium phosphate, and 400 mL of dimethylformamide were added, and stirred at 90° C. for 6 hours. The reaction, solution was diluted with ethyl acetate, and was washed with hydrochloric acid, water, and a saline solution in this order. After drying over sodium, sulfate, the solvent was evaporated. Purification was performed by column chromatography (silica gel) and recrystallization (acetone/methanol, toluene/hexane) to yield 63.8 g of the compound represented by the formula (I-5-3).

To a reaction vessel, 63.4 g of the compound represented by the formula (I-5-3), 250 mL of tetrahydrofuran, and 150 mL of methanol were added 68.2 g of a 25% aqueous sodium hydroxide solution was added dropwise at room temperature and the mixture was stirred for 3 hours. The organic solvent was evaporated from the reaction solution, and the resultant was subjected to acid precipitation with hydrochloric acid, and was washed with water to yield 58.9 g of the compound represented by the formula (I-5-4).

To a reaction vessel, 10.0 g of the compound represented by the formula (I-5-4), 14.2 g of the compound represented by the formula (I-2-5), 580 mg of N,N-dimethylaminopyridine, and 240 mL of dichloromethane were added. 6.6 g of diisopropylcarbodiimide was added dropwise under cooling with ice and the mixture was stirred at room temperature for 7 hours. The reaction solution was filtered, and the filtrate was purified by column chromatography (silica gel) and recrystallization (dichloromethane/methanol) to yield 16.8 g of a compound represented by the formula (I-5-5).

To a reaction vessel, 5.3 g of the compound represented by the formula (I-5-5), 1.3 g of the compound represented by the formula (I-3-2), 60 mg of (±)-10-camphorsulfonic acid, and 25 mL of tetrahydrofuran were added, and stirred at room temperature for 8 hours. The reaction solution was diluted with dichloromethane, and was washed with water and a saline solution in this order, and the solvent was evaporated. Purification was performed by column chromatography (silica gel) and recrystallization (dichloromethane/methanol) to yield 4.3 g of a compound represented by the formula (I-5). Transition temperature (temperature increase: 5° C./min): C 77 S 90 N 109 I $^1$H NMR (CDCl$_3$) δ 0.89 (t, 3H), 1.20-1.35 (m, 10H), 1.61-1.69 (m, 6H), 1.78 (m, 2H), 1.90 (m, 2H), 2.07 (t, 4H), 2.23 (d, 4H), 2.50 (m, 2H), 3.69-3.76 (m, 12H), 3.83-3.87 (m, 8H), 4.11 (t, 4H), 4.32 (t, 6H), 5.82 (d, 2H), 6.15 (q, 2H), 6.42 (d, 2H), 6.83-6.98 (m, 10H), 7.13 (t, 1H), 7.32 (t, 1H), 7.53 (t, 1H), 7.66 (t, 2H), 8.13 (s, 1H) ppm.

Example 6

Production of Compound Represented by the Formula (I-6)

[Chem. 130]

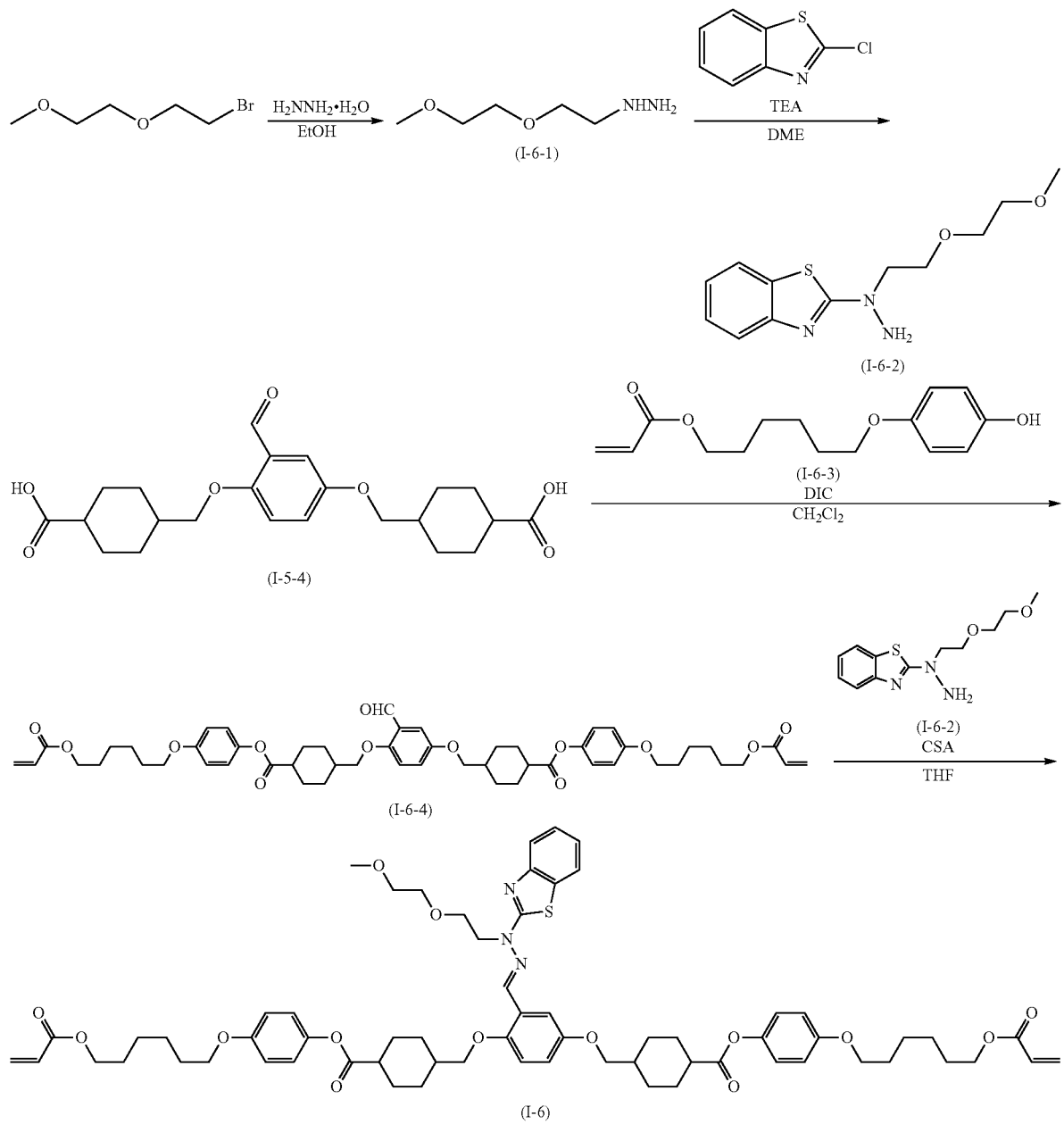

To a reaction vessel, 43.9 g of hydrazine monohydrate and 100 mL of ethanol were added 32.1 g of 1-bromo-2-(2-methoxyethoxyethoxy) ethane was added dropwise at 60° C., and the mixture was stirred at the same temperature for 3 hours. Ethanol was evaporated from the reaction solution to yield 51.9 g of a solid containing the compound represented by the formula (I-6-1).

To a reaction vessel, 18.0 g of 2-chlorobenzothiazole, 10.6 g of triethylamine, and 60 mL of 1,2-dimethoxyethane were added. A solution of 31.5 g of the solid containing the compound, represented by the formula (I-6-1) dissolved in 1,2-dimethoxyethane was added dropwise at room temperature and the mixture was stirred at 60° C. for 11 hours. The reaction solution was diluted with toluene, and was washed with water and a saline solution in this order, and the solvent was evaporated. Purification was performed by recrystallization (hexane) to yield 17.2 g of the compound represented by the formula (I-6-2).

To a reaction vessel, 51.8 g of the compound, represented by the formula (I-5-4), 65.4 g of the compound represented by the formula (I-6-3), 90.9 g of N,N-dimethylaminopyridine, and 500 mL of dichloromethane were added 40.7 g of diisopropylcarbodiimide was added dropwise under cooling with ice and the mixture was stirred at room temperature for 3 hours. The reaction solution was filtered and was washed with hydrochloric acid, water, and a saline solution in this order. Purification was performed by column chromatography (silica gel) and recrystallization (dichloromethane/methanol) to yield 56.5 g of the compound represented by the formula (I-6-4).

To a reaction vessel, 5.0 g of the compound, represented by the formula (I-6-4), 1.5 g of the compound represented by the formula (I-6-2), 60 mg of (±)-10-camphorsulfonic acid, and 100 mL of tetrahydrofuran were added, and stirred at room temperature for 8 hours. The reaction solution was purified by column chromatography (silica gel) and recrystallization (dichloromethane/hexane) to yield 6.4 g of the compound represented by the formula (I-6).

Transition temperature (temperature increase: 5° C./min): C 85 N 128 I $^1$H NMR (CDCl$_3$) δ 1.22-1.28 (m, 4H), 1.44-1.47 (m, 8H), 1.60-1.82 (m, 12H), 1.90 (m, 2H), 2.07 (t, 4H), 2.24 (d, 4H), 2.53 (m, 2H), 3.30 (s, 3H), 3.50 (t, 2H), 3.66 (t, 2H), 3.85-3.39 (m, 6H), 3.93 (t, 4H), 4.17 (t, 4H), 4.53 (t, 2H), 5.82 (d, 2H), 6.13 (q, 2H), 6.40 (d, 2H), 6.83-6.90 (m, 6H), 6.95-6.98 (m, 4H), 7.14 (t, 1H), 7.32 (t, 1H), 7.52 (t, 1H), 7.67 (t, 2H), 8.33 (s, 1H) ppm.

Example 7

Production of Compound Represented by the Formula (I-7)

[Chem. 131]

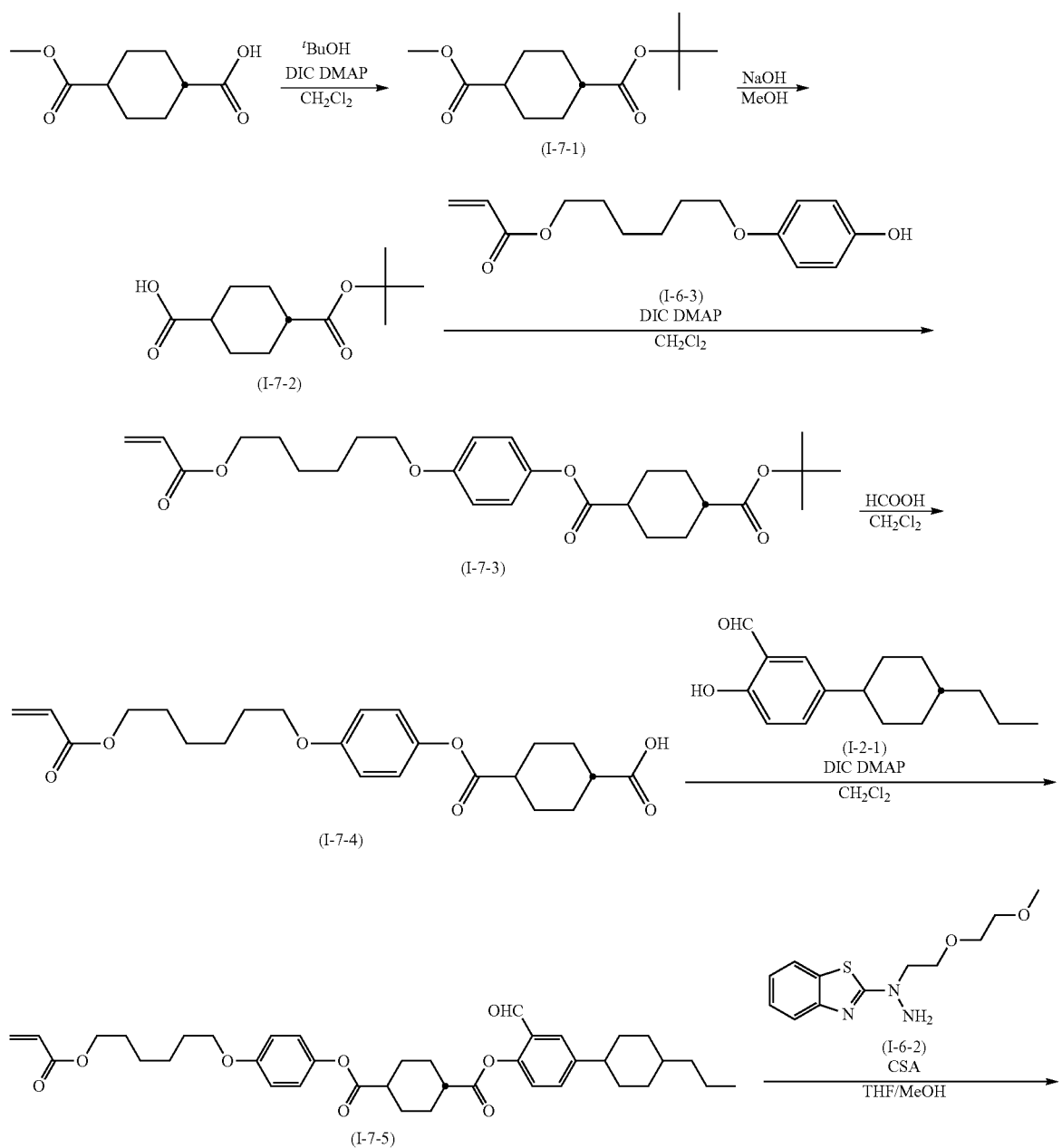

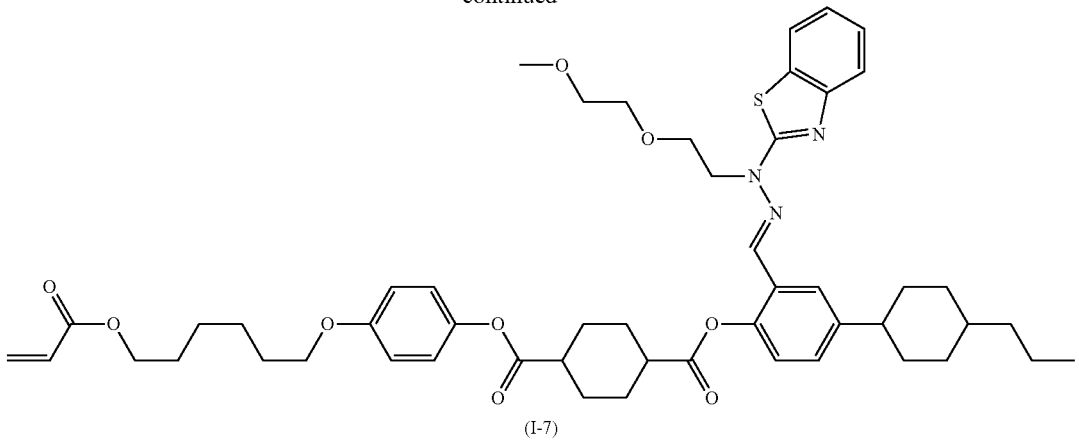

(I-7)

To a reaction vessel, 440.0 g of 4-methoxycarbonylcyclohexane carboxylic acid, 175.1 g of t-butanol, 28.9 g of N,N-diethylaminopyridine, and 1760 mL of dichloromethane were added 357.8 g of diisopropylcarbodiimide was added dropwise under cooling with ice and the mixture was stirred at room temperature for 4 hours.

The reaction solution was filtered, and the filtrate was washed with hydrochloric acid, water, and a saline solution in this order. Purification was performed by column chromatography (silica gel) to yield 416.6 g of a compound represented by the formula (I-7-1).

To a reaction vessel, 416.6 g of the compound represented by the formula (I-7-1) and 1430 mL of methanol were added. 228.8 g of a 30% aqueous sodium hydroxide solution was added dropwise, and the mixture was stirred at room, temperature for 7 hours. Methanol was evaporated, from the reaction solution, and the resultant was subjected to acid precipitation with hydrochloric acid. The precipitation was extracted with dichloromethane, and dichloromethane was evaporated to yield 325.4 g of the compound represented by the formula (I-7-2).

To a reaction vessel, 220.0 g of the compound represented by the formula (I-7-2), 254.7 g of the compound represented by the formula (I-6-3), 5.9 g of N,N-dimethylaminopyridine, and 1300 mL of dichloromethane were added 145.9 g of diisopropylcarbodiimide was added dropwise under cooling with ice, and the mixture was stirred at room temperature for 8 hours. The reaction solution was filtered, and the filtrate was washed with hydrochloric acid, water, and a saline solution in this order. Purification was performed by column chromatography (silica gel) and recrystallization (dichloromethane/methanol) to yield 350.1 q or a compound represented by the formula (I-7-3).

To a reaction vessel, 350.1 g of the compound represented by the formula (I-7-3), 1750 mL of dichloromethane, and 1400 mL of formic acid were added, and the mixture was stirred at room temperature for 5 hours. Dichloromethane was evaporated from the reaction solution, and purification was performed by recrystallization (diisopropyl ether/formic acid) to yield 247.4 g of a compound represented by the formula (I-7-4).

To a reaction vessel, 10.0 g of the compound represented by the formula (I-7-4), 5.9 g of the compound represented by the formula (I-2-1), 290 mg of N,N-dimethylaminopyridine, and 150 mL of dichloromethane were added 3.3 g of diisopropylcarbodiimide was added dropwise under cooling with ice, and the mixture was stirred at room temperature for 3 hours. The reaction solution was filtered, and was washed with hydrochloric acid, water, and a saline solution in this order. Purification was performed by column chromatography (silica gel) and recrystallization (dichloromethane/methanol) to yield 8.0 g of a compound represented by the formula (I-7-5).

To a reaction vessel, 6.0 g of the compound represented by the formula (I-7-5), 2.6 g of the compound represented by the formula (I-6-2), 110 mg of ($\pm$)-10-camphorsulfonic acid, and 60 mL of tetrahydrofuran were added, and stirred at room temperature for 6 hours. The reaction solution was diluted with ethyl acetate, and was washed with water and a saline solution in this order, and the solvent was evaporated. Purification was performed by column chromatography (silica gel) and recrystallization (dichloromethane/methanol) to yield 1.6 g of a compound represented by the formula (I-7). Transition temperature (temperature increase: 5° C./min): C 106 N 125 I $^1$H NMR (CDCl$_3$) δ 0.92 (t, 3H), 1.11 (q, 2H), 1.25 (m, 2H), 1.36 (m, 2H), 1.48 (m, 4H), 1.68-1.81 (m, 12H), 1.93 (t, 4H), 2.32 (m, 3H), 2.58 (m, 2H), 2.71 (m, 1H), 3.30 (s, 3H), 3.48 (m, 2H), 3.62 (m, 2H), 3.85 (t, 2H), 3.94 (t, 2H), 4.17 (t, 2H), 4.47 (t, 2H), 5.82 (d, 2H), 6.12 (q, 2H), 6.40 (d, 2H), 6.87 (d, 2H), 6.96 (m, 3H), 7.16 (t, 1H), 7.22 (m, 1H), 7.33 (t, 1H), 7.70 (q, 2H), 7.88 (d, 1H), 8.01 (s, 1H) ppm.

Example 8

Production of Compound Represented by the Formula (I-8)

[Chem. 132]

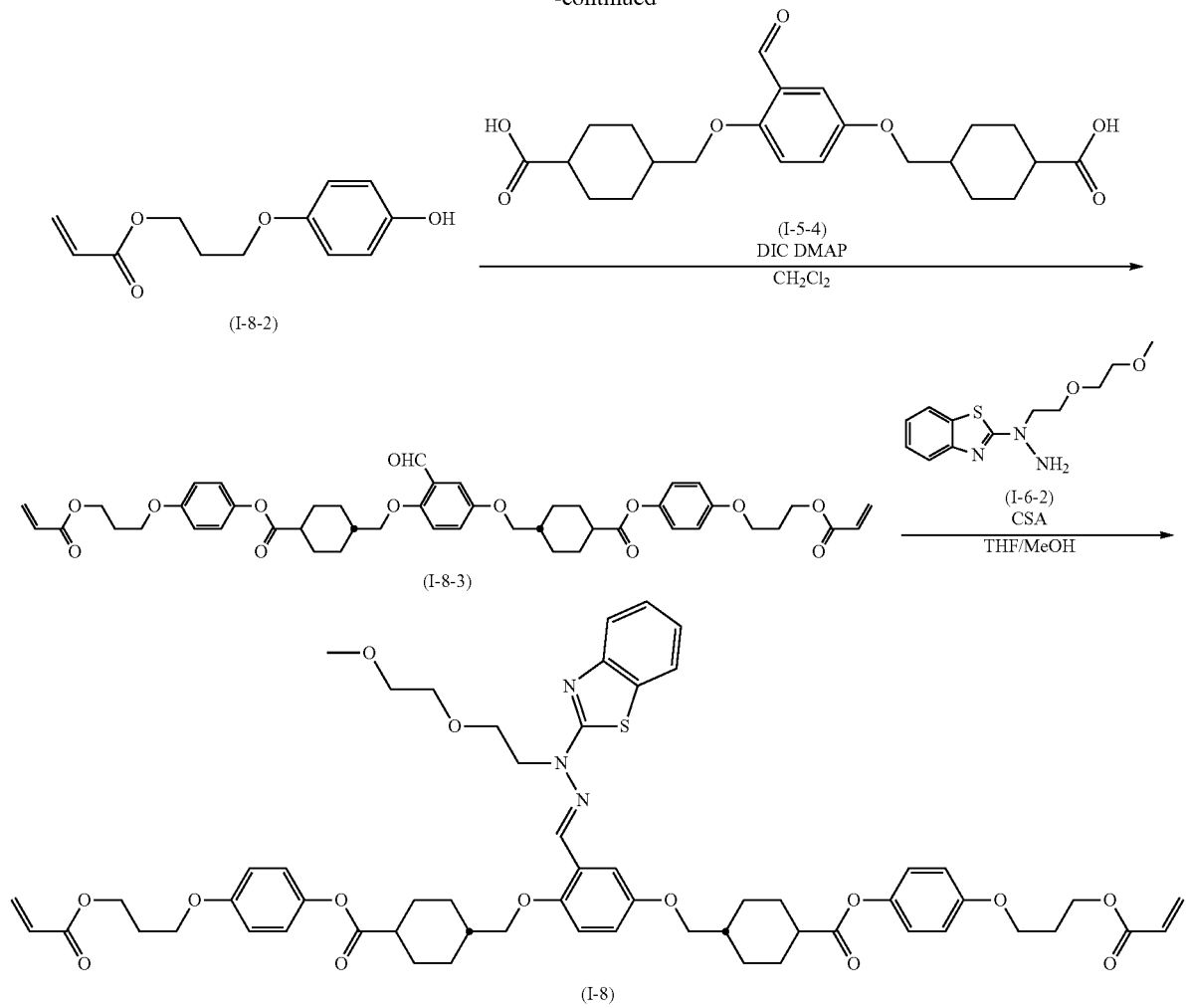

To a reaction vessel, 70.0 g of the compound represented by the formula (I-2-3), 64.2 g of 3-chloropropylacrylate, 140.3 g of cesium carbonate, 350 mL of N, N-dimethylformamide were added, and stirred at 65° C. for 16 hours. The reaction solution was diluted with ethyl acetate, and was washed with water and a saline solution in this order. Purification was performed by column chromatography (alumina) to yield 88.3 g of a compound represented by the formula (I-3-1).

To a reaction vessel, 88.3 g of the compound represented by the formula (I-8-1), 20 mL of 10% hydrochloric acid, 330 mL of methanol, and 330 mL of tetrahydrofuran were added, and stirred at room temperature for 90 minutes. The reaction solution was washed with a saturated aqueous sodium hydrogen carbonate solution, water, and a saline solution in this order, and the solvent was evaporated. Purification was performed by column chromatography (silica gel) and recrystallization (dichloromethane/hexane) to yield 52.9 g of a compound represented by the formula (I-8-2).

To a reaction vessel, 9.6 g of the compound represented by the formula (I-8-2), 9.0 g of the compound represented by the formula (I-5-4), 260 mg of N,N-dimethylaminopyridine, and 200 mL of dichloromethane were added 6.0 g of diisopropylcarbodiimide was added dropwise under cooling with ice and the mixture was stirred at room temperature for 15 hours. The reaction solution was filtered, and the filtrate was washed with hydrochloric acid, water, and a saline solution in this order. Purification was performed by column chromatography (silica gel) and recrystallization (dichloromethane/methanol) to yield 7.9 g of a compound represented by the formula (I-8-3).

To a reaction vessel, 7.9 g of the compound represented by the formula (I-8-3), 2.7 g of the compound represented by the formula (I-6-2), 0.1 g of (±)-10-camphorsulfonic acid, and 50 mL of tetrahydrofuran were added, and stirred at 50° C. The solvent was evaporated from the reaction solution, and was subjected to dispersion-washing with methanol. Purification was performed by column chromatography (silica gel) and recrystallization (dichloromethane/methanol, dichloromethane/hexane) to yield 8.4 g of a compound represented by the formula (I-8).

Transition temperature (temperature increase: 5° C./min): C 89-95 N 145 I $^1$H NMR (CDCl$_3$) δ 1.24 (m, 4H), 1.65 (m, 4H), 1.91 (m, 2H), 2.05-2.25 (m, 12H), 2.55 (m, 2H), 3.30 (s, 3H), 3.51 (m, 2H), 3.67 (m, 2H), 3.84-3.89 (m, 6H), 4.05 (t, 4H), 4.36 (t, 4H), 4.54 (t, 2H), 5.84 (dd, 2H), 6.13 (dd, 2H), 6.41 (dd, 2H), 6.84-6.89 (m, 6H), 6.97-7.00 (m, 4H), 7.14 (t, 1H), 7.33 (t, 1H), 7.52 (d, 1H), 7.67 (dd, 2H), 8.34 (s, 1H) ppm. LCMS: 1076 [M+1]

Example 9
Production of Compound Represented by the Formula (I-9)
[Chem. 133]
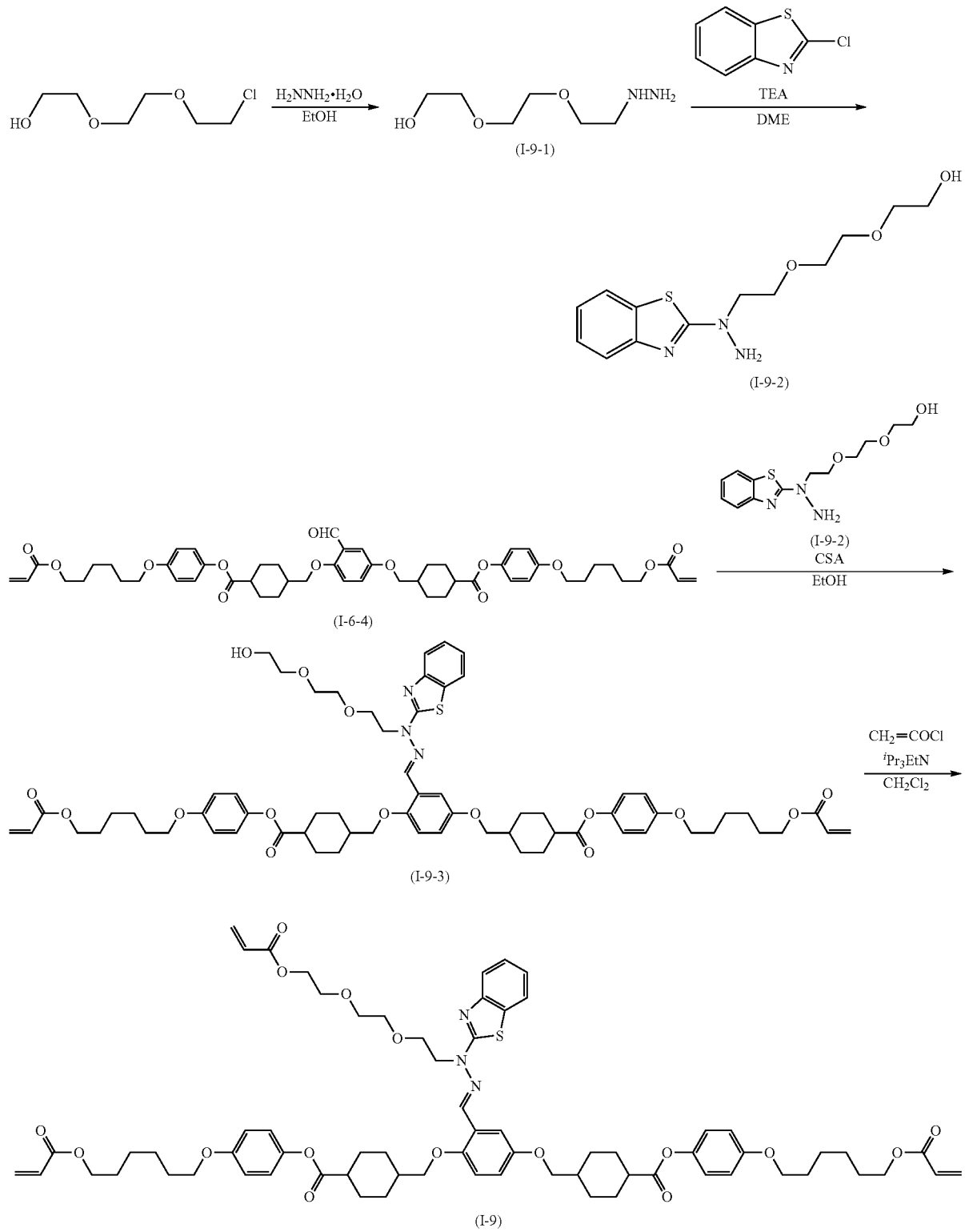

To a reaction vessel, 100 mL of hydrazine monohydrate and 100 mL of ethanol were added. Under heating at 50° C., 10.0 g of 2-[2-(2-chloroethoxy)ethoxy]ethanol was added dropwise and the mixture was stirred at the same temperature for 3 hours. The solvent was evaporated from the reaction solution to yield a mixture containing a compound represented by the formula (I-9-1).

To a reaction vessel, 5.0 g of 2-chlorobenzothiazole, 30 mL of 1,2-dimethoxyethane, and 3.6 g of triethylamine, were added. Under heating at 60° C., the mixture containing the compound represented by the formula (I-9-1) was added, and the resulting mixture was stirred at the same temperature for 2 hours. The reaction solution was diluted with dichloromethane, and was washed with water and a saline solution in this order. After drying over sodium sulfate, the solvent was evaporated to yield 7.0 g of a compound represented by the formula (I-9-2).

To a reaction vessel, 5.0 g of the compound represented by the formula (I-6-4), 1.6 g of the compound represented by the formula (I-9-2), 0.6 g of (±)-10-camphorsulfonic acid, 20 mL of tetrahydrofuran, and 20 mL of ethanol were added, and the mixture was stirred at 50° C. for 10 hours. The solvent was evaporated from the reaction solution, and purification was performed by column chromatography (silica gel) and recrystallization (dichloromethane/methanol) to yield 3.9 g of a compound represented by the formula (I-9-3).

To a reaction vessel, 3.9 g of the compound represented by the formula (I-9-3), 0.6 g of diisopropylethylamine, and 80 mL of dichloromethane were added 0.4 g of acryloyl chloride was added dropwise under cooling with ice, and the mixture was stirred at room temperature for 8 hours. The reaction solution was washed with hydrochloric acid and a saline solution in this order, the solvent was evaporated, and the resultant was subjected to dispersion washing with methanol. Purification was performed by column chromatography (silica gel) and recrystallization (dichloromethane/methanol) to yield 2.5 g of a compound represented by the formula (I-9).

Transition temperature (temperature increase: 5° C./min) C 71 N 115 I $^1$H NMR (CDCl$_3$) δ 1.19-1.29 (m, 4H), 1.41-1.82 (m, 22H), 1.91 (m, 2H), 2.08 (m, 4H), 2.24 (m, 4H), 2.53 (m, 2H), 3.62 (m, 3H), 3.67 (m, 2H), 3.84-3.90 (m, 5H), 3.94 (t, 4H), 4.15-4.19 (m, 6H), 4.53 (t, 2H), 5.76 (dd, 1H), 5.82 (dd, 2H), 6.08 (dd, 1H), 6.12 (dd, 2H), 6.37 (dd, 1H), 6.40 (dd, 2H), 6.84-6.90 (m, 6H), 6.95-6.98 (m, 4H), 7.14 (t, 1H), 7.32 (t, 1H), 7.53 (d, 1H), 7.65 (d, 1H), 7.69 (d, 1H), 8.34 (s, 1H) ppm.

LCMS: 1244 [M+1]

Example 10

Production of Compound Represented by the Formula (I-10)

[Chem. 134]

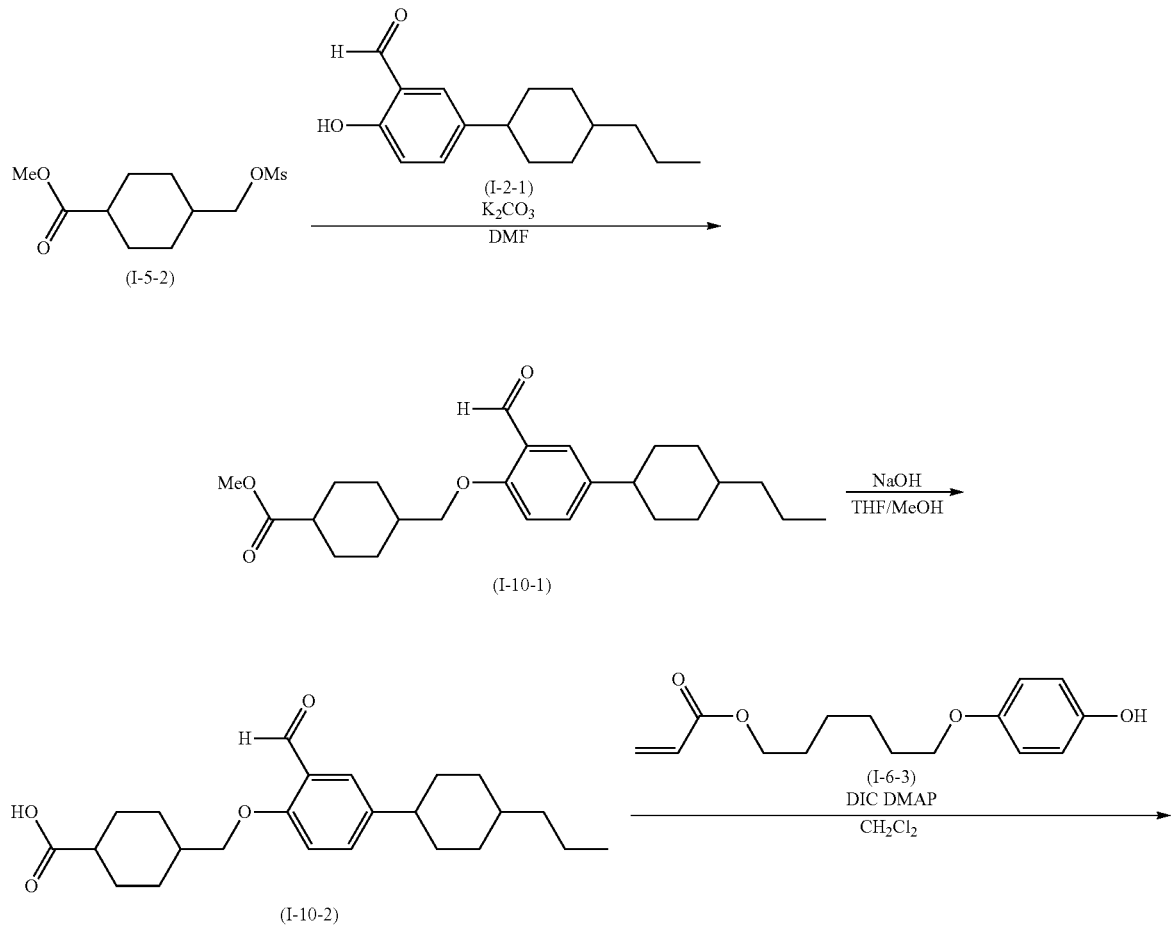

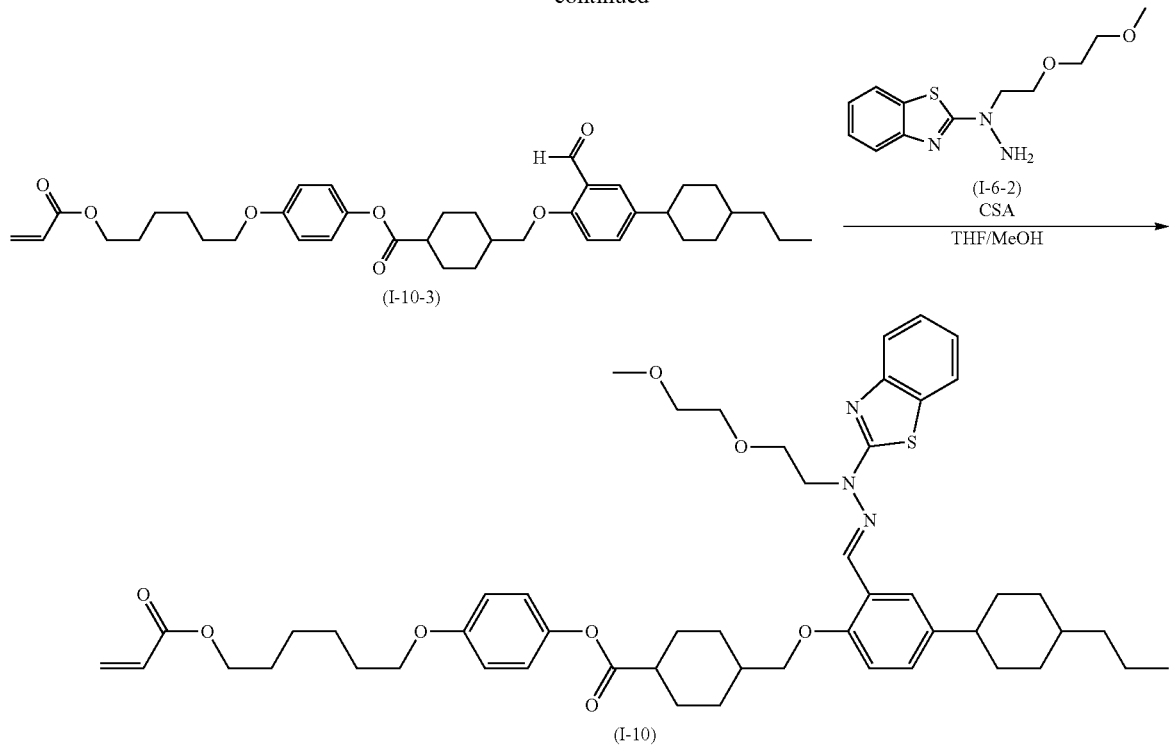

To a reaction vessel, 4.0 g of the compound represented by the formula (I-5-2), 3.9 g of the compound represented by the formula (I-2-1), 3.5 g of potassium carbonate, and 30 mL of N,N-dimethylformamide were added, and stirred at 90° C. for 12 hours. The reaction solution was diluted with dichloromethane, and was washed with water and a saline solution in this order. Purification was performed by column chromatography (silica gel) and recrystallization to yield 5.1 g of a compound represented by the formula (I-10-1).

To a reaction vessel, 5.1 g of the compound represented by the formula (I-10-1), 30 mL of tetrahydrofuran, 30 mL of methanol, and 10 mL of a 25% aqueous sodium hydroxide solution were added, and stirred at 60° C. Hydrochloric acid was added, and the solvent was evaporated. The resultant was washed with water and dried to yield 4.9 g of a compound represented by the formula (I-10-2).

To a reaction vessel, 4.9 g of the compound represented by the formula (I-10-2), 3.4 g of the compound represented by the formula (I-6-3), 100 mg of N,N-dimethylaminopyridine, and 40 mL of dichloromethane were added 1.6 g of diisopropylcarbodiimide was added dropwise under cooling with ice and the mixture was stirred at room temperature. The reaction solution was filtered, and the filtrate was purified by column chromatography (silica gel) and recrystallization to yield 5.7 g of a compound represented by the formula (I-10-3).

To a reaction vessel, 2.5 g of the compound represented by the formula (I-10-3), 1.1 g of the compound represented by the formula (I-6-2), 0.5 g of (±)-10-camphorsulfonic acid, 10 mL of tetrahydrofuran, and 10 mL of ethanol were added, and stirred at 50° C. The solvent was evaporated from the reaction solution, and was subjected to dispersion, washing with methanol. Purification was performed by column chromatography (silica gel) and recrystallization to yield 2.1 g of a compound represented by the formula (I-10). Transition temperature (temperature increase: 5° C./min, temperature decrease: 5° C./min): C 101-105 (N 82) I $^1$H NMR (CDCl$_3$) δ 0.92 (t, 3H), 1.08-1.91 (m, 26H), 2.06 (d, 2H), 2.24 (d, 2H), 2.51 (m, 2H), 3.30 (s, 3H), 3.51 (dd, 2H), 3.67 (dd, 2H), 3.87 (quin, 4H), 3.34 (t, 2H), 4.17 (t, 2H), 4.54 (t, 2H), 5.82 (dd, 1H), 6.12 (dd, 1H), 6.40 (dd, 1H), 6.86 (m, 3H), 6.97 (m, 2H), 7.16 (m, 2H), 7.32 (t, 1H), 7.65 (d, 1H), 7.70 (d, 1H), 7.82 (d, 1H), 8.36 (s, 1H) ppm.

Example 11

Production of Compound Represented by the Formula (I-11)

[Chem. 135]

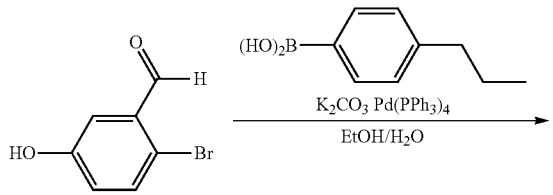

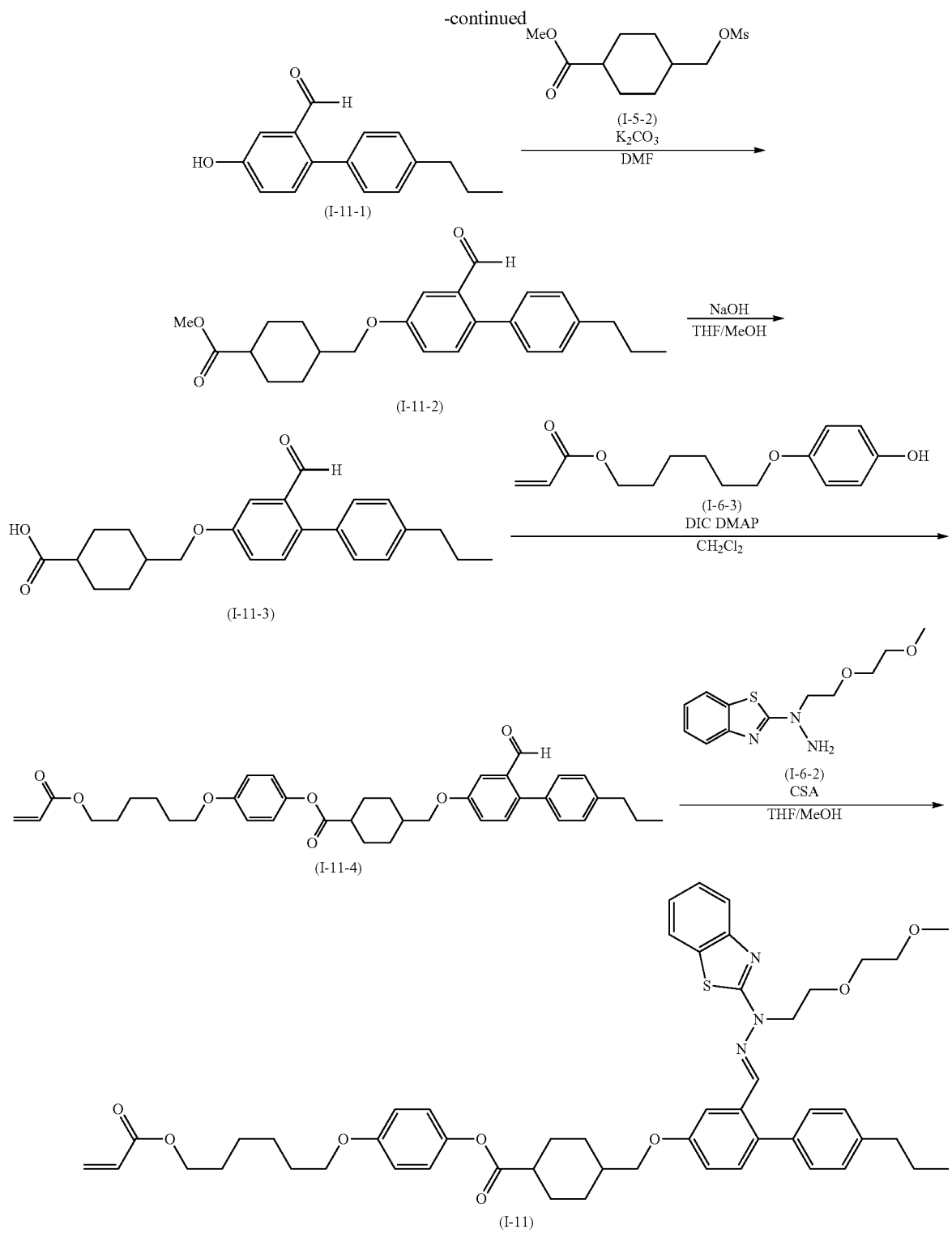

To a reaction vessel, 10.0 g of 2-bromo-5-hydroxybenzaldehyde, 8.2 g of propylphenylboric acid, 10.3 g of potassium carbonate, 1.1 g of tetrakis(triphenylphosphine) palladium(0), 50 mL of ethanol, and 50 mL of water were added and stirred at 60° C. The reaction solution was diluted with ethyl acetate and was washed with hydrochloric acid and a saline water in this order, and the solvent was evaporated. Purification was performed by column chromatography (silica gel) to yield 4.8 g of a compound represented by the formula (I-11-1).

To a reaction vessel, 4.0 g of a compound represented by the formula (I-11-1), 4.2 g of the compound represented by the formula (I-5-2), 3.5 g of potassium carbonate, and 30 mL of N,N-dimethylformamide were added, and stirred at 90°

C. for 12 hours. The reaction solution was diluted with dichloromethane, and was washed with water and a saline solution in this order. Purification was performed by column chromatography (silica gel) and recrystallization to yield 4.6 g of a compound represented by the formula (I-11-2).

To a reaction vessel, 4.6 g of the compound represented by the formula (I-11-2), 30 mL of tetrahydrofuran, 30 mL of methanol, and 10 mL of a 25% aqueous sodium hydroxide solution were added, and stirred at 60° C. Hydrochloric acid was added, and the solvent was evaporated. The resultant was washed with water and dried to yield 4.4 g of a compound represented by the formula (I-11-3).

$^1$H NMR (CDCl$_3$) δ 1.00 (t, 3H), 1.28 (m, 2H), 1.45-1.81 (m, 12H), 1.97 (br, 1H), 2.13 (m, 2H), 2.26 (m, 2H), 2.57 (tt, 1H), 2.65 (t, 2H), 3.27 (s, 3H), 3.37 (m, 2H), 3.50 (m, 2H), 3.70 (t, 2H), 3.95 (q, 4H), 4.17 (t, 2H), 4.33 (t, 2H), 5.82 (dd, 1H), 6.12 (dd, 1H), 6.40 (dd, 1H), 6.87 (d, 2H), 6.38 (m, 3H), 7.15 (t, 1H), 7.25 (m, 5H), 7.32 (t, 1H), 7.64 (m, 2H), 7.69 (d, 1H), 7.91 (s, 1H) ppm.

Example 12

Production of Compound Represented by the Formula (I-12)

[Chem. 136]

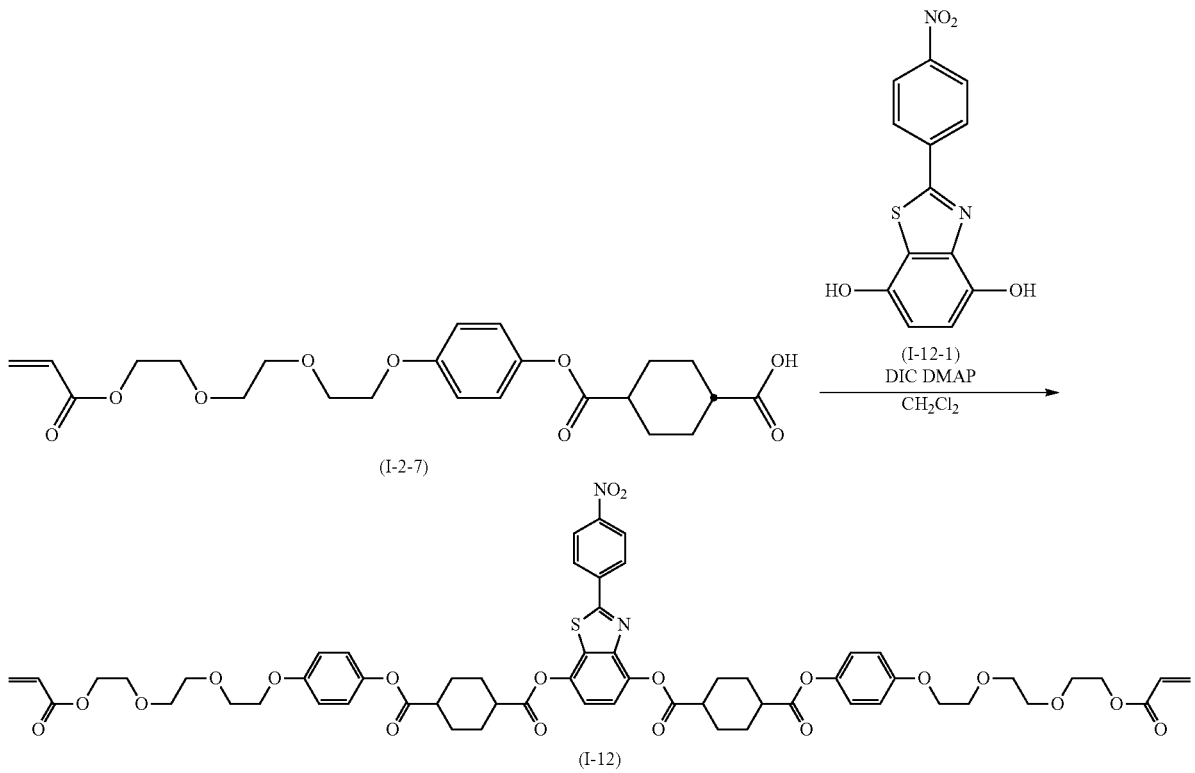

To a reaction vessel, 4.4 g of the compound represented by the formula (I-11-3), 3.1 g of the compound represented by the formula (I-6-3), 100 mg of N,N-dimethylaminopyridine, and 49 mL of dichloromethane were added 1.8 g of diisopropylcarbodiimide was added dropwise, under cooling with ice and the mixture was stirred at room temperature. The reaction solution was filtered, and the filtrate was purified by column chromatography (silica gel) and recrystallization to yield 5.1 g of a compound represented by the formula (I-11-4).

To a reaction vessel, 2.5 g of the compound represented by the formula (I-11-4), 1.1 g of the compound represented by the formula (I-6-2), 0.5 g of (±)-10-camphorsulfonic acid, 10 mL of tetrahydrofuran, and 10 mL of ethanol were added, and the mixture was stirred at 50° C. The solvent was evaporated from the reaction solution, and was subjected to dispersion washing with methanol. Purification was performed by column chromatography (silica gel) and recrystallization to yield 1.8 g of a compound represented by the formula (I-11). Transition temperature (temperature increase: 5° C./min): C 67-100 I A compound represented by the formula (I-12-1) was produced according to a method, disclosed, in PTL2. To a reaction vessel, 47.8 g of the compound represented by the formula (I-2-7), 15.3 g of the compound represented by the formula (I-12-1), 1.3 g of N,N-dimethylaminopyridine, and 300 mL of dichloromethane were added 14.7 g of diisopropylcarbodiimide was added dropwise under cooling with ice and the mixture was stirred at room temperature for 6 hours. The reaction solution was filtered, and the filtrate was washed with hydrochloric acid, water, and a saline solution in this order. Purification was performed by column, chromatography (silica gel) and recrystallization (dichloromethane/methanol) to yield 37.9 g of a compound represented by the formula (I-12).

LCMS: 1153 [M+1]

Example 13

Production of Compound Represented by the Formula (I-13)

[Chem. 137]

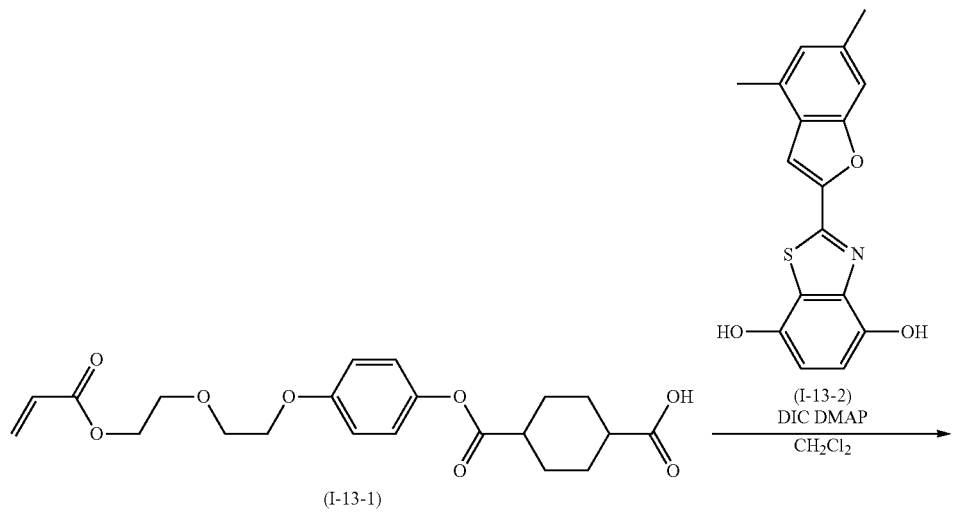

(I-13)

A compound represented by the formula (I-13-1) was produced in the same manner as in the Example 2 except of using 2-(2-chloroethoxy)ethanol in place of 2-[2-(2-chloroethoxy)ethoxy]ethanol. A compound represented by the formula (I-13-2) was produced according to a method disclosed in JP-A-2011-207765.

To a reaction vessel, 12.8 g of the compound represented by the formula (I-13-1), 4.9 g of the compound represented by the formula (I-13-2), 380 mg of N,N-dimethylamine-pyridine, and 100 mL of dichloromethane were added 4.4 g of diisopropylcarbodiimide was added dropwise under cooling with ice and the mixture, was stirred at room temperature for 4 hours. The reaction solution was filtered, and the filtrate was washed with hydrochloric acid, water, and a saline solution in this order. Purification was performed by column chromatography (silica gel) and recrystallization (dichloromethane/methanol) to yield 9.6 g of a compound represented by the formula (I-13).

LCMS: 1088 [M+1]

Example 14

Production of Compound Represented by the Formula (I-14)

[Chem. 138]

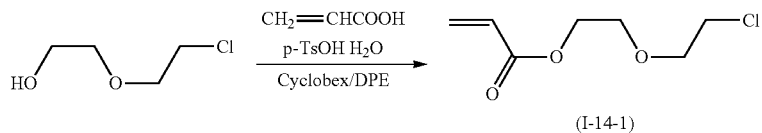

(I-14-1)

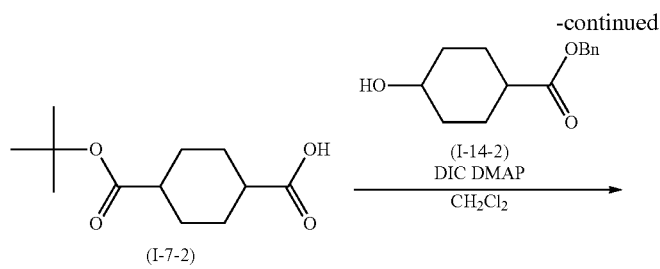
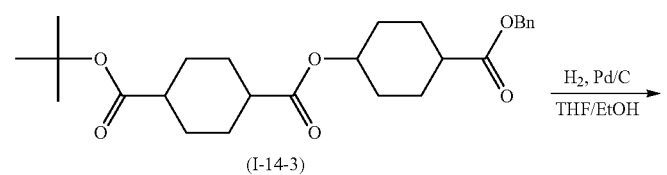
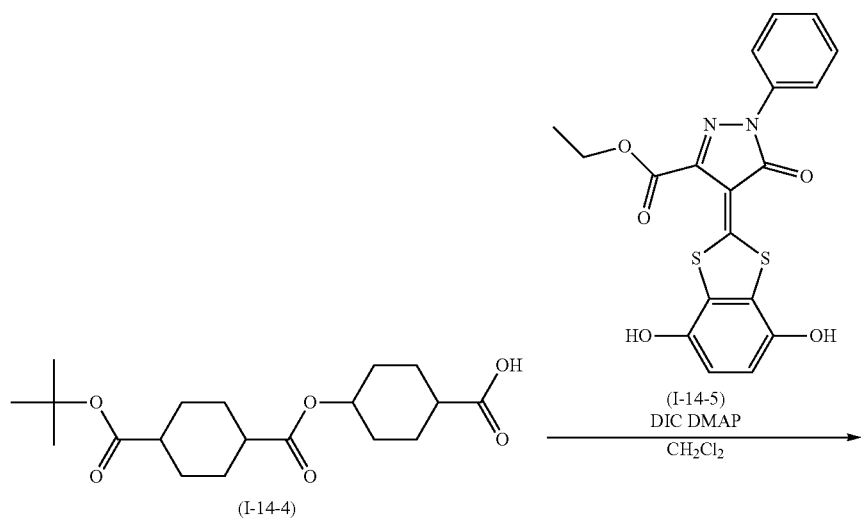
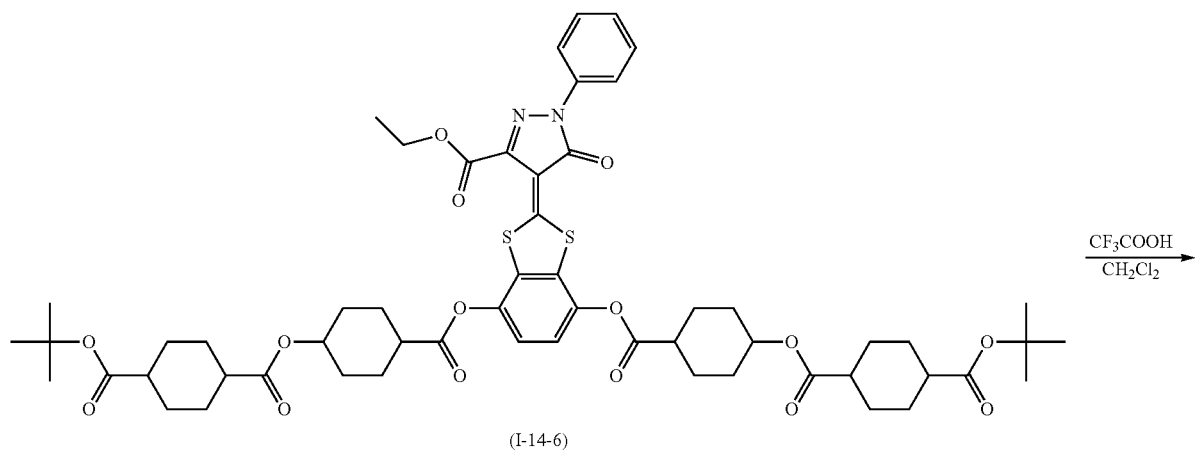

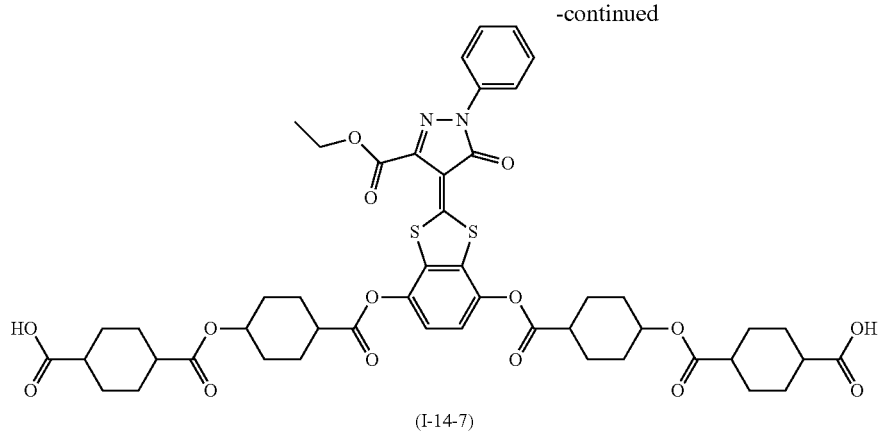

(I-14-7)

(I-14-1)
Cs$_2$CO$_3$
———————→
DMSO

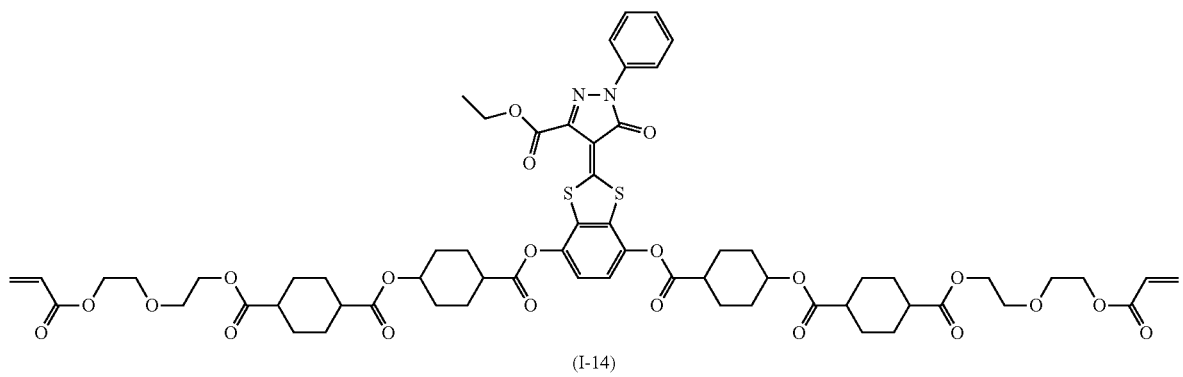

(I-14)

Compounds represented by the formula (I-14-2) and the formula (I-14-5) were produced according to a method disclosed in JP-A-2009-179563.

To a reaction vessel, 100.0 g of 2-(2-chloroethoxy)ethanol, 69.7 g of acrylic acid, 200 mg of 4-methoxyphenol, 7.7 g of p-toluene sulfonic acid monohydrate, 400 mL of cyclohexane, and 100 mL of diisopropyl ether were added, and stirred at 78° C. for 6 hours. The reaction solution was washed with a saturated aqueous sodium hydrogen carbonate solution, water, and a saline solution in this order, and the solvent was evaporated. Purification was performed by column chromatography (silica gel) to yield 131.0 g of a compound represented by the formula (I-14-1).

To a reaction vessel, 50.0 g of the compound, represented by the formula (I-7-2), 51.3 g of the compound represented by the formula (I-14-2), 2.6 g of N,N-dimethylaminopyridine, and 500 mL of dichloromethane were added 33.2 g of diisopropylcarbodiimide was added dropwise under cooling with ice and the mixture stirred at room temperature. The reaction solution was filtered, and the filtrate was purified by column chromatography (silica gel) and recrystallization to yield 65.2 g of a compound represented by the formula (I-14-3).

To an autoclave reaction vessel, 65.2 g of the compound represented by the formula (I-14-3), 3.3 g of 5% palladium/carbon (50% Wet), 200 mL of tetrahydrofuran, and 200 mL of methanol were added, and stirred under 0.5 MPa hydrogen atmosphere, at room temperature for 5 hours. The reaction solution was filtered, and the solvent was evaporated to yield 46.8 g of a compound represented by the formula (I-14-4).

To a reaction vessel, 17.1 g of the compound represented by the formula (I-14-4), 10.0 g of the compound represented by the formula (I-14-5), 590 mg of N,N-dimethylaminopyridine, and 300 mL of dichloromethane were added 6.7 g of diisopropylcarbodiimide was added dropwise under cooling with ice and the mixture was stirred at room temperature. The reaction solution was filtered, and the filtrate was purified by column chromatography (silica gel) to yield 17.3 g of a compound represented by the formula (I-14-6).

To a reaction vessel, 17.3 g of the compound represented by the formula (I-14-6), 50 mL of dichloromethane, and 50 mL of trifluoroacetic acid were added, and stirred for 3 hours. After dichloromethane was evaporated, diisopropyl ether was added, and precipitated solid was filtered to yield 13.2 g of a compound represented by the formula (I-14-7).

To a reaction vessel, 13.2 g of the compound represented by the formula (I-14-7), 5.3 g of the compound represented by the formula (I-14-1), 10.6 g of cesium carbonate, and 60 mL of dimethylsulfoxide were added, and stirred at 60° C. for 12 hours. The reaction solution was diluted with dichloromethane, and was washed with hydrochloric acid, water, and a saline solution in this order. Purification was performed by column chromatography (silica gel) and recrystallization (dichloromethane/methanol) to yield 10.8 g of a compound represented by the formula (I-14).

LCMS: 1259 [M+1]

Example 15
Production of Compound Represented by the Formula (I-15)
[Chem. 139]
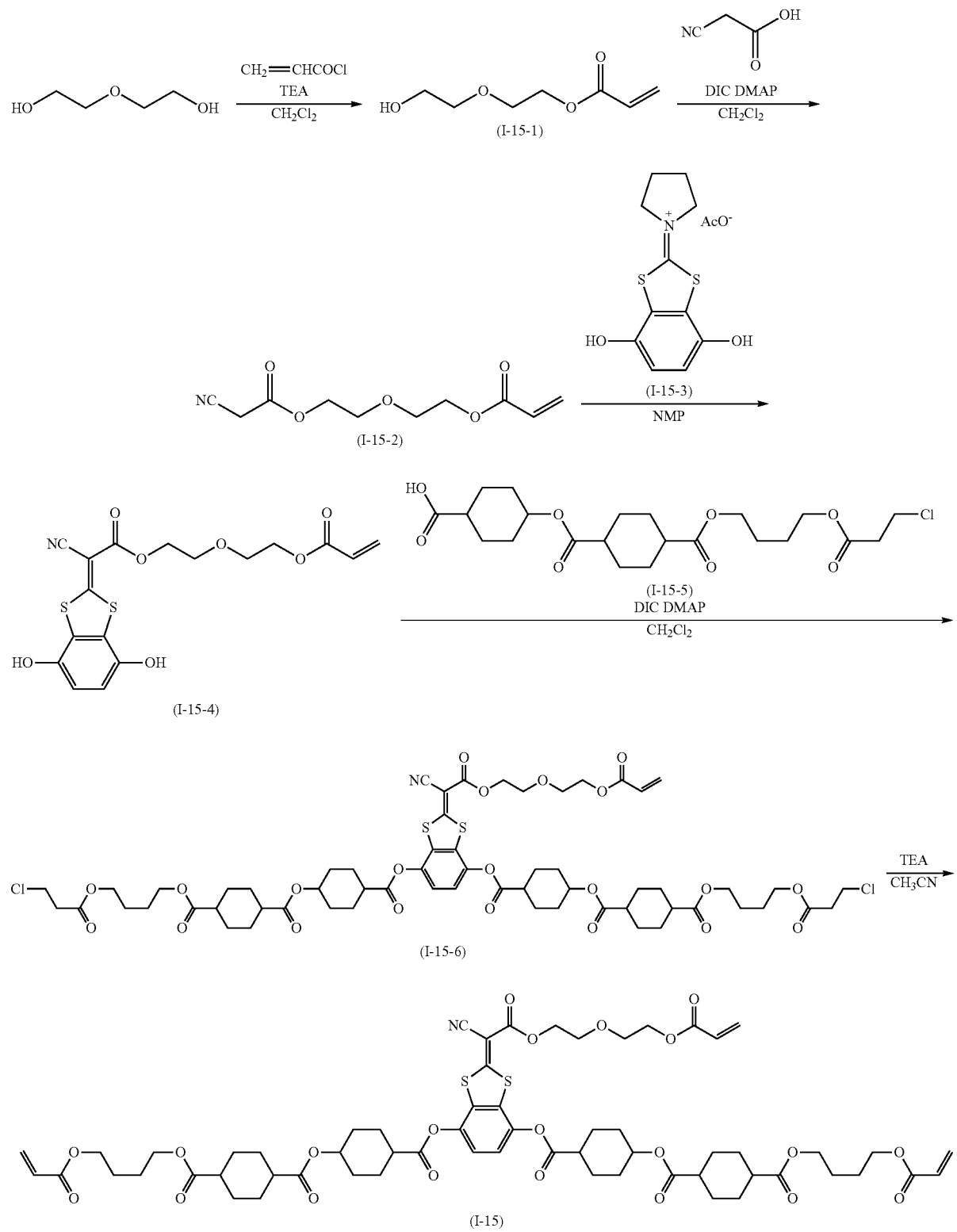

A compound represented by the formula (I-15-3) was produced according to a method described in Journal of Chemical, Crystallography (1997), 27(9), p. 515-526, and a compound represented by the formula (I-15-5) was produced according to a method disclosed in JP-A-2009-179563.

To a reaction vessel, 50.0 g of diethylene glycol, 45.2 g of triethylamine, and 250 mL of dichloromethane were added 38.4 g of acryloyl chloride was added dropwise under cooling with ice and the mixture was stirred at room temperature for 4 hours. The reaction solution was washed with hydrochloric acid and a saline solution in this order, and the solvent was evaporated. Purification was performed by column chromatography (silica gel) to yield 21.7 g of a compound represented by the formula (I-15-1).

To a reaction vessel, 21.7 g of the compound represented by the formula (I-15-1), 11.5 g of cyanoacetic acid, 1.65 g of N,N-dimethylaminopyridine, and 160 mL of dichloromethane were added 18.8 g of diisopropylcarbodiimide was added dropwise under cooling with ice and the mixture was stirred at room temperature for 4 hours. The reaction solution was filtered, and the filtrate was purified by column chromatography (silica gel) to yield 23.4 g of a compound represented by the formula (I-15-2).

To a reaction vessel, 10.7 g of the compound represented by the formula (I-15-2), 10.0 g of the compound represented by the formula (I-15-3), 50 mg of Irganox 1010 (manufactured by BASF), and 100 mL of N-methyl-2-pyrrolidone were added, and stirred at 80° C. for 2 hours. The reaction solution was diluted with ethyl acetate, and was washed with water and a saline solution in this order, and the solvent was evaporated. Purification was performed by column chromatography (silica gel) to yield 10.5 g of a compound represented by the formula (I-15-4).

To a reaction vessel, 10.5 g of the compound, represented by the formula (I-15-4), 23.6 g of the compound represented by the formula (I-15-5), 0.6 g of N,N-dimethylaminopyridine, and 170 mL of dichloromethane were added. 7.1 g of diisopropylcarbodiimide was added dropwise under cooling with ice and the mixture was stirred at room temperature for 6 hours. The reaction solution was filtered, and the filtrate was purified by column chromatography (silica gel) and recrystallization (dichloromethane/methanol) to yield 22.3 g of a compound represented by the formula (I-15-6).

To a reaction vessel, 22.3 g of the compound represented by the formula (I-15-6), 10 mL of triethylamine, and 100 mL of acetonitrile were added, and stirred at 80° C. for 3 hours. The reaction solution was diluted with ethyl acetate, and was washed with hydrochloric acid, water, and a saline solution in this order, and the solvent was evaporated. Purification was performed by column chromatography (silica gel) and recrystallization (dichloromethane/methanol) to yield 12.2 g of a compound represented by the formula (I-15).

LCMS: 1222 [M+1]

Example 16

Production of Compound, Represented by the Formula (I-16)

[Chem. 140]

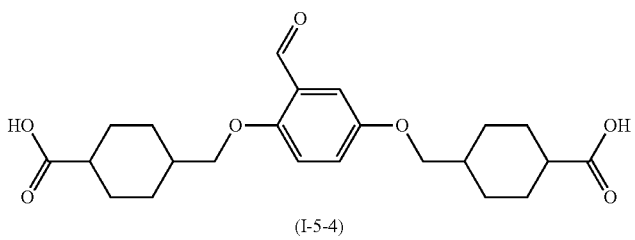

(I-5-4)

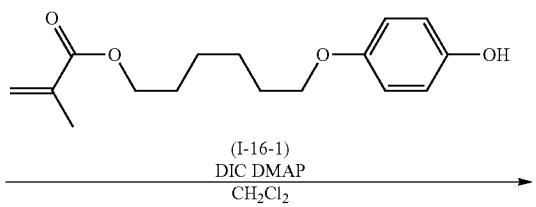

(I-16-1)
DIC DMAP
CH$_2$Cl$_2$

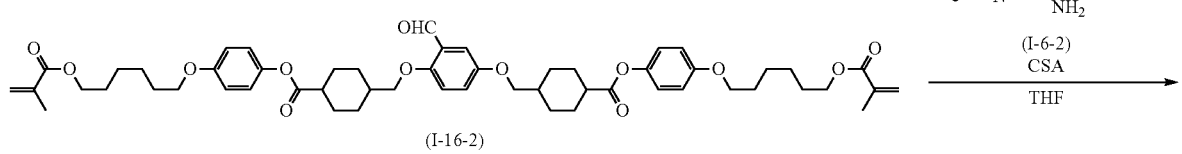

(I-16-2)

-continued

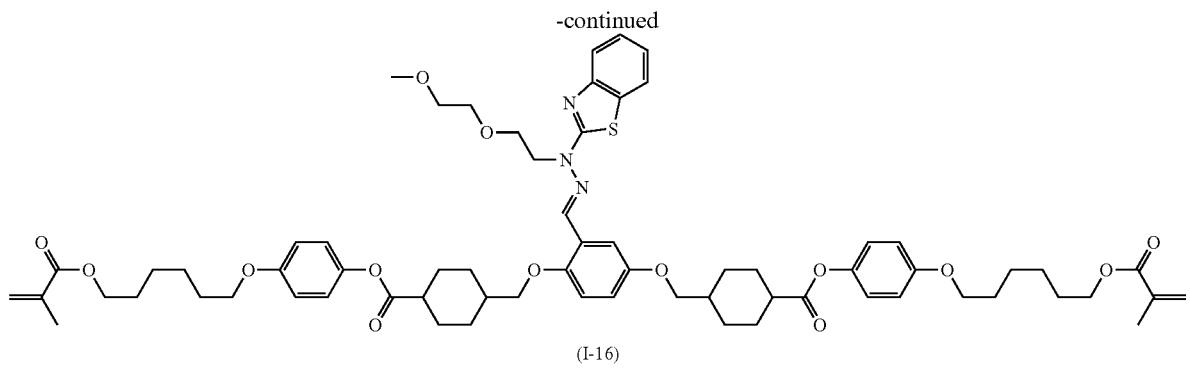

(I-16)

To a reaction vessel, 6.3 g of the Compound represented by the formula (I-5-4), 8.4 g of a compound represented by the formula (I-16-1), 370 mg of N,N-dimethylaminopyridine, and 70 mL of dichloromethane were added 4.2 g of diisopropylcarbodiimide was added dropwise under cooling with ice and the mixture was stirred at room temperature for 7 hours. The reaction solution was filtered, and the filtrate was washed with hydrochloric acid, water, and a saline solution in this order. Purification was performed by column chromatography (silica gel) and recrystallization (dichloromethane/methanol) to yield 10.1 g of a compound represented by the formula (I-16-2).

To a reaction vessel, 10.1 g of the compound represented by the formula (I-16-2), 3.0 g of the compound represented by the formula (I-6-2), 0.1 g of (±)-10-camphorsulfonic acid, and 70 mL of tetrahydrofuran were added, and stirred at 50° C. The solvent was evaporated from the reaction solution, and was subjected to dispersion washing with methanol. Purification was performed by column chromatography (silica gel) and recrystallization to yield 6.9 g of a compound represented by the formula (I-16). LCMS: 1188 [M+1]

Example 17

Production of Compound Represented by the Formula (I-17)

[Chem. 141]

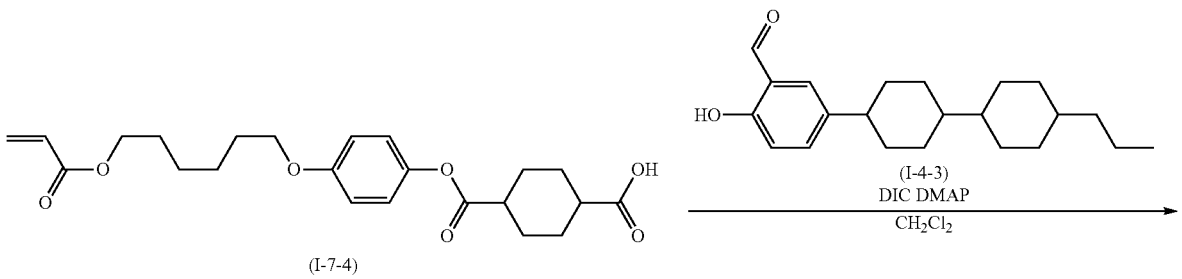

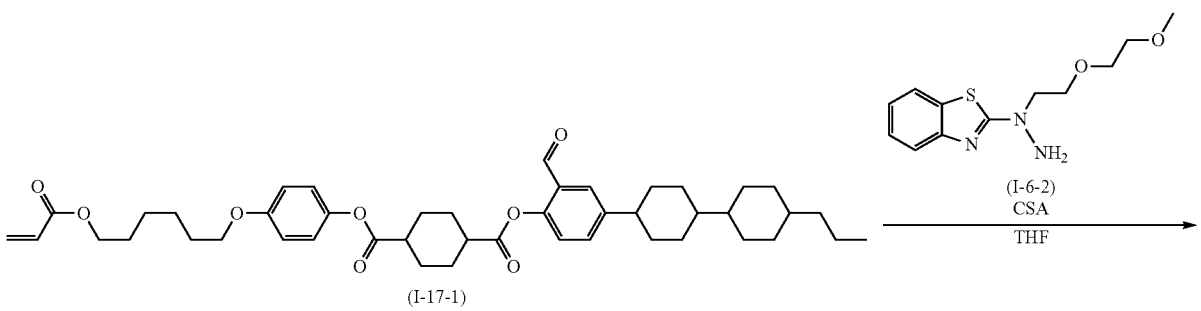

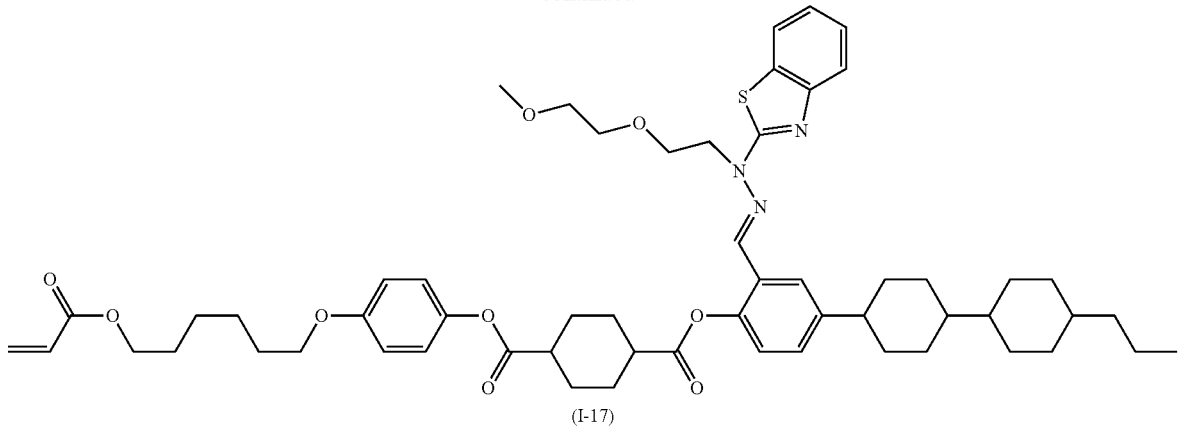

(I-17)

To a reaction vessel, 2.0 g of the compound represented by the formula (I-4-3), 2.5 g of the compound represented by the formula (I-7-4), 400 mg of N,N-dimethylaminopyridine, and 30 mL of dichloromethane were added 0.9 g of diisopropylcarbodiimide was added dropwise under cooling with ice and the mixture was stirred at room temperature. The reaction solution was filtered, and the filtrate was washed with hydrochloric acid, water, and a saline solution in this order. Purification was performed by column chromatography (silica gel) and recrystallization (dichloromethane/hexane) to yield 3.5 g of a compound represented by the formula (I-17-1).

To a reaction vessel, 2.5 g of the compound represented by the formula (I-17-1), 0.9 g of the compound represented by the formula (I-6-2), 0.3 g of (±)-10-camphorsulfonic acid, 50 mL of tetrahydrofuran, and 20 mL of ethanol were added, and stirred at 50° C. The solvent was evaporated from the reaction solution, and was subjected to dispersion washing with methanol. Purification was performed by column chromatography (silica gel) and recrystallization (dichloromethane/methanol) to yield 2.0 q of a compound represented by the formula (I-17).

$^1$H NMR (CDCl$_3$) δ 0.92 (t, 3H), 1.05-1.83 (m, 32H), 1.93 (t, 5H), 2.33 (m, 4H), 2.55 (m, 2H), 2.71 (m, 1H), 3.30 (s, 3H), 3.62 (m, 2H), 3.85 (t, 2H), 3.94 (t, 2H), 4.17 (t, 2H), 4.48 (t, 2H), 5.32 (dd, 1H), 6.12 (dd, 1H), 6.40 (dd, 1H), 6.38 (d, 2H), 6.99 (m, 3H), 7.17 (t, 1H), 7.23 (dd, 1H), 7.34 (t, 1H), 7.66 (d, 1H), 7.71 (d, 1H), 7.89 (d, 1H), 8.02 (s, 1H) ppm.

LCMS: 978 [M+1]

Compounds represented by the formulae (I-18) to (I-99) were produced using the same methods as in Examples 1 to 17 and known methods.

Examples 18 to 34, Comparative Examples 1 to 3

Compounds: represented toy the formulae (I-1) to (I-17) described in Examples 1 to 17, a compound (R-1) disclosed in PTL 1, a compound (R-2) disclosed in PTL 2, and a compound (R-3) disclosed in PTL 3 were compounds to be evaluated.

[Chem. 142]

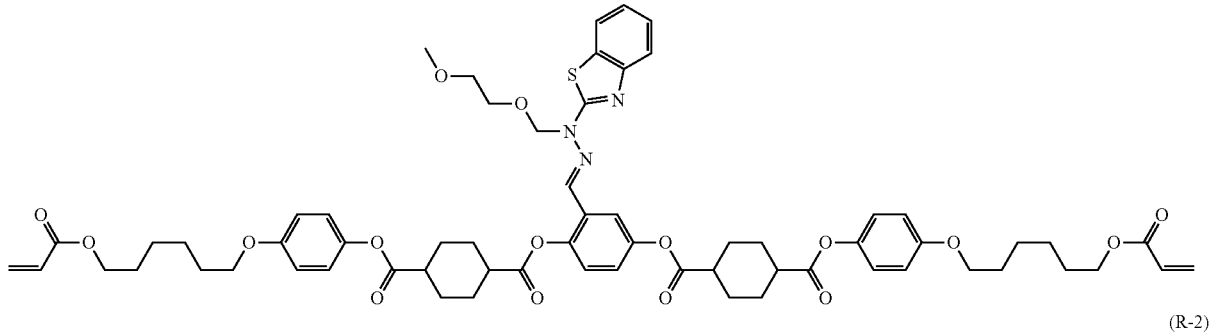

(R-1)

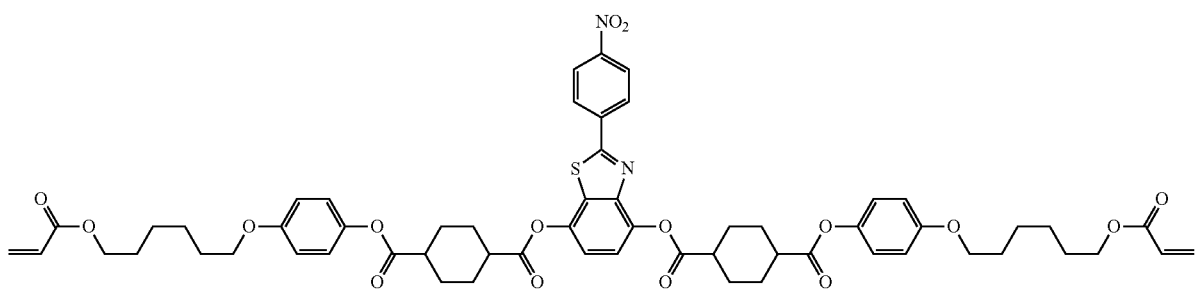

(R-2)

-continued

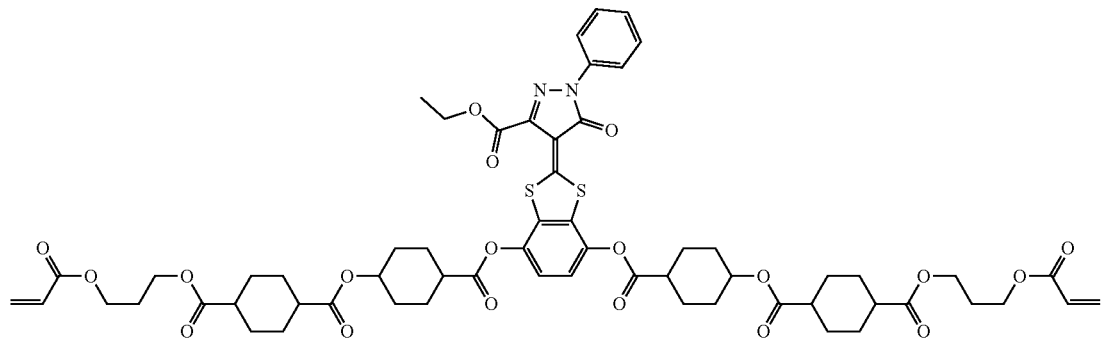
(R-3)

20 wt % solutions of each of the compounds to be evaluated in chloroform, trichloroethane, cyclopentanone, methyl ethyl ketone (MEK), methyl isobutyl ketone (MIBK), and toluene were prepared to check the solubilities of the compound to be evaluated. The results are shown in the following table. A in the table indicates the compound dissolves at room temperature, B indicates the compound does not dissolve at room temperature but dissolves when heated to 60° C., and C indicates the compound does not dissolve even when heated to 60° C.

The table shows that the compounds (I-1) to (I-17) of the present invention have equal, or higher solubilities in various solvents than the comparative compounds (R-1) to (R-3).

Examples 35 to 51, Comparative Examples 4 to 6

A polyimide solution for alignment film was applied on a cycloolefin polymer substrate using a spin coating process, and dried at 60° C. for 10 minutes and baked at 100° C. for

TABLE 1

|  | Compound to be Evaluated | Results of Solubility ||||||
|---|---|---|---|---|---|---|---|
|  |  | Chloroform | Trichloroethane | Cyclopentanone | MEK | MIBK | Toluene |
| Example 18 | Compound (I-1) of the Invention | A | A | A | A | A | A |
| Example 19 | Compound (I-2) of the Invention | A | A | A | A | B | A |
| Example 20 | Compound (I-3) of the Invention | A | A | A | C | C | B |
| Example 21 | Compound (I-4) of the Invention | A | B | B | C | C | B |
| Example 22 | Compound (I-5) of the Invention | A | A | A | B | B | A |
| Example 23 | Compound (I-6) of the Invention | A | A | A | B | B | B |
| Example 24 | Compound (I-7) of the Invention | A | A | A | A | B | A |
| Example 25 | Compound (I-8) of the Invention | A | A | A | B | B | A |
| Example 26 | Compound (I-9) of the Invention | A | A | A | A | B | A |
| Example 27 | Compound (I-10) of the Invention | A | A | A | B | B | A |
| Example 28 | Compound (I-11) of the Invention | A | A | A | B | B | A |
| Example 29 | Compound (I-12) of the Invention | A | A | B | B | C | B |
| Example 30 | Compound (I-13) of the Invention | A | A | B | C | C | B |
| Example 31 | Compound (I-14) of the Invention | A | A | B | B | C | B |
| Example 32 | Compound (I-15) of the Invention | A | A | B | B | C | B |
| Example 33 | Compound (I-16) of the Invention | A | A | A | B | B | A |
| Example 34 | Compound (I-17) of the Invention | A | B | B | C | C | B |
| Comparative Example 1 | Comparative Compound (R-1) | A | B | B | C | C | B |
| Comparative Example 2 | Comparative Compound (R-2) | B | B | C | C | C | B |
| Comparative Example 3 | Comparative Compound (R-3) | A | B | C | C | C | B |

60 minutes to produce a coating film. The obtained coating film was subjected to a rubbing treatment. The rubbing treatment was performed using a commercially available rubbing apparatus.

An application solution was prepared so as to have a composition of 18.9% of each of the compounds to be evaluated, 1% of a photoinitiator Irgacure 907 (manufactured by BASF), 0.1% of 4-methoxyphenol, and 80% of chloroform. The application solution was applied on the rubbed cycloolefin polymer substrate by a spin coating process. The resulting coating was dried at 60° C. for 2 minutes, and then irradiated with ultraviolet light at an intensity of 40 mW/cm$^2$ for 25 seconds using a high pressure mercury lamp, thereby producing a coating film to be evaluated. The coating film was cut in a 2 mm-square grid pattern with a cutter by a cross cutting method in accordance with JIS K5600-5-6, and the adhesiveness of the coating film was measured. The results are shown in the following table. The meanings of the terms in the table was as follows.

Class 0; no peeling is found in any grid square.

Class 1: a little peeling of the coating film is found at intersections of the cutting (less than 5%).

Class 2: the coating film is peeled along the cutting line at intersections (5% or more and less than 15%).

Class 3: the coating film is peeled partially or entirely along the cutting line (15% or more and less than 35%).

Class 4: the coating film is largely peeled partially or entirely along the cutting line (35% or more and less than 65%).

Class 5: more than Class 4 (65% or more).

TABLE 2

| Compound to be Evaluated | Results of adhesiveness |
|---|---|
| Example 35 | Compound (I-1) of the Invention | Class 2 |
| Example 36 | Compound (I-2) of the Invention | Class 2 |
| Example 37 | Compound (I-3) of the Invention | Class 2 |
| Example 38 | Compound (I-4) of the Invention | Class 2 |
| Example 39 | Compound (I-5) of the Invention | Class 2 |
| Example 40 | Compound (I-6) of the Invention | Class 2 |
| Example 41 | Compound (I-7) of the Invention | Class 2 |
| Example 42 | Compound (I-8) of the Invention | Class 2 |
| Example 43 | Compound (I-9) of the Invention | Class 1 |
| Example 44 | Compound (I-10) of the Invention | Class 2 |
| Example 45 | Compound (I-11) of the Invention | Class 2 |
| Example 46 | Compound (I-12) of the Invention | Class 2 |
| Example 47 | Compound (I-13) of the Invention | Class 3 |
| Example 48 | Compound (I-14) of the Invention | Class 3 |
| Example 49 | Compound (I-15) of the Invention | Class 3 |
| Example 50 | Compound (I-16) of the Invention | Class 2 |
| Example 51 | Compound (I-17) of the Invention | Class 2 |
| Comparative Example 4 | Comparative Compound (R-1) | Class 3 |
| Comparative Example 5 | Comparative Compound (R-2) | Class 4 |
| Comparative Example 6 | Comparative Compound (R-3) | Class 4 |

The table shows that the compounds (I-1) to (I-17) of the present invention have an equal or lower likelihood of peeling than the comparative compounds (R-1) to (R-3).

Accordingly, the compound of the present invention is useful as a constituent of a polymerizable composition. In addition, an optically anisotropic body using a polymerizable liquid crystal composition containing the compound of the present invention is useful for applications such as optical film.

The invention claimed is:
1. A polymerizable low wavelength dispersion or polymerizable reverse wavelength dispersion compound having a partial structure represented by the following general formula (AO-1) in a molecule:

(AO-1)

wherein n$^0$ represents an integer of 2 or more; and R$^0$ represents a linear alkylene group having 2 to 20 carbon atoms, a branched alkylene group having 3 to 20 carbon atoms, an arbitrary hydrogen atom in the alkylene group may be substituted with a fluorine atom or a chlorine atom, and plural les may be the same or different,
wherein the compound has, in a molecule, at least one group represented by the following general formula (I-0-R):

(I-0-R)

wherein P$^0$ represents a polymerizable group; k$^0$ represents an integer of 1 to 10; Sp$^0$ represents a linear alkylene group having 1 to 30 carbon atoms, a branched alkylene group having 3 to 30 carbon atoms, or a single bond, one —CH$_2$— or two or more (—CH$_2$—)'s not adjacent to each other in the alkylene group may be each independently substituted with —O—, —S—, —CO—, —COO—, —OCO—, —CO—S—, —S—CO—, —O—CO—O—, —CO—NH—, —NH—CO—, —CF$_2$O—, —OCF$_2$—, —CF$_2$S—, —SCF$_2$—, —CH=CH—COO—, —CH=CH—OCO—, —COO—CH=CH—, —OCO—CH=CH—, —CH=CH—, —N=N—, —CH=N—N=CH—, —CF=CF—, or —C≡C—, and plural Sp$^0$'s, if any, may be the same or different; and (Sp$^0$)$_{k0}$ may be a group having a partial structure represented by the general formula (AO-1), provided that P$^0$—(Sp$^0$)$_{k0}$—contains no —O—O— bond,
wherein the compound is represented by the general formula (I):

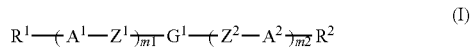

(I)

wherein R$^1$ is the group represented by the general formula (I-0-R) in which)(Sp$^0$)$_{k0}$ includes the partial structure represented by the general formula (AO-1), and
wherein R$^2$ represents a hydrogen atom, a fluorine atom, a chlorine atom, a bromine atom, an iodine atom, a pentafluorosulfuranyl group, a cyano group, a nitro group, an isocyano group, a thioisocyano group, a linear alkyl group having 1 to 20 carbon atoms or a branched alkyl group having 3 to 20 carbon atoms, in which arbitrary hydrogen atoms in the group may be substituted with a fluorine atom and one —CH$_2$— or two or more (—CH$_2$—)'s not adjacent to each other may be each independently substituted with —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH₂S—, —CF₂O—, —OCF₂—, —CF₂S—, —SCF₂—, —COO—CH₂CH₂—, —OCO—CH₂CH₂—, —CH₂CH₂—COO—, —CH₂CH₂—OCO—, —COO—CH₂—, —OCO—CH₂—, —CH₂—COO—, —CH₂—OCO—, —N=N—, or —CH=N—N=CH—;

A¹ and A² each independently represent a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, or 1,3-dioxane-2,5-diyl group, these groups may be unsubstituted or substituted with one or more substituents L's, L represents a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, a linear alkyl group having 1 to 20 carbon atoms or a branched alkyl group having 3 to 20 carbon atoms, in which one —CH₂— or two or more (—CH₂—)'s not adjacent to each other may be each independently substituted with —O—, —S—, —CO—, —COO—, —OCO—, —CO—S—, —S—CO—, —O—CO—O—, —CO—NH— or —NH—CO—, and an arbitrary hydrogen atom in the alkyl group may be substituted with a fluorine atom, and plural L's in the compound, if any, may be the same or different;

Z¹ and Z² each independently represent —O—, —S—, —OCH₂—, —CH₂O—, —CH₂CH₂—, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —SCH₂—, —CH₂S—, —CF₂O—, —OCF₂—, —CF₂S—, —SCF₂—, —CH=CH—COO—, —CH=CH—OCO—, —COO—CH=CH—, —OCO—CH=CH—, —COO—CH₂CH₂—, —OCO—CH₂CH₂—, —CH₂CH₂—COO—, —CH₂CH₂—OCO—, —COO—CH₂—, —OCO—CH₂—, —CH₂—COO—, —CH₂—OCO—, —CH=CH—, —N=N—, —CH=N—, —N=CH—, —CH=N—N=CH—, —CF=CF—, —C≡C—, or a single bond, plural Z¹'s, if any, may be the same or different, and plural Z²'s, if any, may be the same or different;

G¹ represents a divalent group having at least one aromatic ring selected from the group consisting of an aromatic hydrocarbon ring and an aromatic heterering, the number of π electrons contained in the aromatic ring(s) in the group represented by G¹ is 12 or more, and the group represented by G¹ may be unsubstituted or substituted with one or more substituents L^G's, L^G represents a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, a linear alkyl group having 1 to 20 carbon atoms or a branched alkyl group having 3 to 20 carbon atoms, in which one —CH₂— or two or more (—CH₂—)'s not adjacent to each other may be each independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, and an arbitrary hydrogen atom in the alkyl group may be substituted with a fluorine atom, or L^G may represent a group represented by P^{LG}—(Sp^{LG}—X^{LG})_{kLG}— where P^{LG} represents a polymerizable group, Sp^{LG} represents a linear alkylene group having 1 to 10 carbon atoms in which one —CH₂— or two or more (—CH₂—)'s not adjacent to each other may be each independently substituted with —O—, —COO—, or —OCO— or a single bond, plural Sp^{LG}'s, if any, may be the same or different, X^{LG} represents —O—, —S—, —OCH₂—, —CH₂O—, —CO—, —COO—, —OCO—, —CO—S—, —S—CO—, —O—CO—O—, —CO—NH—, —NH—CO—, —SCH₂—, —CH₂S—, —CF₂O—, —OCF₂—, —CF₂S—, —SCF₂—, —CH=CH—COO—, —CH=CH—OCO—, —COO—CH=CH—, —OCO—CH=CH—, —COO—CH₂CH₂—, —OCO—CH₂CH₂—, —CH₂CH₂—COO—, —CH₂CH₂—OCO—, —COO—CH₂—, —OCO—CH₂—, —CH₂—COO—, —CH₂—OCO—, —CH=CH—, —N=N—, —CH=N—N=CH—, —CF=CF—, —C≡C—, or a single bond, plural X^{LG}'s, if any, may be the same or different, and kLG represents an integer of 0 to 10, and plural L^G's in the compound, if any, may be the same or different; and m1 and m2 each independently represent an integer of 0 to 6, provided that m1+m2 is an integer of 0 to 6;

provided that the general formula (I) contains no —O—O— bond, wherein in the general formula (I), G¹ represents a group selected from the following general formulae (M-1) to (M-6):

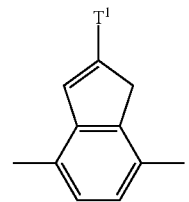

(M-1)

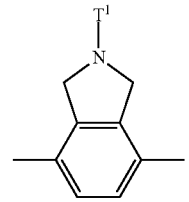

(M-2)

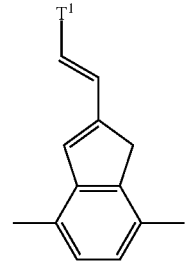

(M-3)

(M-4)
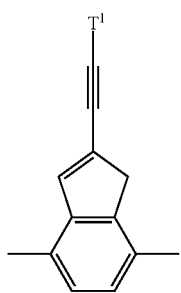

(M-5)
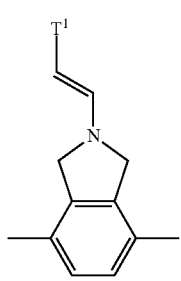

(M-6)
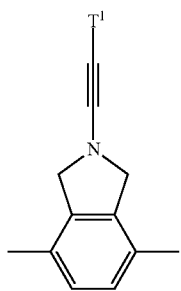

wherein these groups may be unsubstituted or substituted with one or more substituents $L^G$'s as described above; arbitrary (—CH═)'s may be each independently substituted with —N═; (—CH$_2$—)'s each independently represent —O—, —S—, —NR$^T$—, wherein R$^T$ represents a hydrogen atom or an alkyl group having 1 to 20 carbon atoms, —CS—, or —CO—; T$^1$ represents a group selected from the following formulae (T1-1) to (T1-6):

(T1-1)

(T1-2)

(T1-3)
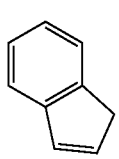

(T1-4)
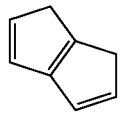

(T1-5)
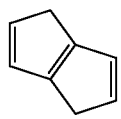

(T1-6)
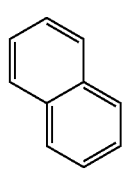

wherein these groups may have a bonding at an arbitrary position, arbitrary (—CH═)'s may be each independently substituted with —N═, (—CH$_2$—)'s each independently represent —O—, —S—, —NR$^T$—, wherein R$^T$ represents a hydrogen atom or an alkyl group having 1 to 20 carbon atoms), —CS—, or —CO—, and these groups may be unsubstituted or substituted with one or more substituents $L^G$'s as described above, or a group selected from the general formulae (M-7) to (M-14):

(M-7)
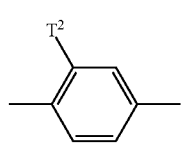

(M-8)
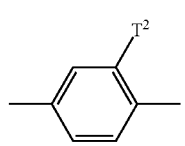

(M-9)
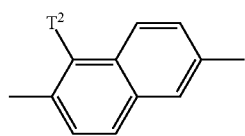

(M-10)
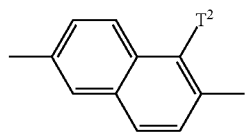

(M-11)
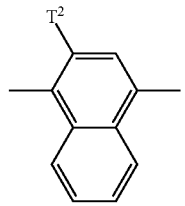

-continued

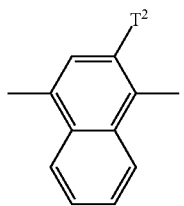
(M-12)

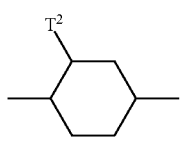
(M-13)

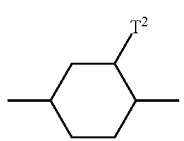
(M-14)

wherein these groups may be unsubstituted or substituted with one or more substituents $L^G$'s as described above, arbitrary (—CH=)'s may be each independently substituted with —N=, (—CH$_2$—)'s each independently represent —O—, —S—, —NR$^T$— wherein R$^T$ represents a hydrogen atom or an alkyl group having 1 to 20 carbon atoms, —CS—, or —CO—; and T$^2$ represents a group selected from the following general formula (T2-1) or (T2-2):

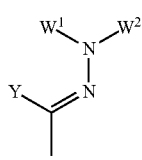
(T2-1)

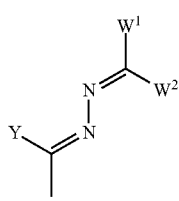
(T2-2)

wherein W$^1$ represents a group having 1 to 40 carbon atoms and containing an aromatic group and/or a nonaromatic group which may be substituted, the aromatic group may be a hydrocarbon ring or a heteroring, and the nonaromatic group may be a hydrocarbon group or a hydrocarbon group in which an arbitrary carbon atom is substituted with a heteroatom provided that oxygen atoms do not directly bind to each other; W$^2$ represents a hydrogen atom, a linear alkyl group having 1 to 20 carbon atoms or a branched alkyl group having 3 to 20 carbon atoms, in which one —CH$_2$— or two or more (—CH$_2$—)'s not adjacent to each other may be each independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CH=CH—, —CF=CF—, or —C≡C—, and an arbitrary hydrogen atom in the alkyl group may be substituted with a fluorine atom, or W$^2$ may represent a group having 2 to 30 carbon atoms and having at least one aromatic group, and the group may be unsubstituted or substituted with one or more substituents $L^W$'s, or W$^2$ may represent a group represented by P$^W$—(Sp$^W$—X$^W$)$_{kW}$— where P$^W$ represents a polymerizable group, Sp$^W$ represents a linear alkylene group having 1 to 30 carbon atoms, a branched alkylene group having 1 to 30 carbon atoms, or a single bond, one —CH$_2$— or two or more (—CH$_2$—)'s not adjacent to each other in the alkylene group may be each independently substituted with —O—, —S—, —CO—, —COO—, —OCO—, —CO—S—, —S—CO—, —O—CO—O—, —CO—NH—, —NH—CO—, —CF$_2$O—, —OCF$_2$—, —CF$_2$S—, —SCF$_2$—, —CH=CH—COO—, —CH=CH—OCO—, —COO—CH=CH—, —OCO—CH=CH—, —CH=CH—, —N=N—, —CH=N—N=CH—, —CF=CF—, or —C≡C, and plural Sp$^W$'s, if any, may be the same or different, X$^W$ represents —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, —C≡C—, or a single bond, plural X$^W$'s, if any, may be the same or different, and kW represents an integer of 0 to 10, and L$^W$ represents a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, a linear alkyl group having 1 to 20 carbon atoms or a branched alkyl group having 3 to 20 carbon atoms, in which one —CH$_2$— or two or more (—CH$_2$—)'s not adjacent to each other may be each independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, and an arbitrary hydrogen atom in the alkyl group may be substituted with a fluorine atom, or L$^W$ may represent a group represented by P$^{LW}$—(Sp$^{LW}$—X$^{LW}$)$_{kLW}$— where P$^{LW}$ represents a polymerizable group, Sp$^{LW}$ represents a linear alkylene group having 1 to 10 carbon atoms in which one —CH$_2$— or two or more (—CH$_2$—)'s not adjacent to each other may be each independently substituted with —O—, —COO—, or —OCO— or a single bond, plural Sp$^{LW}$'s, if any, may be the same or different, X$^{LW}$ represents —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—

—CH=CH—, —COO—CH₂CH₂—, —OCO—CH₂CH₂—, —CH₂CH₂—COO—, —CH₂CH₂—OCO—, —COO—CH₂—, —OCO—CH₂—, —CH₂—COO—, —CH₂—OCO—, —CH=CH—, —N=N—, —CH=N—N=CH—, —CF=CF—, —C≡C—, or a single bond, plural $X^{LW}$'s, if any, may be the same or different, and kLW represents an integer of 0 to 10, and plural $L^W$'s in the compound, if any, may be the same or different;

Y represents a hydrogen atom, a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, a linear alkyl group having 1 to 20 carbon atoms or a branched alkyl group having 3 to 20 carbon atoms, in which one —CH₂— or two or more (—CH₂—)'s not adjacent to each other may be each independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, and an arbitrary hydrogen atom in the alkyl group may be substituted with a fluorine atom, or Y may represent a group represented by $P^Y$—($Sp^Y$—$X^Y$)$_{kY}$— where $P^Y$ represents a polymerizable group, $Sp^Y$ represents a linear alkylene group having 1 to 10 carbon atoms in which one —CH₂— or two or more (—CH₂—)'s not adjacent to each other may be each independently substituted with —O—, —COO—, or —OCO— or a single bond, plural $Sp^Y$'s, if any, may be the same or different, $X^Y$ represents —O—, —S—, —OCH₂—, —CH₂O—, —CO—, —OCO—, —OCO—, —CO—S—, —S—CO—, —O—CO—O—, —CO—NH—, —NH—CO—, —SCH₂—, —CH₂S—, —CF₂O—, —OCF₂—, —CF₂S—, —SCF₂—, —CH=CH—COO—, —CH=CH—OCO—, —COO—CH=CH—, —OCO—CH=CH—, —COO—CH₂CH₂—, —OCO—CH₂CH₂—, —CH₂CH₂—COO—, —CH₂CH₂—OCO—, —COO—CH₂—, —OCO—CH₂—, —CH₂—COO—, —CH₂—OCO—, —CH=CH—, —N=N—, —CH=N—N=CH—, —CF=CF—, —C≡C—, or a single bond, plural $X^Y$'s, if any, may be the same or different, and kY represents an integer of 0 to 10; and $W^1$ and $W^2$ may be linked together to form a ring structure.

2. The compound according to claim 1, wherein in the general formula (I-0-R), $P^0$ represents a group selected from the following formulae (P-1) to (P-14) and (P-16) to (P-20):

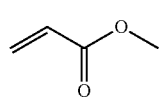
(P-1)

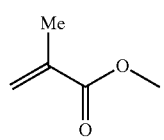
(P-2)

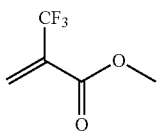
(P-3)

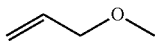
(P-4)

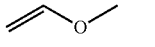
(P-5)

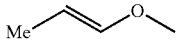
(P-6)

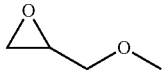
(P-7)

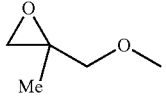
(P-8)

(P-9)

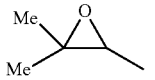
(P-10)

(P-11)

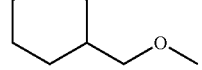
(P-12)

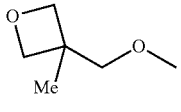
(P-13)

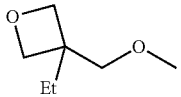
(P-14)

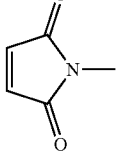
(P-16)

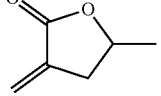
(P-17)

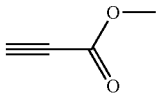
(P-18)

-continued

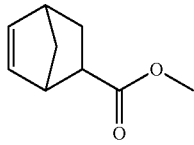
(P-19)

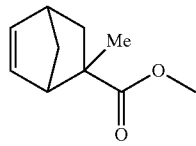
(P-20)

3. The compound according to claim 1, wherein $W^2$ in the general formula (T2-1) or the general formula (T2-2) comprises a partial structure represented by the general formula (AO-1).

4. The compound according to claim 1, wherein in the general formula (I), $G^1$ is represented by the formula (M-7) or (M-8).

5. A composition comprising the compound of claim 1.

6. A liquid crystal composition comprising the compound of claim 1.

7. A polymer comprising a composition of claim 5.

8. An optically anisotropic body comprising the polymer of claim 7.

9. Resins, resin additives, oils, filters, adhesives, pressure-sensitive adhesives, oils and fats, inks, medicines, cosmetics, detergents, building materials, wrapping materials, liquid crystal materials, organic EL materials, organic semiconductor materials, electronic materials, display elements, electronic devices, communication devices, automotive parts, aircraft parts, machine parts, agricultural chemicals and foods using the compound of claim 1, and products using them.

* * * * *